United States Patent
Strum et al.

(10) Patent No.: US 11,090,306 B2
(45) Date of Patent: Aug. 17, 2021

(54) TREATMENT OF RB-NEGATIVE TUMORS USING TOPOISOMERASE INHIBITORS IN COMBINATION WITH CYCLIN DEPENDENT KINASE 4/6 INHIBITORS

(71) Applicant: G1 Therapeutics, Inc., Research Triangle Park, NC (US)

(72) Inventors: Jay Copeland Strum, Hillsborough, NC (US); John E. Bisi, Apex, NC (US); Patrick Joseph Roberts, Durham, NC (US); Jessica A. Sorrentino, Durham, NC (US)

(73) Assignee: G1 Therapeutics, Inc.

( * ) Notice: Subject to any disclaimer, the term of this patent is extended or adjusted under 35 U.S.C. 154(b) by 106 days.

(21) Appl. No.: 16/572,418

(22) Filed: Sep. 16, 2019

(65) Prior Publication Data

US 2020/0022983 A1   Jan. 23, 2020

Related U.S. Application Data

(60) Division of application No. 16/142,574, filed on Sep. 26, 2018, now Pat. No. 10,413,547, which is a continuation of application No. 15/457,667, filed on Mar. 13, 2017, now abandoned, which is a continuation of application No. PCT/US2015/049756, filed on Sep. 11, 2015.

(60) Provisional application No. 62/050,035, filed on Sep. 12, 2014.

(51) Int. Cl.
| | | |
|---|---|---|
| *A61K 31/519* | (2006.01) | |
| *A61K 31/5375* | (2006.01) | |
| *A61K 31/5377* | (2006.01) | |
| *A61K 31/695* | (2006.01) | |
| *A61K 31/4745* | (2006.01) | |

(52) U.S. Cl.
CPC ........ *A61K 31/519* (2013.01); *A61K 31/4745* (2013.01); *A61K 31/5375* (2013.01); *A61K 31/5377* (2013.01); *A61K 31/695* (2013.01)

(58) Field of Classification Search
None
See application file for complete search history.

(56) References Cited

U.S. PATENT DOCUMENTS

| | | |
|---|---|---|
| 5,591,855 A | 1/1997 | Hudkins et al. |
| 5,628,984 A | 5/1997 | Boucher |
| 6,291,504 B1 | 9/2001 | Nugiel et al. |
| 6,369,086 B1 | 4/2002 | Davis |
| 6,610,684 B2 | 8/2003 | Zaharevitz et al. |
| 6,667,346 B2 | 12/2003 | Reddy et al. |
| 6,936,612 B2 | 8/2005 | Barvian et al. |
| 6,962,993 B2 | 11/2005 | Blumenkopf et al. |
| 6,982,277 B2 | 1/2006 | Gudkov et al. |
| 7,208,489 B2 | 4/2007 | Barvain et al. |
| 7,345,171 B2 | 3/2008 | Beylin et al. |
| 7,482,354 B2 | 1/2009 | Traquandi et al. |
| 7,855,211 B2 | 12/2010 | Coates et al. |
| 8,598,186 B2 | 12/2013 | Tavares et al. |
| 8,598,197 B2 | 12/2013 | Tavares et al. |
| 8,691,830 B2 | 4/2014 | Tavares et al. |
| 8,822,683 B2 | 9/2014 | Tavares et al. |
| 8,829,012 B2 | 9/2014 | Tavares et al. |
| 9,102,682 B2 | 8/2015 | Tavares et al. |
| 9,260,442 B2 | 1/2016 | Tavares et al. |
| 9,464,092 B2 | 10/2016 | Strum et al. |
| 9,481,691 B2 | 11/2016 | Tavares et al. |
| 9,487,530 B2 | 11/2016 | Strum et al. |
| 9,499,564 B2 | 11/2016 | Tavares et al. |
| 9,527,857 B2 | 12/2016 | Strum et al. |
| 2002/0042412 A1 | 4/2002 | Zaharevitz et al. |
| 2003/0069430 A1 | 4/2003 | Davis et al. |
| 2003/0073668 A1 | 4/2003 | Booth et al. |
| 2003/0224522 A1 | 12/2003 | de Jong et al. |
| 2003/0229026 A1 | 12/2003 | Al-Awar et al. |
| 2004/0006074 A1 | 1/2004 | Kelley et al. |
| 2004/0048915 A1 | 3/2004 | Engler et al. |
| 2004/0236084 A1 | 11/2004 | Biwersi et al. |
| 2005/0222163 A1 | 10/2005 | Eck et al. |
| 2007/0027147 A1 | 2/2007 | Hayama et al. |
| 2007/0179118 A1 | 8/2007 | Barvian et al. |
| 2007/0207143 A1 | 9/2007 | Dang et al. |

(Continued)

FOREIGN PATENT DOCUMENTS

| | | |
|---|---|---|
| CA | 2656290 | 7/2008 |
| CN | 1278794 A | 1/2001 |

(Continued)

OTHER PUBLICATIONS

Akinleye et al., Ibrutinib and novel BTK inhibitors in clinical development, Journal of Hematology & Oncology, 2013, 6:59.
An, H. X. et al. "Gene amplification and overexpression of CDK4 in sporadic breast carcinomas is associated with high tumor cell proliferation" American Journal of Pathology, 1999; 154: 113-118.
Anderson, M. S. and J. A. Bluestone "The NOD mouse: a model of immune dysregulation" Annu Rev Immunol, 2005; 23: 447-485.
Barginear, M. F. and D. R. Budman "Trastuzumab-DM1: A review of the novel immuno-conjugate for HER2-overexpressing breast cancer" The Open Breast Cancer Journal, 2009; 1:25-30.
Baughn, L. B. et al. "A novel orally active small molecule potently induces G1 arrest in primary myeloma cells and prevents tumor growth by specific inhibition of cyclin-dependent kinase 4/6" Cancer Res, Aug. 1, 2006; 66(15): 7661-7667.

(Continued)

*Primary Examiner* — Jeffrey S Lundgren
*Assistant Examiner* — Michael J Schmitt
(74) *Attorney, Agent, or Firm* — Knowles Intellectual Property Strategies, LLC

(57) ABSTRACT

This invention is in the area of improved therapeutic combinations for and methods of treating selected retinoblastoma (Rb)-negative cancers and Rb-negative abnormal cellular proliferative disorders using particular topoisomerase inhibitors and specific cyclin-dependent kinase 4/6 (CDK4/6) inhibitors. In one aspect, the improved treatment of select Rb-negative cancers is disclosed using specific compounds disclosed herein in combination with a topoisomerase I inhibitor.

6 Claims, 32 Drawing Sheets

(56) References Cited

U.S. PATENT DOCUMENTS

| | | |
|---|---|---|
| 2007/0212736 A1 | 9/2007 | Chen-Kiang et al. |
| 2007/0270362 A1 | 11/2007 | Harlan et al. |
| 2008/0085890 A1 | 4/2008 | Tsou et al. |
| 2008/0161355 A1 | 7/2008 | Curry et al. |
| 2008/0182853 A1 | 7/2008 | Kruman et al. |
| 2010/0105653 A1 | 4/2010 | Besong et al. |
| 2011/0009353 A1 | 1/2011 | Chen-Kiang et al. |
| 2011/0224221 A1 | 9/2011 | Sharpless et al. |
| 2011/0224227 A1 | 9/2011 | Sharpless et al. |
| 2011/0312909 A1 | 12/2011 | Ciomei et al. |
| 2012/0100100 A1 | 4/2012 | Sharpless et al. |
| 2013/0237533 A1* | 9/2013 | Tavares ............... C07D 487/14 514/228.5 |
| 2013/0289031 A1 | 10/2013 | Sanofi |
| 2014/0107114 A1 | 4/2014 | Kim et al. |
| 2014/0271460 A1 | 9/2014 | Strum et al. |
| 2014/0271466 A1 | 9/2014 | Strum et al. |
| 2014/0274896 A1 | 9/2014 | Strum et al. |
| 2014/0275066 A1 | 9/2014 | Strum et al. |
| 2014/0275067 A1 | 9/2014 | Strum et al. |
| 2015/0246925 A1 | 9/2015 | Tavares et al. |
| 2015/0246926 A1 | 9/2015 | Tavares et al. |
| 2015/0297606 A1 | 10/2015 | Strum et al. |
| 2015/0297607 A1 | 10/2015 | Strum et al. |
| 2015/0297608 A1 | 10/2015 | Strum et al. |
| 2015/0299212 A1 | 10/2015 | Strum et al. |
| 2016/0045509 A1 | 2/2016 | Strum et al. |
| 2016/0108054 A1 | 4/2016 | Tavares |
| 2016/0220569 A1 | 8/2016 | Strum et al. |
| 2016/0310499 A1 | 10/2016 | Strum et al. |
| 2017/0037051 A1 | 2/2017 | Strum et al. |
| 2017/0057971 A1 | 3/2017 | Tavares et al. |
| 2017/0057972 A1 | 3/2017 | Tavares |
| 2017/0065597 A1 | 3/2017 | Strum et al. |
| 2017/0100405 A1 | 4/2017 | Strum et al. |
| 2017/0119774 A1 | 5/2017 | Strum et al. |

FOREIGN PATENT DOCUMENTS

| | | |
|---|---|---|
| CN | 1379668 A | 11/2002 |
| JP | 2001-517652 A | 10/2001 |
| JP | 2005-519909 A | 7/2005 |
| JP | 2007-530425 A | 11/2007 |
| JP | 2007-530654 A | 11/2007 |
| WO | WO 1998/033798 A2 | 8/1998 |
| WO | WO 1999/015500 A1 | 4/1999 |
| WO | WO 2001/012188 A1 | 2/2001 |
| WO | WO 2002/044174 A2 | 6/2002 |
| WO | WO 2003/062236 A1 | 7/2003 |
| WO | WO 2005/005426 A1 | 1/2005 |
| WO | WO 2005/040166 A1 | 5/2005 |
| WO | WO 2005/052147 A2 | 6/2005 |
| WO | WO 2005/094830 A1 | 10/2005 |
| WO | WO 2005/105213 A2 | 11/2005 |
| WO | WO 2006/074985 A1 | 7/2006 |
| WO | WO 2006/127587 A1 | 11/2006 |
| WO | WO 2007/025090 A2 | 3/2007 |
| WO | WO 2007/048847 A2 | 5/2007 |
| WO | WO 2007/065820 A1 | 6/2007 |
| WO | WO 2007/124252 A2 | 11/2007 |
| WO | WO 2008/005538 A2 | 1/2008 |
| WO | WO 2008/079933 A2 | 7/2008 |
| WO | WO 2009/003003 A2 | 12/2008 |
| WO | WO 2009/061345 A2 | 5/2009 |
| WO | WO 2009/085185 A1 | 7/2009 |
| WO | WO 2010/012777 A1 | 2/2010 |
| WO | WO 2010/020675 A1 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2011/101409 A1 | 8/2011 |
| WO | WO 2011/103485 A1 | 8/2011 |
| WO | WO 2012/068381 A2 | 5/2012 |
| WO | WO 2012/061156 A1 | 10/2012 |
| WO | WO 2013/148748 A1 | 10/2013 |
| WO | WO 2013/163239 A1 | 10/2013 |
| WO | WO 2014/071109 A1 | 5/2014 |
| WO | WO 2014/144326 A1 | 9/2014 |
| WO | WO 2014/144596 A2 | 9/2014 |
| WO | WO 2014/144740 A2 | 9/2014 |
| WO | WO 2014/144847 A2 | 9/2014 |
| WO | WO 2014/168975 A1 | 10/2014 |
| WO | WO 2015/061407 A1 | 4/2015 |
| WO | WO 2015/161283 A1 | 10/2015 |
| WO | WO 2015/161285 A1 | 10/2015 |
| WO | WO 2015/161287 A1 | 10/2015 |
| WO | WO 2015/161288 A1 | 10/2015 |
| WO | WO 2016/040848 A1 | 3/2016 |
| WO | WO 2016/040858 A1 | 3/2016 |

OTHER PUBLICATIONS

Berge et al. "Pharmaceutical Salts" J. Pharm. Sci., 1977; 66(1): 1-19.

Bernhard, E. J. et al. "Reducing the radiation-induced G2 delay causes HeLa cells to undergo apoptosis instead of mitotic death" Int J Radiat Biol., May 1996; 69(5): 575-584.

Bisi et al., Preclinical Characterization of G1T28: A Novel CDK4/6 Inhibitor for Reduction of Chemotherapy-Induced Myelosuppression, Mol. Cancer Therap. (2016) (15)5: 783-793.

Bisi et al., Preclinical development of G1T38: A novel, potent and selective inhibitor of cyclin dependent kinases 4/6 for use as an oral antineoplastic in patients with CDK4/6 sensitive tumors, Oncotarget. Mar. 15, 2017: doi:10.18632/oncotarget.16216.

Bisi et al., Preclinical development of G1T38: A novel, potent and selective inhibitor of cyclin dependent kinases 4/6 for use as an oral antineoplastic in patients with CDK4/6 sensitive tumors, Oncotarget. Mar. 15, 2017: doi:10.18632/oncotarget.16216, Suppl.

Blagosklonny, M. V. and A. B. Pardee "Exploiting cancer cell cycling for selective protection of normal cells" Cancer Res, Jun. 1, 2001; 61(11): 4301-4305.

Brookes et al. "INK4a-deficient human diploid fibroblasts are resistant to RAS-induced senescence" EMBO J., Jun. 17, 2002; 21(12): 2936-2945.

Bucher, N. and C. D. Britten "G2 checkpoint abrogation and checkpoint kinase-1 targeting in the treatment of cancer" Br J Cancer, Feb. 12, 2008; 98(3): 523-528.

Burdelya et al. "An agonist of toll-like receptor 5 has radioprotective activity in mouse and primate models" Science, Apr. 11, 2008; 320(5873): 226-230.

Casi, G. and D. Neri "Antibody-drug conjugates: basic concepts, examples and future perspectives" Journal of Controlled Release, 2012; 161(2): 422-428.

Chari, R.V. "Targeted cancer therapy: conferring specificity to cytotoxic drugs" Accounts of Chemical Research, 2008; 41(1): 98-107.

Chen, X. et al. "Protection of normal proliferating cells against chemotherapy by staurosporine-mediated, selective, and reversible G1 arrest" J Natl Cancer Inst., Dec. 20, 2000; 92(24): 1999-2008.

Chin et al. "Cooperative effects of INK4a and ras in melanoma susceptibility in vivo" Genes & Development, 1997; 11: 2822-2834.

Chu et al. "Discovery of [4-Amino-2-(1-methanesulfonylpiperidin-4-ylamino)pyrimidin-5-yl](2,3-difluoro-6-methoxyphenyl)methanone (R547), a potent and selective cyclin-dependent kinase inhibitor with significant in vivo antitumor activity" J Med Chem, 200.

Curtin et al. "Distinct Sets of Genetic Alterations in Melanoma" N Engl J Med 2005; 353: 2135-2147.

Daniotti et al. "BRAF alterations are associated with complex mutational profiles in malignant melanoma" Oncogene, 2004; 23: 5968-5977.

Davis, S. T. et al. "Prevention of chemotherapy-induced alopecia in rats by CDK inhibitors" Science, Jan. 5, 2001; 291(5501): 134-137.

Davis, S.T. et al. "Retraction" Science, Dec. 20, 2002; 298(5602): 2327.

Davis, T. A. et al. "Genistein induces radioprotection by hematopoietic stem cell quiescence" Int J Radiat Biol, Sep. 2008; 84(9): 713-726.

(56) References Cited

OTHER PUBLICATIONS

Decker et al. "Expression of Cyclin E in resting and activated B-chronic lymphocytic leukemia cells: cyclin E/cdk2 as protential therapeutic target" British Journal of Hematology, Jan. 13, 2004, 125, 141-148.

Dickson, M. A. and G. K. Schwartz "Development of cell-cycle inhibitors for cancer therapy" Curr Oncol, Mar. 2009; 16(2): 36-43.

Dickson, Mark, et al. "Phase II Trial of the CDK4 Inhibitor PD0332991 in Patients With Advanced CDK4-Amplified Well-Differentiated or Dedifferentiated Liposarcoma." J Clin Oncol. Jun. 1, 2013; 31(16): 2024-2028.

Diehl, J. A. "Cycling to Cancer with Cyclin D1" Cancer Biology and Therapy, 2002; 1(3): 226-231.

El-Diery, W. S. "Meeting report: The international conference on tumor progression and therapeutic resistance" Cancer Res, Jun. 1, 2005; 65(11): 4475-4484.

Elkind, M.M. and H. Sutton "Radiation response of mammalian cells grown in culture. 1. Repair of x-ray damage in surviving Chinese hamster cells" Radiat Res., 1960; 13: 556-593.

Elkind, M.M. and H. Sutton "X-ray damage and recovery in mammalian cells in culture" Nature, 1959; 184: 1293-1295.

Engler et al. "Novel, potent and selective cyclin D1/CDK4 inhibitors: indolo[6,7-a]pyrrolo[3,4-c]carbazoles" Bioorg Med Chem Lett, Jul. 21, 2003; 13(14): 2261-2267.

Finn et al. "PD 0332991, a selective cyclin D kinase 4/6 inhibitor, preferentially inhibits proliferation of luminal estrogen receptor-positive human breast cancer cell lines in vitro" Breast Cancer Research, Oct. 29, 2009; 11(5): R77.

Finn et al. "Results of a randomized phase 2 study of PD 0332991, a cyclin-dependent kinase (CDK) 4/6 inhibitor, in combination with letrozole vs letrozole alone for first-line treatment of ER+/HER2—advanced breast cancer (BC)" Cancer Res, 2012; 72(24 Suppl): Abstract nr S1-6.

Firer, M. A. and G. J. Gellerman Targeted drug delivery for cancer therapy: the other side of antibodies, J. Hematol. Oncol., 2012; 5: 70. [retrieved from http://www.jhoonline.org/content/5/1/70 on Jul. 16, 2014].

Franken et al. "Clonogenic assay of cells in vitro" Nature Protocols, 2006; 1: 2315-2319.

Fry, D. W. et al. "Specific inhibition of cyclin-dependent kinase 4/6 by PD 0332991 and associated antitumor activity in human tumor xenografts" Mol Cancer Ther., Nov. 2004; 3(11): 1427-1438.

Goldberg et al. "Pyrazinoindolone inhibitors of MAPKAP-K2" Bioogranic & Medicinal Chemistry Letters, Dec. 23, 2007, 18, 938-941.

Guillard et al., "Synthesis and biological evaluations of new pyrrolo[2,3-b]pyrimidine as SDI analogs" Heterocyles, 2008, vol. 75(5), pp. 1163-1189.

Guo et al. "Staurosporine modulates radiosensitivity and radiation-induced apoptosis in U937 cells" Int J Radiat Biol., Feb. 2006; 82(2): 97-109.

Hallahan, D. E. et al. "Inhibition of protein kinases sensitizes human tumor cells to ionizing radiation" Radiat Res., Mar. 1992; 129(3): 345-350.

Hamilton et al., Synergistic Anticancer Activity of Topotecan—Cyclin-Dependent Kinase Inhibitor Combinations against Drug-Resistant Small Cell Lung Cancer (SCLC) Cell Lines, Journal of Cancer Therapy (2013) 4: 47-53.

Hamilton et al., Synergism of Cyclin-Dependent Kinase Inhibitors with Camptothecin Derivatives in Small Cell Lung Cancer Cell Lines, Molecules (2014), 19(2): 2077-2088.

Hara, E. et al. "Regulation of p16CDKN2 expression and its implications for cell immortalization and senescence" Mol Cell Biol, Mar. 1996; 16(3): 859-867.

Herodin, F. et al. "Short-term injection of antiapoptotic cytokine combinations soon after lethal gamma-irradiation promotes survival" Blood, Apr. 1, 2003; 101(7): 2609-2616.

Hershman, D et al. "Acute myeloid leukemia or myelodysplastic syndrome following use of granulocyte colony-stimulating factors during breast cancer adjuvant chemotherapy" J Natl Cancer Inst, Feb. 7, 2007; 99(3): 196-205.

Hibbs, M. L. et al. "Multiple defects in the immune system of Lyn-deficient mice, culminating in autoimmune disease" Cell, Oct. 20, 1995; 83(2): 301-311.

Hirose, Y. et al. "Abrogation of the Chk1-mediated G(2) checkpoint pathway potentiates temozolomide-induced toxicity in a p53-independent manner in human glioblastoma cells" Cancer Res, Aug. 1, 2001; 61(15): 5843-5849.

Honma, T. et al. "A novel approach for the development of selective Cdk4 inhibitors: library design based on location of Cdk4 specific amino acid residues" J Med Chem, Dec. 20, 2001; 44(26): 4628-4640.

Honma, T. et al. "Structure-based generation of a new class of potent Cdk4 inhibitors: new de novo design strategy and library design" J Med Chem, Dec. 20, 2001; 44(26): 4615-4627.

Humphreys, B.D. et al. "Intrinsic epithelial cells repair the kidney after injury" Cell Stem Cell, 2008; 2: 284-291.

Humphreys, B.D. et al. "Repair of injured proximal tubule does not involve specialized progenitors" Proc Natl Acad Sci USA, 2011; 108: 9226-9231.

Ikuta, M. et al. "Crystallographic approach to identification of cyclin-dependent kinase 4 (CDK4)-specific inhibitors by using CDK4 mimic CDK2 protein" J Biol Chem, Jul. 20, 2001; 276(29): 27548-27554.

Johnson, D. G. and C. L. Walker "Cyclins and Cell Cycle Checkpoints" Annual Review of Pharmacology and Toxicology, Apr. 1999; 39: 295-312.

Johnson, N. and G. Shapiro "Cyclin-dependent kinase 4/6 inhibition in cancer therapy" Cell Cycle, Nov. 1, 2012; 11(21): 3913-3918.

Johnson, S.M., et al. "Mitigation of hematologic radiation toxicity in mice through pharmacological quiescence induced by CDK4/6 inhibition" J Clin Invest, Jul. 2010; 120(7): 2528-2536.

Johnson et al., Cyclin-dependent kinases (cdks) and the DNA damage response: rationale for cdk inhibitor-chemotherapy combinations as an anticancer strategy for solid tumors, Expert Opin Ther Targets. Nov. 2010; 14(11): 1199-1212.

Karaman, M. W. et al. "A quantitative analysis of kinase inhibitor selectivity" Nat Biotechnol., Jan. 2008; 26(1): 127-132.

Khuri, F. R. "Weighing the hazards of erythropoiesis stimulation in patients with cancer" N Engl J Med, Jun. 14, 2007; 356(24): 2445-2448.

Kiel et al. "SLAM Family Receptors Distinguish Hematopoietic Stem and Progenitor Cells and Reveal Endothelial Niches for Stem Cells" Cell, 2005; 121: 1109-1121.

Kim, S. et al. "Enhancement of radiation effects by flavopiridol in uterine cervix cancer cells" Cancer Res Treat, Jun. 2005; 37(3): 191-195.

Knockaert et al. "Pharmacological inhibitors of cyclin-dependent kinases" Trends Pharmacol Sci, Sep. 2002; 23(9): 417-425.

Kubinyi (3D QSAR in Drug Design: Ligand-Protein Interactions and Molecular Similarity, vol. 2-3, Springer, 1998, 800 pages). p. 243-44.

Kubo, et al. "The p16 status of tumor cell lines identifies small molecule inhibitors specific for cyclin-dependent kinase 4" Clin Cancer Res, 1999; 5: 4279-4286.

Lambert, J. M. Drug-conjugated antibodies for the treatment of cancer British Journal of Clinical Pharmacology, 2013; 76(2): 248-262.

Landis, M.W. et al. Cyclin D1-dependent kinase activity in murine development and mammary tumorigenesis. Cancer Cell, 2006; 9: 13-22.

Laredo, J. et al. "Effect of the protein kinase C inhibitor staurosporine on chemosensitivity to daunorubicin of normal and leukemic fresh myeloid cells" Blood, Jul. 1, 1994; 84(1): 229-237.

Le Deley et al. "Anthracyclines, Mitoxantrone, Radiotherapy, and Granulocyte Colony-Stimulating Factor: Risk Factors for Leukemia and Myelodysplastic Syndrome After Breast Cancer" J Clin Oncol, 2007; 25: 292-300.

(56) References Cited

OTHER PUBLICATIONS

Little, J.B. "Repair of sub-lethal and potentially lethal radiation damage in plateau phase cultures of human cells" Nature, 1969; 224(5221): 804-806.
Lohmann and Gallie "Retinoblastoma" Gene Reviews (2000), retrieved from http://www.ncbi.nlm.nih.gov/books/NBK1452/ on Jul. 10, 2014.
Lopus, M. Antibody-DM1 conjugates as cancer therapeutics, Cancer Letters, 2011; 307(2): 113-118.
Luo, Y. et al. "Blocking Chk1 expression induces apoptosis and abrogates the G2 checkpoint mechanism" Neoplasia, Sep.-Oct. 2001; 3(5): 411-419.
Malumbres, M. an M. Barbacid "Cell cycle, CDKs and cancer: a changing paradigm" Nature Reviews Cancer, Mar. 2009; 9(3): 153-166.
Malumbres, M. and M. Barbacid "Mammalian cyclin-dependent kinases" Trends Biochem. Sci., Nov. 2005; 30(11): 630-641.
McInnes, C. "Progress in the evaluation of CDK inhibitors as anti-tumor agents" Drug Discov Today, Oct. 2008; 13(19-20): 875-881.
McClendon et al., CDK4/6 inhibition antagonizes the cytotoxic response to anthracycline therapy, Cell Cycle 11 (2012):14, 2747-2755.
Meng et al. "Ionizing Radiation and Busulfan Induce Premature Senescence in Murine Bone Marrow Hematopoietic Cells" Cancer Res, 2003; 63: 5414-5419.
Menu, E. et al. "A novel therapeutic combination using PD 0332991 and bortezomib: study in the 5T33MM myeloma model" Cancer Res, Jul. 15, 2008; 68(14): 5519-5523.
Michaud, Karine et al. "Pharmacologic inhibition of cdk4/6 arrests the growth of glioblastoma multiforme intracranial xenografts" Cancer Res, Apr. 15, 2010; 70: 3228-3238.
Morgan, D.O. "Cyclin-dependent Kinases: Engines, Clocks, and Microprocessors" Annual Review of Cell and Developmental Biology, 1997; 13: 261-291.
Na Nakorn et al. "Myeloerythroid-restricted progenitors are sufficient to confer radioprotection and provide the majority of day 8 CFU-S" J Clin Invest, 2002; 109: 1579-1585.
Newland, A. M. "Brentuximab vedotin: a CD30-directed antibody-cytotoxic drug conjugate" Pharmacotherapy, Jan. 2013; 33(1): 93-104.
O'Dwyer, et al. "A phase I dose escalation trial of a daily oral CDK 4/6 inhibitor PD-0332991" J Clin Oncol, 2007; 25(18S): 3550. [Abstract].
Ojeda, F. et al. "Role of protein kinase-C in thymocyte apoptosis induced by irradiation" Int J Radiat Biol., May 1992; 61(5): 663-667.
Park et al. "Toxicogenetics in drug development" Toxicology Letters, Mar. 31, 2001, 120, 281-291.
Parsam et al. "A comprehensive, sensitive and economical approach for the detection of mutations in the RB1 gene in retinoblastoma" Journal of Genetics, Dec. 2009; 88(4): 517-527.
Passegué et al. "Global analysis of proliferation and cell cycle gene expression in the regulation of hematopoietic stem and progenitor cell fates" J Exp Med, 2005; 202: 1599-1611.
Pawlik, T. M. and K. Keyomarsi "Role of cell cycle in mediating sensitivity to radiotherapy" Int J Radiat Oncol Biol Phys, Jul. 15, 2004; 59(4): 928-942.
PCT/US2015/049756 International Search Report dated Feb. 16, 2016.
Pedersen-Bjegaard et al., Genetic pathways in therapy-related myelodysplasia and acute myeloid leukemia, Blood (2002) 99:1909-1912.
Presser, Armin and Antje Hüfner "Trimethylsilyldiazomethane—A Mild and Efficient Reagent for the Methylation of Carboxylic Acids and Alcohols in Natural Products" Monatshefte für Chemie, 2004, 135(8): 1015-1022.
Pommier et al., DNA topoisomerases and their poisoning by anti-cancer and antibacterial drugs, Chem. & Biol. Review 17 (2010) 421-433.
Rader et al., Dual CDK4/CDK6 Inhibition Induces Cell Cycle Arrest and Senescence in Neuroblastoma, Clin Cancer Res (Nov. 15, 2013) 19(22): 6173-82.
Ramsey, M. R. et al. "Expression of p16Ink4a compensates for p18Ink4c loss in cyclin-dependent kinase 4/6-dependent tumors and tissues" Cancer Res, May 15, 2007; 67(10): 4732-4741.
Reddy, H. K. et al. "Cyclin-dependent kinase 4 expression is essential for neu-induced breast tumorigenesis" Cancer Research, 2005; 65: 10174-10178.
Roberts et al. "Multiple Roles of Cyclin-Dependent Kinase 4/6 Inhibitors in Cancer Therapy" JNCI, 2012; 104(6):476-487.
Ruas et al. "CDK4 and CDK6 Delay Senescence by Kinase-Dependent and p16INK4a-Independent Mechanisms" Molecular and Cellular Biology, Jun. 2007; 27(12): 4273-4282.
Samady, L. et al. "Activation of CDK4 gene expression in human breast cancer cells by the Brn-3b POU family transcription factor" Cancer Biology & Therapy, 2004; 3: 317-323.
Sanchez-Martinez, C. et al. "Aryl[a]pyrrolo[3,4-c]carbazoles as selective cyclin D1-CDK4 inhibitors" Bioorg Med Chem Lett, Nov. 3, 2003; 13(21): 3835-3839.
Sanchez-Martinez, C. et al. "Studies on cyclin-dependent kinase inhibitors: indole-[2,3-a]pyrrolo[3,4-c]carbazoles versus bis-indolylmaleimides" Bioorg Med Chem Lett, Nov. 3, 2003; 13(21): 3841-3846.
Sapra, P. and B. Shor "Monoclonal antibody-based therapies in cancer: advances and challenges" Pharmacology & Therapeutics, 2013; 138(3): 452-469.
Sarkar et al. Nonsolvent Application of Ionic Liquids: Organo-Catalysis by 1-Alkyl-3-methylimidazolium Cation Based Room-Temperature Ionic Liquids for Chemoselective N-tert-Butyloxycarbonylation of Amines and the Influence of the C-2 Hydrogen on Catalyti.
Schliemann, C. and D. Neri "Antibody-based targeting of the tumor vasculature" Biochimica et Biophysica Acta, 2007; 1776(2): 175-192.
Schmidt, M. and Z. Fan "Protection against chemotherapy-induced cytotoxicity by cyclin-dependent kinase inhibitors (CKI) in CKI-responsive cells" Oncogene, Sep. 27, 2001; 20(43): 6164-6171.
Schönauer, K. and E. Zibral "Reactions with organophosphorus compounds, 50.: Trimethylsilylethoxymethylene triphenylphosphorane, a novel reagent for the homologation of carbonyl compounds." Tetrahedron Letters, 1983, 24: 573-576.
Schwartz, G.K. et al. "Phase I study of PD 0332991, a cyclin-dependent kinase inhibitor, administered in 3-week cycles (Schedule 2/1)" Br J Cancer, Jun. 7, 2011; 104(12): 1862-1868.
Seed, T. M. "Radiation protectants: current status and future prospects" Health Phys, Nov. 2005; 89(5): 531-545.
Sharma, P.S. et al. "Inhibitors of cyclin dependent kinases: useful targets for cancer treatment" Curr. Cancer Drug Targets, Feb. 2008; 8(1): 53-75.
Sharpless et al. "Both products of the mouse Ink4a/Arf locus suppress melanoma formation in vivo" Oncogene, Aug. 7, 2003; 22(32): 5055-5059.
Sherr, C. J., "Cancer Cell Cycles" Science, Dec. 6, 1996; 274(5293): 1672-1677.
Sherr, Mammalian G1 Cyclins, Cell 73 (1993) 1059-1065.
Shields et al. "Lack of Extracellular Signal-Regulated Kinase Mitogen-Activated. Protein Kinase Signaling Shows a New Type of Melanoma" Cancer Res, 2007; 67: 1502-1512.
Shimamura, T. et al. "Identification of potent 5-pyrimidinyl-2-aminothiazole CDK4, 6 inhibitors with significant selectivity over CDK1, 2, 5, 7, and 9" Bioorg Med Chem Lett., Jul. 15, 2006; 16(14): 3751-3754.
Sielecki et al "Quinazolines as cyclin dependent kinase inhibitors"Bioogranic & Medicinal Chemistry Letters, May 7, 2001, 11, 1157-1160.
Sinclair, W.K. and R.A. Morton "X-ray sensitivity during the cell generation cycle of cultured Chinese hamster cells" Radiat Res., Nov. 1966; 29(3): 450-474.
Singh et al. Discovery and Development of Spleen Tyrosine Kinase (SYK) Inhibitors, J. Med. Chem. 2012, 55, 3614-3643.

(56) References Cited

OTHER PUBLICATIONS

Soni, R. et al. "Selective in vivo and in vitro effects of a small molecule inhibitor of cyclin-dependent kinase 4" J Natl Cancer Inst, Mar. 21, 2001; 93(6): 436-446.
Stone, S. et al. "Reversible, p16-mediated cell cycle arrest as protection from chemotherapy" Cancer Research, Jul. 15, 1996; 56(14): 3199-3202.
Sun, Y. et al. "Antibody-drug conjugates as targeted cancer therapeutics" Acta Pharmaceutica Sinica, 2009; 44(9): 943-952.
Takano, Y. et al. Cyclin D1 overexpression in invasive breast cancers: correlation with cyclin-dependent kinase 4 and oestrogen receptor overexpression, and lack of correlation with mitotic activity Journal of Cancer Research and Clinical Oncology, 1999.
Tate et al., Semi-Mechanistic Pharmacokinetic/Pharmacodynamic Modeling of the Antitumor Activity of LY2835219, a New Cyclin-Dependent Kinase 4/6 Inhibitor, in Mice Bearing Human Tumor Xenografts, Clin Cancer Res (Jul. 15, 2014) 20; 3763.
Teicher, B. A. and R. V. Chart "Antibody conjugate therapeutics: challenges and potential" Clinical Cancer Research, 2011; 17(20): 6389-6397.
Terasima, T. and Li Tolmach "X-ray sensitivity and DNA synthesis in synchronous populations of HeLa cells" Science, 1963, 140: 490-492.
Teyssier, F. et al. "Cell cycle regulation after exposure to ionizing radiation" Bull Cancer., Apr. 1999; 86(4): 345-357. [Abstract].
Toogood, P. L. et al. "Discovery of a potent and selective inhibitor of cyclin-dependent kinase 4/6" J Med Chem, Apr. 7, 2005; 48(7): 2388-2406.
Tsou, H. R. et al. "4-(Phenylaminomethylene)isoquinoline-1,3(2H,4H)-diones as potent and selective inhibitors of the cyclin-dependent kinase 4 (CDK4)" J Med Chem, Jun. 26, 2008: 51(12): 3507-3525.
Tsou, H.R. et al. "Discovery of 4-(benzylaminomethylene)isoquinoline-1,3-(2H,4H)-diones and 4-[(pyridylmethyl)aminomethylene]isoquinoline-1,3-{2H,4H)-diones as potent and selective inhibitors of the cyclin-dependent kinase 4" J Med Chem, Apr. 23, 2009; 52(8): 2289-2310.
Tu, S. et al. "New potential inhibitors of cyclin-dependent kinase 4: design and synthesis of pyrido[2,3-d]pyrimidine derivatives under microwave irradiation" Bioorg Med Chem Lett, Jul. 1, 2006; 16(13): 3578-3581.
Uckun, F. M. et al. "In vivo radioprotective effects of recombinant human granulocyte colony-stimulating factor in lethally irradiated mice" Blood, Feb. 1, 1990; 75(3): 638-645.
Vanderwel, S.N. et al. "Pyrido[2,3-d]pyrimidin-7-ones as specific inhibitors of cyclin-dependent kinase 4" J Med Chem., Apr. 7, 2005; 48(7): 2371-2387.
Vlachakis, D. and S. Kossida "Antibody Drug Conjugate bioinformatics: drug delivery through the letterbox" Comput. Math. Methods Med., 2013; 2013: 282398. Published online on Jun. 19, 2013. [retrieved from http://dx.doi.org/10.1155/2013/282398 on Jul. 16, 2014].
Walker et al. "Virtually 100% of melanoma cell lines harbor alterations at the DNA level within CDKN2A, CDKN2B, or one of their downstream targets" Genes Chromosomes & Cancer, 1998; 22: 157-163.
Wall et al., The isolation and structure of camptothecin, a novel alkaloidal leukemia and tumor inhibitor from Camptotheca acuminate, J. Am. Chem. Soc. (1966) 88: 3888-3890.
Wang et al. "Loss of p21 increases sensitivity to ionizing radiation and delays the onset of lymphoma in atm-deficient mice" Proc Natl Acad Sci, USA, 1997; 94: 14590-14595.
Wang, R. H. et al. "Protein kinase inhibitor staurosporine enhances cytotoxicity of antitumor drugs to cancer cells" Yao Xue Xue Bao, 1996; 31(6): 411-415. [Abstract].
Weiss and Landauer "History and development of radiation-protective agents" International Journal of Radiation Biology, Jul. 2009; 85: 539-573.
Wermuth, The Practice of Medicinal Chemistry, 2d ed. (2003), 768 pages. Chs. 9-10.

White, J.D. et al. "Transformations of Quinic Acid. Asymmetric Synthesis and Absolute Configuration of Mycosporin I and Mycosporingly" Journal of Organic Chemistry, 1995, 60(12): 3600-3611.
Wilson et al. "Hematopoietic Stem Cells Reversibly Switch from Dormancy to Self-Renewal during Homeostasis and Repair" Cell, 2008; 135: 1118-1129.
WIPO International Search Report dated Dec. 10, 2015.
Yu, Q. et al. "Requirement for CDK4 kinase function in breast cancer" Cancer Cell, 2006; 9: 23-32.
Yu, Q. et al. "Specific protection against breast cancers by cyclin D1 ablation" Nature, 2001; 411: 1017-1021.
Zhang, W. et al. "Sensitization of C6 glioma cells to radiation by staurosporine, a potent protein kinase C inhibitor" J Neurooncol., Jan. 1993; 15(1): 1-7.
Zhu, G. et al. "Synthesis, structure-activity relationship, and biological studies of indolocarbazoles as potent cyclin D1-CDK4 inhibitors" J Med Chem., May 22, 2003; 46(11): 2027-2030.
Zhu, G. et al. "Synthesis of quinolinyl/isoquinolinyl[a]pyrrolo [3,4-c]] carbazoles as cyclin D1/CDK4 inhibitors" Bioorg Med Chem Lett, Apr. 7, 2003; 13(7): 1231-1235.
U.S. Pat. No. 8,598,186, B2, U.S. Appl. No. 13/869,520, Tavares et al., Dec. 3, 2013.
U.S. Pat. No. 8,598,197, B2, U.S. Appl. No. 13/869,576, Tavares et al., Dec. 3, 2013.
U.S. Pat. No. 8,691,830, B2, U.S. Appl. No. 13/869,594, Tavares et al., Apr. 8, 2014.
U.S. Pat. No. 8,822,683, B2, U.S. Appl. No. 14/162,637, Tavares et al., Sep. 2, 2014.
U.S. Pat. No. 8,829,012, B2, U.S. Appl. No. 14/162,649, Tavares et al., Sep. 9, 2014.
U.S. Pat. No. 9,102,682, B2, U.S. Appl. No. 14/452,296, Tavares et al., Aug. 11, 2015.
U.S. Pat. No. 9,260,442, B2, U.S. Appl. No. 14/498,796, Tavares, Jan. 27, 2016.
U.S. Pat. No. 9,464,092, B2, U.S. Appl. No. 14/212,911, Strum et al., Oct. 11, 2016.
U.S. Pat. No. 9,481,691, B2, U.S. Appl. No. 14/712,630, Tavares et al., Nov. 1, 2016.
U.S. Pat. No. 9,487,530, B2, U.S. Appl. No. 14/212,430, Strum et al., Nov. 8, 2016.
U.S. Pat. No. 9,499,564, B2, U.S. Appl. No. 14/712,582, Tavares et al., Nov. 22, 2016
U.S. Pat. No. 9,527,857, B2, U.S. Appl. No. 14/214,048, Strum et al., Dec. 27, 2016.
U.S. Pat. No. 9,717,735, B2, U.S. Appl. No. 14/690,180, Strum et al., Aug. 1, 2017.
U.S. Pat. No. 9,745,316, B2, U.S. Appl. No. 14/982,443, Tavares, Aug. 29, 2017.
U.S. Pat. No. 9,856,268, B2, U.S. Appl. No. 15/348,862, Tavares, Jan. 2, 2018.
U.S. Pat. No. 9,931,345, B2, U.S. Appl. No. 15/288,878, Strum et al., Apr. 3, 2018.
U.S. Pat. No. 9,957,276, B2, U.S. Appl. No. 15/348,770, Tavares et al., May 1, 2018.
U.S. Pat. No. 10,076,523, B2, U.S. Appl. No. 15/387,083, Strum et al., Sep. 18, 2018.
U.S. Pat. No. 10,085,992, A1, U.S. Appl. No. 15/342,990, Strum et al., Oct. 2, 2018.
U.S. Pat. No. 10,189,849, B2, U.S. Appl. No. 15/918,834, Tavares et al., Jan. 29, 2019.
U.S. Pat. No. 10,189,850, B2, U.S. Appl. No. 15/918,852, Tavares et al., Jan. 29, 2019.
U.S. Pat. No. 10,189,851, B2, U.S. Appl. No. 15/918,877, Tavares et al., Jan. 29, 2019.
U.S. Pat. No. 10,231,969, B2, U.S. Appl. No. 15/457,699, Strum et al., Mar. 19, 2019.
20170333440, A1, U.S. Appl. No. 15/665,071, Strum, et al., Nov. 23, 2017.
2018/0127431, A1, U.S. Appl. No. 15/860,483, Tavares et al., May 10, 2018.
2018/0221378, A1, U.S. Appl. No. 15/943,278, Strum, et al., Aug. 9, 2018.

(56) References Cited

OTHER PUBLICATIONS

2018/0360840, A1, U.S. Appl. No. 16/112,360, Strum, et al., Dec. 20, 2018.
2018/0360841, A1, U.S. Appl. No. 16/112,362, Strum, et al., Dec. 20, 2018.
2019/0030034, A1, U.S. Appl. No. 16/142,574, Strum, et al., Jan. 31, 2019.
2019/0070185, A1, U.S. Appl. No. 16/178,419, Strum, et al., Mar. 7, 2019.
2019/0119292, A1, U.S. Appl. No. 16/226,430, Tavares et al., Apr. 25, 2019.
2019/0119294, A1, U.S. Appl. No. 16/230,412, Strum, et al., Apr. 25, 2019.
2019/0125752, A1, U.S. Appl. No. 16/228,308, Strum, et al., May 2, 2019.
2019/0135784, A1, U.S. Appl. No. 16/230,388, Strum, et al., May 9, 2019.
2019/0135811, A1, U.S. Appl. No. 16/230,396, Strum, et al., May 9, 2019.
2019/0135820, A1, U.S. Appl. No. 16/230,308, Smith et al., May 9, 2019.

\* cited by examiner

TREATMENT OF RB-NEGATIVE TUMORS USING TOPOISOMERASE INHIBITORS IN COMBINATION WITH CYCLIN DEPENDENT KINASE 4/6 INHIBITORS

CROSS-REFERENCE TO RELATED APPLICATIONS

This application is a divisional application of U.S. application Ser. No. 16/142,574, filed Sep. 26, 2018, which is a continuation of U.S. application Ser. No. 15/457,667, filed Mar. 13, 2017, which is a continuation of International Patent Application No. PCT/US2015/049756, filed Sep. 11, 2015, which claims the benefit of U.S. Provisional Application No. 62/050,035 filed Sep. 12, 2014. Each of these applications is hereby incorporated by reference for all purposes.

FIELD

This invention is in the area of improved therapeutic combinations for and methods of treating selected retinoblastoma (Rb)-negative cancers and Rb-negative abnormal cellular proliferative disorders using particular topoisomerase inhibitors and specific cyclin-dependent kinase 4/6 (CDK4/6) inhibitors. In one aspect, the improved treatment of select Rb-negative cancers is disclosed using specific compounds disclosed herein in combination with a topoisomerase I inhibitor.

BACKGROUND

The regulation of the cell cycle is governed and controlled by specific proteins, which are activated and deactivated mainly through phosphorylation/dephosphorylation processes in a precisely-timed manner. The key proteins that coordinate the initiation, progression, and completion of cell-cycle program are cyclin dependent kinases (CDKs). Cyclin-dependent kinases belong to the serine-threonine protein kinase family. They are heterodimeric complexes composed of a catalytic kinase subunit and a regulatory cyclin subunit. CDK activity is controlled by association with their corresponding regulatory subunits (cyclins) and CDK inhibitor proteins (Cip & Kip proteins, INK4s), by their phosphorylation state, and by ubiquitin-mediated proteolytic degradation (see D. G. Johnson, C. L. Walker, Annu. Rev. Pharmacol. Toxicol. 39 (1999) 295-312; D. O. Morgan, Annu. Rev. Cell Dev. Biol. 13 (1997) 261-291; C. J. Sherr, Science 274 (1996) 1672-1677; T. Shimamura et al., Bioorg. Med. Chem. Lett. 16 (2006) 3751-3754).

There are four CDKs that are significantly involved in cellular proliferation: CDK1, which predominantly regulates the transition from G2 to M phase, and CDK2, CDK4, and CDK6, which regulate the transition from G1 to S phase (Malumbres M, Barbacid M. Cell cycle, CDKs and cancer: a changing paradigm. Nat. Rev. Cancer 2009; 9(3):153-166). In early to mid G1 phase, when the cell is responsive to mitogenic stimuli, activation of CDK4-cyclin D and CDK6-cyclin D induces phosphorylation of the retinoblastoma protein (pRb). Phosphorylation of pRb releases the transcription factor E2F, which enters the nucleus to activate transcription of other cyclins which promote further progression of the cell cycle (see J. A. Diehl, Cancer Biol. Ther. 1 (2002) 226-231; C. J. Sherr, Cell 73 (1993) 1059-1065). CDK4 and CDK6 are closely related proteins with basically indistinguishable biochemical properties (see M. Malumbres, M. Barbacid, Trends Biochem. Sci. 30 (2005) 630-641).

A number of CDK 4/6 inhibitors have been identified, including specific pyrido[2,3-d]pyrimidines, 2-anilinopyrimidines, diaryl ureas, benzoyl-2,4-diaminothiazoles, indolo[6,7-a]pyrrolo[3,4-c]carbazoles, and oxindoles (see P. S. Sharma, R. Sharma, R. Tyagi, Curr. Cancer Drug Targets 8 (2008) 53-75). For example, WO 03/062236 identifies a series of 2-(pyridin-2-ylamino-pyrido[2,3]pyrimidin-7-ones for the treatment of Rb positive cancers that show selectivity for CDK4/6, including 6-acetyl-8-cyclopentyl-5-methyl-2-(5-piperazin-1-yl-pyridin-2-ylammino)-8H-pyrido-[2,3-d]-pyrimidin-7-one (PD0332991), which is currently being tested by Pfizer in late stage clinical trials as an antineoplastic agent against estrogen-positive, HER2-negative breast cancer. Tate, et al. describe the antitumor activity of the CDK4/6 inhibitor abemaciclib (LY2835219) ("Semi-Mechanistic Pharmacokinetic/Pharmacodynamic Modeling of the Antitumor Activity of LY2835219, a New Cyclin-Dependent Kinase 4/6 Inhibitor, in Mice Bearing Human Tumor Xenografts", Clin Cancer Res (Jul. 15, 2014) 20; 3763). Rader, et al. describe the reduced proliferation in neuroblastoma-derived cell lines using the CDK4/6 inhibitor ribociclib (LEE011) ("Dual CDK4/CDK6 Inhibition Induces Cell Cycle Arrest and Senescence in Neuroblastoma", Clin Cancer Res (Nov. 15, 2013) 19(22): 6173-82). VanderWel et al. describe an iodine-containing pyrido[2,3-d]pyrimidine-7-one (CKIA) as a potent and selective CDK4 inhibitor (see VanderWel et al., J. Med. Chem. 48 (2005) 2371-2387). WO 99/15500 filed by Glaxo Group Ltd discloses protein kinase and serine/threonine kinase inhibitors. WO 2010/020675 filed by Novartis AG describes pyrrolopyrimidine compounds as CDK inhibitors. WO 2011/101409 also filed by Novartis describes pyrrolopyrimidines with CDK 4/6 inhibitory activity. WO 2005/052147 filed by Novartis and WO 2006/074985 filed by Janssen Pharma disclose additional CDK4 inhibitors. WO 2012/061156 filed by Tavares and assigned to G1 Therapeutics describes CDK inhibitors. WO 2013/148748 filed by Francis Tavares and assigned to G1 Therapeutics describes Lactam Kinase Inhibitors. PCT Patent Application No. PCT/US2014/029073 filed by Strum et al. and assigned to G1 Therapeutics describes compounds and methods for protection of hematopoietic stem and progenitor cells against ionizing radiation using CDK4/6 inhibitors. In one aspect, PCT/US2014/029073 describes the use of a CDK4/6 inhibitor to protect hematopoietic stem and progenitor cells in a subject with small cell lung cancer undergoing treatment with standard of care chemotherapeutics such as carboplatin, cisplatin, etoposide, topotecan, camptothecin, and irinotecan. PCT Patent Application No. PCT/US2014/028685 filed by Strum et al. and assigned to G1 Therapeutics describes compounds and methods for protection of normal cells during chemotherapy using CDK4/6 inhibitors. PCT Patent Application No. PCT/US2014/029429 filed by Strum et al. and assigned to G1 Therapeutics describes compounds and methods for treating Rb-positive cancers using CDK4/6 inhibitors. PCT Patent Application No. PCT/US2014/029274 filed by Strum et al. and assigned to G1 Therapeutics describes compounds and methods for treating certain cancers with CDK4/6 inhibitors.

Selective CDK4/6 inhibitors are generally designed to target CDK4/6-replication dependent cancers. For example, Michaud et al., reported that the CDK4/6 inhibitor PD-0332991 was inactive against Rb-negative tumors. (Michaud et al., Pharmacologic inhibition of cyclin-dependent kinase 4 and 6 arrests the growth of glioblastoma multiform intracranial xenografts. Cancer Res. 70:3228-3238 (2010)).

Topoisomerase enzymes play a vital role in cellular proliferation and replication, altering the supercoiling of double-stranded DNA by catalyzing the breaking and rejoining of the phosphodiester backbone of DNA strands during the normal cell cycle. DNA strand separation is obligatory to transcribe and replicate genomes by copying each base by RNA and DNA polymerases. (Pommier et al., DNA topoisomerases and their poisoning by anticancer and antibacterial drugs, Chem. & Biol. Review 17 (2010) 421-433). Because of DNA's double-helical structure, replication generated catenated progenies that have to be unlinked by topoisomerases prior to cytokinesis.

Topoisomerases are classified as type I and type II. Type I enzymes cleave one DNA strand at a time and type II both strands to perform their catalytic functions. All topoisomerases cleave the DNA phosphodiester backbone by nucleophilic attack from a catalytic tyrosine residue which becomes linked to the phosphate end (P-Y) of the DNA break. Those reactions are highly reversible and leave the DNA sequence unchanged following topoisomerization (Pommier et al., DNA topoisomerases and their poisoning by anticancer and antibacterial drugs, Chem. & Biol. Review 17 (2010) 421-433).

A number of topoisomerase type I (Top1) inhibitors have been evaluated as anticancer therapeutics. Camptothecin was first identified from the Chinese tree *Camptotheca acuminate* (Wall et al., "The isolation and structure of camptothecin, a novel alkaloidal leukemia and tumor inhibitor from *Camptotheca acuminate*," J. Am. Chem. Soc. (1966) 88: 3888-3890.) A number of camptothecin derivatives, including for example topotecan, irinotecan, belotecan, gimatecan, lurtotecan, diflomotecan, S39625, and exatecan, have been further investigated as anticancer agents (Pommier et al., DNA topoisomerases and their poisoning by anticancer and antibacterial drugs, Chem. & Biol. Review 17 (2010) 421-433).

In addition to the camptothecin derivatives, several non-camptothecin topoisomerase inhibitors have also been investigated as anticancer agents, including the indolocarbazole edotecarin, indenoisoquinolines NSC 706744 (MJ-III-65), NSC 725776 (LMP-776), and NSC 724998 (LMP-400), dibenzonaphthyridiones such as topovale (ARC-111), and the aromathecin rosettacin (Pommier et al., DNA topoisomerases and their poisoning by anticancer and antibacterial drugs, Chem. & Biol. Review 17 (2010) 421-433).

In addition to the Top1 inhibitors, a number of anti-cancer agents have been investigated that target topoisomerase type II (Top2) enzymes, including etoposide, teniposide, and the DNA intercalators doxorubicin, daunorubicin, aclarubicin, amsacrine, dexrazoxane, TAS-103, the quinolone CP-115, 963, the ellipticines including ellipticinium, azatoxins, genistein, VP-16, VM-26, mitoxantrone, amonafidem, and saintopin.

One potential side-effect of the use of topoisomerase inhibitors as anti-cancer agents includes the development of secondary malignancies. For example, the use of etoposide induces treatment-related acute myelocytic leukemia (t-AML) and treatment related myelodysplastic syndromes (t-MDS), which often progress to t-AML (Pedersen-Bjergaard et al., "Genetic pathways in therapy-related myelodysplasia and acute myeloid leukemia," Blood (2002) 99:1909-1912).

Previous studies have examined the potential cytotoxic activity of camptothecin derivatives in combination with CDK inhibitors against small cell lung cancer cell lines.

Hamilton et al. found that the non-specific pan-CDK inhibitors olomoucine, roscovitine, and CDK4I had a synergistic cytotoxic effect on small cell lung cancer cell lines in combination with topotecan ("Synergistic Anticancer Activity of Topotecan-Cyclin-Dependent Kinase Inhibitor Combinations against Drug-Resistant Small Cell Lung Cancer (SCLC) Cell Lines", Journal of Cancer Therapy (2013) 4: 47-53). In additional experiments, Hamilton et al. found that while the pan-CDK inhibitors olomoucine, roscovitine, and CDK4I had a synergistic cytotoxic effect on small cell lung cancer cell lines in combination with various camptothecin derivatives (including rubitecan, 9AC, topotecan, SN38, and CPT109), comparatively, the CDK 4/6 inhibitor PD0332991 had low chemosensitizing activity ("Synergism of Cyclin-Dependent Kinase Inhibitors with Camptothecin Derivatives in Small Cell Lung Cancer Cell Lines" Molecules (2014), 19(2): 2077-2088).

Accordingly, there is an ongoing need for improved compounds, methods, and regimes to treat patients with Rb-negative cancers and abnormal cellular proliferative disorders.

SUMMARY OF THE INVENTION

Methods and compositions are provided to treat abnormal cellular proliferation characterized by the loss, deficiency, or absence of the retinoblastoma tumor suppressor protein (Rb) (Rb-null or Rb-negative), including Rb-negative cancer, wherein a CDK4/6 inhibitor described herein and a topoisomerase I inhibitor is administered in combination to a host resulting in an advantageous anti-tumor effect compared to the use of either the CDK4/6 inhibitor, which does not inhibit Rb-negative cellular proliferation, or the topoisomerase I inhibitor alone. Surprisingly, this advantageous anti-tumor effect is seen at various dosing levels of the CDK4/6 inhibitor, including low-dose levels of the CDK 4/6 inhibitor as described in the Examples below.

Furthermore, provided herein are methods and compositions for reducing the development of secondary malignancies associated with the use of topoisomerase inhibitors wherein a subject undergoing treatment for an Rb-negative cancer with a topoisomerase inhibitor is administered a CDK4/6 inhibitor described herein.

In one embodiment of the invention, a CDK4/6 inhibitor is selected from Formula I, II, III, IV, or V as described herein and administered in a combination or alternation schedule with a topoisomerase I inhibitor. In one non-limiting example, a CDK4/6 inhibitor compound selected from Table 1 below is administered in combination or alternation with a topoisomerase I inhibitor. In one non-limiting example, a CDK4/6 inhibitor selected from Table 1 below is administered in combination or alternation with a topoisomerase I inhibitor selected from the group consisting of (1S,9S)-1-Amino-9-ethyl-5-fluoro-1,2,3,9,12,15-hexahydro-9-hydroxy-4-methyl-1 OH, 13H-benzo(de)pyrano(3',4':6,7)indolizino(1,2-b)quinoline-10,13-dione (exatecan), (7-(4-methylpiperazinomethylene)-10,11-ethylenedioxy-20 (S)-camptothecin (lurtotecan), (R)-5-ethyl-9,10-difluoro-5-hydroxy-4,5-dihydrooxepino[3',4':6,7]indolizino[1,2-b]quinoline-3,15(1H, 13H)-dione (diflomotecan), (4S)-11-((E)-((1,1-Dimethylethoxy)imino)methyl)-4-ethyl-4-hydroxy-1,12-dihydro-14H-pyrano(3',4':6,7)indolizino(1,2-b) quinoline-3,14(4H)-dione (gimatecan), (S)-8-ethyl-8-hydroxy-15-((4-methylpiperazin-1-yl)methyl)-11,14-dihydro-2H-[1,4]dioxino[2,3-g]pyrano[3',4':6,7]indolizino [1,2-b]quinoline-9,12(3H,8H)-dione (lurtotecan), (4S)-4-Ethyl-4-hydroxy-11-[2-[(1-methylethyl)amino]ethyl]-1H- pyrano[3,4:6,7]indolizino[1,2-b]quinoline-3,14(4H, 12H)-dione (belotecan), 6-((1,3-dihydroxypropan-2-yl)amino)-2,10-dihydroxy-12-((2R,3R,4S,5S,6R)-3,4,5-trihydroxy-6-(hydroxymethyl)tetrahydro-2H-pyran-2-yl)-12,13-dihydro-5H-indolo[2,3-a]pyrrolo[3,4-c]carbazole-5,7(6H)-dione (edotecarin), 8,9-dimethoxy-5-(2-N,N-dimethylaminoethyl)-2,3-methylenedioxy-5H-dibenzo(c,h)(1,6)naphthyridin-6-one (topovale), benzo[6,7]indolizino[1,2-b]quinolin-11(13H)-one (rosettacin), (S)-4-ethyl-4-hydroxy-11-(2-(trimethylsilyl)ethyl)-1H-pyrano[3',4':6,7]indolizino[1,2-b]quinoline-3,14(4H, 12H)-dione (cositecan), tetrakis{(4S)-9-[((1,4'-bipiperidinyl]-1'-carbonyl)oxy]-4,11-diethyl-3,14-dioxo-3,4,12,14-tetrahydro-1H-pyrano[3',4':6,7]indolizino[1,2-b]quinolin-4-yl} N,N',N'',N'''-{methanetetrayltetrakis[methylenepoly(oxyethylene)oxy(1-oxoethylene)]} tetraglycinate tetrahydrochloride (etirinotecan pegol), (S)-10-amino-4-ethyl-4-hydroxy-1H-pyrano[3',4':6,7]indolizino[1,2-b]quinoline-3,14(4H, 12H)-dione (9-aminocamptothecin), 10-hydroxy-camptothecin (HOCPT), or (S)-11-(tert-butyldimethylsilyl)-4-ethyl-4,9-dihydroxy-1H-pyrano[3',4':6,7]indolizino[1,2-b]quinoline-3,14(4H, 12H)-dione (silatecan), (R)-9-chloro-5-ethyl-5-hydroxy-10-methyl-12-((4-methylpiperidin-1-yl)methyl)-4,5-dihydrooxepino[3',4':6,7]indolizino[1,2-b]quinoline-3,15(1H,13H)-dione (elmotecan). In one embodiment, the CDK4/6 inhibitor is selected from compounds Q, T, U, and GG, or a combination thereof. In one embodiment, the CDK4/6 inhibitor is selected from compounds X and BB, or a combination thereof.

The subject treated according to the present invention may suffer from a proliferative disorder or disease such as cancer characterized by the loss, deficiency, or absence of the retinoblastoma (Rb) tumor suppressor protein (Rb-null or Rb-negative). The cancer may be characterized by reduced expression of the retinoblastoma tumor suppressor protein or a retinoblastoma family member protein or proteins (such as, but not limited to p107 and p130). Due to the lack or deficiency of Rb, these cancers are generally CDK4/6 replication independent, and not growth inhibited upon exposure to a CDK4/6 inhibitor such as the CDK4/6 inhibitors described herein.

In one embodiment, the subject is undergoing treatment for an Rb-negative or Rb-deficient cancer, including but not limited to, small cell lung cancer, triple-negative breast cancer, HPV-positive head and neck cancer, retinoblastoma, Rb-negative bladder cancer, Rb-negative prostate cancer, osteosarcoma, or cervical cancer. In one embodiment, the cancer is selected from a gastric, glioma, non-small cell lung, esophageal, liver, breast, neuroblastoma, ovarian, sarcoma, for example, but not limited to Ewing sarcoma, pancreatic, lymphoma, prostate, or hematological cancer, for example, but not limited to acute lymphoblastic leukemia and acute myeloid leukemia, that has a loss, deficiency, or absence of the retinoblastoma (Rb) tumor suppressor protein.

In one aspect of the invention, a subject is suffering from small cell lung carcinoma and administered a CDK4/6 inhibitor selected from Formula I, II, III, IV, or V as described herein, in a combination or alternation schedule with a topoisomerase I inhibitor. In one embodiment, the topoisomerase I inhibitor is selected from exatecan, lurtotecan, diflomotecan, gimatecan, belotecan, edotecarin, topovale, rosettacin, cositecan, etirinotecan pegol, silatecan, 9-aminocamptothecin, elmotecan, HOCPT, or a combination thereof. In one embodiment of the invention, a subject suffering from small cell lung carcinoma is administered a CDK4/6 inhibitor selected from Formula I, II, III, IV, or V, in combination or alternation with exatecan, lurtotecan, diflomotecan, gimatecan, belotecan, edotecarin, topovale, rosettacin, cositecan, etirinotecan pegol, silatecan, 9-aminocamptothecin, HOCPT, or a combination thereof. In another embodiment of the invention, a subject suffering from small cell lung carcinoma is administered a CDK4/6 inhibitor selected from compounds Q, T, U, GG, X, and BB, or a combination thereof, in combination or alternation with exatecan, lurtotecan, diflomotecan, gimatecan, belotecan, edotecarin, topovale, rosettacin, cositecan, etirinotecan pegol, silatecan, 9-aminocamptothecin, elmotecan, HOCPT, or a combination thereof. In one embodiment of the invention, a subject suffering from small cell lung carcinoma is administered a CDK4/6 inhibitor selected from compounds Q, T, U, GG, X, and BB, or a combination thereof, in combination or alternation with exatecan. In one embodiment of the invention, a subject suffering from small cell lung carcinoma is administered a CDK4/6 inhibitor selected from compounds Q, T, U, GG, X, and BB, or a combination thereof, in combination or alternation with lurtotecan. In one embodiment of the invention, a subject suffering from small cell lung carcinoma is administered a CDK4/6 inhibitor selected from compounds Q, T, U, GG, X, and BB, or a combination thereof, in combination or alternation with diflomotecan. In a further embodiment of the invention, a subject suffering from small cell lung carcinoma is administered a CDK4/6 inhibitor selected from compounds Q, T, U, GG, X, and BB, or a combination thereof, in combination or alternation with belotecan. In one embodiment of the invention, a subject suffering from small cell lung carcinoma is administered a CDK4/6 inhibitor selected from compounds Q, T, U, GG, X, and BB, or a combination thereof, in combination or alternation with edotecarin. In one embodiment of the invention, a subject suffering from small cell lung carcinoma is administered a CDK4/6 inhibitor selected from compounds Q, T, U, GG, X, and BB, or a combination thereof, in combination or alternation with topovale. In one embodiment of the invention, a subject suffering from small cell lung carcinoma is administered a CDK4/6 inhibitor selected from compounds Q, T, U, GG, X, and BB, or a combination thereof, in combination or alternation with rosettacin. In one embodiment of the invention, a subject suffering from small cell lung carcinoma is administered a CDK4/6 inhibitor selected from compounds Q, T, U, GG, X, and BB, or a combination thereof, in combination or alternation with cositecan. In one embodiment of the invention, a subject suffering from small cell lung carcinoma is administered a CDK4/6 inhibitor selected from compounds Q, T, U, GG, X, and BB, or a combination thereof, in combination or alternation with etirinotecan pegol. In yet another embodiment of the invention, a subject suffering from small cell lung carcinoma is administered a CDK4/6 inhibitor selected from compounds Q, T, U, GG, X, and BB, or a combination thereof, in combination or alternation with silatecan. In one embodiment of the invention, a subject suffering from small cell lung carcinoma is administered a CDK4/6 inhibitor selected from compounds Q, T, U, GG, X, and BB, or a combination thereof, in combination or alternation with 9-aminocamptothecin. In one embodiment of the invention, a subject suffering from small cell lung carcinoma is administered a CDK4/6 inhibitor selected from compounds Q, T, U, GG, X, and BB, or a combination thereof, in combination or alternation with elmotecan. In one embodiment of the invention, a subject suffering from small cell lung carcinoma is administered a CDK4/6 inhibitor selected from compounds Q, T, U, GG, X, and BB, or a combination thereof, in combination or alternation with HOCPT.

In another aspect of the invention, a CDK4/6 inhibitor is selected from Formula I, II, III, IV, or V as described herein, and administered in a combination or alternation schedule with a topoisomerase I inhibitor to a subject having an Rb-negative cervical cancer. In one embodiment, the topoisomerase I inhibitor is selected from topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In one embodiment of the invention, a subject suffering from Rb-negative cervical cancer and administered a CDK4/6 inhibitor selected from compounds Q, T, U, GG, X, and BB, or a combination thereof, in combination or alternation with topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In an additional embodiment of the invention, a subject suffering from Rb-negative cervical cancer and administered a CDK4/6 inhibitor selected from compounds Q, T, U, GG, X, and BB, or a combination thereof, in combination or alternation with topotecan.

In one aspect of the invention, a CDK4/6 inhibitor is selected from Formula I, II, III, IV, or V as described herein, and administered in a combination or alternation schedule with a topoisomerase I inhibitor to a subject having an Rb-negative ovarian cancer. In one embodiment, the topoisomerase I inhibitor is selected from topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In another embodiment of the invention, a subject suffering from Rb-negative ovarian cancer and administered a CDK4/6 inhibitor selected from compounds Q, T, U, GG, X, and BB, or a combination thereof, in combination or alternation with topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In a further embodiment of the invention, a subject suffering from Rb-negative ovarian cancer and administered a CDK4/6 inhibitor selected from compounds Q, T, U, GG, X, and BB, or a combination thereof, in combination or alternation with topotecan.

In a further aspect of the invention, a CDK4/6 inhibitor is selected from Formula I, II, III, IV, or V as described herein, and administered in a combination or alternation schedule with a topoisomerase I inhibitor to a subject having an Rb-negative neuroblastoma. In one embodiment, the topoisomerase I inhibitor is selected from topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In another embodiment of the invention, a subject suffering from Rb-negative neuroblastoma and administered a CDK4/6 inhibitor selected from compounds Q, T, U, GG, X, and BB, or a combination thereof, in combination or alternation with topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In an additional embodiment of the invention, a subject suffering from Rb-negative neuroblastoma and administered a CDK4/6 inhibitor selected from compounds Q, T, U, GG, X, and BB, or a combination thereof, in combination or alternation with topotecan.

In one aspect of the invention, a CDK4/6 inhibitor is selected from Formula I, II, III, IV, or V as described herein, and administered in a combination or alternation schedule with a topoisomerase I inhibitor to a subject having an Rb-negative sarcoma, for example, Ewing sarcoma. In one embodiment, the topoisomerase I inhibitor is selected from topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In another embodiment of the invention, a subject suffering from Rb-negative sarcoma and administered a CDK4/6 inhibitor selected from compounds Q, T, U, GG, X, and BB, or a combination thereof, in combination or alternation with topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In an additional embodiment of the invention, a subject suffering from Rb-negative sarcoma and administered a CDK4/6 inhibitor selected from compounds Q, T, U, GG, X, and BB, or a combination thereof, in combination or alternation with topotecan.

In another aspect of the invention, a CDK4/6 inhibitor is selected from Formula I, II, III, IV, or V as described herein, and administered in a combination or alternation schedule with a topoisomerase I inhibitor to a subject having an Rb-negative leukemia, for example, acute myeloid leukemia (AML) or acute lympoblastic leukemia (ALL). In one embodiment, the topoisomerase I inhibitor is selected from topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In another embodiment of the invention, a subject suffering from Rb-negative leukemia and administered a CDK4/6 inhibitor selected from compounds Q, T, U, GG, X, and BB, or a combination thereof, in combination or alternation with topotecan, exatecan, lurtotecan, diflomotecan, gimatecan, belotecan, edotecarin, topovale, rosettacin, cositecan, etirinotecan pegol, 9-aminocamptothecin, silatecan, elmotecan, HOCPT, or a combination thereof. In a further embodiment of the invention, a subject suffering from Rb-negative leukemia and administered a CDK4/6 inhibitor selected from compounds Q, T, U, GG, X, and BB, or a combination thereof, in combination or alternation with topotecan.

In one embodiment of the invention, a CDK4/6 inhibitor is selected from Formula I, II, III, IV, or V as described herein, and administered in a combination or alternation schedule with diflomotecan to a subject having an Rb-negative breast, small cell lung, or prostate cancer.

In another embodiment of the invention, a CDK4/6 inhibitor is selected from Formula I, II, III, IV, or V as described herein, and administered in a combination or alternation schedule with gimatecan to a subject having an Rb-negative glioblastoma or small cell lung cancer.

In one embodiment of the invention, a CDK4/6 inhibitor is selected from Formula I, II, III, IV, or V as described herein, and administered in a combination or alternation schedule with lurtotecan to a subject having an Rb-negative small cell lung cancer or ovarian cancer.

In a further embodiment of the invention, a CDK4/6 inhibitor is selected from Formula I, II, III, IV, or V as described herein, and administered in a combination or alternation schedule with exatecan to a subject having an Rb-negative sarcoma, for example Ewing's sarcoma, pancreatic, gastric, or liver cancer.

In an additional embodiment of the invention, a CDK4/6 inhibitor is selected from Formula I, II, III, IV, or V as described herein, and administered in a combination or alternation schedule with belotecan to a subject having an Rb-negative small cell lung, cervical, non-small cell lung, or ovarian cancer.

In one embodiment of the invention, a CDK4/6 inhibitor is selected from Formula I, II, III, IV, or V as described herein, and administered in a combination or alternation schedule with cositecan to a subject having an Rb-negative cervical, non-small cell lung, glioblastoma, melanoma, or ovarian cancer.

In one embodiment of the invention, a CDK4/6 inhibitor is selected from Formula I, II, III, IV, or V as described herein, and administered in a combination or alternation schedule with etirinotecan pegol to a subject having an Rb-negative non-small cell lung, small cell lung, glioblastoma, or breast cancer.

In another embodiment of the invention, a CDK4/6 inhibitor is selected from Formula I, II, III, IV, or V as described herein, and administered in a combination or alternation schedule with 9-aminocamptothecin to a subject having an Rb-negative leukemia, ovarian, esophageal, gastric, lymphoma, or small cell lung cancer.

In one embodiment of the invention, a CDK4/6 inhibitor is selected from Formula I, II, III, IV, or V as described herein, and administered in a combination or alternation schedule with silatecan to a subject having an Rb-negative glioblastoma.

In one embodiment of the invention, a CDK4/6 inhibitor is selected from Formula I, II, III, IV, or V as described herein, and administered in a combination or alternation schedule with topotecan to a subject having an Rb-negative small cell lung cancer. In one embodiment, the CDK 4/6 inhibitor is selected from compounds Q, T, U, GG, X, and BB.

In one aspect of the invention, a CDK4/6 inhibitor is selected from Formula I, II, III, IV, or V as described herein, and administered in a combination or alternation schedule with a topoisomerase II inhibitor to a subject suffering from an Rb-negative cancer. In one non-limiting example, a CDK4/6 inhibitor compound selected from Table 1 below is administered in combination or alternation with a topoisomerase II inhibitor. In one non-limiting example, a CDK4/6 inhibitor selected from Table 1 below is administered in combination or alternation with a topoisomerase II inhibitor selected from etoposide, teniposide, and the DNA intercalators doxorubicin, daunorubicin, aclarubicin, amsacrine, dexrazoxane, TAS-103, the quinolone CP-115,963, the ellipticines including ellipticinium, azatoxins, genistein, VP-16, VM-26, mitoxantrone, amonafidem, or saintopin.

In one embodiment of the invention, the combination therapy described herein can be administered in a concerted regimen with at least one other chemotherapeutic agent, targeted anti-neoplastic agent, immunotherapeutic agent, or a hematopoietic growth factor agent for beneficial, additive, or further synergistic effects against the abnormal cellular proliferation.

In certain embodiments, a CDK4/6 inhibitor described herein is administered to the subject prior to treatment with the topoisomerase inhibitor, during treatment with the topoisomerase inhibitor, after administration of the topoisomerase inhibitor, or a combination thereof. In one embodiment, a CDK4/6 inhibitor described herein is administered to the subject less than about 24 hours, 20 hours, 16 hours, 12 hours, 8 hours, 4 hours, 2 hours, 1 hour, 30 minutes or less prior to treatment with the topoisomerase inhibitor. In one embodiment, the CDK4/6 inhibitor is administered up to 4 hours prior to treatment with the topoisomerase inhibitor. In one embodiment, the CDK4/6 inhibitor is administered approximately 30 minutes prior to treatment with the topoisomerase inhibitor. In one embodiment, the CDK4/6 inhibitor is administered at approximately the same time as the topoisomerase inhibitor. In one embodiment, the CDK4/6 inhibitor is administered within 30 minutes, 1 hour, 2 hours, 4 hours, 8 hours, 12 hours, 16 hours, 20 hours, or 24 hours after treatment with the topoisomerase inhibitor.

In summary, the present invention includes the following features:

A) Methods for treating a host suffering from an Rb-negative proliferative disorder, for example but not limited to an Rb-negative cancer, comprising administering an effective amount of a compound of Formula I, II, III, IV, or V, or a salt, isotopic analog, or prodrug thereof, including a compound selected from Table 1 as described herein, in combination with a topoisomerase inhibitor;

B) A pharmaceutically acceptable composition for use as a chemotherapeutic comprising a CDK4/6 inhibitor described herein, or a salt, isotopic analog, or prodrug thereof, and a topoisomerase inhibitor;

C) Use of a CDK4/6 inhibitor described herein, or a pharmaceutically acceptable composition, salt, isotopic analog, or prodrug thereof, in combination with a topoisomerase inhibitor, in the manufacture of a medicament for use as a chemotherapeutic to treat a subject with an Rb-negative abnormal cellular proliferation disorder, including an Rb-negative cancer;

D) Processes for the preparation of therapeutic products that contain an effective amount of a CDK 4/6 inhibitor compound described herein in combination with a topoisomerase inhibitor, for use in the treatment of a subject having an Rb-negative abnormal cellular proliferation disorder, such as an Rb-negative cancer, and;

E) A method for manufacturing a medicament selected from a CDK4/6 inhibitor described herein in combination with a topoisomerase inhibitor, intended for therapeutic use as a chemotherapeutic for the treatment of an Rb-negative abnormal cellular proliferation disorder, such as an Rb-negative cancer.

BRIEF DESCRIPTION OF THE DRAWINGS

FIG. 14 is a graph showing animal weight change (%) vs. time (days) in a CDK4/6 independent tumor mouse model (NCI-H69 SCLC xenograft model). Tumor-bearing mice were treated with Compound T vehicle and topotecan vehicle (Group 1; closed squares), Compound T (100 mg/kg) and topotecan vehicle (Group 2; open squares), Compound T (100 mg/kg) and topotecan (0.6 mg/kg) (Group 3; closed triangles), Compound T (50 mg/kg) and topotecan (0.6 mg/kg) (Group 4; open triangles), Compound T (10 mg/kg) and topotecan (0.6 mg/kg) (Group 5; closed circles) or Compound T vehicle and topotecan (0.6 mg/kg) (Group 6; open circles). As discussed in Example 157, the percent weight gain versus Day 0 in each group of animals was similar.

DETAILED DESCRIPTION OF THE INVENTION

Figure 1:
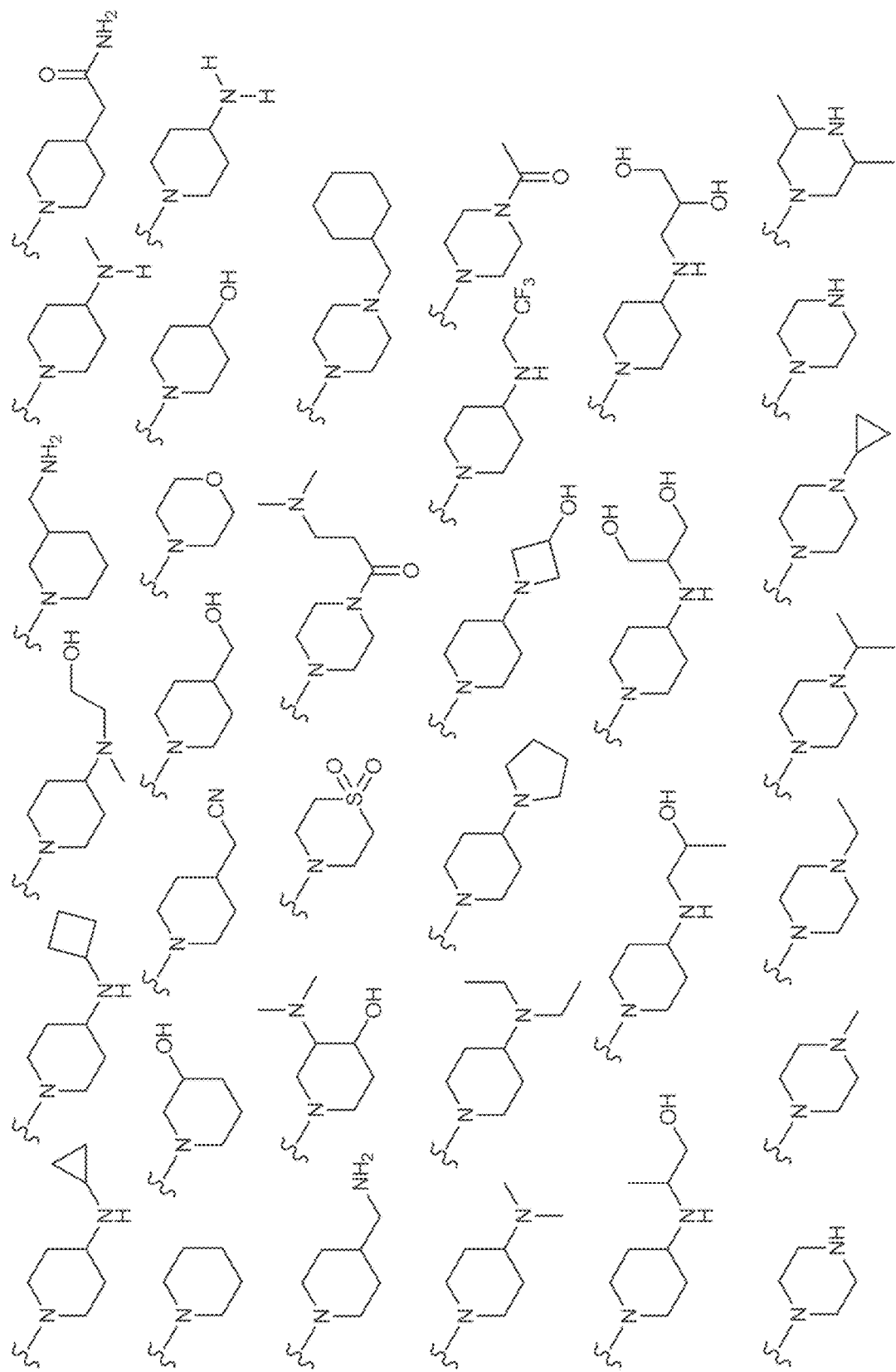
FIGS. 1-3 illustrate several exemplary embodiments of $R^2$ of the compounds of CDK4/6 inhibitors useful in the present invention.

Methods and compositions are provided to treat abnormal cellular proliferation characterized by the loss, deficiency, or absence of the retinoblastoma tumor suppressor protein (Rb)(Rb-null or Rb-negative), including Rb-negative cancer, wherein a CDK4/6 inhibitor described herein and a topoisomerase inhibitor, for example a topoisomerase I inhibitor, is administered in combination or alternation to a subject resulting in an advantageous effect compared to the use of either the CDK4/6 inhibitor or topoisomerase inhibitor alone. In a typical embodiment, the subject is a human.

Definitions

Unless otherwise stated, the following terms used in this application, including the specification and claims, have the definitions given below. As used in the specification and the appended claims, the singular forms "a," "an" and "the" include plural referents unless the context clearly dictates otherwise. Definition of standard chemistry terms may be found in reference works, including Carey and Sundberg (2007) *Advanced Organic Chemistry 5th Ed*. Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in *March's Advanced Organic Chemistry: Reactions, Mechanisms, and Structure, 6th Edition*, M. B. Smith and J. March, John Wiley & Sons, Inc., Hoboken, N.J., 2007.

The term "alkyl," either alone or within other terms such as "haloalkyl" and "alkylamino," embraces linear or branched radicals having one to about twelve carbon atoms. "Lower alkyl" radicals have one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylene" embraces bridging divalent linear and branched alkyl radicals. Examples include methylene, ethylene, propylene, isopropylene and the like.

The term "alkenyl" embraces linear or branched radicals having at least one carbon-carbon double bond of two to about twelve carbon atoms. "Lower alkenyl" radicals having two to about six carbon atoms. Examples of alkenyl radicals include ethenyl, propenyl, allyl, propenyl, butenyl and 4-methylbutenyl. The terms "alkenyl" and "lower alkenyl," embrace radicals having "cis" and "trans" orientations, or alternatively, "E" and "Z" orientations.

The term "alkynyl" denotes linear or branched radicals having at least one carbon-carbon triple bond and having two to about twelve carbon atoms. "Lower alkynyl" radicals having two to about six carbon atoms. Examples of such radicals include propargyl, butynyl, and the like.

Alkyl, alkenyl, and alkynyl radicals may be optionally substituted with one or more functional groups such as halo, hydroxy, nitro, amino, cyano, haloalkyl, aryl, heteroaryl, heterocyclo and the like.

The term "alkylamino" embraces "N-alkylamino" and "N,N-dialkylamino" where amino groups are independently substituted with one alkyl radical and with two alkyl radicals, respectively. "Lower alkylamino" radicals have one or two alkyl radicals of one to six carbon atoms attached to a nitrogen atom. Suitable alkylamino radicals may be mono or dialkylamino such as N-methylamino, N-ethylamino, N.N-dimethylamino, N,N-diethylamino and the like.

The term "halo" means halogens such as fluorine, chlorine, bromine or iodine atoms.

The term "haloalkyl" embraces radicals wherein any one or more of the alkyl carbon atoms is substituted with one or more halo as defined above. Examples include monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means an alkyl radical having all hydrogen atoms replaced with fluoro atoms. Examples include trifluoromethyl and pentafluoroethyl.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. An aryl group may be optionally substituted with one or more functional groups such as halo, hydroxy, nitro, amino, cyano, haloalkyl, aryl, heteroaryl, heterocyclo and the like.

The term "heterocyclyl" (or "heterocyclo") embraces saturated, and partially saturated heteroatom-containing ring radicals, where the heteroatoms may be selected from nitrogen, sulfur and oxygen. In one embodiment, heterocyclic rings comprise monocyclic 6-8 membered rings, as well as 5-16 membered bicyclic ring systems (which can include bridged fused and spiro-fused bicyclic ring systems). It does not include rings containing -O-O-.-O-S- or -S-S- portions. Said "heterocyclyl" group may have one or more substituents such as hydroxyl, Boc, halo, haloalkyl, cyano, lower alkyl, lower aralkyl, oxo, lower alkoxy, amino, lower alkylamino, and the like. In one embodiment, said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like. In an alternate embodiment, a heterocyclic ring comprises a monocyclic 3-6 membered ring.

Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclo groups include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1D'-benzo[d]isothiazol-6-yl, dihydropyranyl, dihydrofuryl and dihydrothiazolyl, and the like.

Heterocyclo groups also includes radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. Said "heteroaryl" group may have one or more substituents such as hydroxyl, Boc, halo, haloalkyl, cyano, lower alkyl, lower aralkyl, oxo, lower alkoxy, amino, lower alkylamino, and the like.

The term "heteroarylalkyl" denotes alkyl radicals substituted with a heteroaryl group. Examples include pyridylmethyl and thienylethyl.

The term "sulfonyl", whether used alone or linked to other terms such as alkylsulfonyl, denotes respectively divalent radicals —SO$_2$—.

The terms "carboxy" or "carboxyl", whether used alone or with other terms, such as "carboxyalkyl", denotes —C(O)—OH.

The term "carbonyl", whether used alone or with other terms, such as "aminocarbonyl", denotes —C(O)—.

The term "aminocarbonyl" denotes an amide group of the Formula —C(O)—NH2.

The terms "heterocycloalkyl" embrace heterocyclic-substituted alkyl radicals. Examples include piperidylmethyl and morpholinylethyl.

The term "arylalkyl" embraces aryl-substituted alkyl radicals. Examples include benzyl, diphenylmethyl and phenylethyl. The aryl in said aralkyl may be additionally substituted with halo, alkyl, alkoxy, halkoalkyl and haloalkoxy.

The term "cycloalkyl" includes saturated carbocyclic groups of 3 to 10 carbons. Lower cycloalkyl groups include $C_3$-$C_6$ rings. Examples include cyclopentyl, cyclopropyl, and cyclohexyl. Cycloalkyl groups may be optionally substituted with one or more functional groups such as halo, hydroxy, nitro, amino, cyano, haloalkyl, aryl, heteroaryl, heterocyclo and the like.

The term "cycloalkylalkyl" embraces cycloalkyl-substituted alkyl radicals. "Lower cycloalkylalkyl" radicals are cycloalkyl radicals attached to alkyl radicals having one to six carbon atoms. Examples of include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Examples include cyclopentenyl, cyclopentadienyl, cyclohexenyl and cycloheptadienyl.

The term "comprising" is meant to be open ended, including the indicated component but not excluding other elements.

The term "oxo" as used herein contemplates an oxygen atom attached with a double bond.

The term "nitro" as used herein contemplates —NO$_2$.

The term "cyano" as used herein contemplates —CN.

As used herein, the term "prodrug" means a compound which when administered to a host in vivo is converted into the parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

Throughout the specification and claims, a given chemical formula or name shall encompass all optical and stereoisomers, as well as racemic mixtures where such isomers and mixtures exist, unless otherwise noted.

The term "selective CDK4/6 inhibitor" used in the context of the compounds described herein includes compounds that inhibit CDK4 activity, CDK6 activity, or both CDK4 and CDK6 activity at an $IC_{50}$ molar concentration at least about 500 times less than the $IC_{50}$ molar concentration necessary to inhibit to the same degree of CDK2 activity in a standard phosphorylation assay. In alternative embodiments, the $IC_{50}$ molar concentration is at least about 1000, or 1500, 1800 or 2000 times less than the $IC_{50}$ molar concentration necessary to inhibit to the same degree of CDK2 activity in a standard phosphorylation assay.

As used herein the term "chemotherapy" or "chemotherapeutic agent" refers to treatment with a cytostatic or cytotoxic agent (i.e., a compound) to reduce or eliminate the growth or proliferation of undesirable cells, for example cancer cells. Thus, as used herein, "chemotherapy" or "chemotherapeutic agent" refers to a cytotoxic or cytostatic agent used to treat a proliferative disorder, for example cancer.

The host is typically a human, although it is to be understood the methods described herein are effective for other animals, such as mammals and vertebrate species. More particularly, the term host can include animals either for veterinary purposes or used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

Active Compounds

In one embodiment, the invention is directed to methods of administering a CDK4/6 inhibitor in combination or alternation with a topoisomerase I inhibitor to treat an Rb-negative cellular proliferation disorder, such as cancer, wherein the CDK4/6 inhibitor is selected from Formula I, II, III, IV, or V:

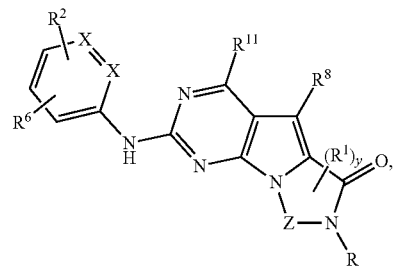

or a pharmaceutically acceptable salt thereof;
wherein:
Z is —$(CH_2)_x$— wherein x is 1, 2, 3 or 4 or —O—$(CH_2)_z$— wherein z is 2, 3 or 4; each X is independently CH or N;
each X' is independently CH or N;
X" is independently $CH_2$, S or NH, arranged such that the moiety is a stable 5-membered ring;
R, $R^8$, and $R^{11}$ are independently H, $C_1$-$C_3$ alkyl or haloalkyl, cycloalkyl or cycloalkyl containing one or more heteroatoms selected from N, O or S; -(alkylene)m-$C_3$-$C_8$ cycloalkyl, -(alkylene)$_m$-aryl, -(alkylene)$_m$-heterocyclo, -(alkylene)$_m$-heteroaryl, -(alkylene)$_m$-$NR^3R^4$, -(alkylene)$_m$-C(O)—$NR^3R^4$; -(alkylene)$_m$-O-$R^5$, -(alkylene)$_m$-S(O)$_n$-$R^5$, or -(alkylene)$_m$-S(O)$_n$-$NR^3R^4$ any of which may be optionally independently substituted with one or more $R^x$ groups as allowed by valance, and wherein two $R^x$ groups bound to the same or adjacent atoms may optionally combine to form a ring;
each $R^1$ is independently aryl, alkyl, cycloalkyl or haloalkyl, wherein each of said alkyl, cycloalkyl and haloalkyl groups optionally includes O or N heteroatoms in place of a carbon in the chain and two $R^1$'s on adjacent ring atoms or on the same ring atom together with the ring atom(s) to which they are attached optionally form a 3-8-membered cycle;
y is 0, 1, 2, 3 or 4;
$R^2$ is -(alkylene)$_m$-heterocyclo, -(alkylene)$_m$-heteroaryl, -(alkylene)$_m$-$NR^3R^4$, -(alkylene)$_m$-C(O)—$NR^3R^4$; -(alkylene)$_m$-C(O)—O-alkyl; -(alkylene)$_m$-O—$R^5$, -(alkylene)$_m$-S(O)$_n$—$R^5$, or -(alkylene)$_m$-S(O)$_n$—$NR^3R^4$ any of which may be optionally independently substituted with one or more $R^x$ groups as allowed by valance, and wherein two $R^x$ groups bound to the same or adjacent atom may optionally combine to form a ring and wherein m is 0 or 1 and n is 0, 1 or 2;
$R^3$ and $R^4$ at each occurrence are independently:
  (i) hydrogen or
  (ii) alkyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance, and wherein two $R^x$ groups bound to the same or adjacent atom may optionally combine to form a ring; or $R^3$ and $R^4$ together with the nitrogen atom to which they are attached may combine to form a heterocyclo ring optionally independently substituted with one or more $R^x$ groups as allowed by valance, and wherein two $R^x$ groups bound to the same or adjacent atom may optionally combine to form a ring;
$R^5$ and $R^{5*}$ at each occurrence is:
  (i) hydrogen or
  (ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance; $R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-O-alkylene-OR$^5$, -(alkylene)$_m$-S(O)$_n$—R$^5$, -(alkylene)$_m$-NR$^3$R$^4$, -(alkylene)$_m$-CN, -(alkylene)$_m$-C(O)—R$^5$, -(alkylene)$_m$-C(S)—R$^5$, -(alkylene)$_m$-C(O)—OR$^5$, -(alkylene)$_m$-O—C(O)—R$^5$, -(alkylene)$_m$-C(S)—OR$^5$, -(alkylene)$_m$-C(O)-(alkylene)$_m$-NR$^3$R$^4$, -(alkylene)$_m$-C(S)—NR$^3$R$^4$, -(alkylene)$_m$-N(R$^3$)—C(O)—NR$^3$R$^4$, -(alkylene)$_m$-N(R$^3$)—C(S)—NR$^3$R$^4$, -(alkylene)$_m$-N(R$^3$)—C(O)—R$^5$, -(alkylene)$_m$-N(R$^3$)—C(S)—R$^5$, -(alkylene)$_m$-O—C(O)—NR$^3$R$^4$, -(alkylene)$_m$-O—C(S)—NR$^3$R$^4$, -(alkylene)$_m$-SO$_2$—NR$^3$R$^4$, -(alkylene)$_m$-N(R$^3$)—SO$_2$—R$^5$, -(alkylene)$_m$-N(R$^3$)—SO$_2$—NR$^3$R$^4$, -(alkylene)$_m$-N(R$^3$)—C(O)—OR$^5$) -(alkylene)$_m$-N(R$^3$)—C(S)—OR$^5$, or -(alkylene)$_m$-N(R$^3$)—SO$_2$—R$^5$; wherein:

said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-OR$^5$, -(alkylene)$_m$-S(O)$_n$-R$^{5*}$, -(alkylene)$_m$-NR$^{3*}$R$^{4*}$, -(alkylene)$_m$-C(O)—R$^{5*}$, -(alkylene)$_m$-C(=S)R$^{5*}$, -(alkylene)$_m$-C(=O)OR$^{5*}$, -(alkylene)$_m$-OC(=O)R$^5$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$-O—C(O)—NR$^{3*}$R$^{4*}$, -(alkylene)$_m$-O—C(S)—NR$^{3*}$R$^{4*}$, -(alkylene)$_m$-SO$_2$—NR$^{3*}$R$^{4*}$, -(alkylene)$_m$-N(R$^{3*}$)—S$_2$—R$^{5*}$, -(alkylene)$_m$-N(R$^{3*}$)—SO$_2$—NR$^{3*}$R$^{4*}$, -(alkylene)$_m$-N(R$^{3*}$)—C(O)—OR$^{5*}$, -(alkylene)$_m$-N(R$^{3*}$)—C(S)—OR$^{5*}$, or -(alkylene)$_m$-N(R$^{3*}$)—S$_2$—R$^{5*}$, n is 0, 1 or 2, and
m is 0 or 1;

R$^{3*}$ and R$^{4*}$ at each occurrence are independently:
(i) hydrogen or
(ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance; or R$^{3*}$ and R$^{4*}$ together with the nitrogen atom to which they are attached may combine to form a heterocyclo ring optionally independently substituted with one or more R$^x$ groups as allowed by valance; and R$^6$ is H or lower alkyl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atoms may optionally combine to form a ring; and R$^{10}$ is (i) NHR$^A$, wherein R$^A$ is unsubstituted or substituted C$_1$-C$_8$ alkyl, cycloalkylalkyl, or -TT-RR, C$_1$-C$_8$ cycloalkyl or cycloalkyl containing one or more heteroatoms selected from N, O, and S; TT is an unsubstituted or substituted C$_1$-C$_8$ alkyl or C$_3$-C$_8$ cycloalkyl linker; and RR is a hydroxyl, unsubstituted or substituted C$_1$-C$_6$ alkoxy, amino, unsubstituted or substituted C$_1$-C$_6$ alkylamino, unsubstituted or substituted di-C$_1$-C$_6$ alkylamino, unsubstituted or substituted C$_6$-C$_{10}$ aryl, unsubstituted or substituted heteroaryl comprising one or two 5- or 6-member rings and 1-4 heteroatoms selected from N, O and S, unsubstituted or substituted C$_3$-C$_{10}$ carbocycle, or unsubstituted or substituted heterocycle comprising one or two 5- or 6-member rings and 1-4 heteroatoms selected from N, O and S; or (ii) —C(O)—R$^{12}$ or —C(O)O—R$^{13}$, wherein R$^{12}$ is NHR$^A$ or R$^A$ and R$^{13}$ is R$^A$;

or a pharmaceutically acceptable salt, prodrug or isotopic variant, for example, partially or fully deuterated form thereof.

In some aspects, the CDK4/6 inhibitor used in the combination is Formula I or Formula II and R$^6$ is absent.

In some aspects, the CDK4/6 inhibitor used in the combination is of Formula III:

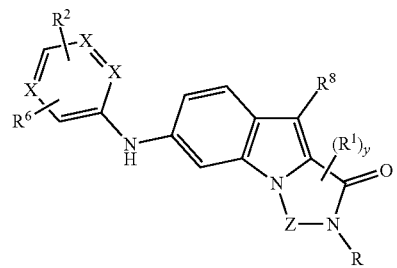

and the variables are as defined for compounds of Formulae I and II and or a pharmaceutically acceptable salt, prodrug, or isotopic variant, for example, partially or fully deuterated form thereof.

In some aspects, R$^x$ is not further substituted.

In some aspects, R$^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atom may optionally combine to form a ring and wherein m is 0 or 1 and n is 0, 1 or 2.

In some aspects, R$^8$ is hydrogen or C$_1$-C$_3$ alkyl.

In some aspects, R is hydrogen or C$_1$-C$_3$ alkyl.

In some aspects, R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ any of which may be optionally independently substituted with one or more R$^x$ groups as allowed by valance, and wherein two R$^x$ groups bound to the same or adjacent atom may optionally combine to form a ring.

In some aspects, R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ without further substitution.

In some aspects, m in R$^2$ is 1. In a further aspect, the alkylene in R$^2$ is methylene.

In some aspects, R$^2$ is

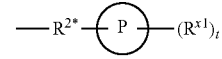

wherein:
R$^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- or -(alkylene)$_m$-NH-(alkylene)$_m$- wherein each m is independently 0 or 1;

P is a 4- to 8-membered mono- or bicyclic saturated heterocyclyl group;

each $R^{x1}$ is independently -(alkylene)$_m$-(C(O))$_m$-(alkylene)$_m$-(N(R$^N$))$_m$-(alkyl)$_m$ wherein each m is independently 0 or 1 provided at least one m is 1, —(C(O))—O-alkyl, -(alkylene)$_m$-cycloalkyl wherein m is 0 or 1, —N(R$^N$)-cycloalkyl, —C(O)-cycloalkyl, -(alkylene)$_m$-heterocyclyl wherein m is 0 or 1, or —N(R$^N$)-heterocyclyl, —C(O)-heterocyclyl, —S(O)$_2$-(alkylene)$_m$ wherein m is 1 or 2, wherein:

$R^N$ is H, $C_1$ to $C_4$ alkyl or $C_1$ to $C_6$ heteroalkyl, and wherein two $R^{x1}$ can, together with the atoms to which they attach on P, which may be the same atom, form a ring; and t is 0, 1 or 2.

In some aspects, each $R^{x1}$ is only optionally substituted by unsubstituted alkyl, halogen or hydroxy.

In some aspects, $R^{x1}$ is hydrogen or unsubstituted $C_1$-$C_4$ alkyl.

In some aspects, at least one $R^{x1}$ is -(alkylene)$_m$-heterocyclyl wherein m is 0 or 1.

In some aspects, $R^2$ is

—R$^{2*}$—N P* —(R$^{x1}$)$_t$ wherein P* is a 4- to 8-membered mono- or bicyclic saturated heterocyclyl group.

In some aspects, $R^2$ is

—R$^{2*}$—N   NH (R$^{x1}$)$_t$.

In some aspects, $R^2$ is

—R$^{2*}$—N   N—R$^{x1}$.

In some aspects, $R^2$ is

—R$^{2*}$—( P )—( P1 )—(R$^{x2}$)$_s$ wherein:
$R^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- or -(alkylene)$_m$-NH-(alkylene)$_m$- wherein each m is independently 0 or 1;

P is a 4- to 8-membered mono- or bicyclic saturated heterocyclyl group;

P1 is a 4- to 6-membered monocyclic saturated heterocyclyl group;

each $R^{x2}$ is independently hydrogen or alkyl; and s is 0, 1 or 2.

In some aspects, $R^2$ is

—R$^{2*}$—N   P1 —(R$^{x2}$)$_s$.

In some aspects, P1 includes at least one nitrogen.

In some aspects, any alkylene in $R^{2*}$ in any previous aspect is not further substituted.

Figure 2:
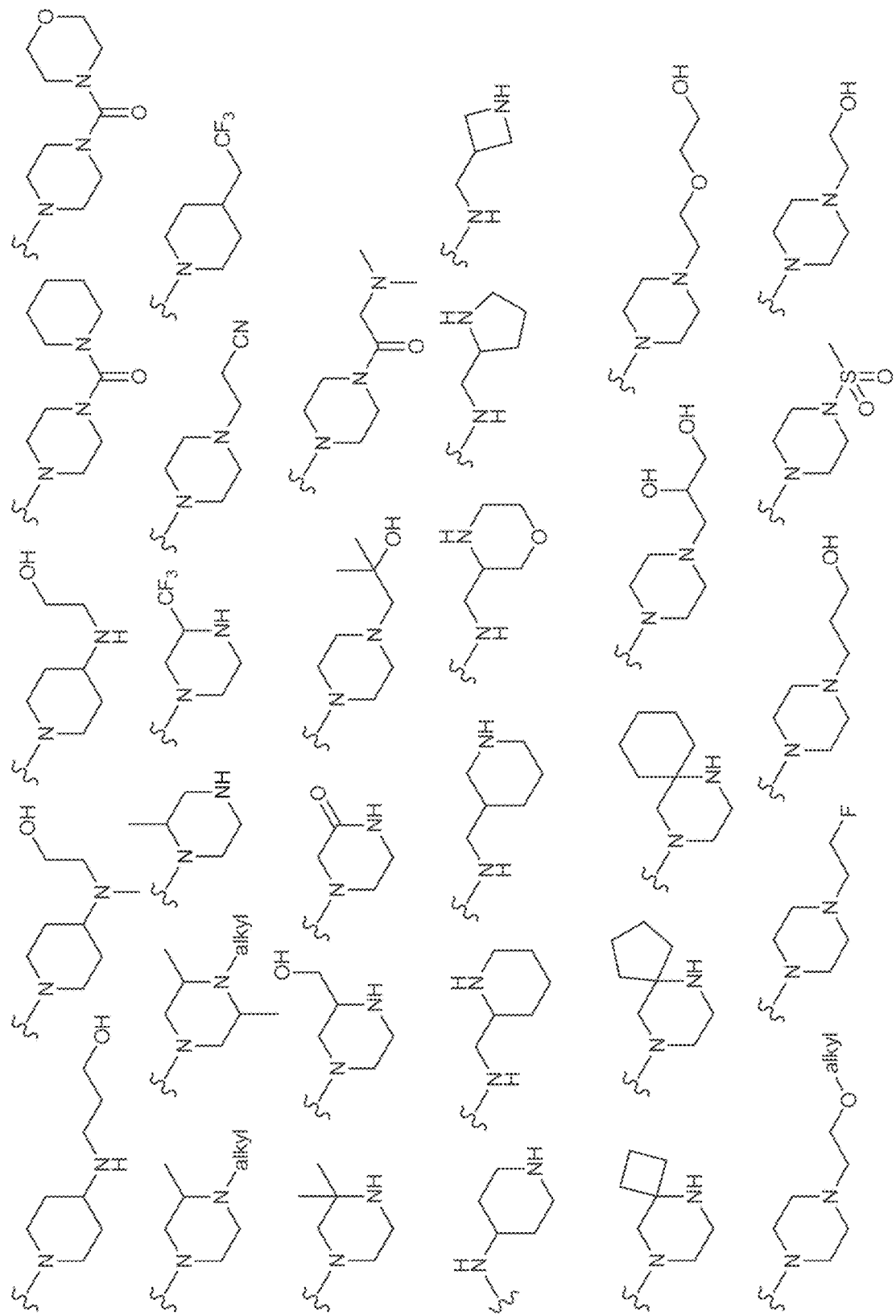
Figure 3:
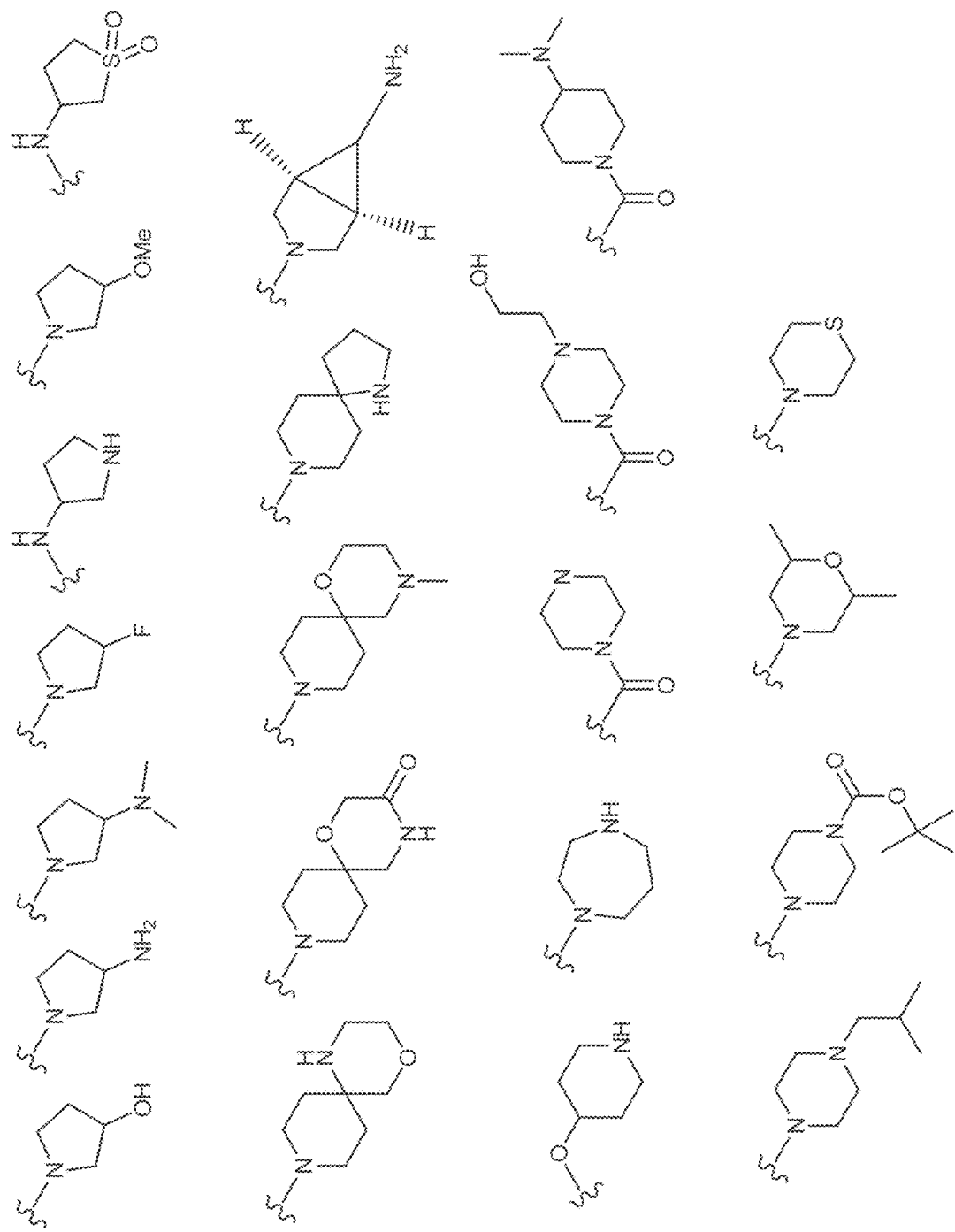
Figure 4A:
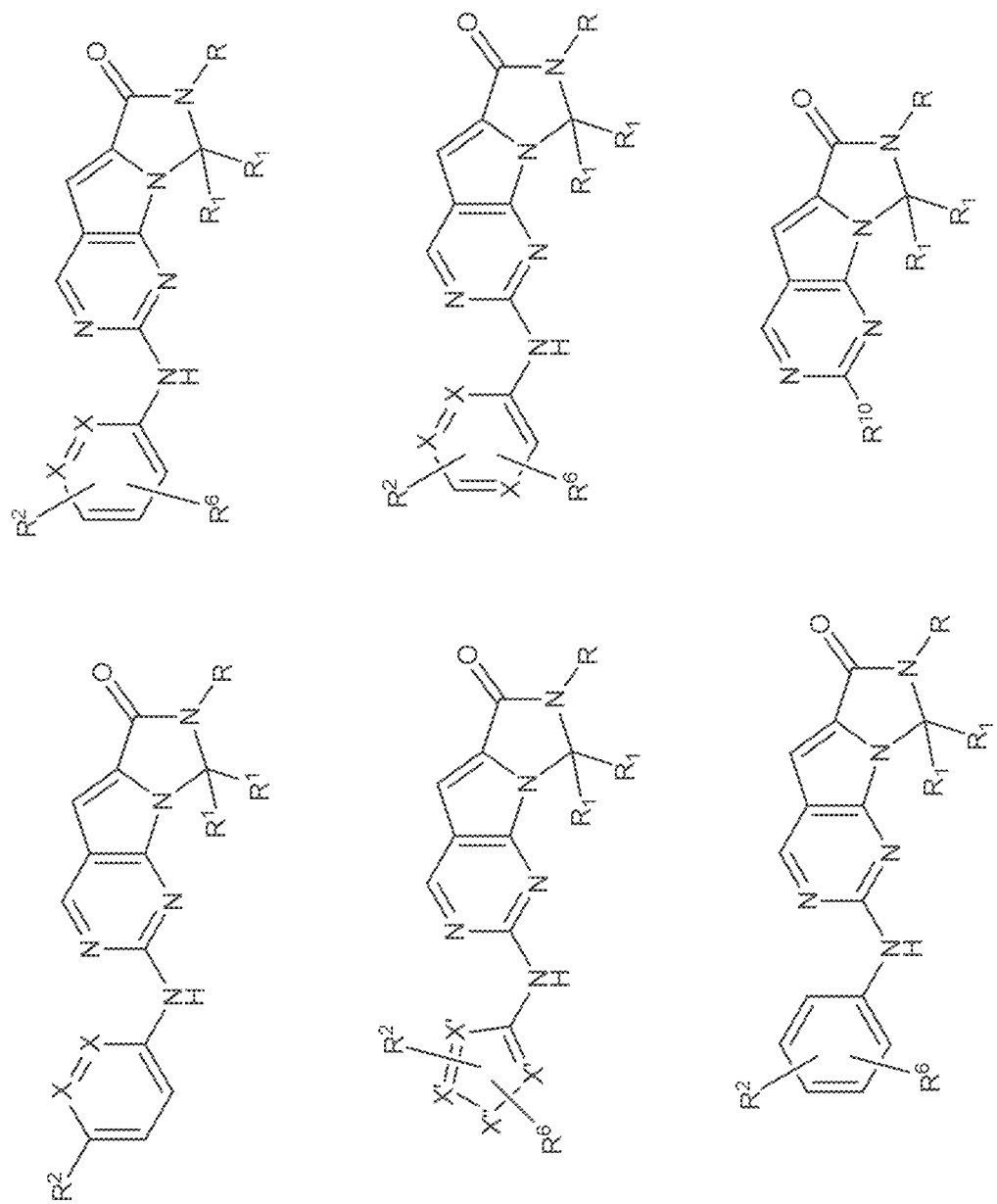
FIGS. 4A-4C, 5A-5D, 6A-6C, 7A-7B, and 8A-8F illustrate several exemplary embodiments of the core structure CDK4/6 inhibitors useful in the present invention of the compounds of the invention.
Figure 4B:
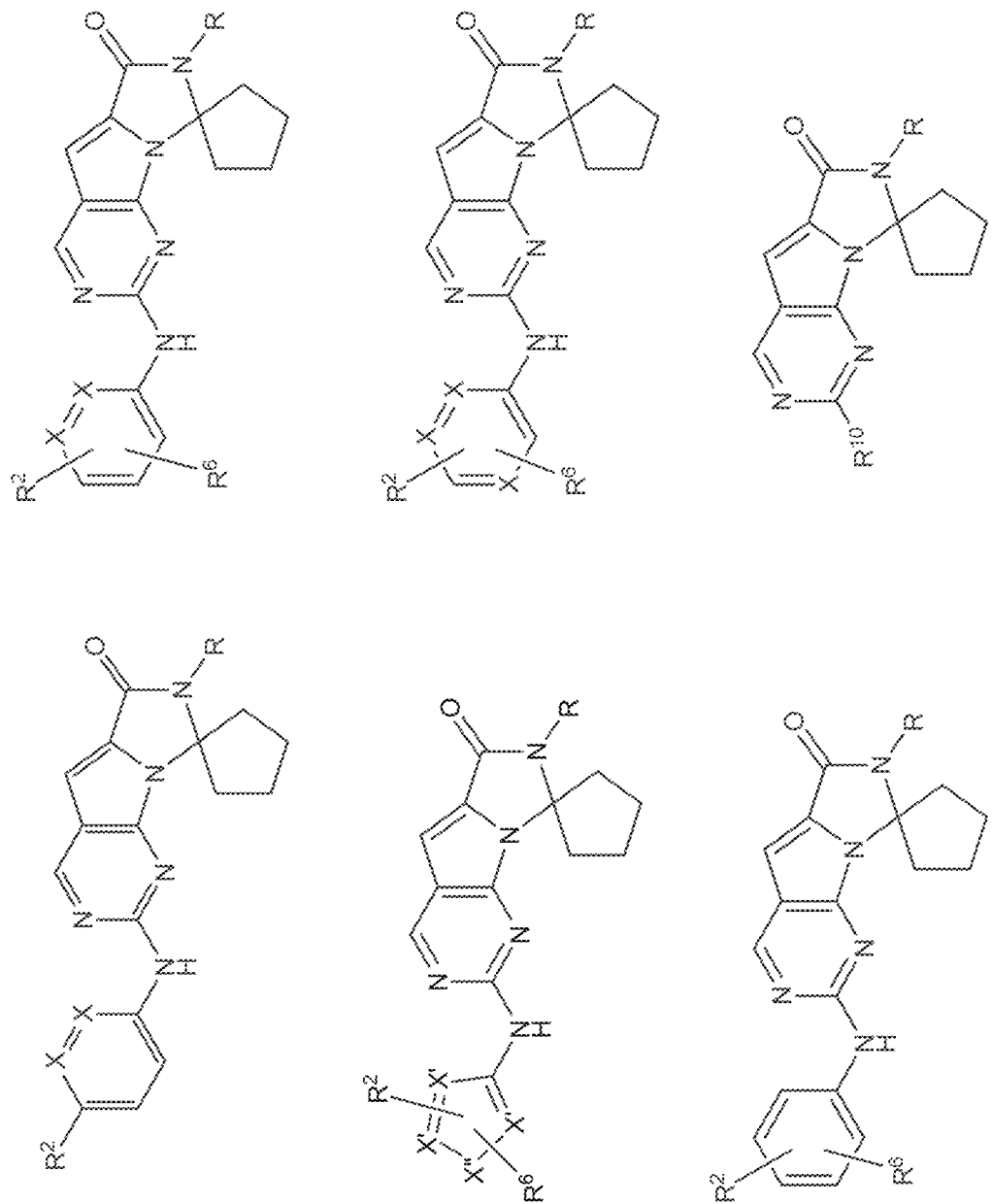
Figure 4C:
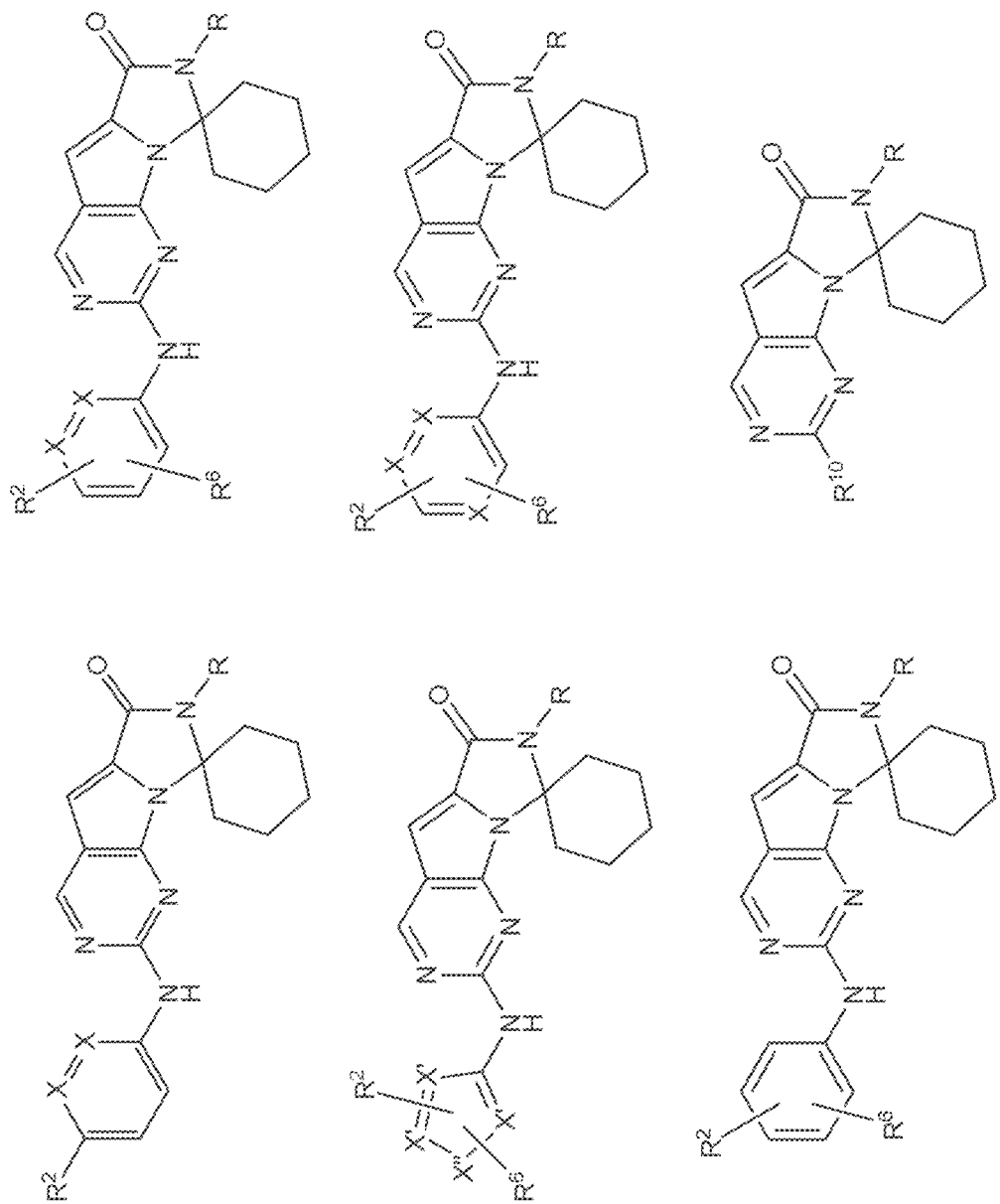
Figure 5A:
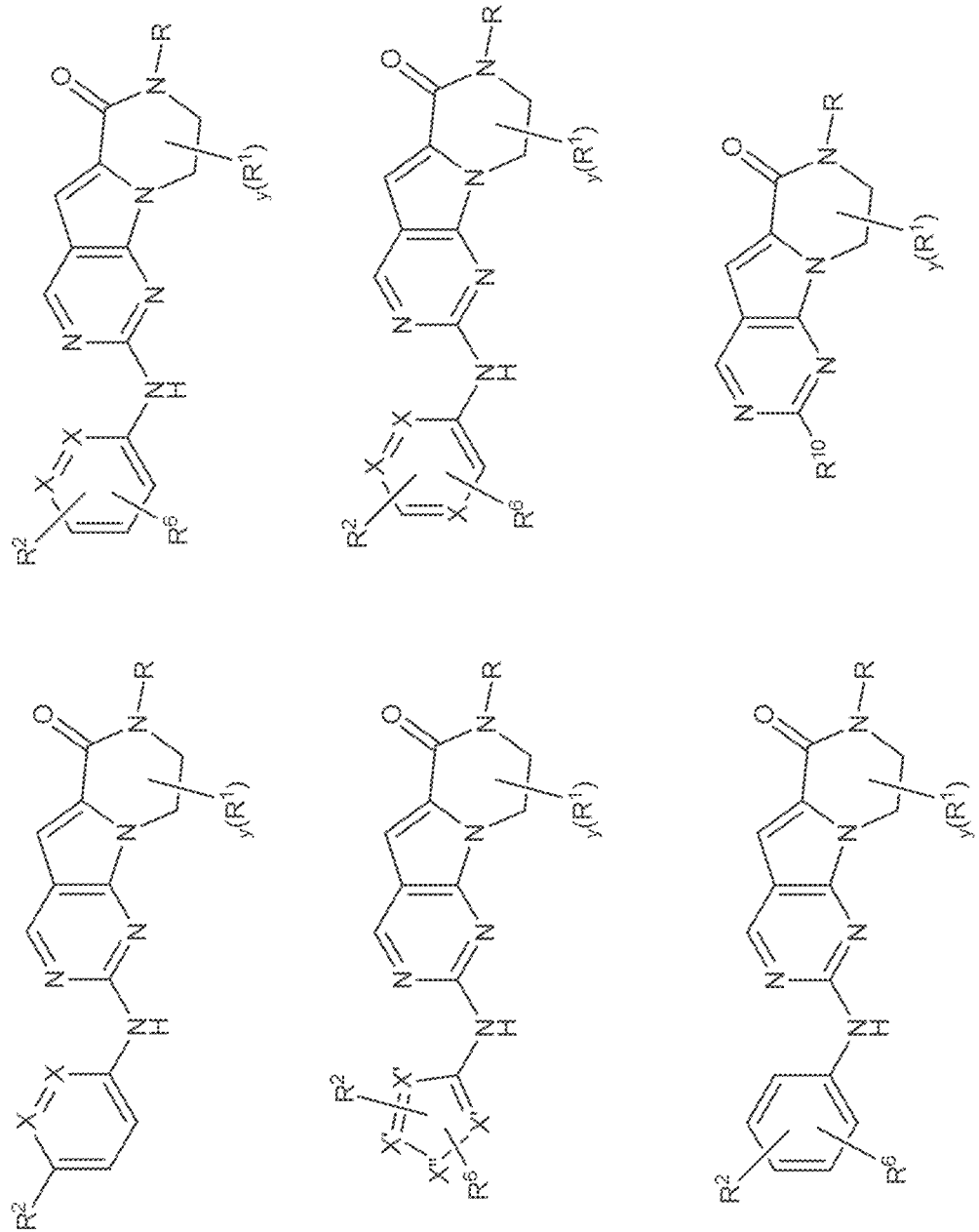
Figure 5B:
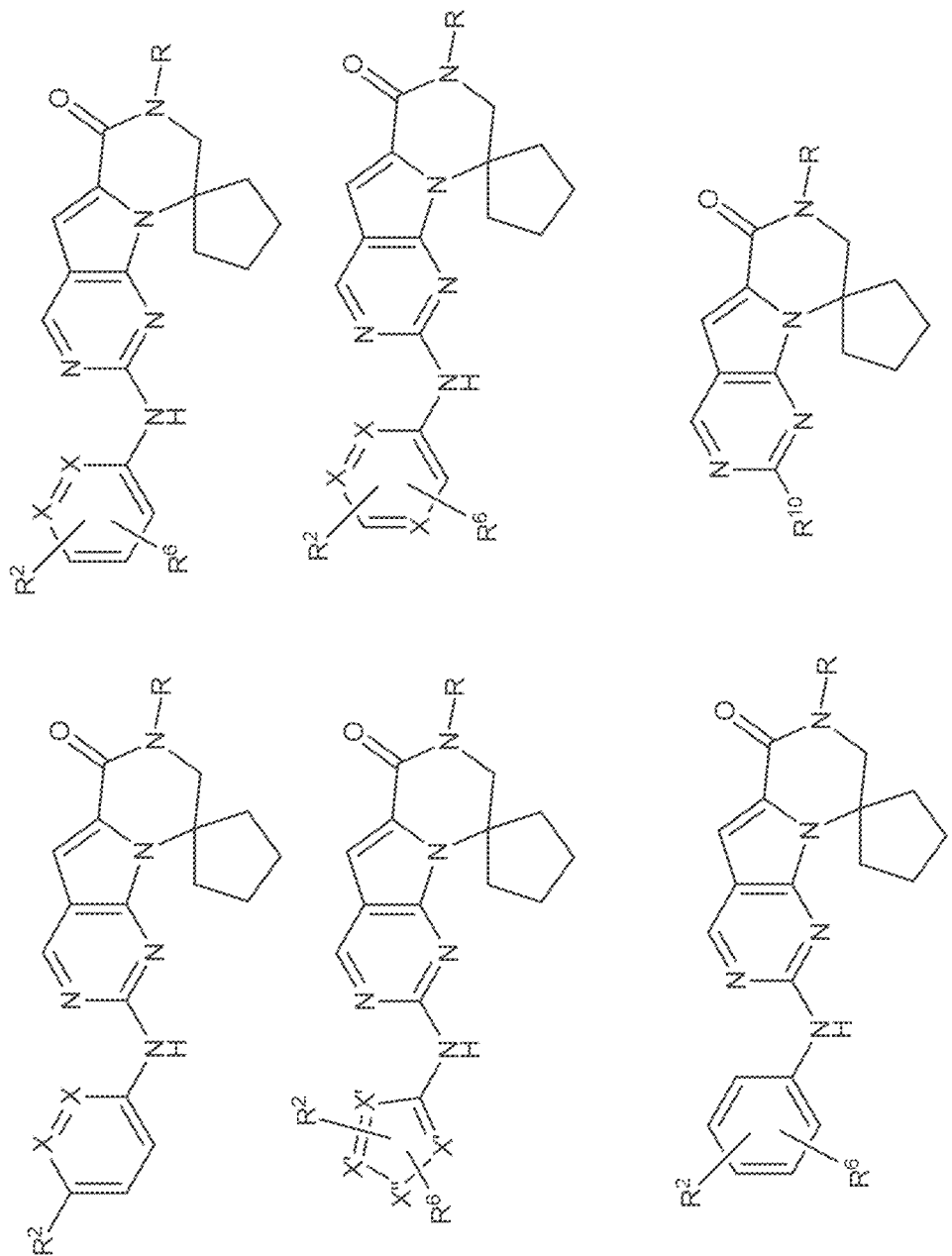
Figure 5C:
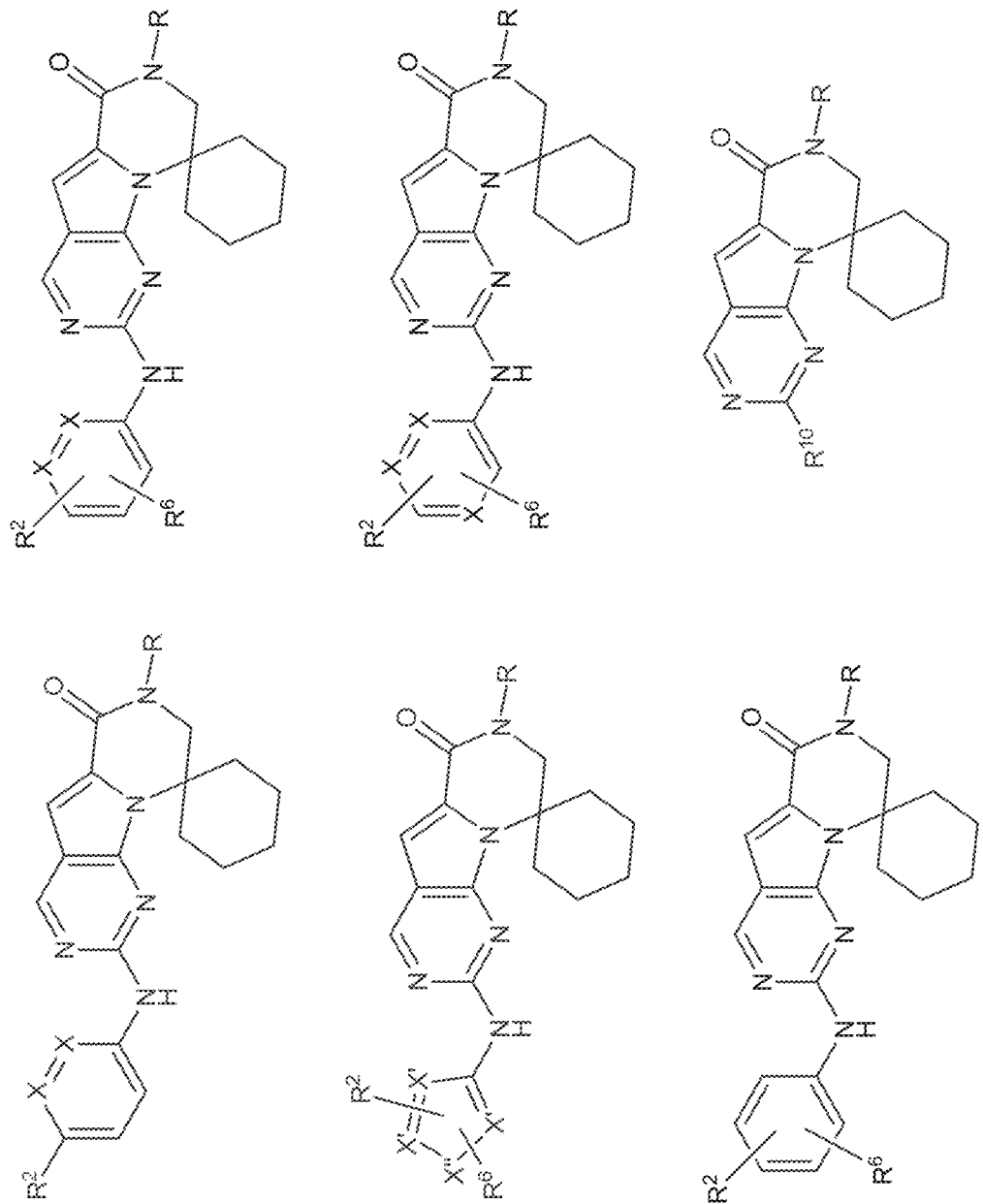
Figure 5D:
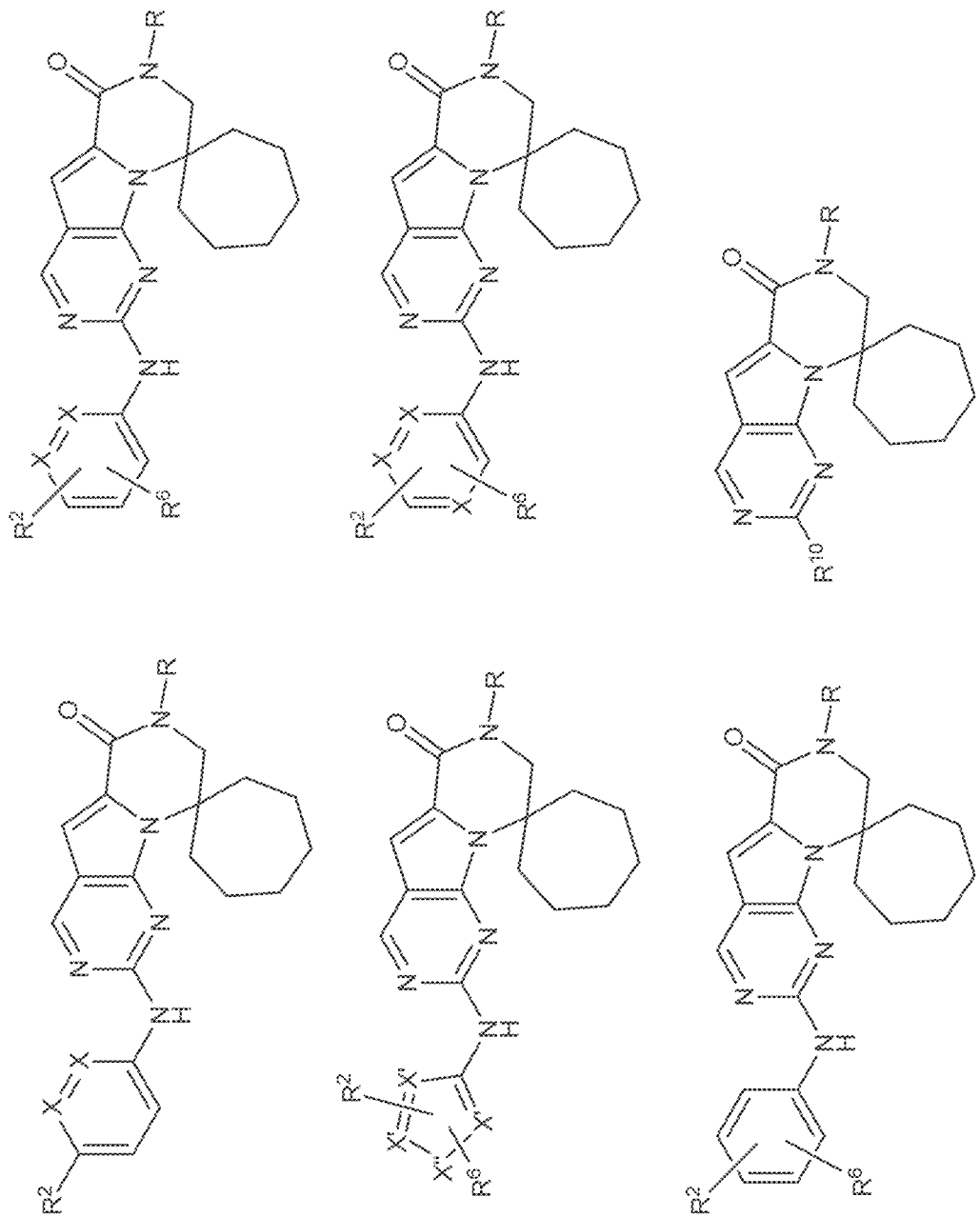
Figure 6A:
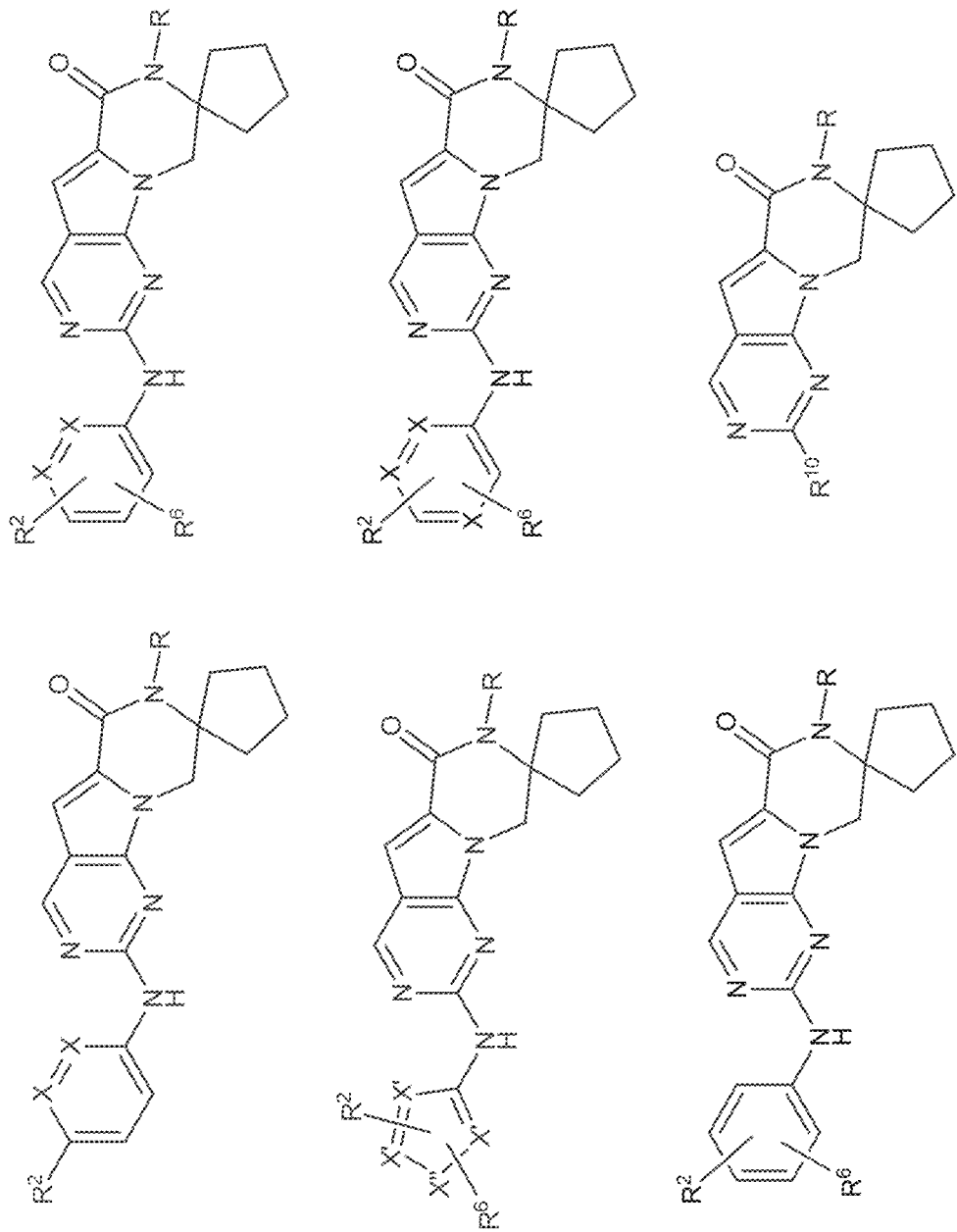
Figure 6B:
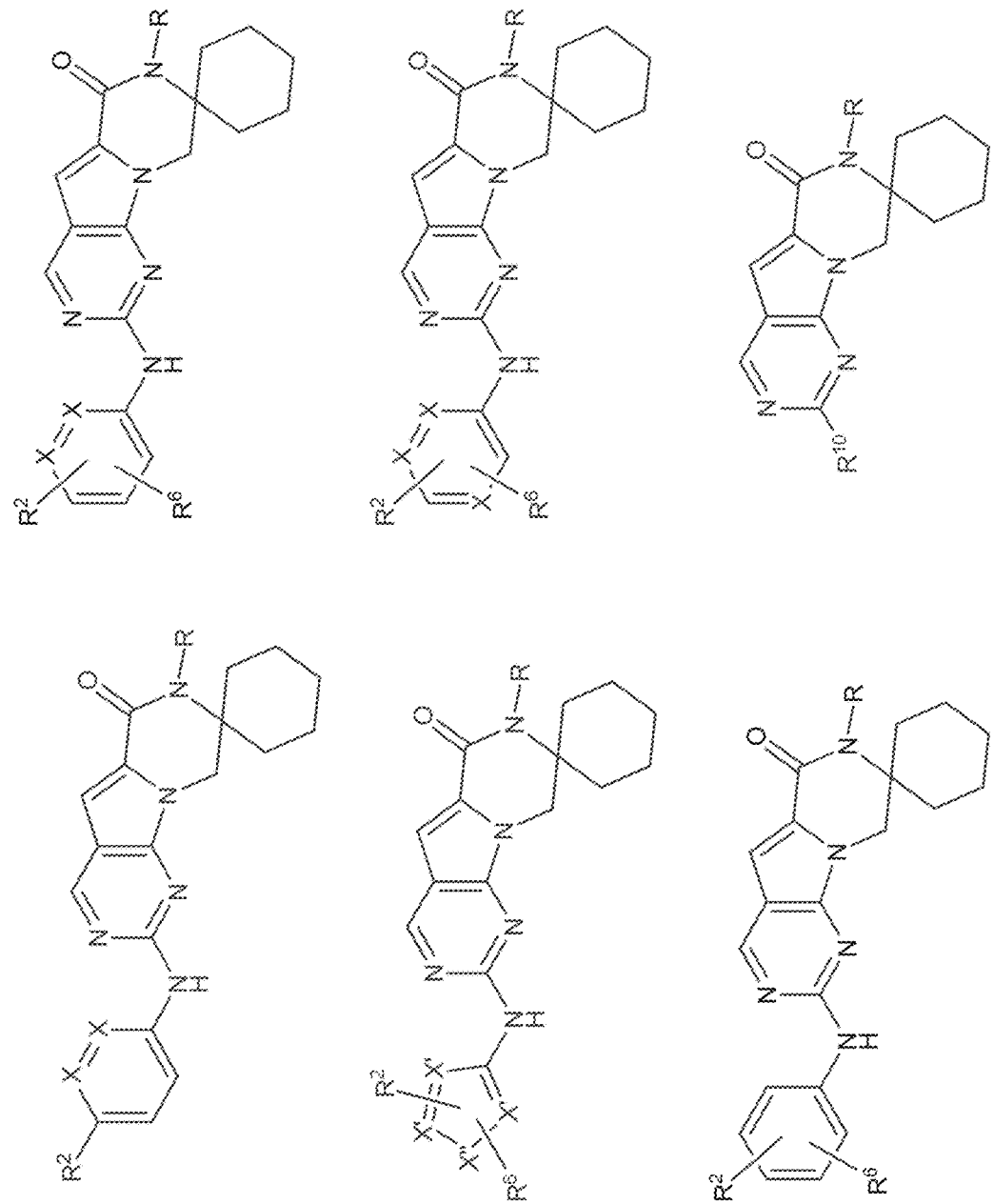
Figure 6C:
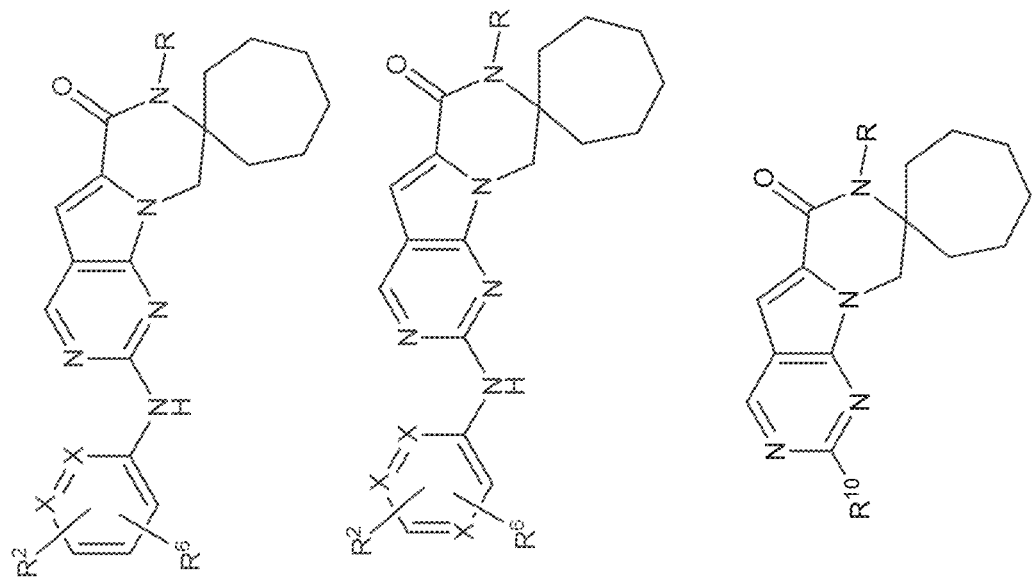
Figure 6C:
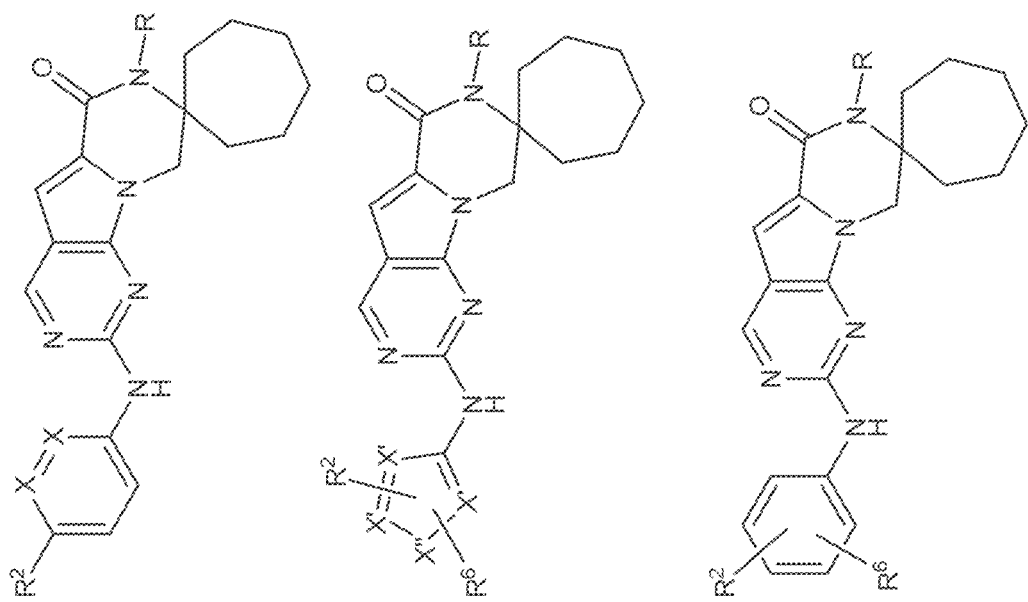
Figure 7A:
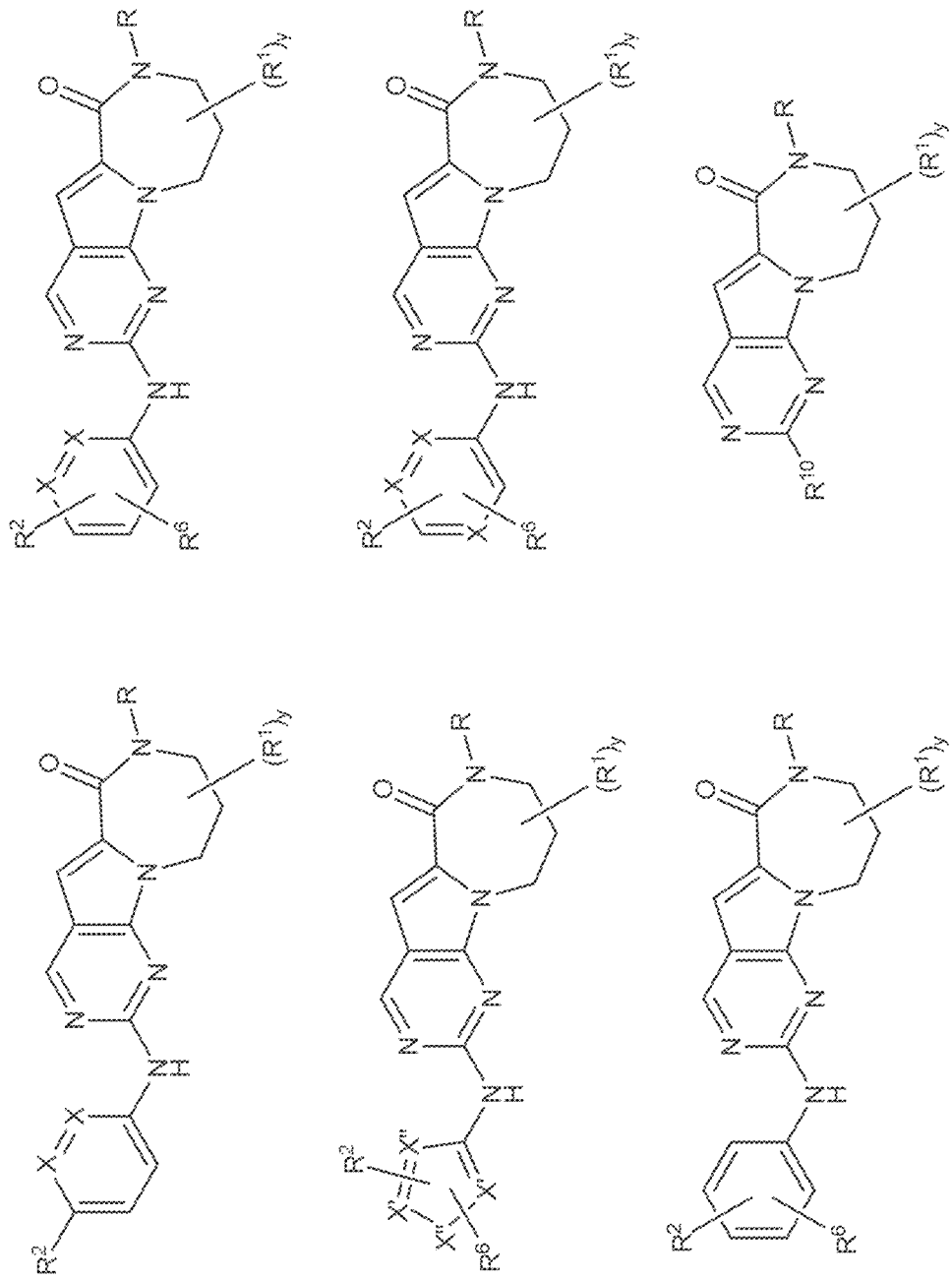
Figure 7B:
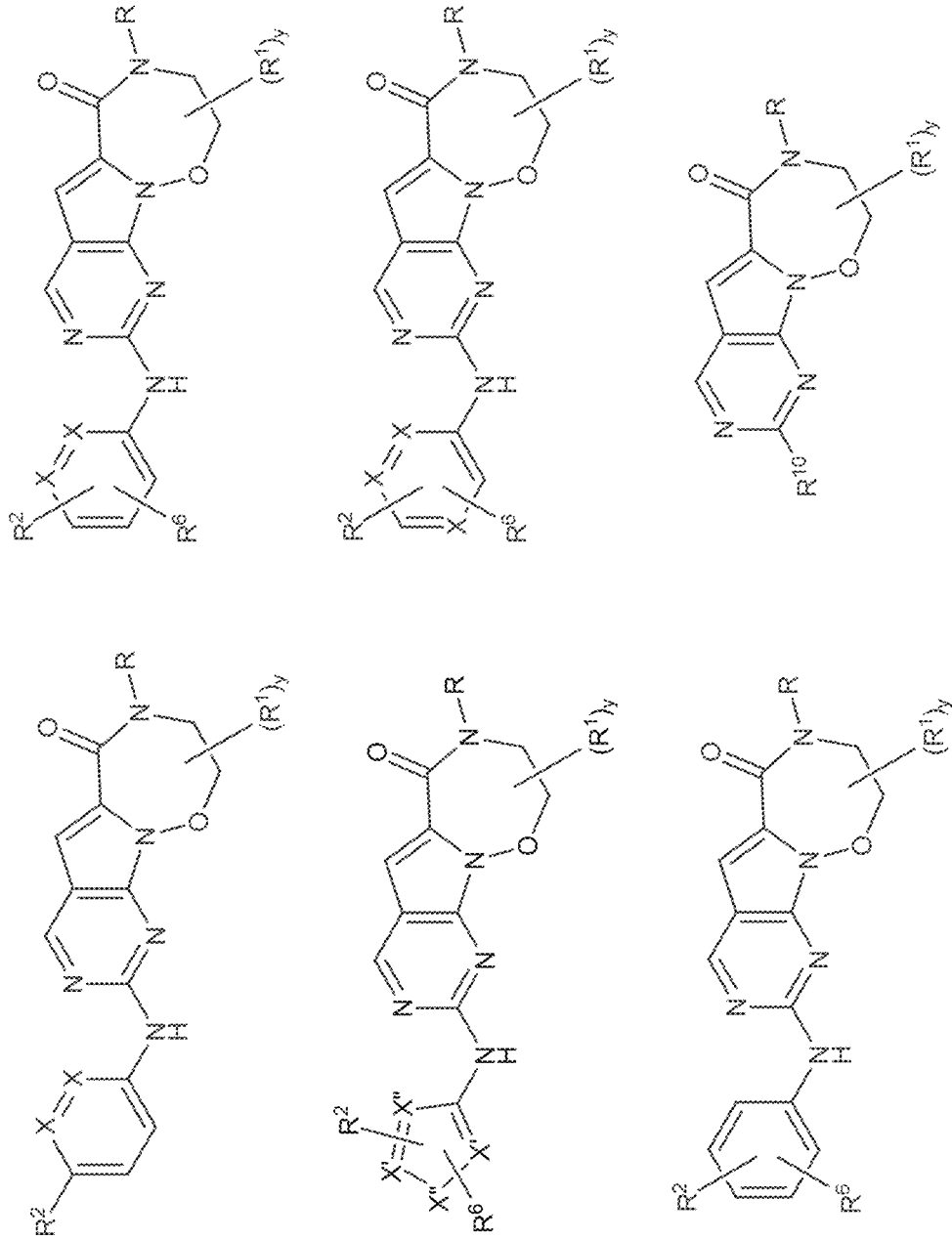
Figure 8A:
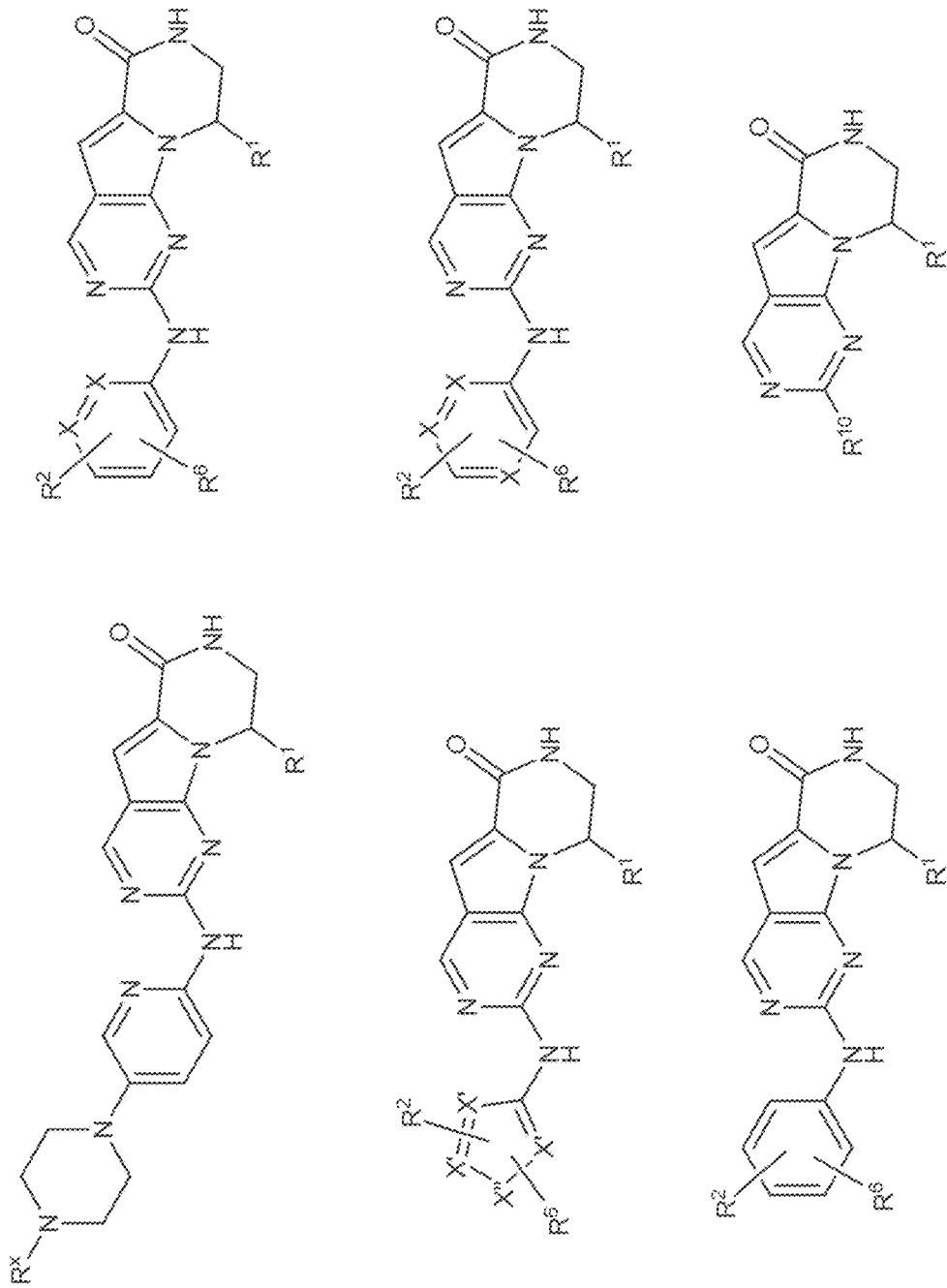
Figure 8B:
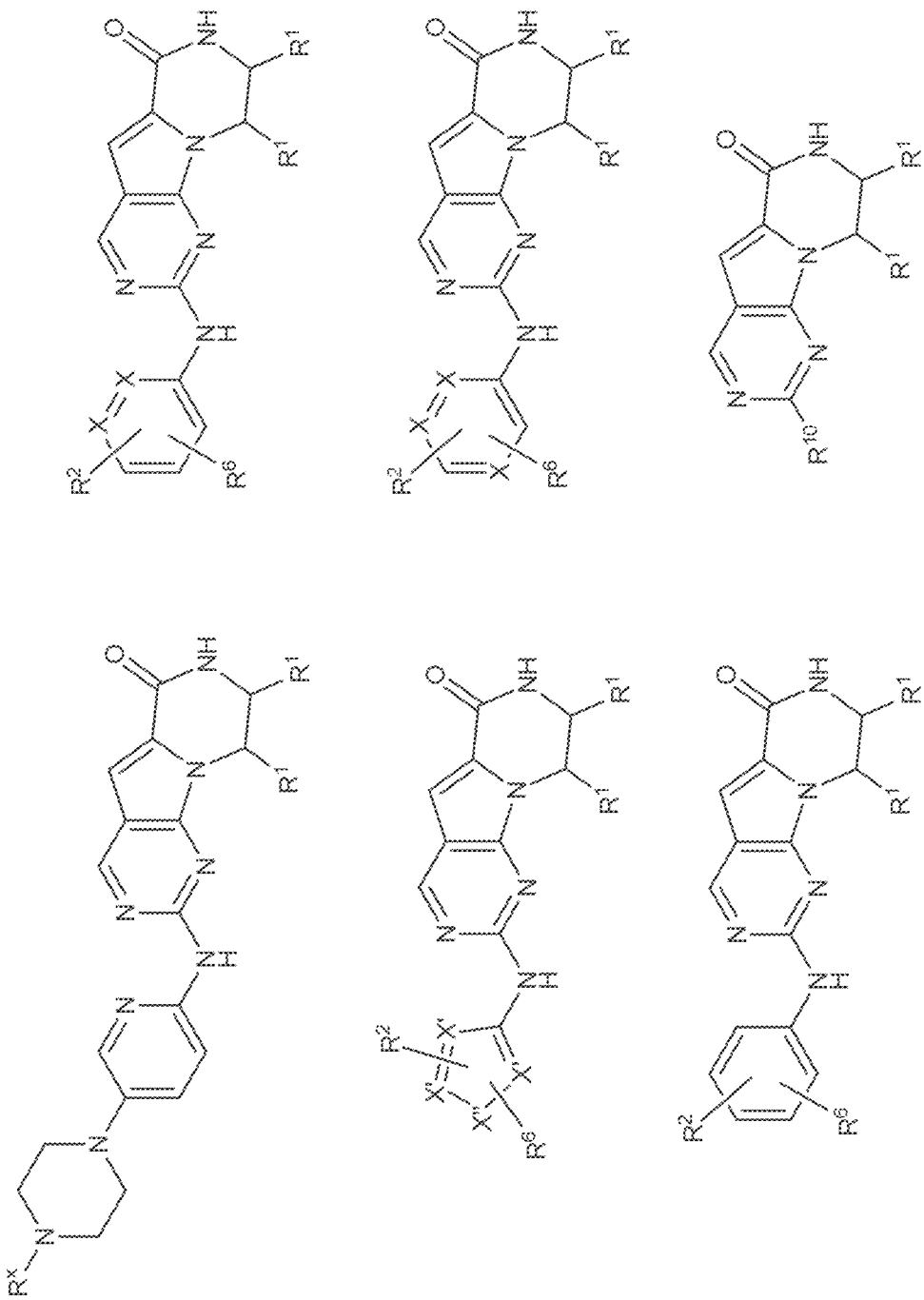
Figure 8C:
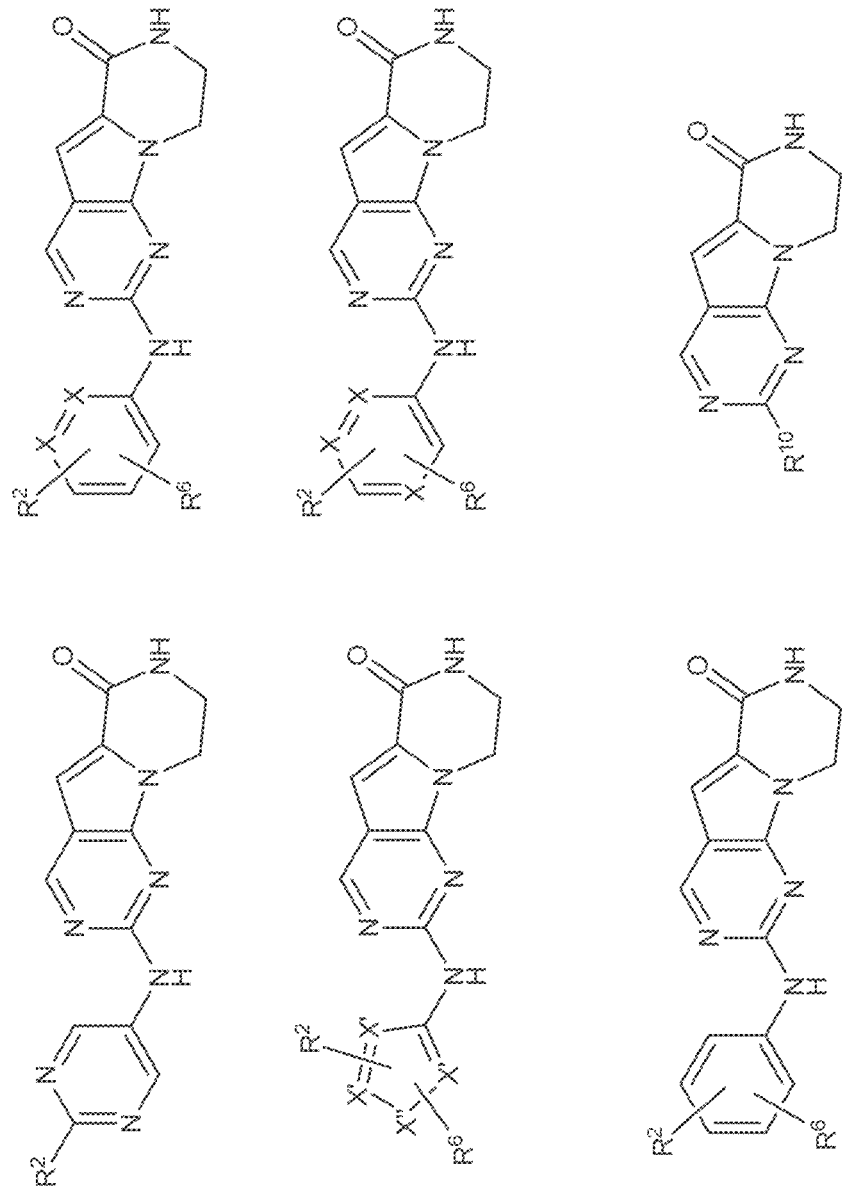
Figure 8D:
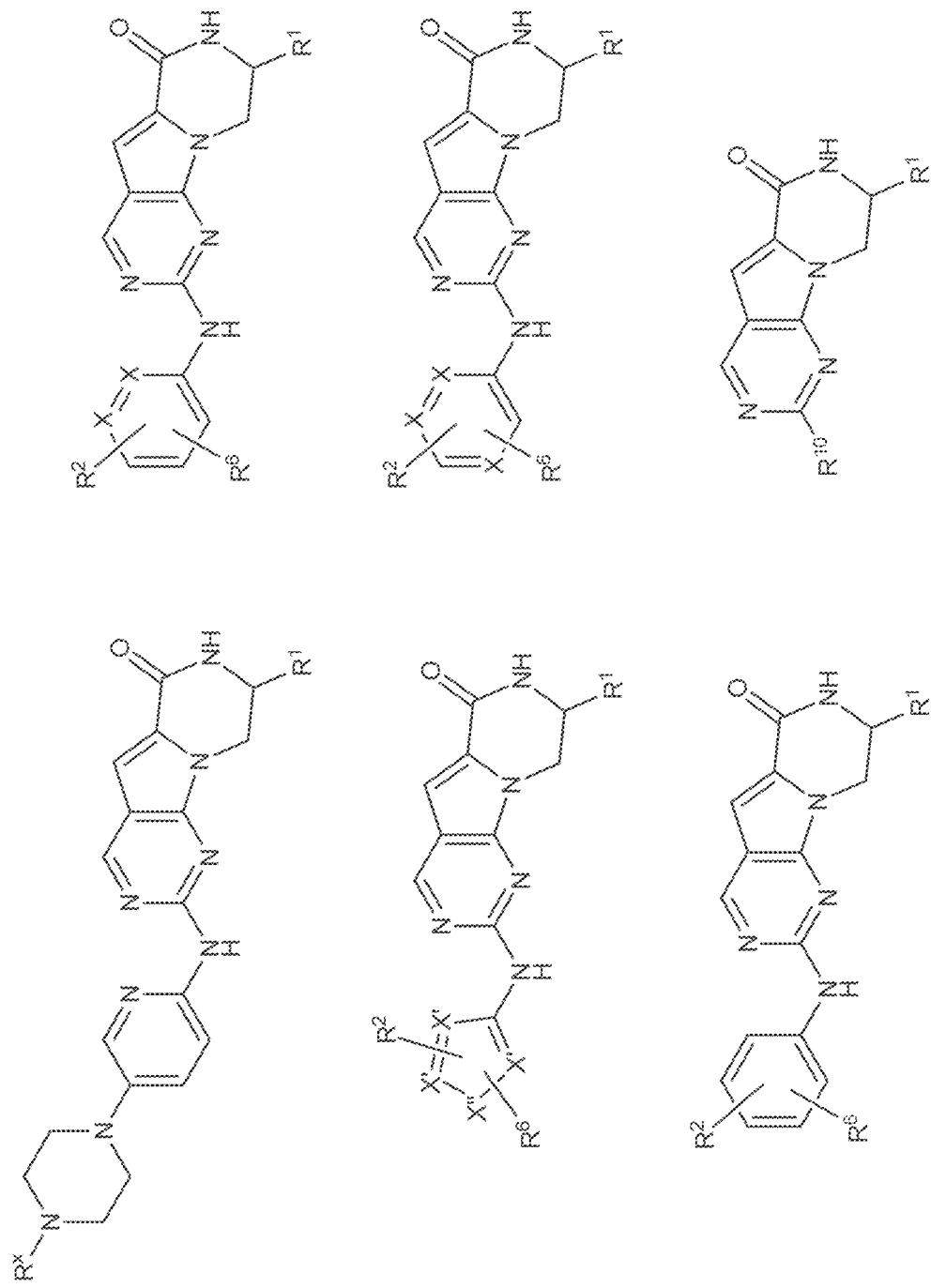
Figure 8E:
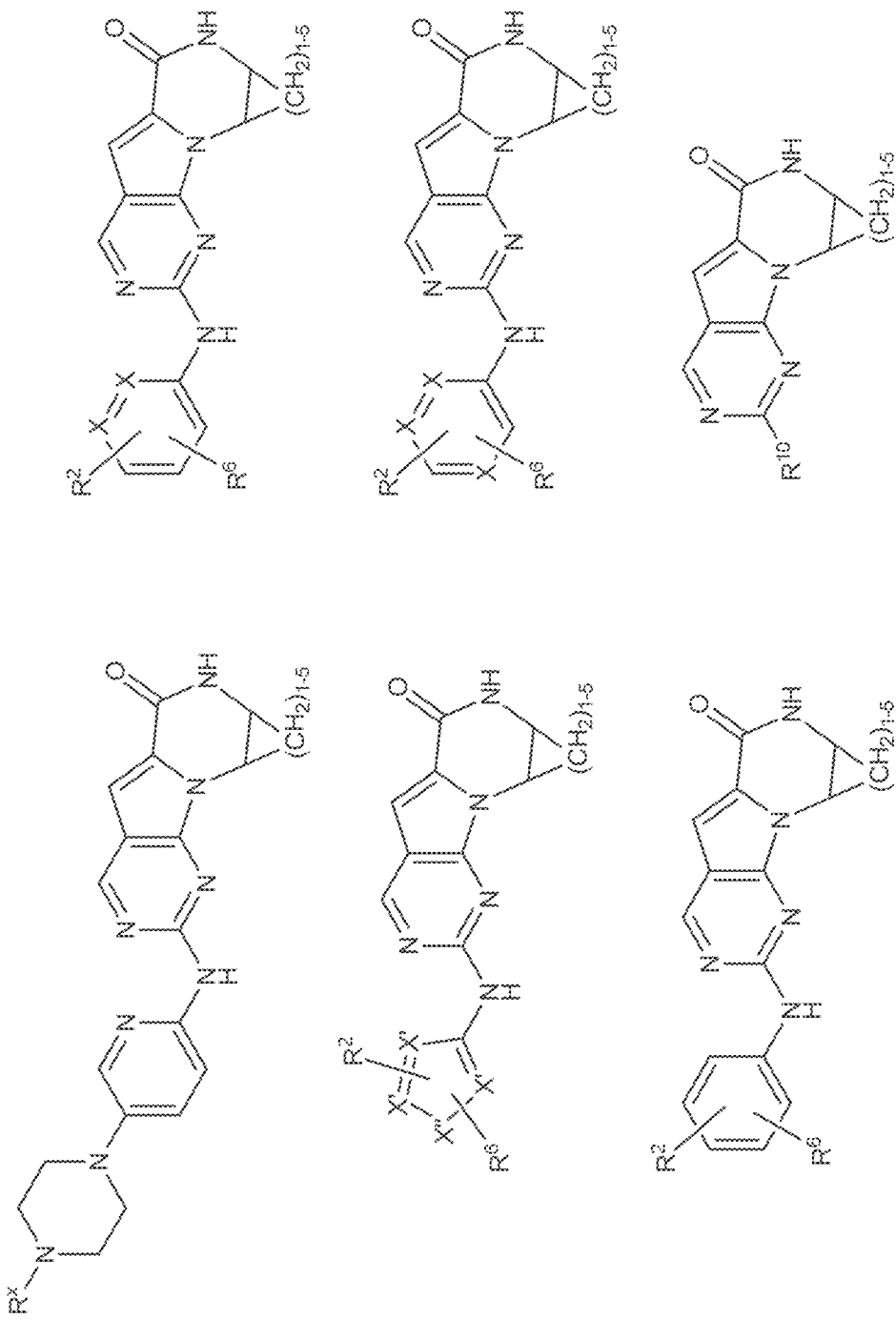
Figure 8F:
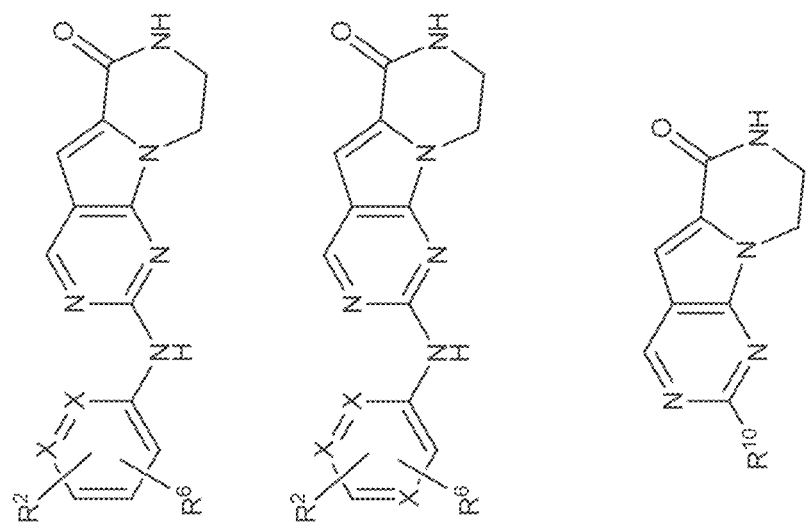
Figure 8F:
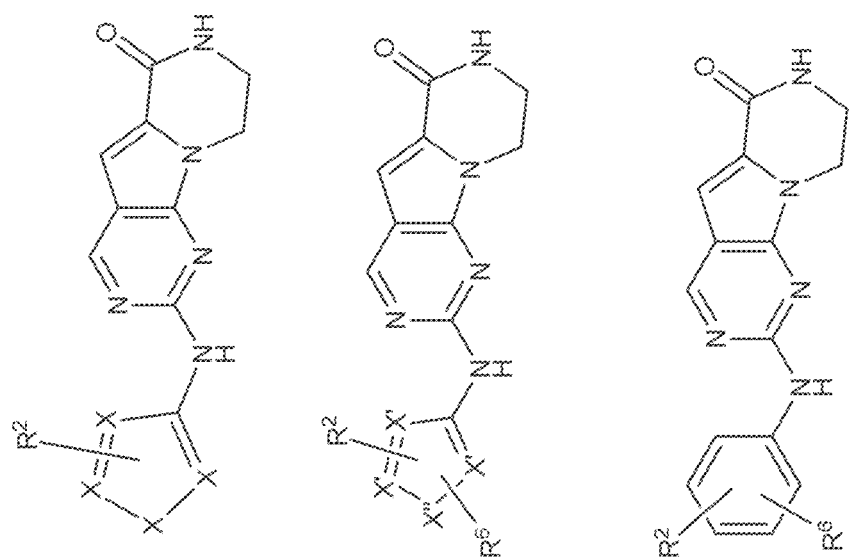

In some aspects, $R^2$ is selected from the structures depicted in FIGS. 1-3.

In some aspects, $R^2$ is

[structures depicted]

In some aspects, the CDK4/6 inhibitor used has general Formula I and more specifically one of the general structures in FIGS. 4-8 wherein the variables are as previously defined.

In some aspects, the CDK4/6 inhibitor used has general Formula Ia:

Ia

[structure with R$^2$, X, N, NH, N, y(R$^1$), R]

wherein $R^1$, $R^2$, R and y are as previously defined.

In some embodiments, the CDK4/6 inhibitor used has Formula Ia and $R^2$ is

—R$^{2*}$—N P* —(R$^{x1}$)$_t$ wherein P* is a 4- to 8-membered mono- or bicyclic saturated heterocyclyl group and $R^{2*}$, $R^{x1}$ and t are as previously defined.

In some embodiments, the CDK4/6 inhibitor used has Formula Ia and R² is

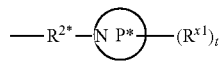

wherein P* is a 4- to 8-membered mono- or bicyclic saturated heterocyclyl group, R^{x1} is hydrogen or unsubstituted $C_1$-$C_4$ alkyl and R²* is as previously defined.

In some embodiments, the CDK4/6 inhibitor used has Formula Ib:

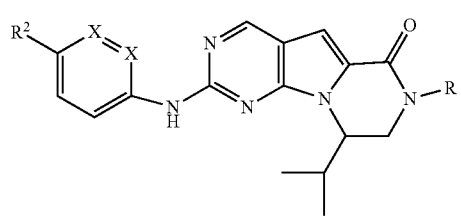

wherein R² and R are as previously defined.

In some embodiments, the CDK4/6 inhibitor used has Formula Ib and R² is

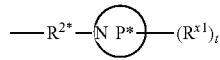

wherein P* is a 4- to 8-membered mono- or bicyclic saturated heterocyclyl group and R²*, R^{x1} and t are as previously defined.

In some embodiments, the CDK4/6 inhibitor used has Formula Ib and R² is

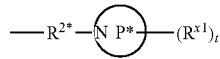

wherein P* is a 4- to 8-membered mono- or bicyclic saturated heterocyclyl group, R^{x1} is hydrogen or $C_1$-$C_4$ alkyl and R²* is as previously defined.

In some embodiments, the CDK4/6 inhibitor used has Formula Ic:

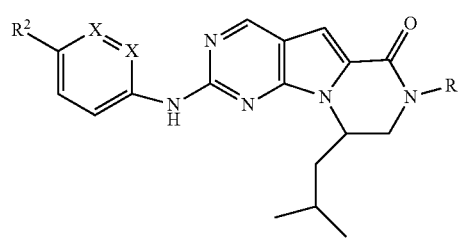

wherein R² and R are as previously defined.

In some embodiments, the CDK4/6 inhibitor used has Formula Ic and R² is

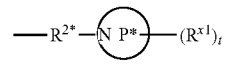

wherein P* is a 4- to 8-membered mono- or bicyclic saturated heterocyclyl group and R²*, R^{x1} and t are as previously defined.

In some embodiments, the CDK4/6 inhibitor used has Formula Ic and R² is

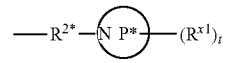

wherein P* is a 4- to 8-membered mono- or bicyclic saturated heterocyclyl group, R^{x1} is hydrogen or $C_1$-$C_4$ alkyl and R²* is as previously defined.

In some embodiments, the CDK4/6 inhibitor used has Formula Id:

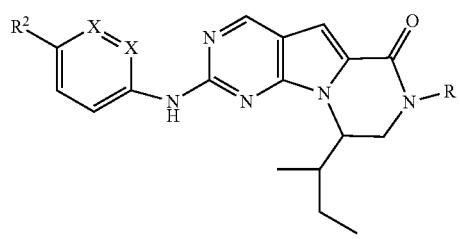

wherein R² and R are as previously defined.

In some embodiments, the CDK4/6 inhibitor used has Formula Id and R² is

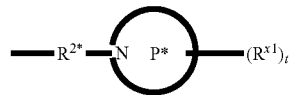

wherein P* is a 4- to 8-membered mono- or bicyclic saturated heterocyclyl group and R²*, R^{x1} and t are as previously defined.

In some embodiments, the CDK4/6 inhibitor used has Formula Id and R² is

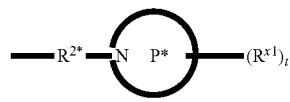

wherein P* is a 4- to 8-membered mono- or bicyclic saturated heterocyclyl group, R^{x1} is hydrogen or $C_1$-$C_4$ alkyl and R²* is as previously defined.

In some embodiments, the CDK4/6 inhibitor used has Formula Ie:

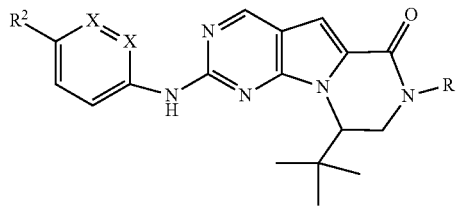

In some embodiments, the CDK4/6 inhibitor used has Formula Ie and $R^2$ is

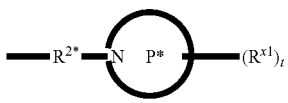

wherein P* is a 4- to 8-membered mono- or bicyclic saturated heterocyclyl group and $R^{2*}$, $R^{x1}$ and t are as previously defined.

In some embodiments, the CDK4/6 inhibitor used has Formula Ie and $R^2$ is

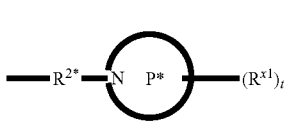

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the CDK4/6 inhibitor used has Formula If:

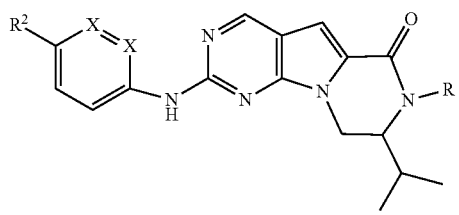

In some embodiments, the CDK4/6 inhibitor used has Formula If and $R^2$ is

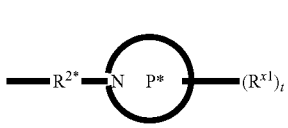

wherein P* is a 4- to 8-membered mono- or bicyclic saturated heterocyclyl group and $R^{2*}$, $R^{x1}$ and t are as previously defined.

In some embodiments, the CDK4/6 inhibitor used has Formula If and $R^2$ is

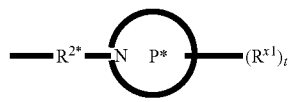

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ig:

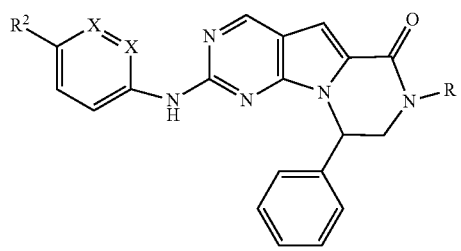

In some embodiments, the CDK4/6 inhibitor used has Formula Ig and $R^2$ is

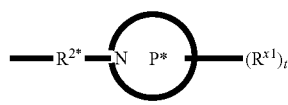

wherein P* is a 4- to 8-membered mono- or bicyclic saturated heterocyclyl group and $R^{2*}$, $R^{x1}$ and t are as previously defined.

In some embodiments, the CDK4/6 inhibitor used has Formula Ig and $R^2$ is

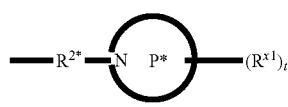

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the CDK4/6 inhibitor used has Formula Ih:

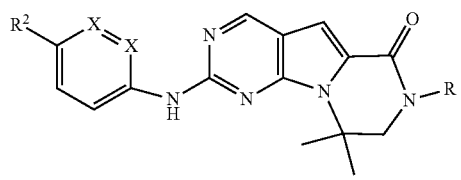

In some embodiments, the CDK4/6 inhibitor used has Formula Ih and $R^2$ is

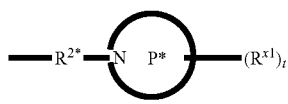

wherein P* is a 4- to 8-membered mono- or bicyclic saturated heterocyclyl group and $R^{2*}$, $R^{x1}$ and t are as previously defined.

In some embodiments, the CDK4/6 inhibitor used has Formula Ih and $R^2$ is

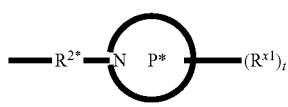

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the CDK4/6 inhibitor used has Formula Ii:

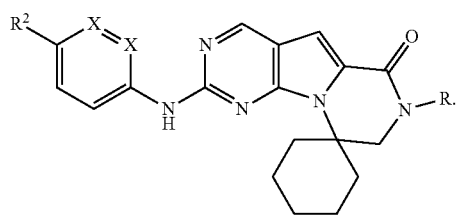

In some embodiments, the CDK4/6 inhibitor used has Formula Ii and $R^2$ is

wherein P* is a 4- to 8-membered mono- or bicyclic saturated heterocyclyl group and $R^{2*}$, $R^{x1}$ and t are as previously defined.

In some embodiments, the CDK4/6 inhibitor used has Formula Ii and $R^2$ is

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the CDK4/6 inhibitor used has Formula Ij:

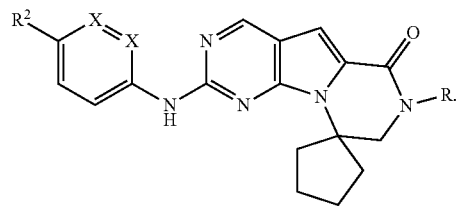

In some embodiments, the CDK4/6 inhibitor used has Formula Ij and $R^2$ is

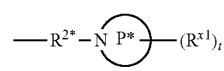

wherein P* is a 4- to 8-membered mono- or bicyclic saturated heterocyclyl group.

In some embodiments, the CDK4/6 inhibitor used has Formula Ij and $R^2$ is

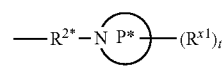

wherein P* is a 4- to 8-membered mono- or bicyclic saturated heterocyclyl group, $R^{x1}$ is hydrogen or $C_1$-$C_4$ alkyl.

In some embodiments, R is hydrogen in Formula Ia, Formula Ib, Formula Ic, Formula Id, Formula Ie, Formula If, Formula Ig, Formula Ih, Formula Ii, and Formula Ij.

In some embodiments, R is alkyl in Formula Ia, Formula Ib, Formula Ic, Formula Id, Formula Ie, Formula If, Formula Ig, Formula Ih, Formula Ii, and Formula Ij.

In some embodiments, the CDK4/6 inhibitor used has Formula Ij and R is H, and both X are N.

In some embodiments, the CDK4/6 inhibitor used has the structure:

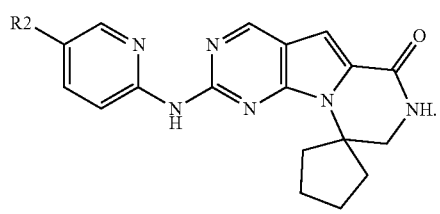

In some embodiments, the CDK4/6 inhibitor used has Formula Ik and $R^2$ is

wherein P* is a 4- to 8-membered mono- or bicyclic saturated heterocyclyl group.

In some embodiments, the CDK4/6 inhibitor used has Formula Ik and $R^2$ is

wherein P* is a 4- to 8-membered mono- or bicyclic saturated heterocyclyl group, $R^{x1}$ is hydrogen or $C_1$-$C_4$ alkyl.

In some embodiments, the CDK4/6 inhibitor used has Formula Il:

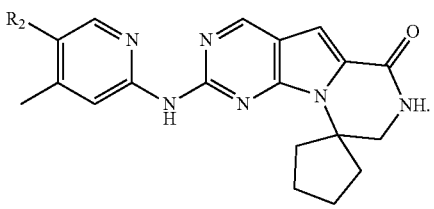

In some embodiments, the CDK4/6 inhibitor used has Formula Il and $R^2$ is

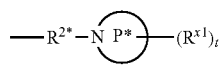

wherein P* is a 4- to 8-membered mono- or bicyclic saturated heterocyclyl group.

In some embodiments, the CDK4/6 inhibitor used has Formula Il and $R^2$ is

wherein P* is a 4- to 8-membered mono- or bicyclic saturated heterocyclyl group, $R^{x1}$ is hydrogen or $C_1$-$C_4$ alkyl.

In some embodiments the CDK4/6 inhibitor used has Formula Im:

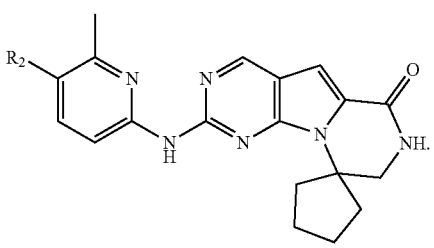

In some embodiments, the CDK4/6 inhibitor used has Formula Im and $R^2$ is

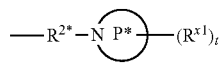

wherein P* is a 4- to 8-membered mono- or bicyclic saturated heterocyclyl group.

In some embodiments, the CDK4/6 inhibitor used has Formula Im and $R^2$ is

wherein P* is a 4- to 8-membered mono- or bicyclic saturated heterocyclyl group, $R^{x1}$ is hydrogen or $C_1$-$C_4$ alkyl.

In some embodiments, the CDK4/6 inhibitor used has Formula IIa:

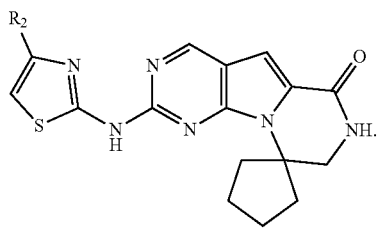

In some embodiments, the CDK4/6 inhibitor used has Formula IIa and $R^2$ is

wherein P* is a 4- to 8-membered mono- or bicyclic saturated heterocyclyl group.

In some embodiments, the CDK4/6 inhibitor used has Formula IIa and $R^2$ is

wherein P* is a 4- to 8-membered mono- or bicyclic saturated heterocyclyl group, $R^{x1}$ is hydrogen or $C_1$-$C_4$ alkyl.

In some embodiments, the CDK4/6 inhibitor used has Formula IIb:

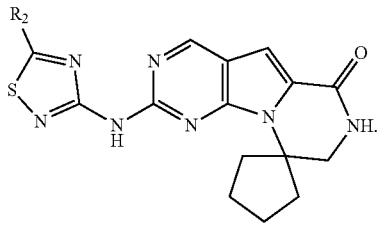

In some embodiments, the CDK4/6 inhibitor used has Formula Im and $R^2$ is

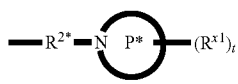

wherein P* is a 4- to 8-membered mono- or bicyclic saturated heterocyclyl group.

In some embodiments, the CDK4/6 inhibitor used has Formula Im and $R^2$ is

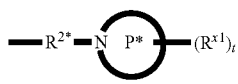

wherein P* is a 4- to 8-membered mono- or bicyclic saturated heterocyclyl group, $R^{x1}$ is hydrogen or $C_1$-$C_4$ alkyl.

In some aspects, the CDK4/6 inhibitor used is:

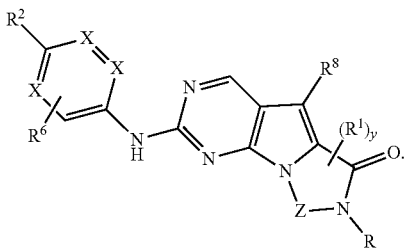

Further specific CDK4/6 inhibitor compounds that can be used in combination with topoisomerase inhibitors and can be used in the disclosed methods of treatment and compositions include the structures listed in Table 1 below.

TABLE 1

Nonlimiting Examples of Compounds of Formula I, II, III, IV, or V

| Structure Reference | Structure |
|---|---|
| A | 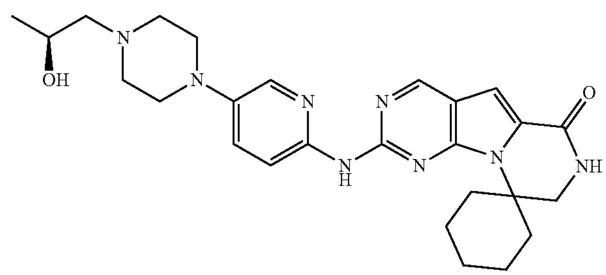 [SMILES: C[C@H](O)CN1CCN(c2ccc(Nc3ncc4cc5n(c4n3)C3(CCCCC3)CNC5=O)nc2)CC1] |
| B | 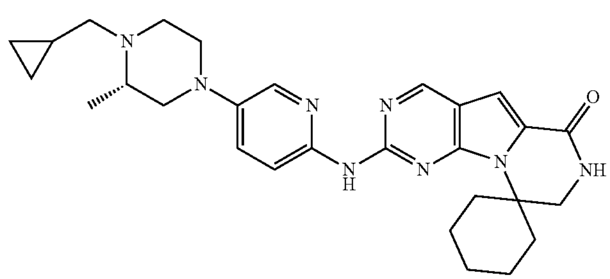 [SMILES: C[C@H]1CN(c2ccc(Nc3ncc4cc5n(c4n3)C3(CCCCC3)CNC5=O)nc2)CCN1CC1CC1] |
| C | 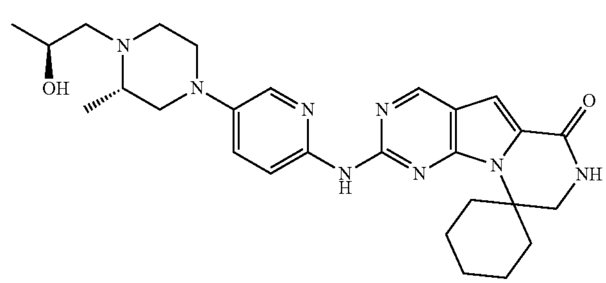 [SMILES: C[C@H](O)CN1CCN(c2ccc(Nc3ncc4cc5n(c4n3)C3(CCCCC3)CNC5=O)nc2)C[C@@H]1C] |

TABLE 1-continued
Nonlimiting Examples of Compounds of Formula I, II, III, IV, or V
| Structure Reference | Structure |
|---|---|
| D | 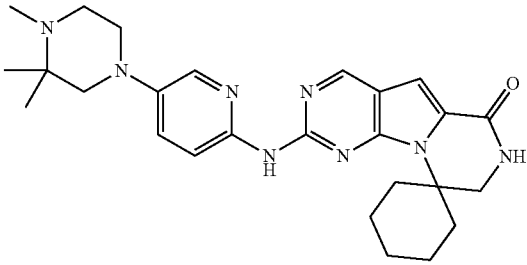 [SMILES: CN1CCN(c2ccc(Nc3ncc4cc5n(c4n3)C3(CCCCC3)CNC5=O)nc2)CC1(C)C] |
| E | 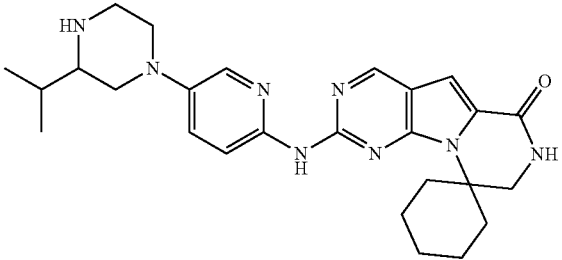 [SMILES: CC(C)C1CN(c2ccc(Nc3ncc4cc5n(c4n3)C3(CCCCC3)CNC5=O)nc2)CCN1] |
| F | 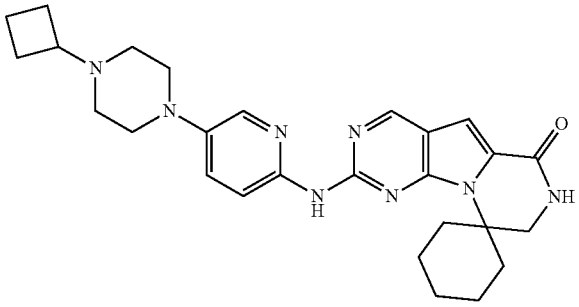 [SMILES: O=C1NCC2(CCCCC2)n2c1cc1cnc(Nc3ccc(N4CCN(C5CCC5)CC4)cn3)nc12] |
| G | 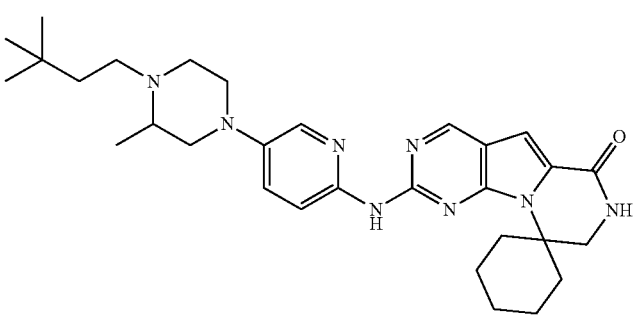 [SMILES: CC1CN(c2ccc(Nc3ncc4cc5n(c4n3)C3(CCCCC3)CNC5=O)nc2)CCN1CCC(C)(C)C] |
| H | 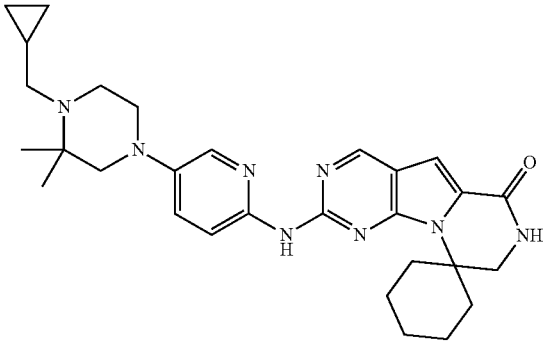 [SMILES: CC1(C)CN(c2ccc(Nc3ncc4cc5n(c4n3)C3(CCCCC3)CNC5=O)nc2)CCN1CC1CC1] |

TABLE 1-continued
Nonlimiting Examples of Compounds of Formula I, II, III, IV, or V
| Structure Reference | Structure |
|---|---|
| I | 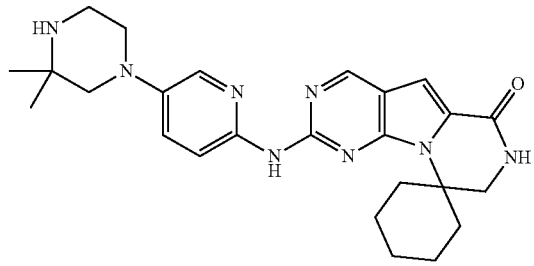 [SMILES: CC1(C)CN(c2ccc(Nc3ncc4cc5n(c4n3)C3(CCCCC3)CNC5=O)nc2)CCN1] |
| J | 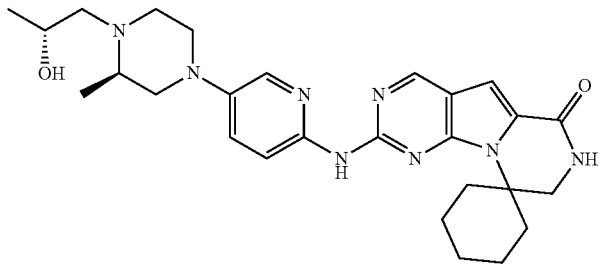 [SMILES: C[C@@H]1CN(c2ccc(Nc3ncc4cc5n(c4n3)C3(CCCCC3)CNC5=O)nc2)CCN1C[C@@H](C)O] |
| K | 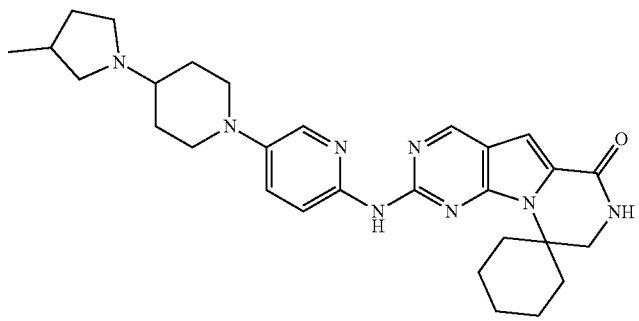 [SMILES: CC1CCN(C2CCN(c3ccc(Nc4ncc5cc6n(c5n4)C4(CCCCC4)CNC6=O)nc3)CC2)C1] |
| L | 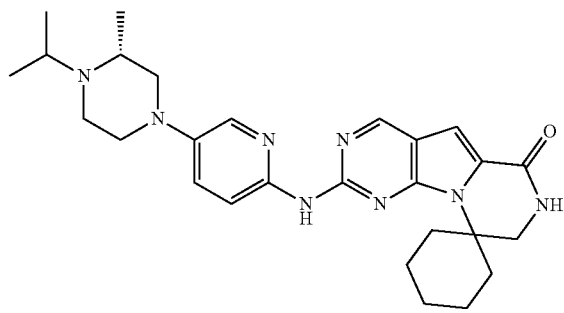 [SMILES: CC(C)N1CCN(c2ccc(Nc3ncc4cc5n(c4n3)C3(CCCCC3)CNC5=O)nc2)C[C@H]1C] |
| M | 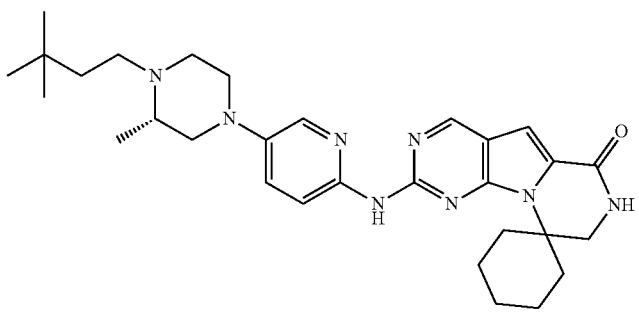 [SMILES: C[C@H]1CN(c2ccc(Nc3ncc4cc5n(c4n3)C3(CCCCC3)CNC5=O)nc2)CCN1CCC(C)(C)C] |

TABLE 1-continued
Nonlimiting Examples of Compounds of Formula I, II, III, IV, or V
| Structure Reference | Structure |
|---|---|
| N | 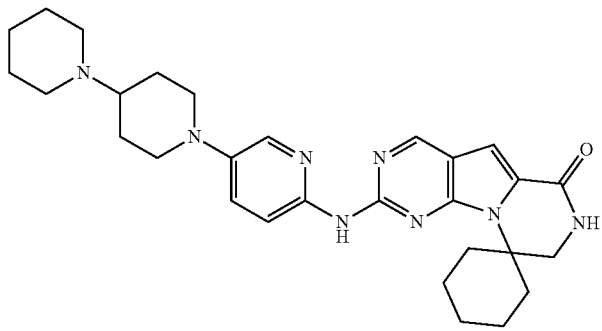 [SMILES: O=C1NCC2(CCCCC2)n2c1cc1cnc(Nc3ccc(N4CCC(N5CCCCC5)CC4)cn3)nc12] |
| O | 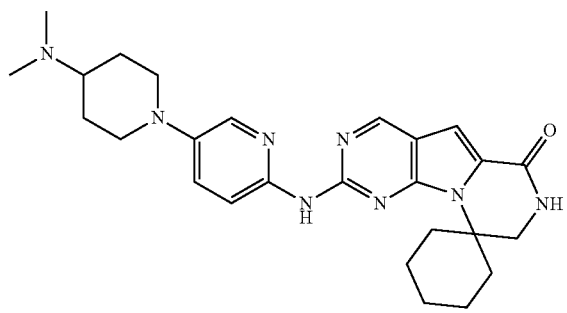 [SMILES: CN(C)C1CCN(c2ccc(Nc3ncc4cc5n(c4n3)C3(CCCCC3)CNC5=O)nc2)CC1] |
| P | 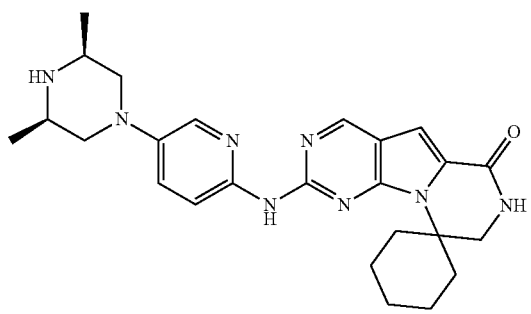 [SMILES: C[C@@H]1CN(c2ccc(Nc3ncc4cc5n(c4n3)C3(CCCCC3)CNC5=O)nc2)C[C@H](C)N1] |
| Q | 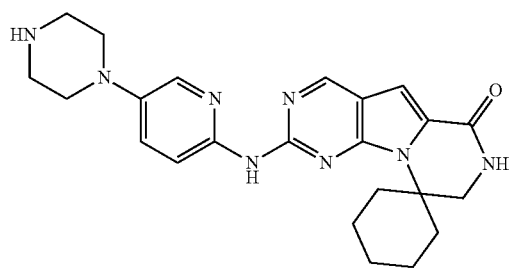 [SMILES: O=C1NCC2(CCCCC2)n2c1cc1cnc(Nc3ccc(N4CCNCC4)cn3)nc12] |
| R | 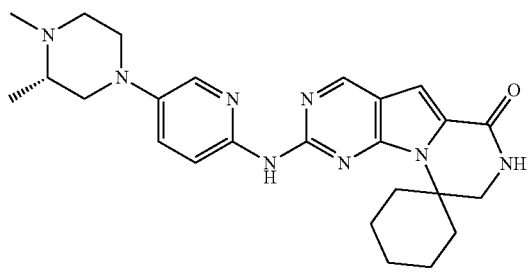 |

TABLE 1-continued
Nonlimiting Examples of Compounds of Formula I, II, III, IV, or V
| Structure Reference | Structure |
|---|---|
| S | 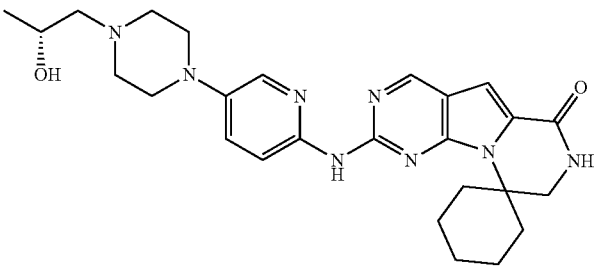 [SMILES: C[C@@H](O)CN1CCN(c2ccc(Nc3ncc4cc5n(c4n3)C3(CCCCC3)CNC5=O)nc2)CC1] |
| T | 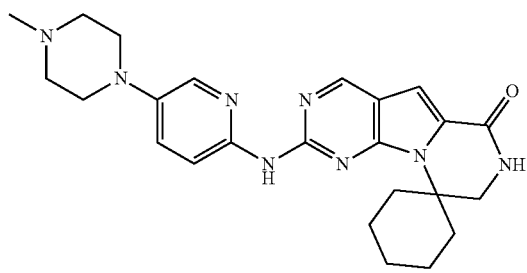 [SMILES: CN1CCN(c2ccc(Nc3ncc4cc5n(c4n3)C3(CCCCC3)CNC5=O)nc2)CC1] |
| U | 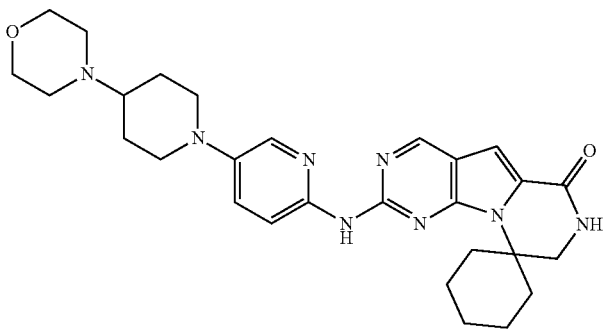 [SMILES: O=C1NCC2(CCCCC2)n2c1cc1cnc(Nc3ccc(N4CCC(N5CCOCC5)CC4)cn3)nc12] |
| V | 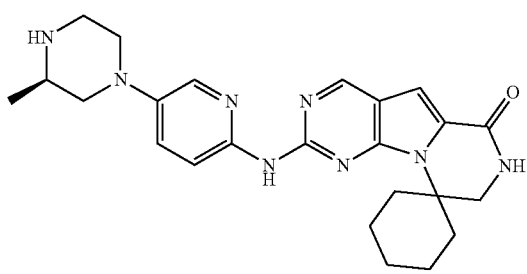 [SMILES: C[C@@H]1CN(c2ccc(Nc3ncc4cc5n(c4n3)C3(CCCCC3)CNC5=O)nc2)CCN1] |
| W | 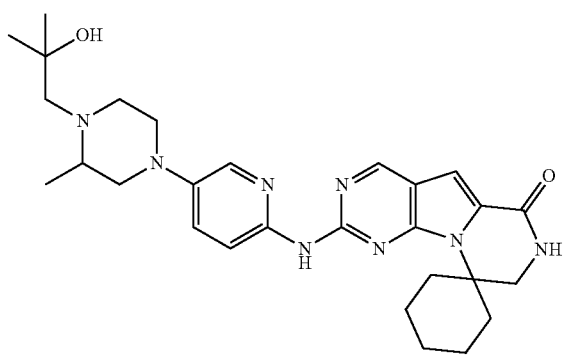 [SMILES: CC1CN(c2ccc(Nc3ncc4cc5n(c4n3)C3(CCCCC3)CNC5=O)nc2)CCN1CC(C)(C)O] |

TABLE 1-continued
Nonlimiting Examples of Compounds of Formula I, II, III, IV, or V
| Structure Reference | Structure |
|---|---|
| X | 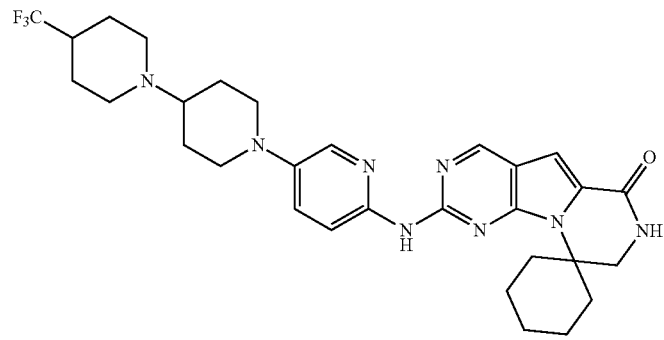 [SMILES: O=C1NCC2(CCCCC2)n2c1cc1cnc(Nc3ccc(N4CCC(N5CCC(C(F)(F)F)CC5)CC4)cn3)nc12] |
| Y | 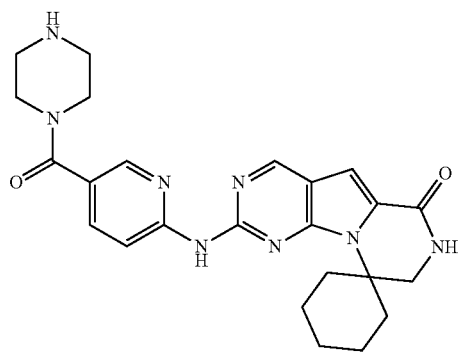 [SMILES: O=C1NCC2(CCCCC2)n2c1cc1cnc(Nc3ccc(C(=O)N4CCNCC4)cn3)nc12] |
| Z | 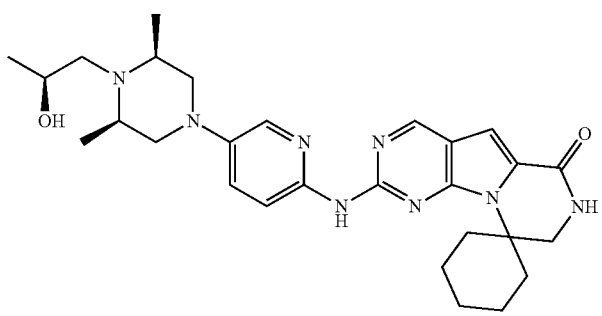 [SMILES: C[C@H](O)CN1[C@H](C)CN(c2ccc(Nc3ncc4cc5n(c4n3)C3(CCCCC3)CNC5=O)nc2)C[C@@H]1C] |
| AA | 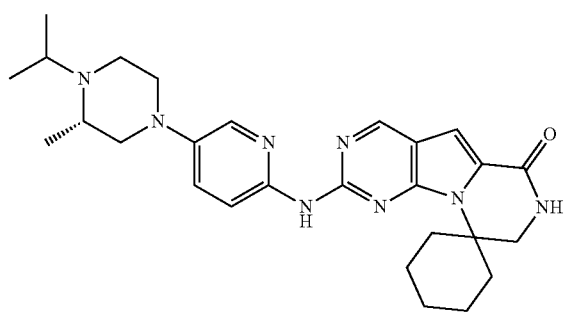 [SMILES: CC(C)N1CCN(c2ccc(Nc3ncc4cc5n(c4n3)C3(CCCCC3)CNC5=O)nc2)C[C@@H]1C] |

TABLE 1-continued
Nonlimiting Examples of Compounds of Formula I, II, III, IV, or V
| Structure Reference | Structure |
| --- | --- |
| BB | 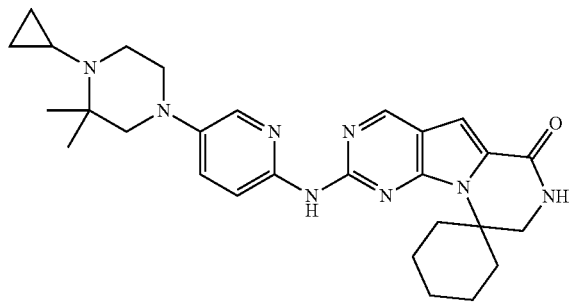 [SMILES: CC1(C)CN(c2ccc(Nc3ncc4cc5n(c4n3)C3(CCCCC3)CNC5=O)nc2)CCN1C1CC1] |
| CC | 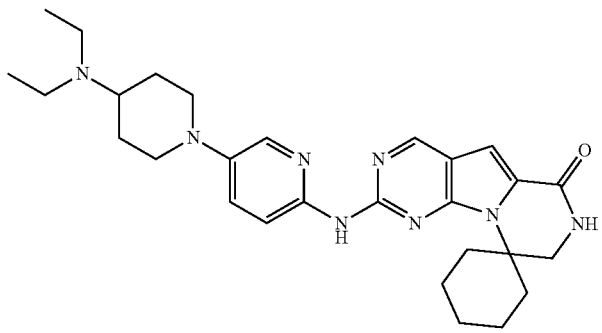 [SMILES: CCN(CC)C1CCN(c2ccc(Nc3ncc4cc5n(c4n3)C3(CCCCC3)CNC5=O)nc2)CC1] |
| DD | 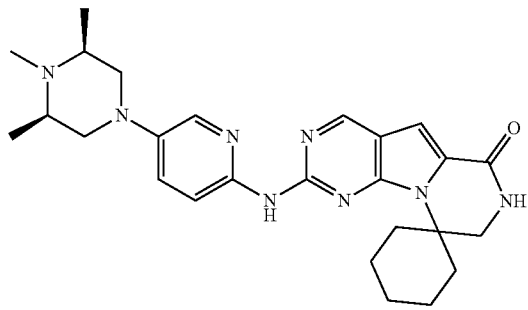 [SMILES: C[C@@H]1CN(c2ccc(Nc3ncc4cc5n(c4n3)C3(CCCCC3)CNC5=O)nc2)C[C@H](C)N1C] |
| EE | 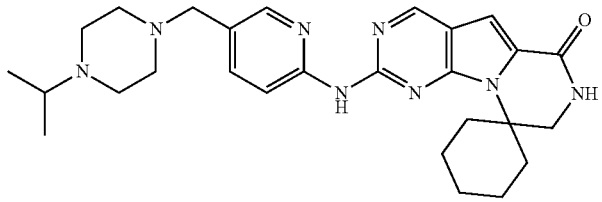 [SMILES: CC(C)N1CCN(Cc2ccc(Nc3ncc4cc5n(c4n3)C3(CCCCC3)CNC5=O)nc2)CC1] |
| FF | 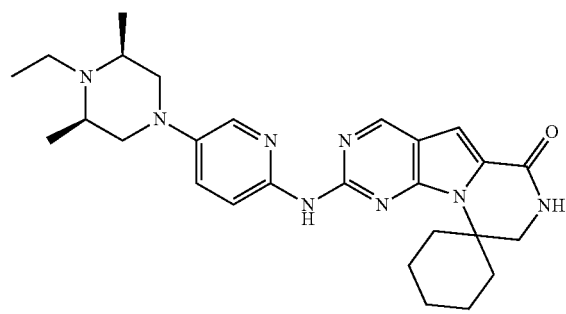 [SMILES: CCN1[C@H](C)CN(c2ccc(Nc3ncc4cc5n(c4n3)C3(CCCCC3)CNC5=O)nc2)C[C@@H]1C] |

TABLE 1-continued
Nonlimiting Examples of Compounds of Formula I, II, III, IV, or V
| Structure Reference | Structure |
|---|---|
| GG | 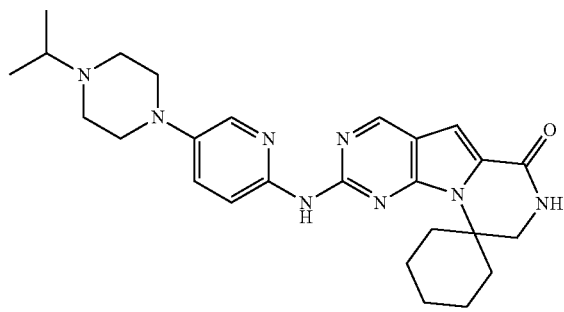 [SMILES: CC(C)N1CCN(c2ccc(Nc3ncc4cc5n(c4n3)C3(CCCCC3)CNC5=O)nc2)CC1] |
| HH | 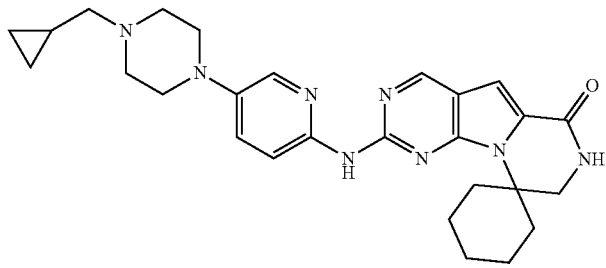 [SMILES: O=C1NCC2(CCCCC2)n2c1cc1cnc(Nc3ccc(N4CCN(CC5CC5)CC4)cn3)nc12] |
| II | 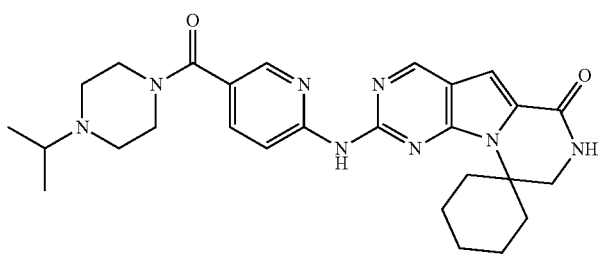 [SMILES: CC(C)N1CCN(C(=O)c2ccc(Nc3ncc4cc5n(c4n3)C3(CCCCC3)CNC5=O)nc2)CC1] |
| JJ | 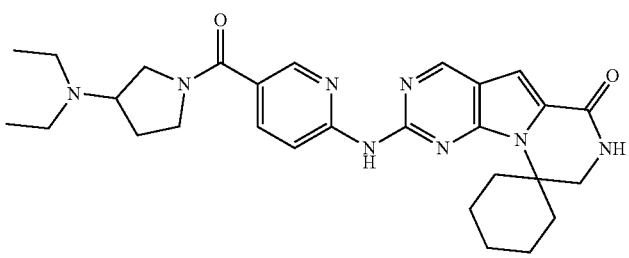 [SMILES: CCN(CC)C1CCN(C(=O)c2ccc(Nc3ncc4cc5n(c4n3)C3(CCCCC3)CNC5=O)nc2)C1] |
| KK | 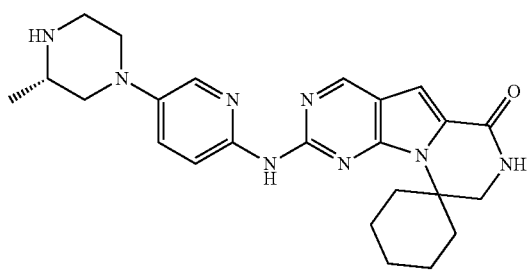 [SMILES: C[C@H]1CN(c2ccc(Nc3ncc4cc5n(c4n3)C3(CCCCC3)CNC5=O)nc2)CCN1] |

TABLE 1-continued
Nonlimiting Examples of Compounds of Formula I, II, III, IV, or V
| Structure Reference | Structure |
|---|---|
| LL | 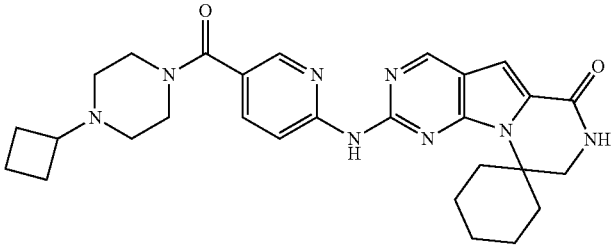 [SMILES: O=C1NCC2(CCCCC2)n2c1cc1cnc(Nc3ccc(C(=O)N4CCN(C5CCC5)CC4)cn3)nc12] |
| MM | 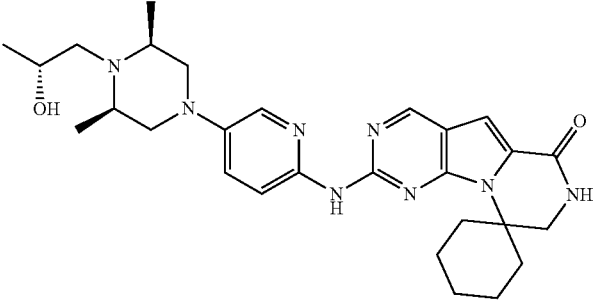 [SMILES: C[C@@H]1CN(c2ccc(Nc3ncc4cc5n(c4n3)C3(CCCCC3)CNC5=O)nc2)C[C@H](C)N1C[C@@H](C)O] |
| NN | 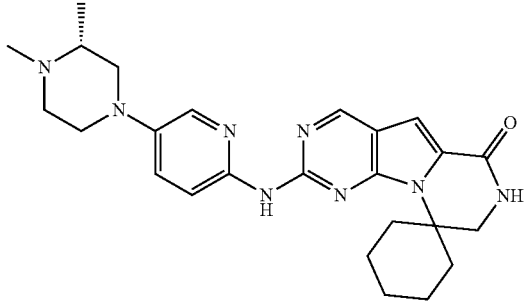 [SMILES: C[C@@H]1CN(c2ccc(Nc3ncc4cc5n(c4n3)C3(CCCCC3)CNC5=O)nc2)CCN1C] |
| OO | 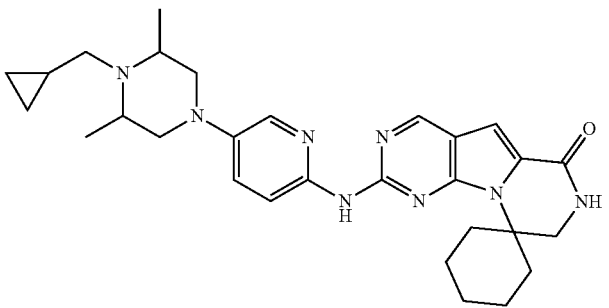 [SMILES: CC1CN(c2ccc(Nc3ncc4cc5n(c4n3)C3(CCCCC3)CNC5=O)nc2)CC(C)N1CC1CC1] |
| PP | 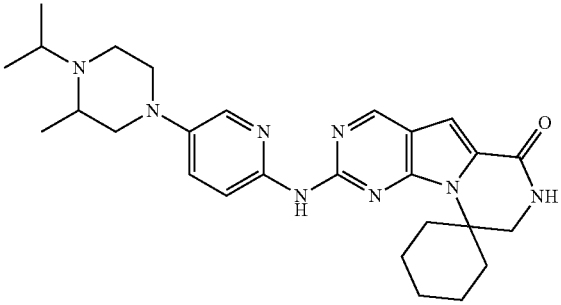 [SMILES: CC(C)N1CCN(c2ccc(Nc3ncc4cc5n(c4n3)C3(CCCCC3)CNC5=O)nc2)CC1C] |

TABLE 1-continued

Nonlimiting Examples of Compounds of Formula I, II, III, IV, or V

| Structure Reference | Structure |
|---|---|
| QQ | 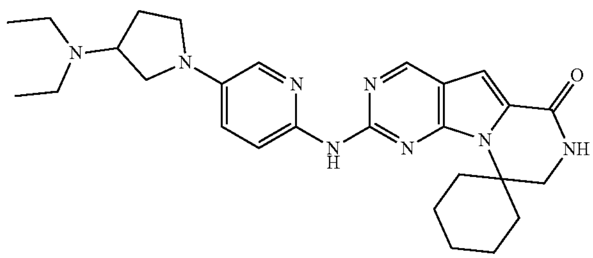 [SMILES: CCN(CC)C1CCN(c2ccc(Nc3ncc4cc5n(c4n3)C3(CCCCC3)CNC5=O)nc2)C1] |
| RR | 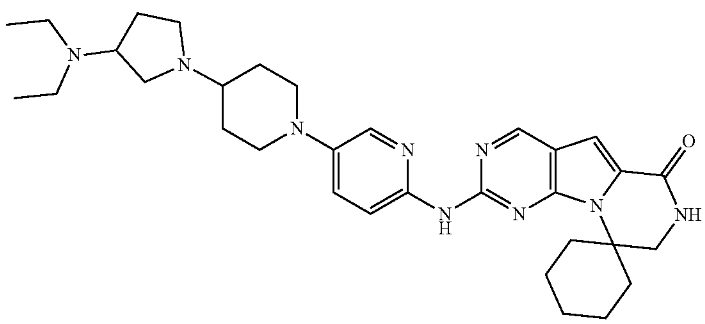 |
| SS | 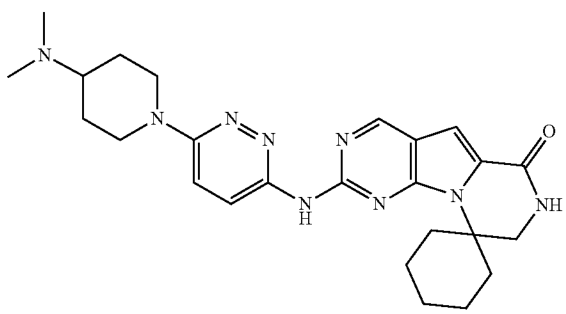 [SMILES: CN(C)C1CCN(c2ccc(Nc3ncc4cc5n(c4n3)C3(CCCCC3)CNC5=O)nn2)CC1] |
| TT | 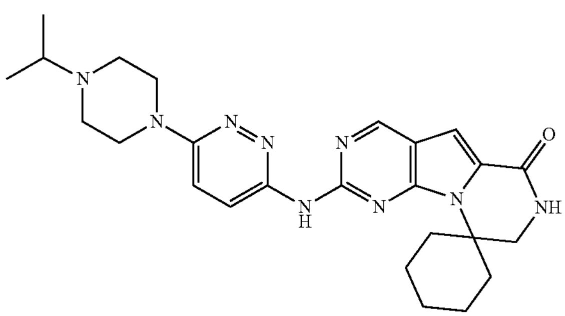 [SMILES: CC(C)N1CCN(c2ccc(Nc3ncc4cc5n(c4n3)C3(CCCCC3)CNC5=O)nn2)CC1] |
| UU | 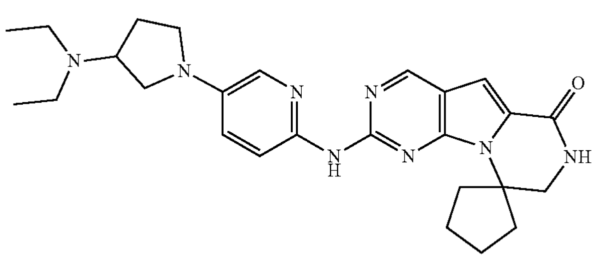 [SMILES: CCN(CC)C1CCN(c2ccc(Nc3ncc4cc5n(c4n3)C3(CCCC3)CNC5=O)nc2)C1] |

TABLE 1-continued
Nonlimiting Examples of Compounds of Formula I, II, III, IV, or V
| Structure Reference | Structure |
|---|---|
| VV | 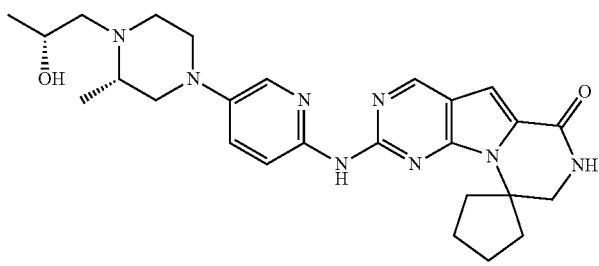 [SMILES: C[C@@H](O)CN1CCN(c2ccc(Nc3ncc4cc5n(c4n3)C3(CCCC3)CNC5=O)nc2)C[C@@H]1C] |
| WW | 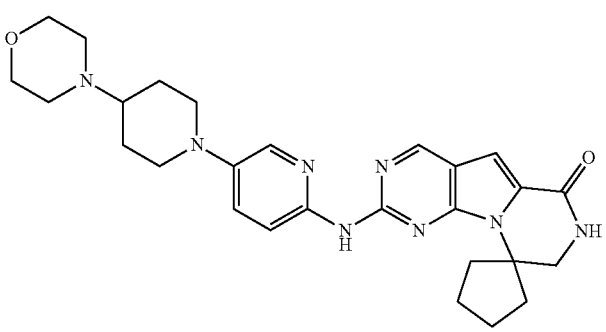 [SMILES: O=C1NCC2(CCCC2)n2c1cc1cnc(Nc3ccc(N4CCC(N5CCOCC5)CC4)cn3)nc12] |
| XX | 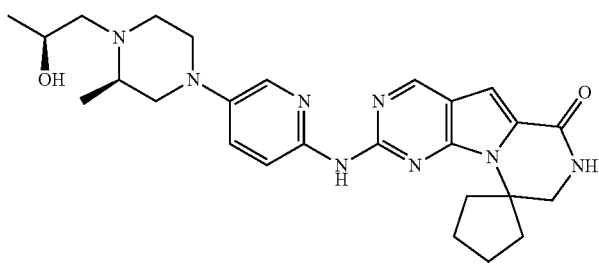 [SMILES: C[C@H](O)CN1CCN(c2ccc(Nc3ncc4cc5n(c4n3)C3(CCCC3)CNC5=O)nc2)C[C@H]1C] |
| YY | 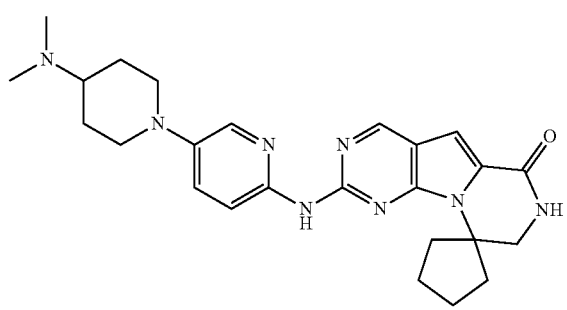 |
| ZZ | 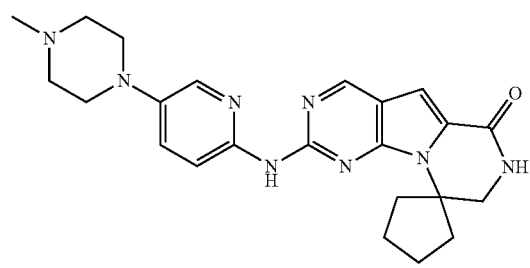 [SMILES: CN1CCN(c2ccc(Nc3ncc4cc5n(c4n3)C3(CCCC3)CNC5=O)nc2)CC1] |

TABLE 1-continued

Nonlimiting Examples of Compounds of Formula I, II, III, IV, or V

| Structure Reference | Structure |
|---|---|
| AAA | 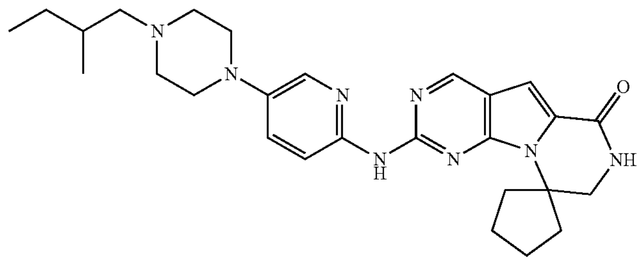 [SMILES: CCC(C)CN1CCN(c2ccc(Nc3ncc4cc5n(c4n3)C3(CCCC3)CNC5=O)nc2)CC1] |
| BBB | 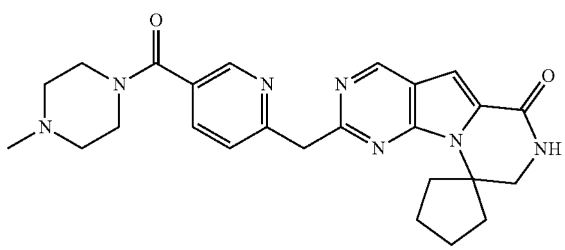 [SMILES: CN1CCN(C(=O)c2ccc(Cc3ncc4cc5n(c4n3)C3(CCCC3)CNC5=O)nc2)CC1] |
| CCC | 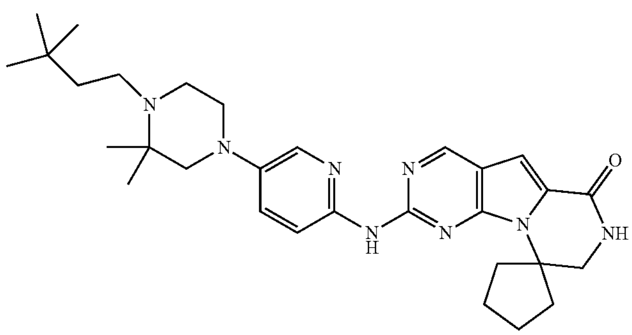 [SMILES: CC(C)(C)CCN1CCN(c2ccc(Nc3ncc4cc5n(c4n3)C3(CCCC3)CNC5=O)nc2)CC1(C)C] |
| DDD | 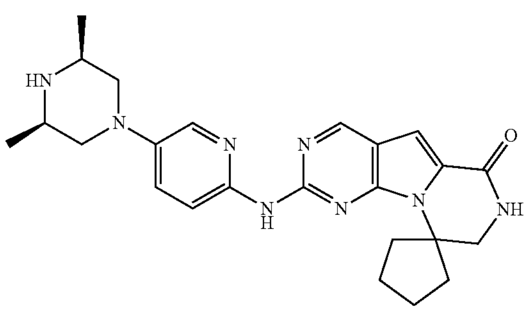 [SMILES: C[C@@H]1CN(c2ccc(Nc3ncc4cc5n(c4n3)C3(CCCC3)CNC5=O)nc2)C[C@H](C)N1] |
| EEE | 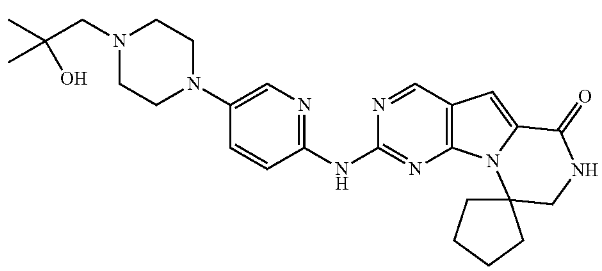 [SMILES: CC(C)(O)CN1CCN(c2ccc(Nc3ncc4cc5n(c4n3)C3(CCCC3)CNC5=O)nc2)CC1] |

TABLE 1-continued
Nonlimiting Examples of Compounds of Formula I, II, III, IV, or V
| Structure Reference | Structure |
|---|---|
| FFF | 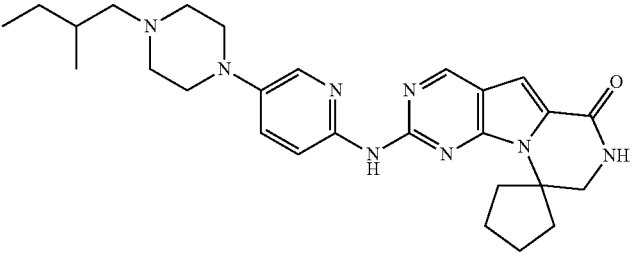 [SMILES: CCC(C)CN1CCN(c2ccc(Nc3ncc4cc5n(c4n3)C3(CCCC3)CNC5=O)nc2)CC1] |
| GGG | 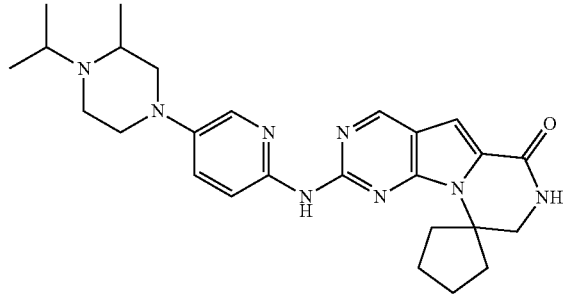 [SMILES: CC(C)N1CCN(c2ccc(Nc3ncc4cc5n(c4n3)C3(CCCC3)CNC5=O)nc2)CC1C] |
| HHH | 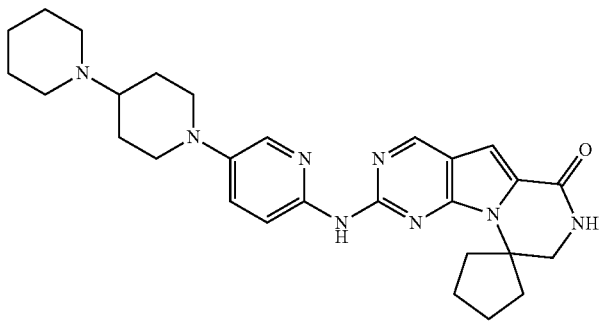 [SMILES: O=C1NCC2(CCCC2)n2c1cc1cnc(Nc3ccc(N4CCC(N5CCCCC5)CC4)cn3)nc12] |
| III | 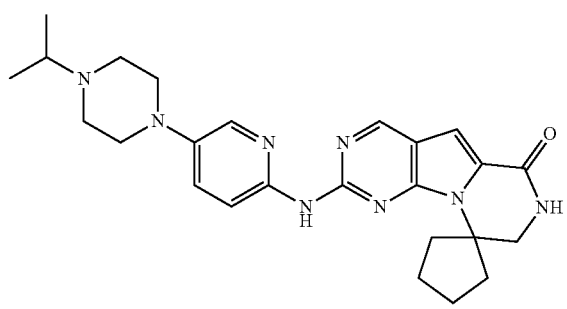 [SMILES: CC(C)N1CCN(c2ccc(Nc3ncc4cc5n(c4n3)C3(CCCC3)CNC5=O)nc2)CC1] |
| JJJ | 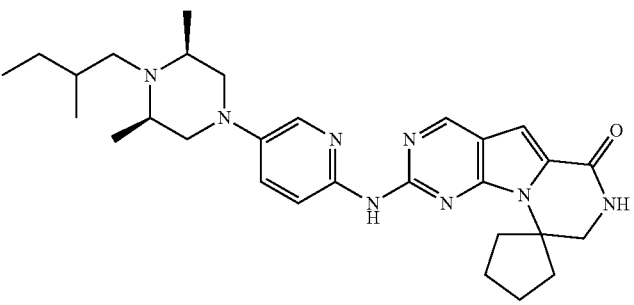 [SMILES: CCC(C)CN1[C@H](C)CN(c2ccc(Nc3ncc4cc5n(c4n3)C3(CCCC3)CNC5=O)nc2)C[C@@H]1C] |

TABLE 1-continued
Nonlimiting Examples of Compounds of Formula I, II, III, IV, or V
| Structure Reference | Structure |
|---|---|
| KKK | 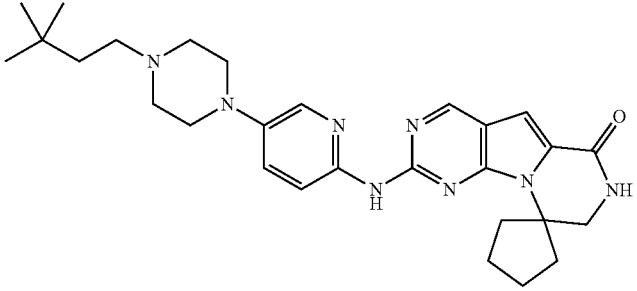 [SMILES: CC(C)(C)CCN1CCN(c2ccc(Nc3ncc4cc5n(c4n3)C3(CCCC3)CNC5=O)nc2)CC1] |
| LLL | 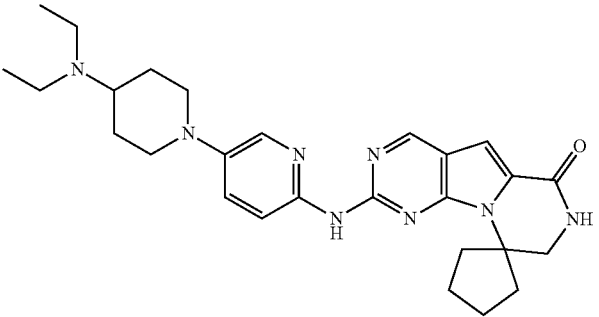 [SMILES: CCN(CC)C1CCN(c2ccc(Nc3ncc4cc5n(c4n3)C3(CCCC3)CNC5=O)nc2)CC1] |
| MMM | 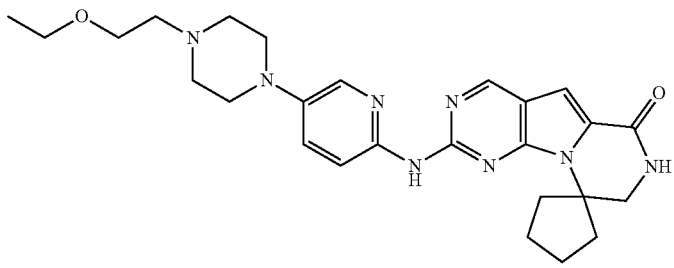 [SMILES: CCOCCN1CCN(c2ccc(Nc3ncc4cc5n(c4n3)C3(CCCC3)CNC5=O)nc2)CC1] |
| NNN | 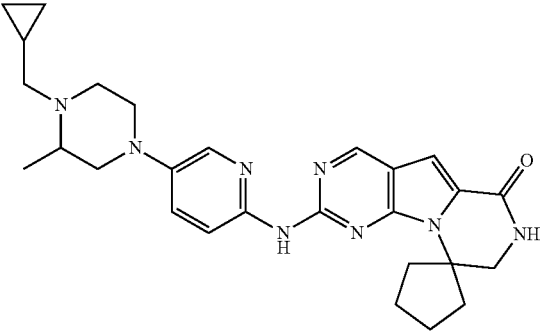 [SMILES: CC1CN(c2ccc(Nc3ncc4cc5n(c4n3)C3(CCCC3)CNC5=O)nc2)CCN1CC1CC1] |
| OOO | 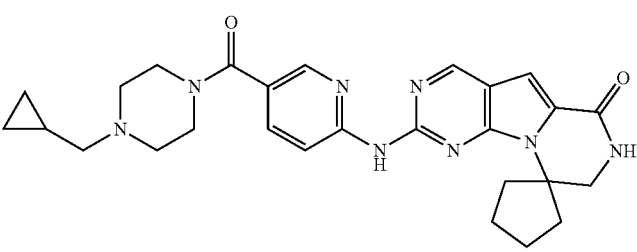 [SMILES: O=C1NCC2(CCCC2)n2c1cc1cnc(Nc3ccc(C(=O)N4CCN(CC5CC5)CC4)cn3)nc12] |

TABLE 1-continued
Nonlimiting Examples of Compounds of Formula I, II, III, IV, or V
| Structure Reference | Structure |
|---|---|
| PPP | 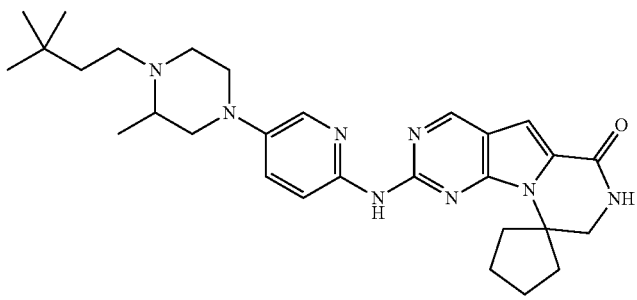 [SMILES: CC1CN(c2ccc(Nc3ncc4cc5n(c4n3)C3(CCCC3)CNC5=O)nc2)CCN1CCC(C)(C)C] |
| QQQ | 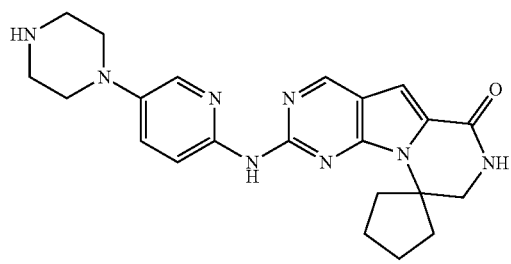 [SMILES: O=C1NCC2(CCCC2)n2c1cc1cnc(Nc3ccc(N4CCNCC4)cn3)nc12] |
| RRR | 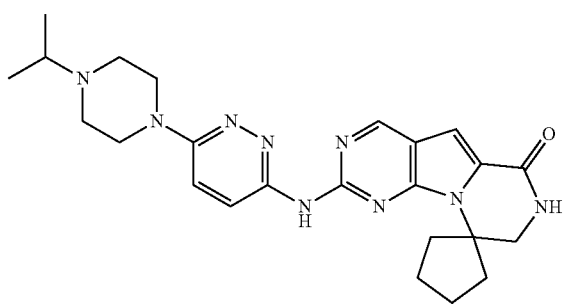 |
| SSS | 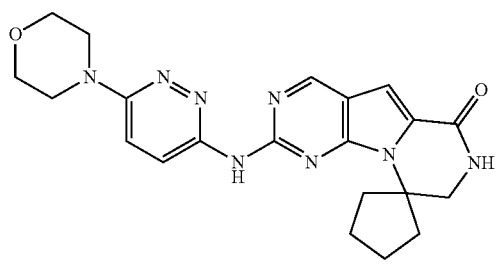 [SMILES: O=C1NCC2(CCCC2)n2c1cc1cnc(Nc3ccc(N4CCOCC4)nn3)nc12] |
| TTT | 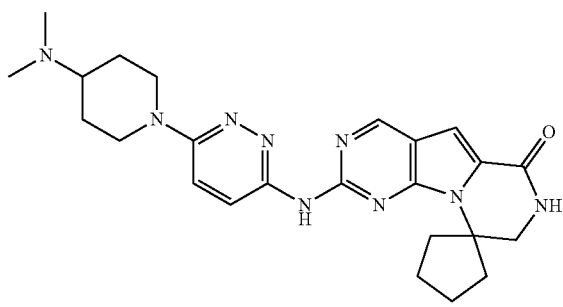 [SMILES: CN(C)C1CCN(c2ccc(Nc3ncc4cc5n(c4n3)C3(CCCC3)CNC5=O)nn2)CC1] |

TABLE 1-continued

Nonlimiting Examples of Compounds of Formula I, II, III, IV, or V

| Structure Reference | Structure |
|---|---|
| UUU | 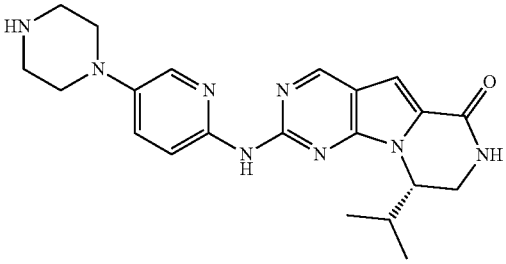 [SMILES: CC(C)[C@H]1CNC(=O)c2cc3cnc(Nc4ccc(N5CCNCC5)cn4)nc3n21] |
| VVV | 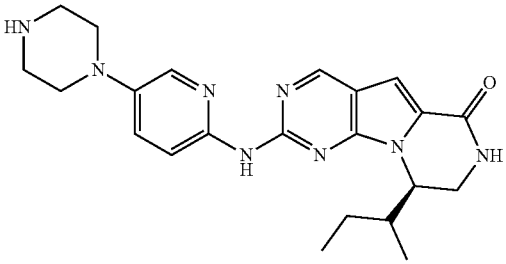 [SMILES: CCC(C)[C@@H]1CNC(=O)c2cc3cnc(Nc4ccc(N5CCNCC5)cn4)nc3n21] |
| WWW | 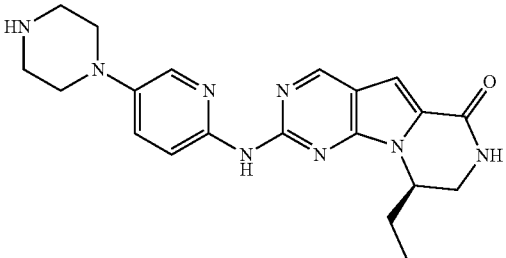 |
| XXX | 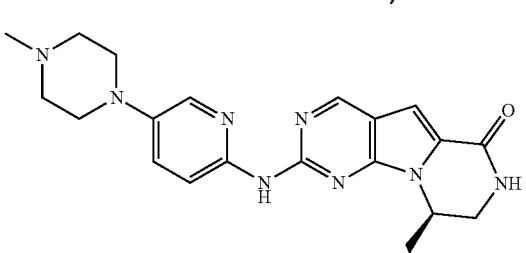 |

The CDK4/6 inhibitors for use in the described methods are highly selective, potent CDK4/6 inhibitors, with minimal CDK2 inhibitory activity. In a range of embodiments, a compound for use in the methods described herein has a CDK4/CycD1 IC$_{50}$ inhibitory concentration value that is >1500 times, >1800 times, >2000 times, >2200 times, >2500 times, >2700 times, >3000 times, >3200 times or greater lower than its respective IC$_{50}$ concentration value for CDK2/CycE inhibition. In another range of embodiments, a compound for use in the methods described herein has an IC$_{50}$ concentration value for CDK4/CycD1 inhibition that is about <1.50 nM, <1.25 nM, <1.0 nM, <0.90 nM, <0.85 nM, <0.80 nM, <0.75 nM, <0.70 nM, <0.65 nM, <0.60 nM, <0.55 nM, or less. In yet a range of embodiments, a CDK4/6 inhibitor for use in the methods described herein has an IC$_{50}$ concentration value for CDK2/CycE inhibition that is about >1.0 μM, >1.25 μM, >1.50 μM, >1.75 μM, >2.0 μM, >2.25 μM, >2.50 μM, >2.75 μM, >3.0 μM, >3.25 μM, >3.5 μM or greater. In still other embodiments, a compound for use in the methods described herein has an IC$_{50}$ concentration value for CDK2/CycA IC$_{50}$ that is >0.80 μM, >0.85 μM, >0.90 μM, >0.95 μM, >0.1.0 μM, >1.25 μM, >1.50 μM, >1.75 μM, >2.0 μM, >2.25 μM, >2.50 μM, >2.75 μM, >3.0 μM or greater.

Additional CDK4/6 inhibitors that may be useful in certain combinations of the present invention include abemaciclib, palbociclib, and ribociclib. Abemaciclib (N-[5-[(4-ethylpiperazin-1-yl)methyl]pyridin-2-yl]-5-fluoro-4-(7- fluoro-2-methyl-3-propan-2-ylbenzimidazol-5-yl)
pyrimidin-2-amine) is described in U.S. Pat. No. 7,855,211
incorporated herein, and has the chemical structure:

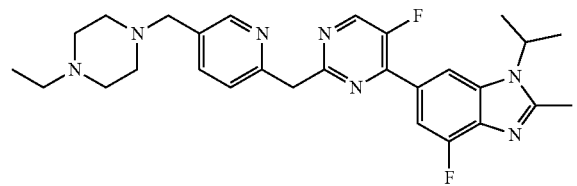

Palbociclib (6-Acetyl-8-cyclopentyl-5-methyl-2-{[5-(1-piperazinyl)-2-pyridinyl]amino}pyrido[2,3-d]pyrimidin-7 (8H)-one) is described in U.S. Pat. No. 7,208,489 incorporated herein, and has the chemical structure:

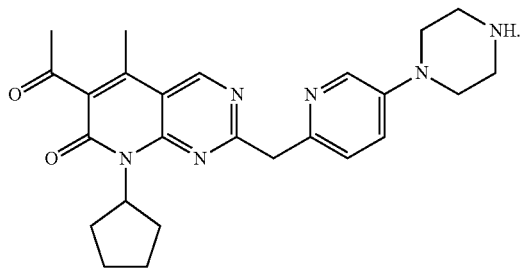 [SMILES: CC(=O)c1c(C)c2cnc(Cc3ccc(N4CCNCC4)cn3)nc2n(C2CCCC2)c1=O]

Ribociclib (7-cyclopentyl-N,N-dimethyl-2-[(5-piperazin-1-ylpyridin-2-yl)amino]pyrrolo[2,3-d]pyrimidine-6-carboxamide) is described in U.S. Pat. Application No. 2010/0105653 incorporated herein, and has the chemical structure:

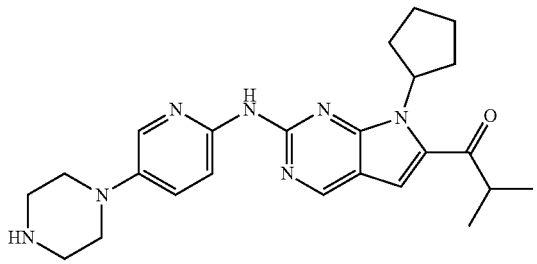

Topoisomerase I Inhibitors

DNA is normally a coiled double helix of two strands and is periodically uncoiled in the process of replication during cell division or in the process of reading the code to make protein. Two enzymes that play a role in this uncoiling and recoiling process are topoisomerase I and topoisomerase II. They also play a significant role in fixing DNA damage that occurs as a result of exposure to DNA damaging agents, for example, radiation exposure or chemotherapeutics.

Topoisomerase I attaches to DNA and breaks one strand of the double helix that can rotate around its own axis to revert supercoiling. Topoisomerase II binds to a DNA double strand and makes a gate allowing a second DNA double helix pass.

Topoisomerase I inhibitors target the enzyme topoisomerase I (Top1) by trapping the catalytic intermediate of the Top1-DNA reaction, the cleavage complex. Topoisomerase I inhibitors, such as camptothecin, form a ternary complex, since they can trap the enzyme and DNA together Many topoisomerase inhibitors are natural products extracted from plants, such as camptothecin, isolated from *Camptotheca accuminata*, and several alkaloids, such as evodiamine, isolated from *Evodia rutaecarpa*. Topotecan and irinotecan are camptothecin derivatives that have been used for ovarian and colorectal cancer treatments, respectively. These inhibitors target topo I and bind to DNA, forming a cleavable complex. The collision between this ternary complex and a replication fork generates DNA double-strand breaks, which may be related to the S-phase cytotoxicity, the G2/M cell cycle arrest and DNA damage that activates repair proteins.

In one aspect, an advantageous treatment of select Rb-negative cancers is disclosed using specific CDK4/6 inhibitor compounds in combination with a topoisomerase inhibitor. In one embodiment, the topoisomerase inhibitor is a topoisomerase I inhibitor or a topoisomerase I and II dual inhibitor. In one embodiment, the topoisomerase inhibitor is a topoisomerase II inhibitor.

In one embodiment, the topoisomerase inhibitor is selected from a topoisomerase I inhibitor. Known topoisomerase I inhibitors useful in the present invention include (S)-10-[(dimethylamino)methyl]-4-ethyl-4,9-dihydroxy-1H-pyrano[3',4':6,7]indolizino[1,2-b]quinoline-3,14(4H, 12H)-dione monohydrochloride (topotecan), (S)-4-ethyl-4-hydroxy-1H-pyrano[3',4':6,7]indolizino[1,2-b]quinoline-3, 14-(4H, 12H)-dione (camptothecin), (1S,9S)-1-Amino-9-ethyl-5-fluoro-1,2,3,9,12,15-hexahydro-9-hydroxy-4-methyl-1 OH, 13H-benzo(de)pyrano(3',4':6,7)indolizino(1, 2-b)quinoline-10,13-dione (exatecan), (7-(4-methylpiperazinomethylene)-10,11-ethylenedioxy-20(S)-camptothecin (lurtotecan), or (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate (irinotecan), (R)-5-ethyl-9,10-difluoro-5-hydroxy-4,5-dihydrooxepino[3',4':6,7]indolizino[1,2-b] quinoline-3,15(1H, 13H)-dione (diflomotecan), (4S)-11-((E)-((1,1-Dimethylethoxy)imino)methyl)-4-ethyl-4-hydroxy-1,12-dihydro-14H-pyrano(3',4':6,7)indolizino(1,2-b)quinoline-3,14(4H)-dione (gimatecan), (S)-8-ethyl-8-hydroxy-15-((4-methylpiperazin-1-yl)methyl)-11,14-dihydro-2H-[1,4]dioxino[2,3-g]pyrano[3',4':6,7]indolizino [1,2-b]quinoline-9,12(3H,8H)-dione (lurtotecan), (4S)-4-Ethyl-4-hydroxy-11-[2-[(1-methylethyl)amino]ethyl]-1H-pyrano[3?,4?:6,7]indolizino[1,2-b]quinoline-3,14(4H, 12H)-dione (belotecan), 6-((1,3-dihydroxypropan-2-yl) amino)-2,10-dihydroxy-12-((2R,3R,4S,5S,6R)-3,4,5-trihydroxy-6-(hydroxymethyl)tetrahydro-2H-pyran-2-yl)-12,13-dihydro-5H-indolo[2,3-a]pyrrolo[3,4-c]carbazole-5,7(6H)-dione (edotecarin), 8,9-dimethoxy-5-(2-N,N-dimethylaminoethyl)-2,3-methylenedioxy-5H-dibenzo(c,h) (1,6)naphthyridin-6-one (topovale), benzo[6,7]indolizino[1, 2-b]quinolin-11(13H)-one (rosettacin), (S)-4-ethyl-4-hydroxy-11-(2-(trimethylsilyl)ethyl)-1H-pyrano[3',4':6,7] indolizino[1,2-b]quinoline-3,14(4H, 12H)-dione (cositecan), tetrakis{(4S)-9-[([1,4'-bipiperidinyl]-1'-carbonyl)oxy]-4,11-diethyl-3,14-dioxo-3,4,12,14-tetrahydro-1H-pyrano[3',4':6,7]indolizino[1,2-b]quinolin-4-yl} N,N',N", N'''-{methanetetrayltetrakis[methylenepoly(oxyethylene) oxy(1-oxoethylene)]}tetraglycinate tetrahydrochloride (etirinotecan pegol), 10-hydroxy-camptothecin (HOCPT), 9-nitrocamptothecin (rubitecan), SN38 (7-ethyl-10-hydroxycamptothecin), and 10-hydroxy-9-nitrocamptothecin (CPT109), (R)-9-chloro-5-ethyl-5-hydroxy-10-methyl-12-

((4-methylpiperidin-1-yl)methyl)-4,5-dihydrooxepino[3',4': 6,7]indolizino[1,2-b]quinoline-3,15(1H,13H)-dione (elmotecan).

In a particular embodiment, the topoisomerase inhibitor is the topoisomerase I inhibitor (S)-10-[(dimethylamino) methyl]-4-ethyl-4,9-dihydroxy-1H pyrano[3',4':6,7]indolizino[1,2-b]quinoline-3,14(4H,12H)-dione monohydrochloride (topotecan hydrochloride).

In one embodiment of the invention, a CDK4/6 inhibitor is selected from Formula I, II, III, IV, or V as described herein, abemaciclib, palbociclib, or ribociclib, and administered in a combination or alternation schedule with a topoisomerase inhibitor to a subject having an Rb-negative cancer. In one embodiment of the invention, a CDK4/6 inhibitor is selected from Formula I, II, III, IV, or V as described herein, abemaciclib, palbociclib, or ribociclib, and administered in a combination or alternation schedule with a topoisomerase inhibitor to a subject having an Rb-negative gastric, glioma, breast, non-small cell lung, small cell lung, esophageal, or liver cancer.

Furthermore, provided herein are methods and compositions for reducing the development of secondary malignancies associated with the use of topoisomerase inhibitors wherein a subject undergoing treatment for an Rb-negative cancer with a topoisomerase inhibitor is provided a CDK4/6 inhibitor described herein. In one embodiment, the topoisomerase inhibitor is a topoisomerase I inhibitor. In one embodiment, the topoisomerase inhibitor is a topoisomerase I and II dual inhibitor. In one embodiment, the CDK4/6 inhibitor is selected from compounds Q, T, U, GG, X, and BB, or a combination thereof.

Isotopic Substitution

The present invention includes the use of CDK4/6 inhibitors in combination with topoisomerase I or II inhibitors for the treatment of Rb-negative proliferative disorders. In certain aspects, the compounds used include compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2H$) and tritium ($^3H$) may be used anywhere in the described structures. Alternatively or in addition, isotopes of carbon, e.g., $^{13}C$ and $^{14}C$, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1H$), deuterium ($^2H$) and tritium ($^3H$). Thus, reference herein to a compound encompasses all potential isotopic forms unless the context clearly dictates otherwise.

The term "isotopic analog" refers to an analog that is a "deuterated analog", a "$^{13}C$-labeled analog," or a "deuterated/$^{13}C$-labeled analog." The term "deuterated analog" means a compound described herein, whereby a H-isotope, i.e., hydrogen/protium ($^1H$), is substituted by a H-isotope, i.e., deuterium ($^2H$). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location.

Further specific isotopic analog compounds that fall within the present invention and that can be used in the disclosed methods of treatment and compositions include the structures of Formula I, II, III, IV, or V listed in Table 1 above and/or the topoisomerase I inhibitors described above.

Rb-Negative Cancers and Proliferative Disorders

In particular, the active compounds described herein can be used in combination with one or more additional chemotherapeutic agents to treat a subject suffering from a Rb-negative cancer or other Rb-negative abnormal cellular proliferative disorder. Cancers and disorders of such type can be characterized by (e.g., that has cells that exhibit) the absence of a functional Retinoblastoma protein. Such cancers and disorders are classified as being Rb-negative. Rb-negative abnormal cellular proliferation disorders, and variations of this term as used herein, refer to disorders or diseases caused by uncontrolled or abnormal cellular division which are characterized by the absence of a functional Retinoblastoma protein, which can include cancers.

Such Rb-negative cancers can include, but are not limited to, small cell lung cancer, retinoblastoma, HPV positive malignancies like cervical cancer and certain head and neck cancers, MYC amplified tumors such as Burkitts' Lymphoma, and triple negative breast cancer; certain classes of sarcoma, for example Ewing's sarcoma, certain classes of non-small cell lung carcinoma, certain classes of melanoma, certain classes of pancreatic cancer, certain classes of leukemia, for example acute myelogenous leukemia (AML) or acute lymphoblatic leukemia (ALL), certain classes of lymphoma, certain classes of brain cancer, certain classes of colon cancer, certain classes of prostate cancer, certain classes of ovarian cancer, certain classes of uterine cancer, certain classes of thyroid and other endocrine tissue cancers, certain classes of salivary cancers, certain classes of thymic carcinomas, certain classes of kidney cancers, certain classes of bladder cancers, and certain classes of testicular cancers. In a specific embodiment, the Rb-negative leukemia is acute myeloid leukemia. In additional nonlimiting embodiments, the host may be suffering from an acute or chronic Rb-negative leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

The presence or absence of a normal functioning of the retinoblastoma (Rb) tumor suppressor protein can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line or surrogate tissue sample that is utilized e.g., for example Western Blot and ELISA may be used with any or all types of tissues, cell lines or surrogate tissues, whereas the IHC method would be more appropriate wherein the tissue utilized in the methods of the present invention was a tumor biopsy. FACs analysis would be most applicable to samples that were single cell suspensions such as cell lines and isolated peripheral blood mononuclear cells. See for example, US 20070212736 "Functional Immunohistochemical Cell Cycle Analysis as a Prognostic Indicator for Cancer". Alternatively, molecular genetic testing may be used for determination of retinoblastoma gene status. Molecular genetic testing for retinoblastoma includes the following as described in Lohmann and Gallie "Retinoblastoma. Gene Reviews" (2010) http://www.ncbi.nlm.nih.gov/bookshelf/br.fcgi?book=gene&part=retinoblastoma or Parsam et al. "A comprehensive, sensitive and economical approach for the detection of mutations in the RB 1 gene in retinoblastoma" Journal of Genetics, 88(4), 517-527 (2009).

In a specific embodiment, the Rb-negative cancer is small cell lung carcinoma.

In a specific embodiment, the Rb-negative cancer is cervical cancer.

In a specific embodiment, the Rb-negative cancer is neuroblastoma.

In a specific embodiment, the Rb-negative cancer is a sarcoma, for example, Ewing sarcoma.

In a specific embodiment, the Rb-negative cancer is an ovarian cancer.

In a specific embodiment, the Rb-negative cancer is a gastric cancer.

In a specific embodiment, the Rb-negative cancer is glioblastoma.

In a specific embodiment, the Rb-negative cancer is breast cancer.

In a specific embodiment, the Rb-negative cancer is triple-negative breast cancer.

In a specific embodiment, the Rb-negative cancer is a non-small cell lung cancer.

In a specific embodiment, the Rb-negative cancer is an esophageal cancer.

In a specific embodiment, the Rb-negative cancer is Burkitts' Lymphoma.

In a specific embodiment, the Rb-negative cancer is a melanoma.

In a specific embodiment, the Rb-negative cancer is pancreatic cancer.

In a specific embodiment, the Rb-negative cancer is leukemia, for example acute myelogenous leukemia (AML) or acute lymphoblastic leukemia (ALL).

In a specific embodiment, the Rb-negative cancer is brain cancer.

In a specific embodiment, the Rb-negative cancer is colon cancer.

In a specific embodiment, the Rb-negative cancer is prostate cancer.

In a specific embodiment, the Rb-negative cancer is uterine cancer.

In a specific embodiment, the Rb-negative cancer is thyroid and other endocrine tissue cancers.

In a specific embodiment, the Rb-negative cancer is salivary cancers.

In a specific embodiment, the Rb-negative cancer is a thymic carcinoma.

In a specific embodiment, the Rb-negative cancer is kidney cancer.

In a specific embodiment, the Rb-negative cancer is bladder cancer.

In a specific embodiment, the Rb-negative cancer is testicular cancer.

The methods of treatment described herein can be used in further combination with one or more additional chemotherapeutic agents to treat a subject suffering from an Rb-negative cancer.

Combination Therapy

In one aspect of the invention, the combination of a CDK4/6 inhibitor described herein and a topoisomerase I inhibitor to treat an Rb-negative cellular proliferation disorder can be further beneficially administered in combination with another therapeutic regimen for beneficial, additive, or synergistic effect.

The additional therapy can be an immunotherapy. In another embodiment, the combination is used with another pharmaceutical or a biologic agent (for example an antibody) to increase the efficacy of treatment with a combined or a synergistic approach. In an embodiment, the CDK4/6 inhibitor and topoisomerase I inhibitor can be used with T-cell vaccination, which typically involves immunization with inactivated auto-reactive T cells to eliminate an Rb-negative cancer cell population as described herein. In another embodiment, the combination is used in further combination with a bispecific T-cell Engager (BiTE), which is an antibody designed to simultaneously bind to specific antigens on endogenous T cells and Rb-negative cancer cells as described herein, linking the two types of cells.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Another group of cancer therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a cancer cell, and the cell-killing substance is taken up by the cell. FDA-approved conjugated MAbs that work this way include ado-trastuzumab emtansine, which targets the HER-2 molecule to deliver the drug DM1, which inhibits cell proliferation, to HER-2 expressing metastatic breast cancer cells.

Immunotherapies with T cells engineered to recognize cancer cells via bispecific antibodies (bsAbs) or chimeric antigen receptors (CARs) are approaches with potential to ablate both dividing and non/slow-dividing subpopulations of cancer cells.

Bispecific antibodies, by simultaneously recognizing target antigen and an activating receptor on the surface of an immune effector cell, offer an opportunity to redirect immune effector cells to kill cancer cells. The other approach is the generation of chimeric antigen receptors by fusing extracellular antibodies to intracellular signaling domains. Chimeric antigen receptor-engineered T cells are able to specifically kill tumor cells in a MHC-independent way.

In some embodiments, the combination can be administered to the subject in further combination with an additional chemotherapeutic agent. In one embodiment, the use of the compounds described herein is combined in a therapeutic regime with other agents.

Further additional chemotherapeutic agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apoptotic inducing compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus, sirolimus, and deforolimus. Examples of P13 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN1117 (INK1117), Pictilisib, Taselisib (GDC-0032), Buparlisib, SAR245408 (XL147), SAR245409 (XL765), Palomid 529, ZSTK474, PWT33597, RP6530, CUDC-907, and AEZS-136. Examples of MEK inhibitors include but are not limited to Trametinib, Selumetinib, MEK162, GDC-0973 (XL518), and PD0325901. Examples of RAS inhibitors include but are not limited to Reolysin and siGl2D LODER. Examples of ALK inhibitors include but are not limited to Crizotinib, Ceritinib (Zykadia), AP26113, and LDK378. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

In one embodiment, the CDK4/6 inhibitor and topoisomerase I inhibitor can be further combined with a chemotherapeutic selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the additional therapeutic agent is an anti-inflammatory agent, a chemotherapeutic agent, a radiotherapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil, dacarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorubicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), palbociclib (PD0332991), ribociclib (LEE011), abemaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

Further treatment regimen includes the administration of at least one additional kinase inhibitor. In one embodiment, the at least one additional kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3K inhibitors that may be used in the present invention are well known. Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)-N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13, 16-tetraazaoctadecan-18-oate), PF-05212384 (N-[4-[[4-(Dimethylamino)-1-piperidinyl]carbonyl]phenyl]-N'-[4-(4, 6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3 aR,6E, 9S,9aR,1 OR, 11 aS)-6-[[bis(prop-2-enyl)amino] methylidene]-5-hydroxy-9-(methoxymethyl)-9a, 11a-dimethyl-1,4,7-trioxo-2,3,3a,9,10,11-hexahydroindeno[4, 5h]isochromen-10-yl]acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109 having the formula:

Compound 292

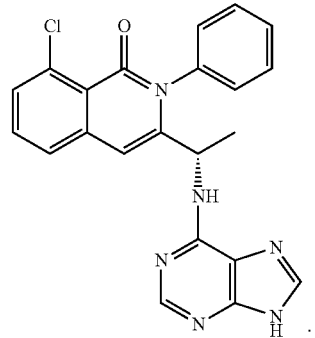

In one embodiment, the CDK4/6 inhibitor is combined in a single dosage form with the PIk3 inhibitor.

BTK inhibitors for use in the present invention are well known. Examples of BTK inhibitors include ibrutinib (also known as PCI-32765)(Imbmvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-5604-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX- 774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2 (1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference. In one embodiment, the CDK4/6 inhibitor is combined in a single dosage form with the BTK inhibitor.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein). In one embodiment, the CDK4/6 inhibitor is combined in a single dosage form with the Syk inhibitor.

MEK inhibitors for use in the present invention are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl] azetidin-3-ol), refametinib/BAY869766/RDEAl 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methyl sulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088, and additional MEK inhibitors as described below. In one embodiment, the CDK4/6 inhibitor is combined in a single dosage form with the MEK inhibitor.

Raf inhibitors for use in the present invention are well known, and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-

(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3 (trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib). In one embodiment, the CDK4/6 inhibitor is combined in a single dosage form with the Raf inhibitor.

In one embodiment, the at least one additional chemotherapeutic agent combined or alternated with the CDK4/6 inhibitor is a programmed death protein 1 (PD-1) inhibitor or programmed death protein ligand 1 or 2 inhibitor. PD-1 inhibitors are known in the art, and include, for example, nivolumab (BMS), pembrolizumab (Merck), pidilizumab (CureTech/Teva), AMP-244 (Amplimmune/GSK), BMS-936559 (BMS), and MEDI4736 (Roche/Genentech), and MPDL3280A (Genentech). In one embodiment, the CDK4/6 inhibitor is combined in a single dosage form with the PD-1 inhibitor.

In one embodiment, the at least one additional chemotherapeutic agent combined or alternated with the CDK4/6 inhibitor is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenyl sulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen). In one embodiment, the CDK4/6 inhibitor is combined in a single dosage form with the at least one BCL-2 inhibitor.

In one aspect of the present invention, the combination therapy described herein can be additionally combined with at least one immunosuppressive agent. The immunosuppressive agent is preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHO-CLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In certain embodiments, the combination treatment described herein is administered to the subject prior to treatment with another chemotherapeutic agent, during treatment with another chemotherapeutic agent, after administration of another chemotherapeutic agent, or a combination thereof.

Drug Conjugates

In one embodiment, the activity of the CDK4/6 inhibitor and/or topoisomerase I inhibitor can be augmented through conjugation to an agent that targets the diseased or abnormally proliferating cell or otherwise enhances activity, delivery, pharmacokinetics or other beneficial property.

For example, the CDK4/6 inhibitor and/or topoisomerase I inhibitor can be administered as an antibody-drug conjugates (ADC). In certain embodiments, a CDK4/6 inhibitor and/or topoisomerase I inhibitor can be administered in conjugation or combination with an antibody or antibody fragment. Fragments of an antibody can be produced through chemical or genetic mechanisms. The antibody fragment can be an antigen binding fragment. For example, the antigen binding fragment can be selected from an Fab, Fab', (Fab')$_2$, or Fv. The antibody fragment can be a Fab. Monovalent F(ab) fragments have one antigen binding site. The antibody can be a divalent (Fab')$_2$ fragment, which has two antigen binding regions that are linked by disulfide bonds. In one embodiment, the antigen fragment is a (Fab'). Reduction of F(ab')$_2$ fragments produces two monovalent Fab' fragments, which have a free sulfhydryl group that is useful for conjugation to other molecules.

A CDK4/6 inhibitor and/or topoisomerase I inhibitor described herein can be administered in conjugation or combination with a Fv fragment. Fv fragments are the smallest fragment made from enzymatic cleavage of IgG and IgM class antibodies. Fv fragments have the antigen-binding site made of the VH and VC regions, but they lack the $CH_1$ and CL regions. The VH and VL chains are held together in Fv fragments by non-covalent interactions.

In one embodiment, a CDK4/6 inhibitor and/or topoisomerase I inhibitor as described herein can be administered in combination with an antibody fragment selected from the group consisting of an ScFv, domain antibody, diabody, triabody, tetrabody, Bis-scFv, minibody, Fab2, or Fab3 antibody fragment. In one embodiment, the antibody fragment is a ScFv. Genetic engineering methods allow the production of single chain variable fragments (ScFv), which are Fv type fragments that include the VH and VL domains linked with a flexible peptide When the linker is at least 12 residues long, the ScFv fragments are primarily monomeric. Manipulation of the orientation of the V-domains and the linker length creates different forms of Fv molecules. Linkers that are 3-11 residues long yield scFv molecules that are unable to fold into a functional Fv domain. These molecules can associate with a second scFv molecule, to create a bivalent diabody. In one embodiment, the antibody fragment administered in combination with a CDK4/6 inhibitor and/or topoisomerase I inhibitor described herein is a bivalent diabody. If the linker length is less than three residues, scFv molecules associate into triabodies or tetrabodies. In one embodiment, the antibody fragment is a triabody. In one embodiment, the antibody fragment is a tetrabody. Multivalent scFvs possess greater functional binding affinity to their target antigens than their monovalent counterparts by having binding to two more target antigens, which reduces the off-rate of the antibody fragment. In one embodiment, the antibody fragment is a minibody. Minibodies are scFv-$CH_3$ fusion proteins that assemble into bivalent dimers. In one embodiment, the antibody fragment is a Bis-scFv fragment. Bis-scFv fragments are bispecific. Miniaturized ScFv fragments can be generated that have two different variable domains, allowing these Bis-scFv molecules to concurrently bind to two different epitopes.

In one embodiment, a CDK4/6 inhibitor and/or topoisomerase I inhibitor described herein is administered in conjugation or combination with a bispecific dimer (Fab2) or trispecific dimer (Fab3). Genetic methods are also used to create bispecific Fab dimers (Fab2) and trispecific Fab trimers (Fab3). These antibody fragments are able to bind 2 (Fab2) or 3 (Fab3) different antigens at once.

In one embodiment, a CDK4/6 inhibitor and/or topoisomerase I inhibitor described herein is administered in conjugation or combination with an rIgG antibody fragment. rIgG antibody fragments refers to reduced IgG (75,000 daltons) or half-IgG. It is the product of selectively reducing just the hinge-region disulfide bonds. Although several disulfide bonds occur in IgG, those in the hinge-region are most accessible and easiest to reduce, especially with mild reducing agents like 2-mercaptoethylamine (2-MEA). Half-IgG are frequently prepared for the purpose of targeting the exposing hinge-region sulfhydryl groups that can be targeted for conjugation, either antibody immobilization or enzyme labeling.

In other embodiments, a CDK4/6 inhibitor and/or topoisomerase I inhibitor described herein can be linked to a radioisotope to increase efficacy, using methods well known in the art. Any radioisotope that is useful against Rb-negative cancer cells can be incorporated into the conjugate, for example, but not limited to, $^{131}I$, $^{123}I$, $^{192}Ir$, $^{32}P$, $^{90}Sr$, $^{198}Au$, $^{226}Ra$, $^{90}Y$, $^{241}Am$, $^{252}Cf$, $^{60}Co$, or $^{137}Cs$.

Of note, the linker chemistry can be important to efficacy and tolerability of the drug conjugates. The thio-ether linked T-DM1 increases the serum stability relative to a disulfide linker version and appears to undergo endosomal degradation, resulting in intra-cellular release of the cytotoxic agent, thereby improving efficacy and tolerability, See, Barginear, M. F. and Budman, D. R., Trastuzumab-DM1: A review of the novel immune-conjugate for HER2-overexpressing breast cancer, The Open Breast Cancer Journal, 1:25-30, 2009.

Examples of early and recent antibody-drug conjugates, discussing drugs, linker chemistries and classes of targets for product development that may be used in the present invention can be found in the reviews by Casi, G. and Neri, D., Antibody-drug conjugates: basic concepts, examples and future perspectives, J. Control Release 161(2):422-428, 2012, Chari, R. V., Targeted cancer therapy: conferring specificity to cytotoxic drugs, Acc. Chem. Rev., 41(1):98-107, 2008, Sapra, P. and Shor, B., Monoclonal antibody-based therapies in cancer: advances and challenges, Pharmacol. Ther., 138(3):452-69, 2013, Schliemann, C. and Neri, D., Antibody-based targeting of the tumor vasculature, Biochim. Biophys. Acta., 1776(2):175-92, 2007, Sun, Y., Yu, F., and Sun, B. W., Antibody-drug conjugates as targeted cancer therapeutics, Yao Xue Xue Bao, 44(9):943-52, 2009, Teicher, B. A., and Chari, R. V., Antibody conjugate therapeutics: challenges and potential, Clin. Cancer Res., 17(20): 6389-97, 2011, Firer, M. A., and Gellerman, G. J., Targeted drug delivery for cancer therapy: the other side of antibodies, J. Hematol. Oncol., 5:70, 2012, Vlachakis, D. and Kossida, S., Antibody Drug Conjugate bioinformatics: drug delivery through the letterbox, Comput. Math. Methods Med., 2013; 2013:282398, Epub 2013 Jun. 19, Lambert, J. M., Drug-conjugated antibodies for the treatment of cancer, Br. J. Clin. Pharmacol., 76(2):248-62, 2013, Concalves, A., Tredan, O., Villanueva, C. and Dumontet, C., Antibody-drug conjugates in oncology: from the concept to trastuzumab emtansine (T-DM1), Bull. Cancer, 99(12):1183-1191, 2012, Newland, A. M., Brentuximab vedotin: a CD-30-directed antibody-cytotoxic drug conjugate, Pharmacotherapy, 33(1): 93-104, 2013, Lopus, M., Antibody-DM1 conjugates as cancer therapeutics, Cancer Lett., 307(2):113-118, 2011, Chu, Y. W. and Poison, A., Antibody-drug conjugates for the treatment of B-cell non-Hodgkin's lymphoma and leukemia, Future Oncol., 9(3):355-368, 2013, Bertholjotti, I., Antibody-drug conjugate—a new age for personalized cancer treatment, Chimia, 65(9): 746-748, 2011, Vincent, K. J., and Zurini, M., Current strategies in antibody engineering: Fc engineering and pH-dependent antigen binding, bispecific antibodies and antibody drug conjugates, Biotechnol. J., 7(12):1444-1450, 2012, Haeuw, J. F., Caussanel, V., and Beck, A., Immunoconjugates, drug-armed antibodies to fight against cancer, Med. Sci., 25(12):1046-1052, 2009 and Govindan, S. V., and Goldenberg, D. M., Designing immunoconjugates for cancer therapy, Expert Opin. Biol. Ther., 12(7):873-890, 2012.

Pharmaceutical Compositions and Dosage Forms

The CDK4/6 inhibitor and topoisomerase I inhibitor described herein, or its salt, isotopic analog, or prodrug can be administered in an effective amount to the host using any suitable approach which achieves the desired therapeutic result. The amount and timing of active compound administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases. Pharmaceutical formulations can be prepared for any desired route of administration including, but not limited to, oral, intravenous, or aerosol administration, as discussed in greater detail below.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage can be the amount of compound needed to provide a serum concentration of the active compound of up to between about 1 and 5, 10, 20, 30, or 40 µM. In some embodiments, a dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 µmol/kg to about 50 µmol/kg, or, optionally, between about 22 µmol/kg and about 33 µmol/kg of the compound for intravenous or oral administration. An oral dosage form can include any appropriate amount of active material, including for example from 5 mg to, 50, 100, 200, or 500 mg per tablet or other solid dosage form.

In accordance with the presently disclosed methods, pharmaceutically active compounds as described herein can be administered orally as a solid or as a liquid, or can be administered intramuscularly, intravenously, or by inhalation as a solution, suspension, or emulsion. In some embodiments, the compounds or salts also can be administered by inhalation, intravenously, or intramuscularly as a liposomal suspension. When administered through inhalation the active compound or salt can be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

The pharmaceutical formulations can comprise a CDK4/6 inhibitor and/or topoisomerase I inhibitor described herein or a pharmaceutically acceptable salt thereof, in any pharmaceutically acceptable carrier. If a solution is desired, water may be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of solutions, suspensions, tablets, pills, capsules, powders, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the host matter described herein, there are provided injectable, stable, sterile formulations comprising an active compound as described herein, or a salt thereof, in a unit dosage form in a sealed container. The compound or salt is provided in the form of a lyophilizate, which is capable of being reconstituted with a suitable pharmaceutically acceptable carrier to form liquid formulation suitable for injection thereof into a host. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulations can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. In one embodiment, the solid particles provide for controlled release through the use of a degradable polymer. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Pharmaceutical formulations also are provided which provide a controlled release of a compound described herein, including through the use of a degradable polymer, as known in the art.

When the pharmaceutical formulations suitable for administration as an aerosol is in the form of a liquid, the formulations can comprise a water-soluble active compound in a carrier that comprises water. A surfactant can be present, which lowers the surface tension of the formulations sufficiently to result in the formation of droplets within the desired size range when hosted to nebulization.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Preparation of CDK4/6 Inhibitors

Syntheses

The disclosed CDK4/6 inhibitors can be made by the following general schemes:

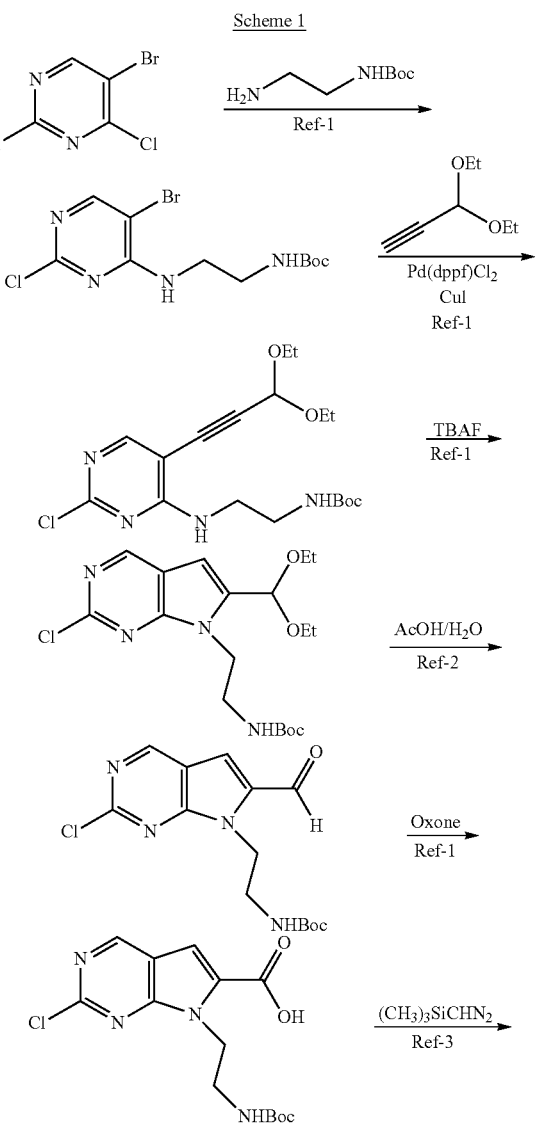

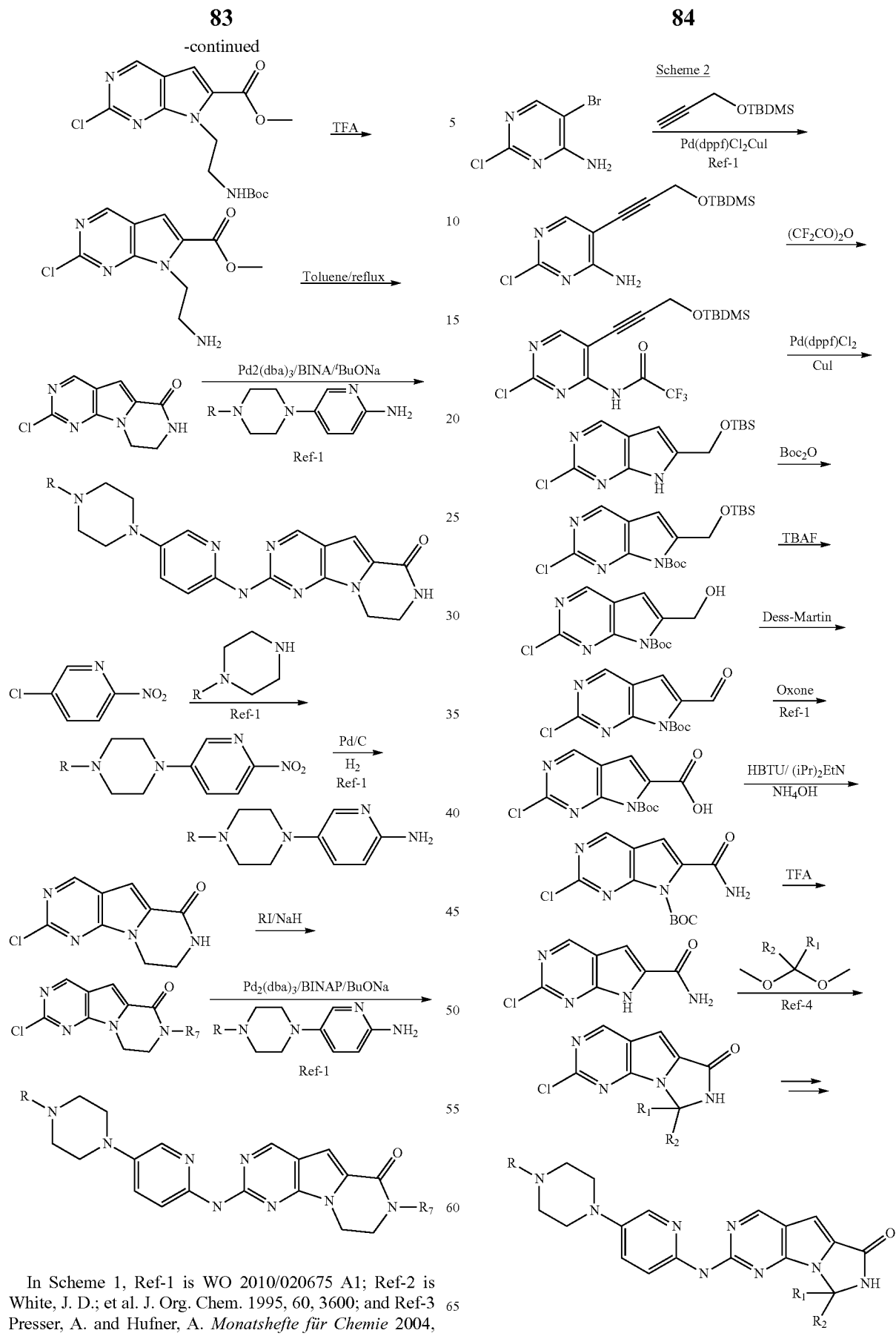
In Scheme 1, Ref-1 is WO 2010/020675 A1; Ref-2 is White, J. D.; et al. J. Org. Chem. 1995, 60, 3600; and Ref-3 Presser, A. and Hufner, A. *Monatshefte für Chemie* 2004, 135, 1015.

85
-continued
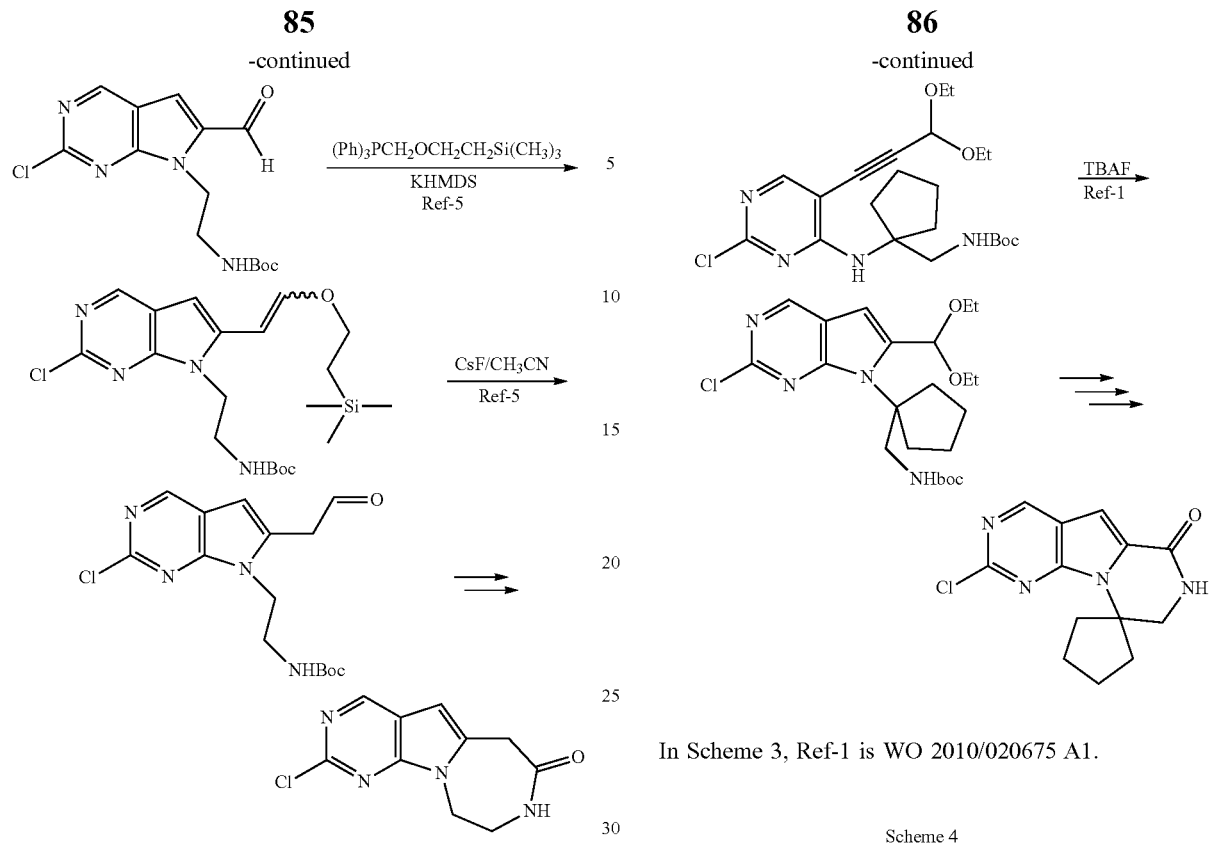
In Scheme 2, Ref-1 is WO 2010/020675 A1; Ref-4 is WO 2005/040166 A1; and Ref-5 is Schoenauer, K and Zbiral, E. Tetrahedron Letters 1983, 24, 573.
Scheme 3
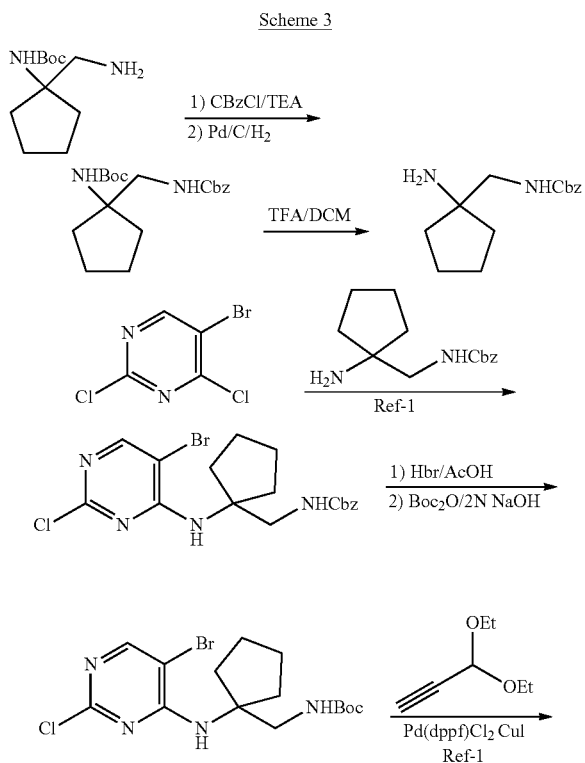
86
-continued
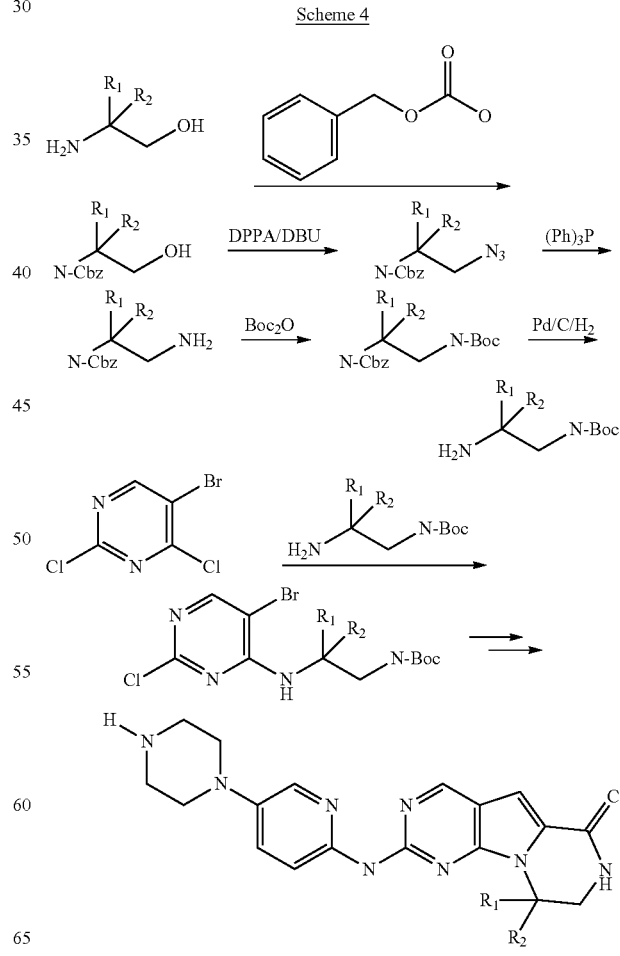
In Scheme 3, Ref-1 is WO 2010/020675 A1.

Scheme 5
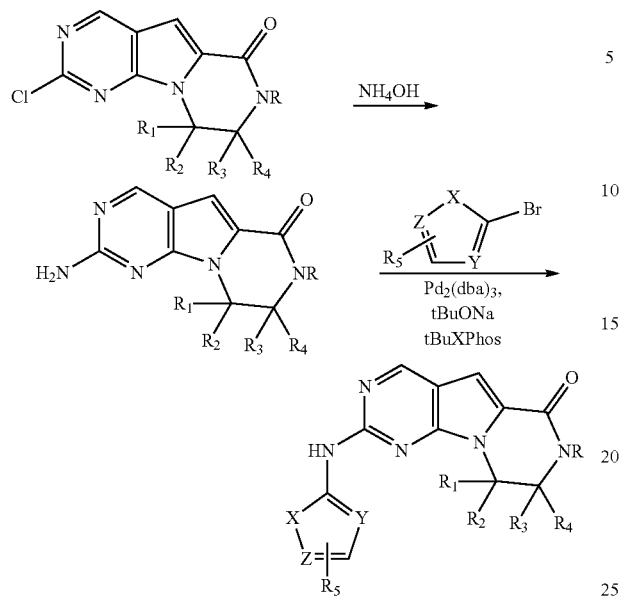
Scheme 6
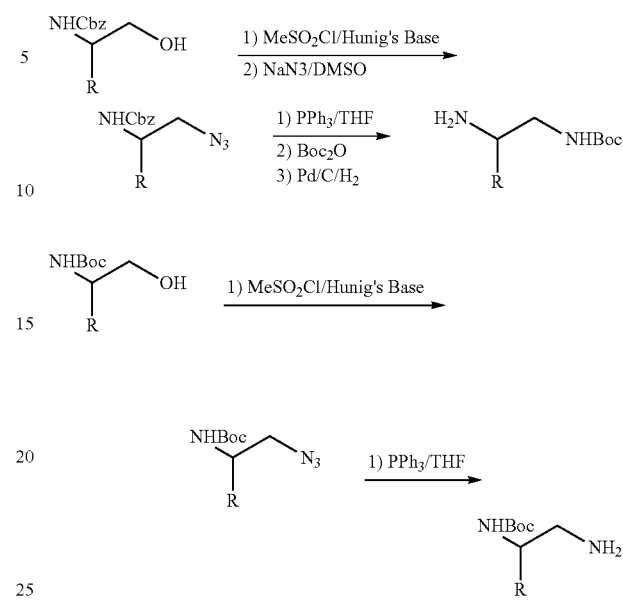
Scheme 7
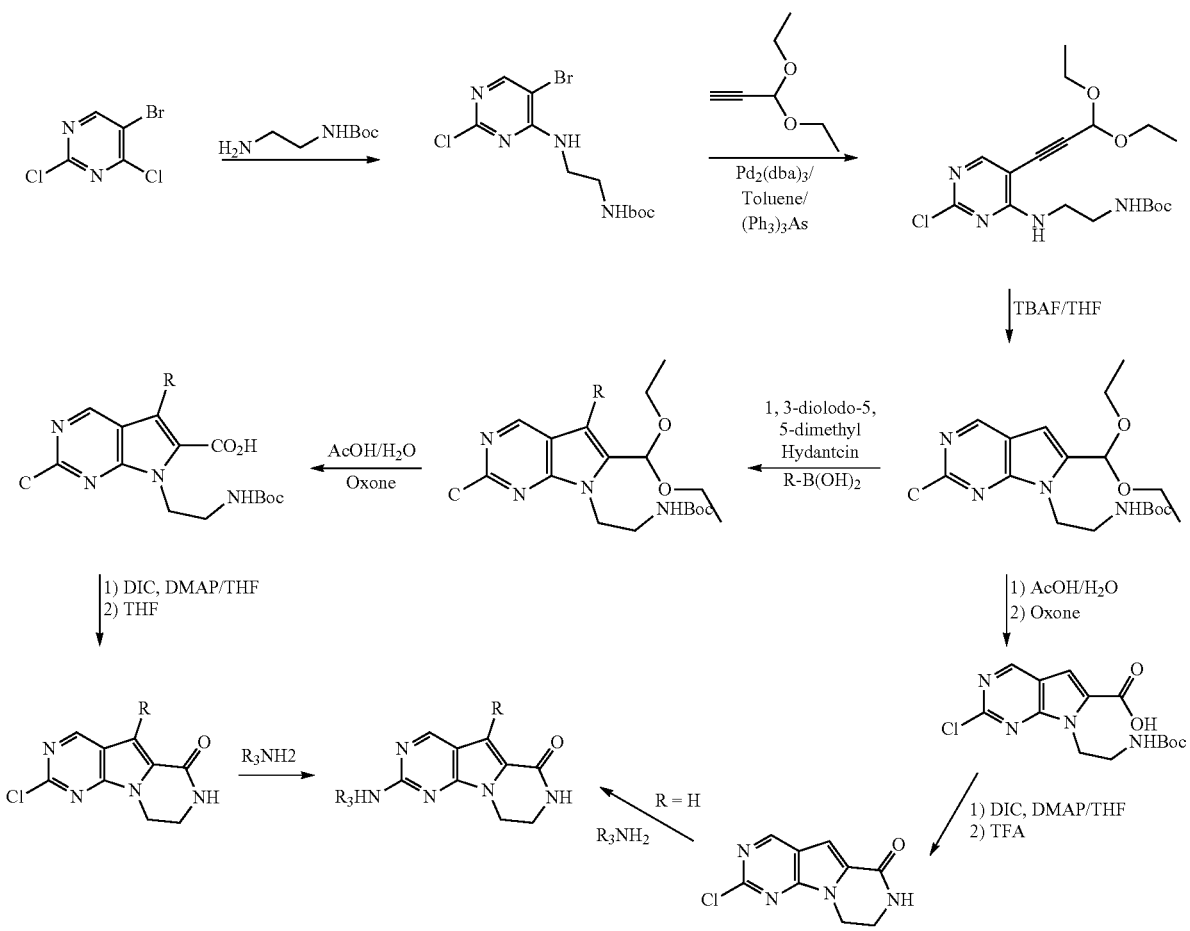

Scheme 8

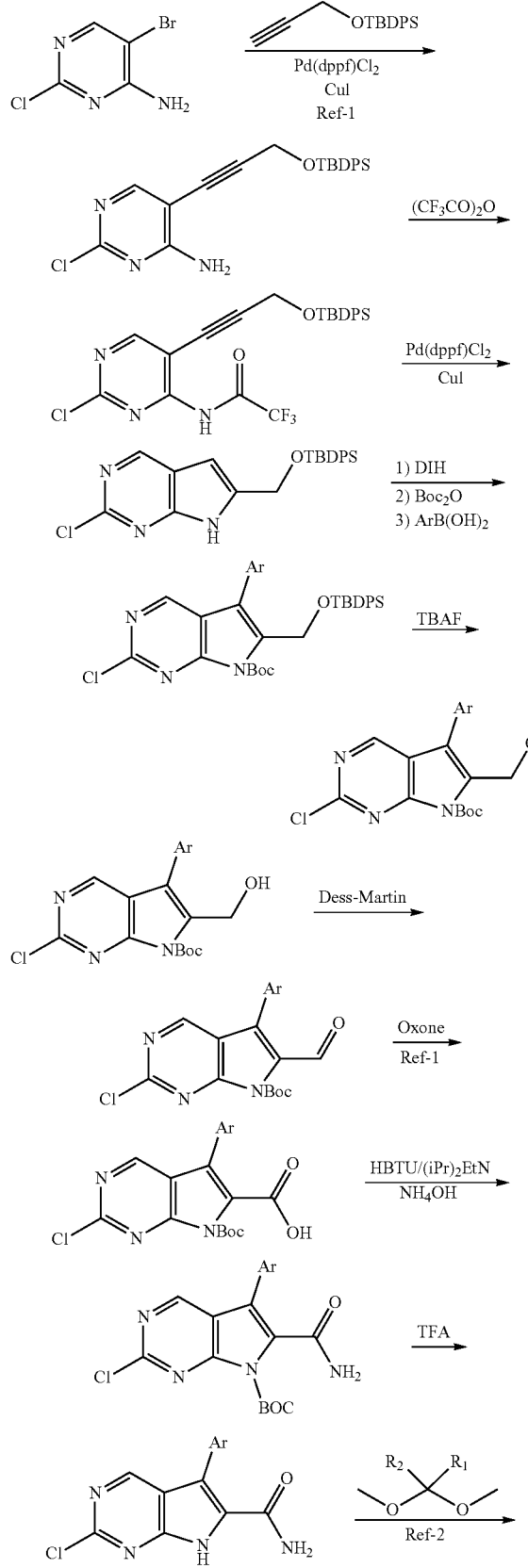

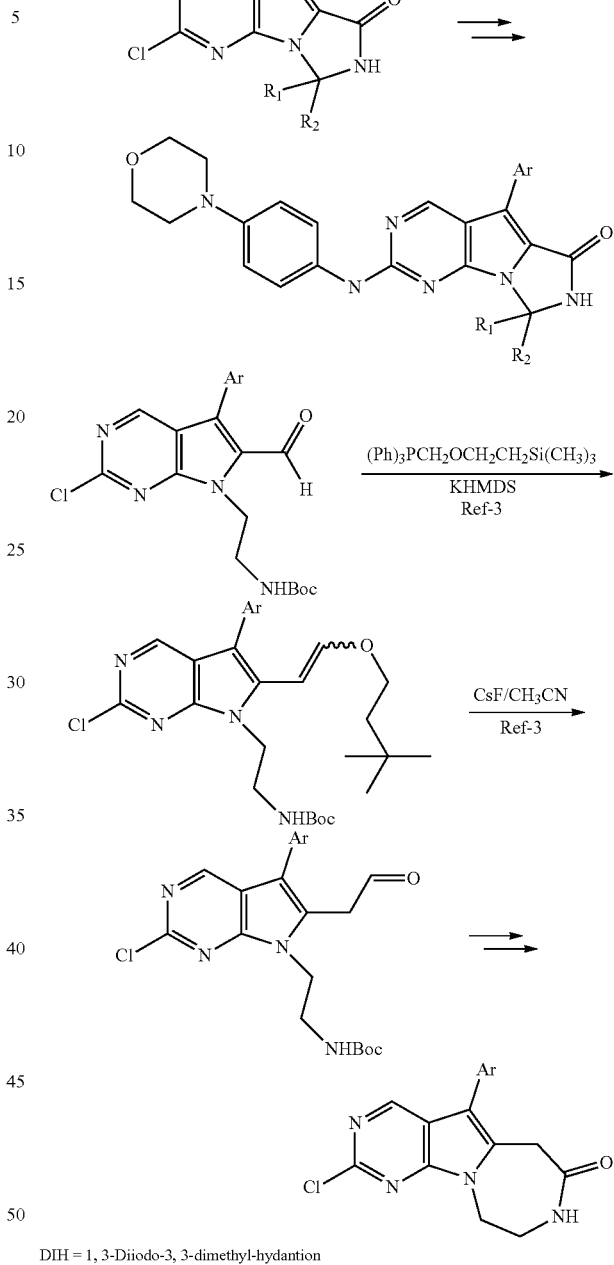

DIH = 1, 3-Diiodo-3, 3-dimethyl-hydantion

In Scheme 8, Ref-1 is WO 2010/020675 A1; Ref-2 is WO 2005/040166 A1; and Ref-3 is Schoenauer, K and Zbiral, E. Tetrahedron Letters 1983, 24, 573.

Alternatively, the lactam can be generated by reacting the carboxylic acid with a protected amine in the presence of a strong acid and a dehydrating agent, which can be together in one moiety as a strong acid anhydride. Examples of strong acid anhydrides include, but are not limited to, trifluoroacetic acid anhydride, tribromoacetic acid anhydride, trichloroacetic acid anhydride, or mixed anhydrides. The dehydrating agent can be a carbodiimide based compound such as but not limited to DCC (N,N-dicyclohexylcarbodiimide), EDC (1-ethyl-3-(3-dimethylaminopropyl)carbodiimide or DIC (N,N-diisopropylcarbodiimide). An additional step may be necessary to take off the N-protecting group and the methodologies are known to those skilled in the art.

Alternatively, the halogen moiety bonded to the pyrimidine ring can be substituted with any leaving group that can be displaced by a primary amine, for example to create an intermediate for a final product such as Br, I, F, SMe, $SO_2Me$, SOalkyl, $SO_2$alkyl. See, for example, PCT/US2013/037878 to Tavares.

Other amine intermediates and final amine compounds can be synthesized by those skilled in the art. It will be appreciated that the chemistry can employ reagents that comprise reactive functionalities that can be protected and de-protected and will be known to those skilled in the art at the time of the invention. See, for example, Greene, T. W. and Wuts, P. G. M., Greene's Protective Groups in Organic Synthesis, $4^{th}$ edition, John Wiley and Sons.

Scheme 9

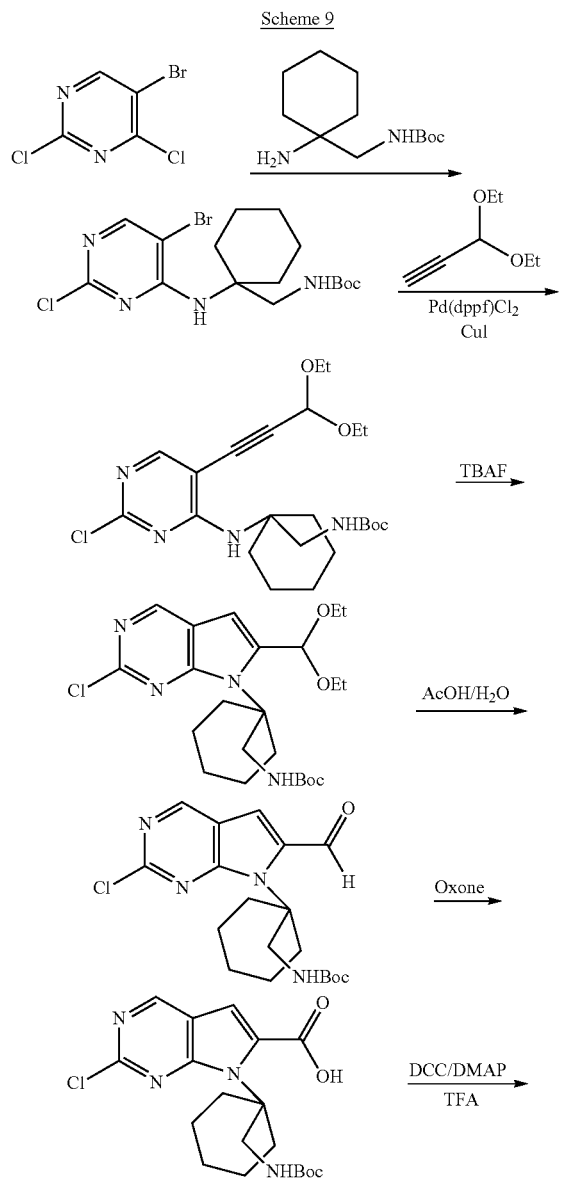

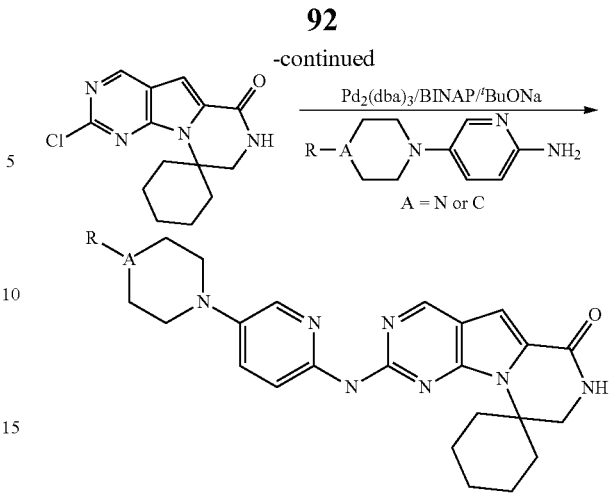

CDK4/6 Inhibitors of the present invention can be synthesized according to the generalized Scheme 9. Specific synthesis and characterization of the Substituted 2-aminopyrmidines can be found in, for instance, WO2012/061156.

Compounds T, Q, GG, and U were prepared as above and were characterized by mass spectrometry and NMR as shown below:

Compound T

1H NMR (600 MHz, DMSO-d6) □ ppm 1.47 (br. s., 6H) 1.72 (br. s., 2H) 1.92 (br. s., 2H) 2.77 (br. s., 3H) 3.18 (br. s., 2H) 3.46 (br. s., 2H) 3.63 (br. s., 2H) 3.66 (d, J=6.15 Hz, 2H) 3.80 (br. s., 2H) 7.25 (s, 1H) 7.63 (br. s., 2H) 7.94 (br. s., 1H) 8.10 (br. s., 1H) 8.39 (br. s., 1H) 9.08 (br. s., 1H) 11.59 (br. s., 1H). LCMS ESI (M+H) 447.

Compound Q

1H NMR (600 MHz, DMSO-d6) □ ppm 0.82 (d, J=7.32 Hz, 2H) 1.08-1.37 (m, 3H) 1.38-1.64 (m, 2H) 1.71 (br. s., 1H) 1.91 (br. s., 1H) 2.80 (br. s., 1H) 3.12 (s, 1H) 3.41 (br. s., 4H) 3.65 (br. s., 4H) 4.09 (br. s., 1H) 7.26 (s, 1H) 7.52-7.74 (m, 2H) 7.94 (br. s., 1H) 8.13 (br. s., 1H) 8.40 (br. s., 1H) 9.09 (br. s., 1H) 9.62 (br. s., 1H) 11.71 (br. s., 1H). LCMS ESI (M+H) 433.

Compound GG

1H NMR (600 MHz, DMSO-d6) □ ppm 0.85 (br. s., 1H) 1.17-1.39 (m, 7H) 1.42-1.58 (m, 2H) 1.67-1.84 (m, 3H) 1.88-2.02 (m, 1H) 2.76-2.93 (m, 1H) 3.07-3.22 (m, 1H) 3.29-3.39 (m, 1H) 3.41-3.61 (m, 4H) 3.62-3.76 (m, 4H) 3.78-3.88 (m, 1H) 4.12 (br. s., 1H) 7.28 (s, 1H) 7.60-7.76 (m, 2H) 7.98 (s, 1H) 8.13 (br. s., 1H) 8.41 (s, 1H) 9.10 (br. s., 1H) 11.21 (br. s., 1H) 11.54 (s, 1H). LCMS ESI (M+H) 475.

Compound U

1H NMR (600 MHz, DMSO-d6) □ ppm 0.84 (t, J=7.61 Hz, 2H) 1.13-1.39 (m, 4H) 1.46 (d, J=14.05 Hz, 2H) 1.64-1.99 (m, 6H) 2.21 (br. s., 1H) 2.66-2.89 (m, 2H) 3.06 (br. s., 1H) 3.24-3.36 (m, 1H) 3.37-3.50 (m, 2H) 3.56-3.72 (m, 2H) 3.77-4.00 (m, 4H) 4.02-4.19 (m, 2H) 7.25 (s, 1H) 7.50-7.75 (m, 2H) 7.89 (d, J=2.93 Hz, 1H) 8.14 (d, J=7.32 Hz, 1H) 8.38 (br. s., 1H) 9.06 (s, 1H) 11.53 (br. s., 1H). LCMS ESI (M+H) 517.

EXAMPLES

Intermediates B, E, K, L, 1A, 1F and 1CA were synthesized according to U.S. Pat. No. 8,598,186 entitled CDK Inhibitors to Tavares, F. X. and Strum, J. C.

The patents WO 2013/148748 entitled Lactam Kinase Inhibitors to Tavares, F. X., WO 2013/163239 entitled Synthesis of Lactams to Tavares, F. X., and U.S. Pat. No.

Example 1

Synthesis of tert-butyl N-[2-[(5-bromo-2-chloro-pyrimidin-4yl)amino]ethyl]carbamate, Compound 1

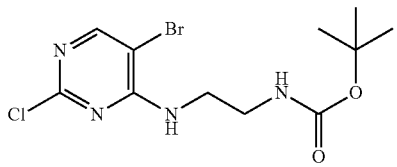 [SMILES: CC(C)(C)OC(=O)NCCNc1nc(Cl)ncc1Br]

To a solution of 5-bromo-2,4-dichloropyrimidine (3.2 g, 0.0135 mol) in ethanol (80 mL) was added Hunig's base (3.0 mL) followed by the addition of a solution of N-(tert-butoxycarbonyl)-1,2-diaminoethane (2.5 g, 0.0156 mole) in ethanol (20 mL). The contents were stirred overnight for 20 hrs. The solvent was evaporated under vacuum. Ethyl acetate (200 mL) and water (100 mL) were added and the layers separated. The organic layer was dried with magnesium sulfate and then concentrated under vacuum. Column chromatography on silica gel using hexane/ethyl acetate (0-60%) afforded tert-butyl N-[2-[(5-bromo-2-chloro-pyrimidin-4-yl)amino]ethyl]carbamate. $^1$HNMR (d6-DMSO) δ ppm 8.21 (s, 1H), 7.62 (brs, 1H), 7.27 (brs, 1H), 3.39 (m, 2H), 3.12 (m, 2H), 1.34 (s, 9H). LCMS (ESI) 351 (M+H).

Example 2

Synthesis of tert-butyl N-[2-[[2-chloro-5-(3,3-diethoxyprop-1-ynyl)pyrimidin-4-yl]amino]ethyl]carbamate, Compound 2

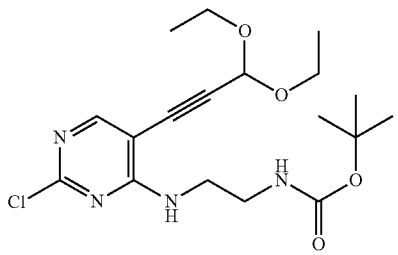 [SMILES: CCOC(C#Cc1cnc(Cl)nc1NCCNC(=O)OC(C)(C)C)OCC]

To tert-butyl N-[2-[(5-bromo-2-chloro-pyrimidin-4-yl)amino]ethyl]carbamate (1.265 g, 3.6 mmol) in THF (10 mL) was added the acetal (0.778 mL, 5.43 mmol), Pd(dppf)CH$_2$Cl$_2$ (148 mg), and triethylamine (0.757 mL, 5.43 mmol). The contents were degassed and then purged with nitrogen. To this was then added CuI (29 mg). The reaction mixture was heated at reflux for 48 hrs. After cooling, the contents were filtered over CELITE$^T$ and concentrated. Column chromatography of the resulting residue using hexane/ethyl acetate (0-30%) afforded tert-butyl N-[2-[[2-chloro-5-(3,3-diethoxyprop-1-ynyl)pyrimidin-4-yl]amino]ethyl]carbamate. 1HNMR (d6-DMSO) δ ppm 8.18 (s, 1H), 7.63 (brs, 1H), 7.40 (brs, 1H), 5.55 (s, 1H), 3.70 (m, 2H), 3.60 (m, 2H), 3.42 (m, 2H), 3.15 (m, 2H), 1.19-1.16 (m, 15H). LCMS (ESI) 399 (M+H).

Example 3

Synthesis of tert-butyl N-[2-[2-chloro-6-(diethoxymethyl)pyrrolo[2,3-d]pyrimidin-7-yl]ethyl]carbamate, Compound 3

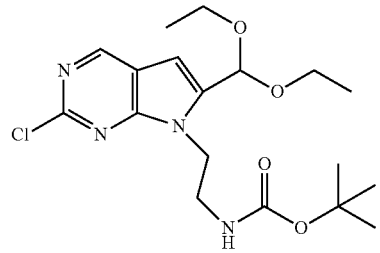 [SMILES: CCOC(OCC)c1cc2cnc(Cl)nc2n1CCNC(=O)OC(C)(C)C]

To a solution of the coupled product (2.1 g, 0.00526 mole) in THF (30 mL) was added TBAF solid (7.0 g). The contents were heated to and maintained at 65 degrees for 2 hrs. Concentration followed by column chromatography using ethyl acetate/hexane (0-50%) afforded tert-butyl N-[2-[2-chloro-6-(diethoxymethyl)pyrrolo[2,3-d]pyrimidin-7-yl]ethyl]carbamate as a pale brown liquid (1.1 g). $^1$HNMR (d6-DMSO) δ ppm 8.88 (s, 1H), 6.95 (brs, 1H), 6.69 (s, 1H), 5.79 (s, 1H), 4.29 (m, 2H), 3.59 (m, 4H), 3.34 (m, 1H), 3.18 (m, 1H), 1.19 (m, 9H), 1.17 (m, 6H). LCMS (ESI) 399 (M+H).

Example 4

Synthesis of tert-butyl N-[2-(2-chloro-6-formyl-pyrrolo [2,3-d]pyrimidin-7-yl)ethyl]carbamate, Compound 4

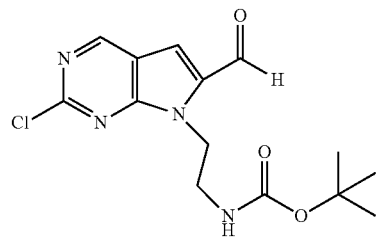 [SMILES: CC(C)(C)OC(=O)NCCn1c(C=O)cc2cnc(Cl)nc21]

To the acetal (900 mg) from the preceding step was added AcOH (8.0 mL) and water (1.0 mL). The reaction was stirred at room temperature for 16 hrs. Conc. and column chromatography over silica gel using ethyl acetate/hexanes (0-60%) afforded tert-butyl N-[2-(2-chloro-6-formyl-pyrrolo[2,3-d]pyrimidin-7-yl)ethyl]carbamate as a foam (0.510 g). $^1$HNMR (d6-DMSO) δ ppm 9.98 (s, 1H), 9.18 (s, 1H), 7.66 (s, 1H), 6.80 (brs, 1H), 4.52 (m, 2H), 4.36 (m, 2H), 1.14 (s, 9H). LCMS (ESI) 325 (M+H).

[Note: reference to 8,598,186 entitled CDK Inhibitors to Tavares, F. X. and Strum, J. C. are incorporated by reference herein in their entirety.]

Example 5

Synthesis of 7-[2-(tert-butoxycarbonylamino)ethyl]-2-chloro-pyrrolo[2,3-d]pyrimidine-6-carboxylic acid, Compound 5

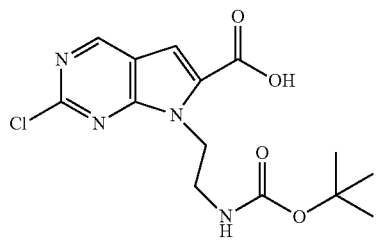 [SMILES: CC(C)(C)OC(=O)NCCn1c(C(=O)O)cc2cnc(Cl)nc21]

To the aldehyde (0.940 g) from the preceding step in DMF (4 mL) was added oxone (1.95 g, 1.1 eq). The contents were stirred at room temp for 7 hrs. Silica gel column chromatography using hexane/ethyl acetate (0-100%) afforded 7-[2-(tert-butoxycarbonylamino)ethyl]-2-chloro-pyrrolo[2,3-d]pyrimidine-6-carboxylic acid (0.545 g). $^1$HNMR (d6-DMSO) δ ppm 9.11 (s, 1H), 7.39 (s, 1H), 4.38 (m, 2H), 4.15 (m, 2H), 1.48 (m, 9H). LCMS (ESI) 341 (M+H).

Example 6

Synthesis of methyl 7-[2-(tert-butoxycarbonylamino)ethyl]-2-chloro-pyrrolo[2,3-d]pyrimidine-6-carboxylate, Compound 6

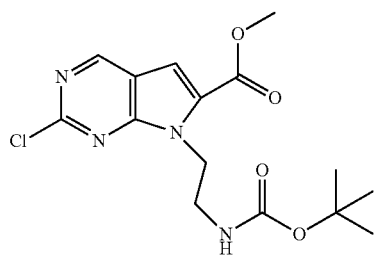 [SMILES: COC(=O)c1cc2cnc(Cl)nc2n1CCNC(=O)OC(C)(C)C]

To a solution of 2-chloro-7-propyl-pyrrolo[2,3-d]pyrimidine-6-carboxylic acid (0.545 g, 0.00156 mole) from the preceding step in toluene (3.5 mL) and MeOH (1 mL) was added TMS-diazomethane (1.2 mL). After stirring overnight at room temperature, the excess of TMS-diazomethane was quenched with acetic acid (3 mL) and the reaction was concentrated under vacuum. The residue was purified by silica gel column chromatography with hexane/ethyl acetate (0-70%) to afford methyl 7-[2-(tert-butoxycarbonylamino) ethyl]-2-chloro-pyrrolo[2,3-d]pyrimidine-6-carboxylate as an off white solid (0.52 g). $^1$HNMR (d6-DMSO) δ ppm 9.10 (s, 1H), 7.45 (s, 1H), 6.81 (brs, 1H) 4.60 (m, 2H), 3.91 (s, 3H), 3.29 (m, 2H), 1.18 (m, 9H) LCMS (ESI) 355 (M+H).

Example 7

Synthesis of Chloro Tricyclic Amide, Compound 7

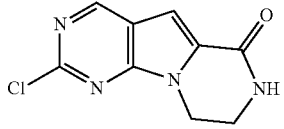 [SMILES: O=C1NCCn2c1cc1cnc(Cl)nc12]

To methyl 7-[2-(tert-butoxycarbonylamino)ethyl]-2-chloro-pyrrolo[2,3-d]pyrimidine-6-carboxylate (0.50 g, 0.0014 mole) from the preceding step in dichloromethane (2.0 mL) was added TFA (0.830 mL). The contents were stirred at room temperature for 1 hr. Concentration under vacuum afforded the crude amino ester which was suspended in toluene (5 mL) and Hunig's base (0.5 mL). The contents were heated at reflux for 2 hrs. Concentration followed by silica gel column chromatography using hexane/ethyl acetate (0-50%) afforded the desired chloro tricyclic amide (0.260 g). $^1$HNMR (d6-DMSO) δ ppm 9.08 (s, 1H), 8.48 (brs, 1H), 7.21 (s, 1H) 4.33 (m, 2H), 3.64 (m, 2H). LCMS (ESI) 223 (M+H).

Example 8

Synthesis of Chloro-N-Methyltricyclic Amide, Compound 8

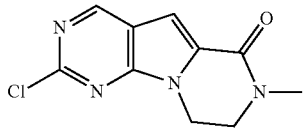 [SMILES: CN1CCn2c(cc3cnc(Cl)nc32)C1=O]

To a solution of the chloro tricycliclactam, Compound 7, (185 mg, 0.00083 mole) in DMF (2.0 mL) was added sodium hydride (55% dispersion in oil, 52 mg). After stirring for 15 mins, methyl iodide (62 µL, 1.2 eq). The contents were stirred at room temperature for 30 mins. After the addition of methanol (5 mL), sat NaHCO$_3$ was added followed by the addition of ethyl acetate. Separation of the organic layer followed by drying with magnesium sulfate and concentration under vacuum afforded the N-methylated amide in quantitative yield. $^1$HNMR (d6-DMSO) δ ppm 9.05 (s, 1H), 7.17 (s, 1H) 4.38 (m, 2H), 3.80 (m, 2H), 3.05 (s, 3H). LCMS (ESI) 237 (M+H).

Example 9

Synthesis of 1-methyl-4-(6-nitro-3-pyridyl)piperazine, Compound 9

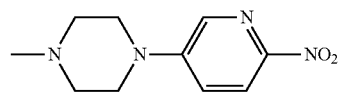

To 5-bromo-2-nitropyridine (4.93 g, 24.3 mmole) in DMF (20 mL) was added N-methylpiperazine (2.96 g, 1.1 eq)

followed by the addition of DIPEA (4.65 mL, 26.7 mmole). The contents were heated at 90 degrees for 24 hrs. After addition of ethyl acetate (200 mL), water (100 mL) was added and the layers separated. Drying followed by concentration afforded the crude product which was purified by silica gel column chromatography using (0-10%) DCM/Methanol. ¹HNMR (d6-DMSO) δ ppm 8.26 (s, 1H), 8.15 (1H, d, J=9.3 Hz), 7.49 (1H, d, J=9.4 Hz), 3.50 (m, 4H), 2.49 (m, 4H), 2.22 (s, 3H).

Example 10

Synthesis of 5-(4-methylpiperazin-1-yl)pyridin-2-amine, Compound 10

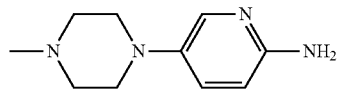

To 1-methyl-4-(6-nitro-3-pyridyl)piperazine (3.4 g) in ethyl acetate (100 mL) and ethanol (100 mL) was added 10% Pd/C (400 mg) and then the reaction was stirred under hydrogen (10 psi) overnight. After filtration through CELITE™, the solvents were evaporated and the crude product was purified by silica gel column chromatography using DCM/7N ammonia in MeOH (0-5%) to afford 5-(4-methylpiperazin-1-yl)pyridin-2-amine (2.2 g). ¹HNMR (d6-DMSO) δ ppm 7.56 (1H, d, J=3 Hz), 7.13 (1H, m), 6.36 (1H, d, J=8.8 Hz), 5.33 (brs, 2H), 2.88 (m, 4H), 2.47 (m, 4H), 2.16 (s, 3H).

Example 11

Synthesis of tert-butyl 4-(6-amino-3-pyridyl)piperazine-1-carboxylate, Compound 11

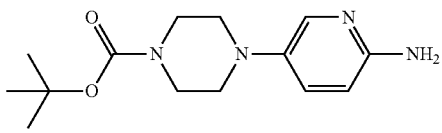 [SMILES: CC(C)(C)OC(=O)N1CCN(c2ccc(N)nc2)CC1]

This compound was prepared as described in WO 2010/020675 A1.

Example 12

Synthesis of tert-butyl N-[2-(benzyloxycarbonylamino)-3-methyl-butyl]carbamate, Compound 12

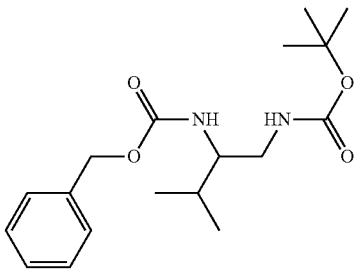 [SMILES: CC(C)C(CNC(=O)OC(C)(C)C)NC(=O)OCc1ccccc1]

To benzyl N-[1-(hydroxymethyl)-2-methyl-propyl]carbamate (11.0 g, 0.0464 mole) in dioxane (100 mL) cooled to 0° C. was added diphenylphosphoryl azide (10.99 mL, 1.1 eq) followed by the addition of DBU (8.32 mL, 1.2 eq). The contents were allowed to warm to room temperature and stirred for 16 hrs. After the addition of ethyl acetate (300 mL) and water (100 mL), the organic layer was separated and washed with satd. NaHCO₃ (100 mL). The organic layer was then dried (magnesium sulfate) and concentrated under vacuum. To this intermediate in DMSO (100 mL) was added sodium azide (7.54 g) and the contents then heated to 90 degrees for 2 hrs. After addition of ethyl acetate and water the layers were separated. The organic layer was dried with magnesium sulfate followed by concentration under vacuum to afford an oil that was purified by silica gel column chromatography using hexane/ethyl acetate (0-70%) to afford benzyl N-[1-(azidomethyl)-2-methyl-propyl]carbamate 6.9 g as a colorless oil.

To benzyl N-[1-(azidomethyl)-2-methyl-propyl]carbamate (6.9 g, 0.0263 mole) in THF (100 mL) was added triphenyl phosphine (7.59 g, 1.1 eq). The contents were stirred for 20 hrs. After addition of water (10 mL), and stirring for an additional 6 hrs, ethyl acetate was added and the layers separated. After drying with magnesium sulfate and concentration under vacuum, the crude product was purified by silica gel column chromatography using DCM/MeOH (0-10%) to afford benzyl N-[1-(aminomethyl)-2-methyl-propyl]carbamate as a yellow oil.

To benzyl N-[1-(aminomethyl)-2-methyl-propyl]carbamate (4.65 g, 0.019 mole) in THF (70 mL) was added 2N NaOH (20 mL) followed by the addition of di-tert-butyl dicarbonate (5.15 g, 1.2 eq). After stirring for 16 hrs, ethyl acetate was added and the layers were separated. After drying with magnesium sulfate and concentration under vacuum, the crude product was purified using hexane/ethyl acetate (0-40%) over a silica gel column to afford intermediate A, tert-butyl N-[2-(benzyloxycarbonylamino)-3-methyl-butyl]carbamate, (6.1 g). ¹HNMR (600 MHz, CHLOROFORM-d) δ ppm 0.89 (d, J=6.73 Hz, 3H) 0.92 (d, J=6.73 Hz, 3H) 1.38 (s, 9H) 1.70-1.81 (m, 1H) 3.18 (d, J=5.56 Hz, 2H) 3.47-3.60 (m, 1H) 4.76 (s, 1H) 4.89 (d, J=7.90 Hz, 1H) 5.07 (s, 2H) 7.25-7.36 (m, 5H). LCMS (ESI) 337 (M+H).

Example 13

Synthesis of tert-butyl N-[2-(benzyloxycarbonylamino)-4-methyl-pentyl]carbamate, Compound 13

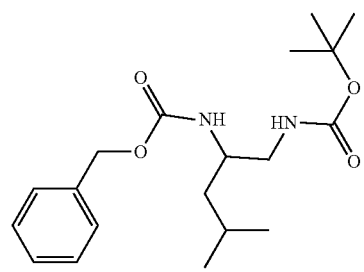 [SMILES: CC(C)CC(CNC(=O)OC(C)(C)C)NC(=O)OCc1ccccc1]

To a solution of benzyl N-[1-(hydroxymethyl)-3-methyl-butyl]carbamate (6.3 g, 0.025 mole) in DCM (100 mL) was added diisopropylethyl amine (5.25 mL, 1.2 eq) followed by the addition of methane sulfonylchloride (2.13 mL, 1.1 eq) at 0 degrees. After stirring for 3 hrs, water (100 mL) was added and the organic layer separated. After drying with magnesium sulfate and concentration under vacuum, the crude [2-(benzyloxycarbonylamino)-4-methyl-pentyl]methanesulfonate which was taken directly to the next step.

To the crude [2-(benzyloxycarbonylamino)-4-methyl-pentyl] methanesulfonate from the above reaction in DMF (50 mL), was added sodium azide 2.43 g. The reaction mixture was then heated to 85 degrees for 3 hrs. After cooling, ethyl acetate (300 mL) and water was added. The organic layer was separated, dried with magnesium sulfate and then concentrated under vacuum to afford the crude benzyl N-[1-(azidomethyl)-3-methyl-butyl]carbamate. To this crude intermediate was added THF (100 mL) followed by triphenylphosphine 7.21 g and stirred under nitrogen for 16 hrs. After addition of water (10 mL), and stirring for an additional 6 hrs, ethyl acetate was added and the layers separated. After drying with magnesium sulfate and concentration under vacuum, the crude product was columned using DCM/MeOH (0-10%) to afford benzyl N-[1-(aminomethyl)-3-methyl-butyl]carbamate (4.5 g).

To benzyl N-[1-(aminomethyl)-3-methyl-butyl]carbamate (4.5 g, 0.018 mole) in THF (60 mL) was added 2N NaOH (18 mL) followed by the addition of di-tert-butyl dicarbonate (4.19 g, 1.07 eq). After stirring for 16 hrs, ethyl acetate was added and the layers separated. After drying with magnesium sulfate and concentration under vacuum, the crude product was taken to the next step. $^1$HNMR (600 MHz, CHLOROFORM-d) δ ppm 0.89 (d, J=6.73 Hz, 6H) 1.25-1.34 (m, 1 H) 1.39 (s, 9H) 1.57-1.71 (m, 2H) 3.04-3.26 (m, 2H) 3.68-3.80 (m, 1H) 4.72-4.89 (m, 2H) 5.06 (s, 2H) 7.25-7.38 (m, 5H). LCMS (ESI) 351 (M+H).

Example 14

Synthesis of tert-butyl N-[(2R)-2-(benzyloxycarbonylamino)-3-methyl-butyl]carbamate, Compound 14

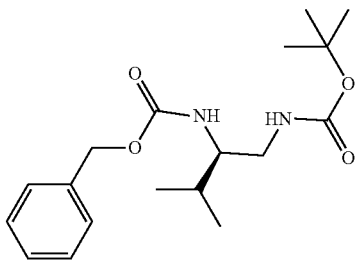 [SMILES: CC(C)[C@H](CNC(=O)OC(C)(C)C)NC(=O)OCc1ccccc1]

Compound 14 was synthesized from benzyl N-[(1R)-1-(hydroxymethyl)-2-methyl-propyl]carbamate using similar synthetic steps as that described for Compound 13. The analytical data (NMR and mass spec) was consistent with that for Compound 12.

Example 15

Synthesis of tert-butyl N-[(2S)-2-(benzyloxycarbonylamino)-3-methyl-butyl]carbamate, Compound 15

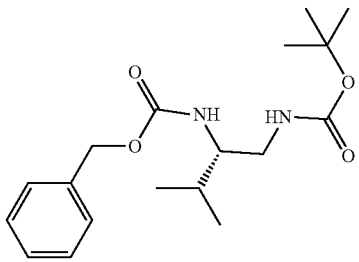 [SMILES: CC(C)[C@@H](CNC(=O)OC(C)(C)C)NC(=O)OCc1ccccc1]

Compound 15 was synthesized from benzyl N-[(1S)-1-(hydroxymethyl)-2-methyl-propyl]carbamate using similar synthetic steps as that described for Compound 13. The analytical data (NMR and mass spec) was consistent with that for Compound 12.

Example 16

Synthesis of tert-butyl N-[(1S)-1-(aminomethyl)-2-methyl-propyl]carbamate, Compound 16

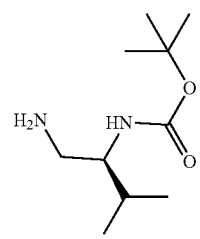

To a solution of tert-butyl N-[(1S)-1-(hydroxymethyl)-2-methyl-propyl]carbamate carbamate (6.3 g, 0.025 mole) in THF (100 mL) was added diisopropylethyl amine (5.25 mL, 1.2 eq) followed by the addition of methane sulfonylchloride (2.13 mL, 1.1 eq) at 0 degrees. After stirring for 3 hrs, water (100 mL) was added and the organic layer separated. After drying with magnesium sulfate and concentration under vacuum, the crude [(2S)-2-(tert-butoxycarbonylamino)-3-methyl-butyl] methanesulfonate was taken directly to the next step.

To the crude [(2S)-2-(tert-butoxycarbonylamino)-3-methyl-butyl] methanesulfonate from the above reaction in DMSO (50 mL), was added sodium azide (2.43 g). The reaction mixture was then heated to 85 degrees for 3 hrs. After cooling, ethyl acetate (300 mL) and water were added. The organic layer was separated, dried with magnesium sulfate and then concentrated under vacuum to afford the crude benzyl N-[1-(azidomethyl)-3-methyl-butyl]carbamate. To this crude intermediate was added THF (100 mL) followed by triphenylphosphine (7.21 g) and the reaction was stirred under nitrogen for 16 hrs. After addition of water (10 mL), and stirring for an additional 6 hrs, ethyl acetate was added and the layers separated. After drying with magnesium sulfate and concentration under vacuum, the crude product was purified by silica gel column chromatography using DCM/MeOH (0-10%) to afford benzyl N-[1-(aminomethyl)-3-methyl-butyl] carbamate (4.5 g). LCMS (ESI) 203 (M+H).

Example 17

Synthesis of tert-butyl N-[(1R)-1-(aminomethyl)-2-methyl-propyl]carbamate, Compound 17

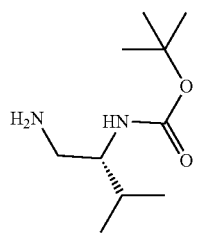

Compound 17 was synthesized from tert-butyl N-[(1R)-1-(hydroxymethyl)-2-methyl-propyl]carbamate using a similar synthetic sequence as described for Compound 16. The analytical data (NMR and mass spec) was consistent with Compound 16.

Example 18

Synthesis of tert-butyl N-[(2S)-2-(benzyloxycarbonylamino)-4-methyl-pentyl]carbamate, Compound 18

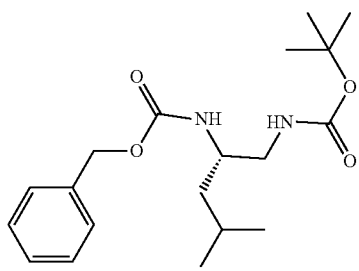 [SMILES: CC(C)C[C@@H](CNC(=O)OC(C)(C)C)NC(=O)OCc1ccccc1]

Compound 18 was synthesized from benzyl N-[(1S)-1-(hydroxymethyl)-3-methyl-butyl]carbamate using a similar synthetic sequence as described for Compound 13. The analytical data (NMR and mass spec) was consistent with Compound 13.

Example 19

Synthesis of tert-butyl N-[(2S)-2-(benzyloxycarbonylamino)-2-phenyl-ethyl]carbamate, Compound 19

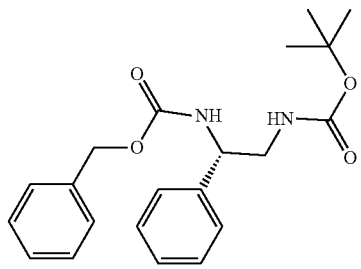 [SMILES: CC(C)(C)OC(=O)NC[C@@H](NC(=O)OCc1ccccc1)c1ccccc1]

Compound 19 was synthesized from benzyl N-[(1S)-2-hydroxy-1-phenyl-ethyl]carbamate using a similar synthetic sequence as described for Compound 13. $^1$HNMR (600 MHz, DMSO-d6) δ ppm 1.20-1.33 (m, 9H) 3.11 (t, J=6.29 Hz, 2H) 4.59-4.68 (m, 1H) 4.88-5.01 (m, 2H) 6.81 (t, J=5.42 Hz, 1H) 7.14-7.35 (m, 10H) 7.69 (d, J=8.49 Hz, 1H). LCMS (ESI) 371 (M+H).

Example 20

Synthesis of tert-butyl N-[(2S)-2-(benzyloxycarbonylamino)-3-methyl-pentyl]carbamate, Compound 20

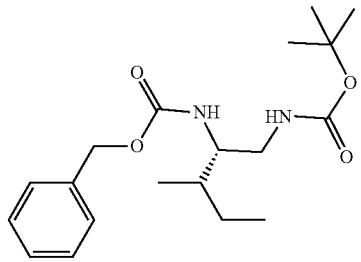 [SMILES: CCC(C)[C@@H](CNC(=O)OC(C)(C)C)NC(=O)OCc1ccccc1]

Compound 20 was synthesized from benzyl N-[(1S)-1-(hydroxymethyl)-2-methyl-butyl]carbamate using a similar synthetic sequence as described for Compound 13. $^1$HNMR (600 MHz, CHLOROFORM-d) δ ppm 0.85-0.92 (m, 6H) 1.05-1.15 (m, 1H) 1.35-1.41 (m, 9H) 1.45-1.56 (m, 2H) 3.14-3.24 (m, 2H) 3.54-3.64 (m, 1H) 4.78 (s, 1H) 4.96 (d, J=7.91 Hz, 1H) 5.06 (s, 2H) 7.27-7.37 (m, 5H). LCMS (ESI) 351 (M+H).

Example 21

Synthesis of tert-butyl N-[(2S)-2-(benzyloxycarbonylamino)-3,3-dimethyl-butyl]carbamate, Compound 21

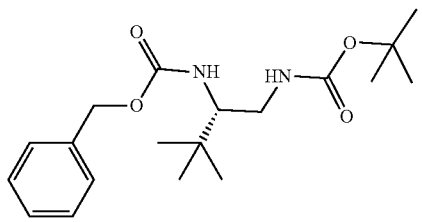 [SMILES: CC(C)(C)OC(=O)NC[C@@H](NC(=O)OCc1ccccc1)C(C)(C)C]

Compound 21 was synthesized from benzyl N-[(1S)-1-(hydroxymethyl)-2,2-dimethyl-propyl]carbamate using a similar synthetic sequence as described for Compound 13. LCMS (ESI) 351.

Example 22

Synthesis of tert-butyl N-[[1-(benzyloxycarbonylamino)cyclohexyl]methyl]carbamate, Compound 22

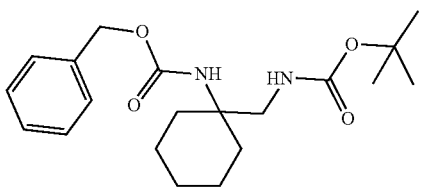 [SMILES: CC(C)(C)OC(=O)NCC1(NC(=O)OCc2ccccc2)CCCCC1]

To a solution of benzyl N-[1-(aminomethyl)cyclohexyl]carbamate (10.0 g, 0.0381 mole) in THF (150 mL) was added di-tert-butyl dicarbonate (9.15 g, 1.1 eq) and the contents were stirred at room temperature for 16 hrs. Ethyl acetate and water were then added. The organic layer was separated, dried over magnesium sulfate and then concentrated under vacuum to afford tert-butyl N-[[1-(benzyloxycarbonylamino)cyclohexyl]methyl]carbamate (13.1 g). $^1$HNMR (600 MHz, DMSO-d6) δ ppm 0.92-1.54 (m, 17H) 1.76-2.06 (m, 2H) 3.09 (d, J=6.15 Hz, 2H) 4.92 (s, 2H) 6.63 (d, J=17.27 Hz, 1H) 7.16-7.49 (m, 6H). LCMS (ESI) 363 (M+H).

Example 23

Synthesis of tert-butyl N-[[1-(benzyloxycarbonylamino)cyclopentyl]methyl]carbamate, Compound 23

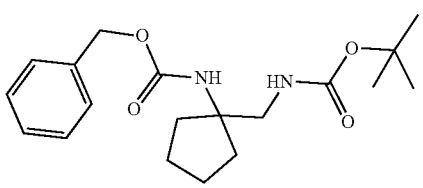 [SMILES: CC(C)(C)OC(=O)NCC1(NC(=O)OCc2ccccc2)CCCC1]

tert-butyl N-[[1-(benzyloxycarbonylamino)cyclopentyl]methyl]carbamate was synthesized in an analogous manner to tert-butyl N-[[1-(benzyloxycarbonylamino) cyclohexyl]methyl]carbamate. LCMS (ESI) 349 (M+H).

Example 24

Synthesis of 2-nitro-5-[4-(1-piperidyl)-1-piperidyl]pyridine, Compound 24

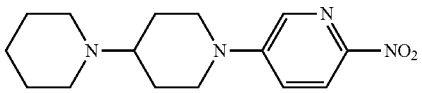 [SMILES: O=[N+]([O-])c1ccc(N2CCC(N3CCCCC3)CC2)cn1]

To 5-bromo-2-nitropyridine (1.2 g, 5.9 mmol) in DMSO (4 mL) was added 1-(4-piperidyl)piperidine (1.0 g, 5.9 mmole) and triethylamine (0.99 mL, 7.1 mmole). The contents were heated to 120° C. in a CEM Discovery microwave system for 3 hours. The crude reaction was then purified by silica gel column chromatography with DCM/methanol (0-20%) to afford 2-nitro-5-[4-(1-piperidyl)-1-piperidyl] pyridine as an oil (457 mg). $^1$HNMR (600 MHz, DMSO-d6) δ ppm 1.26-1.36 (m, 2H) 1.43 (m, 6H) 1.76 (m, 2H) 2.37 (m, 5H) 2.94 (t, J=12.74 Hz, 2H) 4.06 (d, J=13.47 Hz, 2H) 7.41 (dd, J=9.37, 2.64 Hz, 1H) 8.08 (d, J=9.37 Hz, 1H) 8.20 (d, J=2.64 Hz, 1H).

Example 25

Synthesis of 5-[4-(1-piperidyl)-1 piperidyl]pyridin-2-amine, Compound 25

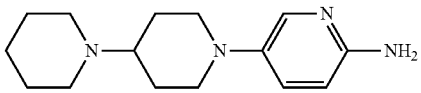

5-[4-(1-piperidyl)-1-piperidyl]pyridin-2-amine was prepared in a manner similar to that used in the synthesis of 5-(4-methylpiperazin-1-yl)pyridin-2-amine. $^1$HNMR (600 MHz, DMSO-d6) δ ppm 1.13-1.37 (m, 6H) 1.40-1.63 (m, 6H) 1.71 (m, 2H), 2.24 (m, 1H) 2.43 (m, 2H) 3.33 (d, J=12.30 Hz, 2H) 5.31 (s, 2H) 6.33 (d, J=8.78 Hz, 1H) 7.10 (dd, J=8.78, 2.93 Hz, 1H) 7.55 (d, J=2.64 Hz, 1H). LCMS (ESI) 261 (M+H).

Example 26

Synthesis of 4-[1-(6-nitro-3-pyridyl)-4-piperidyl]morpholine, Compound 26

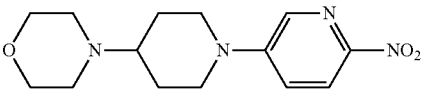

4-[1-(6-nitro-3-pyridyl)-4-piperidyl]morpholine was synthesized in a manner similar to that used in the synthesis of 2-nitro-5-[4-(1-piperidyl)-1-piperidyl]pyridine. $^1$HNMR (600 MHz, DMSO-d6) δ ppm 1.41 (m, 2H) 1.82 (m, 2H)

2.42 (m, 5H) 2.98 (t, J=12.44 Hz, 2H) 3.52 (s, 4H) 4.04 (d, J=12.88 Hz, 2H) 7.42 (d, J=9.37 Hz, 1H) 8.08 (d, J=9.08 Hz, 1H) 8.21 (s, 1H).

Example 27

Synthesis of 5-(4-morpholino-1-piperidyl)pyridin-2-amine, Compound 27

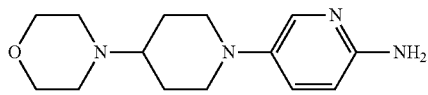 [SMILES: Nc1ccc(N2CCC(N3CCOCC3)CC2)cn1]

5-(4-morpholino-1-piperidyl)pyridin-2-amine was prepared in a manner similar to that used in the synthesis of 5-(4-methylpiperazin-1-yl)pyridin-2-amine. $^1$HNMR (600 MHz, DMSO-d6) δ ppm 1.34-1.52 (m, 2H) 1.78 (m, 2H) 2.14 (m, 1H) 2.43 (m, 4H) 3.32 (d, J=12.30 Hz, 4H) 3.47-3.59 (m, 4H) 5.32 (s, 2H) 6.34 (d, J=8.78 Hz, 1H) 7.11 (dd, J=8.93, 2.78 Hz, 1H) 7.47-7.62 (m, 1H). LCMS (ESI) 263 (M+H).

Example 28

Synthesis of 4-[1-(6-nitro-3-pyridyl)-4-piperidyl]thiomorpholine, Compound 28

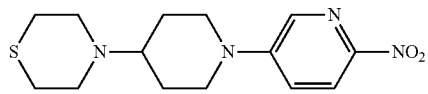

4-[1-(6-nitro-3-pyridyl)-4-piperidyl] thiomorpholine was synthesized in a manner similar to that used in the synthesis of 2-nitro-5-[4-(1-piperidyl)-1-piperidyl]pyridine. $^1$HNMR (600 MHz, DMSO-d6) δ ppm 1.40-1.52 (m, 2H) 1.71 (m, 2H) 2.49-2.55 (m, 4H) 2.56-2.63 (m, 1H) 2.68-2.75 (m, 4H) 2.88-2.98 (m, 2H) 4.09 (d, J=13.18 Hz, 2H) 7.42 (dd, J=9.22, 3.07 Hz, 1H) 8.08 (d, J=9.37 Hz, 1H) 8.20 (d, J=3.22 Hz, 1H).

Example 29

Synthesis of 5-(4-thiomorpholino-1-piperidyl)pyridin-2-amine, Compound 29

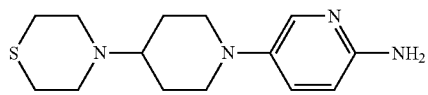 [SMILES: O=[N+]([O-])c1ccc(N2CCC(N3CCSCC3)CC2)cn1]

5-(4-thiomorpholino-1-piperidyl) pyridin-2-amine was prepared in a manner similar to that used in the synthesis of 5-(4-methylpiperazin-1-yl)pyridin-2-amine. $^1$HNMR (600 MHz, DMSO-d6) δ ppm 1.47-1.59 (m, 2H) 1.65 (m, 2H) 2.22-2.38 (m, 1H) 2.50-2.59 (m, 6H) 2.68-2.82 (m, 4H) 3.33 (d, J=12.00 Hz, 2H) 5.31 (s, 2H) 6.33 (d, J=9.08 Hz, 1H) 7.10 (dd, J=8.78, 2.93 Hz, 1H) 7.55 (d, J=2.64 Hz, 1H). LCMS (ESI) 279 (M+H).

Example 30

Synthesis of 2-nitro-5-(1-piperidyl)pyridine, Compound 30

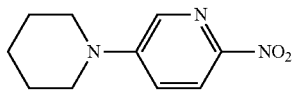

2-nitro-5-(1-piperidyl) pyridine was synthesized in a manner similar to that used in the synthesis of 2-nitro-5-[4-(1-piperidyl)-1-piperidyl]pyridine. $^1$HNMR (600 MHz, DMSO-d6) δ ppm 1.56 (m, 6H) 3.49 (d, J=4.39 Hz, 4H) 7.30-7.47 (m, 1H) 8.02-8.12 (m, 1H) 8.15-8.26 (m, 1H).

Example 31

Synthesis of 5-(1-piperidyl)pyridin-2-amine, Compound 31

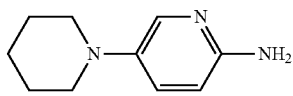 [SMILES: Nc1ccc(N2CCCCC2)cn1]

5-(1-piperidyl) pyridin-2-amine was prepared in a manner similar to that used in the synthesis of 5-(4-methylpiperazin-1-yl)pyridin-2-amine. $^1$HNMR (600 MHz, DMSO-d6) δ ppm 1.39-1.46 (m, 2H) 1.51-1.62 (m, 4H) 2.75-2.92 (m, 4H) 5.30 (s, 2H) 6.34 (d, J=8.78 Hz, 1H) 7.09 (dd, J=8.78, 2.93 Hz, 1H) 7.54 (d, J=2.93 Hz, 1H). LCMS (ESI) 178 (M+H).

Example 32

Synthesis of 4-(6-nitro-3-pyridyl) thiomorpholine, Compound 32

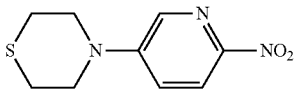 [SMILES: O=[N+]([O-])c1ccc(N2CCSCC2)cn1]

4-(6-nitro-3-pyridyl) thiomorpholine was synthesized in a manner similar to that used in the synthesis of 2-nitro-5-[4-(1-piperidyl)-1-piperidyl]pyridine. $^1$HNMR (600 MHz, DMSO-d6) δ ppm 2.56-2.69 (m, 4H) 3.79-3.92 (m, 4H) 7.43 (dd, J=9.22, 3.07 Hz, 1H) 8.10 (d, J=9.37 Hz, 1H) 8.20 (d, J=2.93 Hz, 1H).

Example 33

Synthesis of 5-thiomorpholinopyridin-2-amine, Compound 33

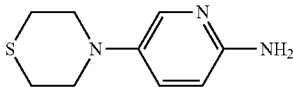 [SMILES: Nc1ccc(N2CCSCC2)cn1]

5-thiomorpholinopyridin-2-amine was prepared in a manner similar to that used in the synthesis of 5-(4-methylpiperazin-1-yl) pyridin-2-amine. ¹HNMR (600 MHz, DMSO-d6) δ ppm 2.59-2.73 (m, 4H) 3.04-3.20 (m, 4H) 5.41 (s, 2H) 6.35 (d, J=8.78 Hz, 1H) 7.10 (dd, J=8.78, 2.93 Hz, 1H) 7.57 (d, J=2.64 Hz, 1H). LCMS (ESI) 196 (M+H).

Example 34

Synthesis of tert-butyl (4R)-5-(6-nitro-3-pyridyl)-2,5-diazabicyclo[2.2.1]heptane-2-carboxylate, Compound 34

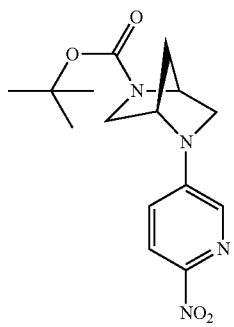 [SMILES: CC(C)(C)OC(=O)N1C[C@H]2CC1CN2c1ccc([N+](=O)[O-])nc1]

tert-butyl (4R)-5-(6-nitro-3-pyridyl)-2,5-diazabicyclo[2.2.1]heptane-2-carboxylate was synthesized in a manner similar to that used in the synthesis of 2-nitro-5-[4-(1-piperidyl)-1-piperidyl]pyridine. ¹HNMR (600 MHz, DMSO-d6) δ ppm 1.33 (d, J=32.21 Hz, 11H) 1.91 (m, 2H) 3.15 (d, J=10.25 Hz, 1H) 3.58 (m, 1H) 4.46 (m, 1H) 4.83 (s, 1H) 7.16 (s, 1H) 7.94 (s, 1H) 8.05-8.16 (m, 1H).

Example 35

Synthesis of tert-butyl (4R)-5-(6-amino-3-pyridyl)-2,5-diazabicyclo[2.2.1]heptane-2-carboxylate, Compound 35

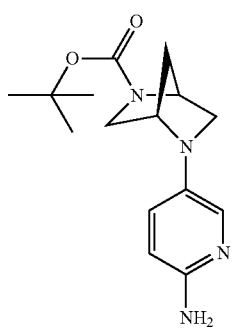

tert-butyl (4R)-5-(6-amino-3-pyridyl)-2,5-diazabicyclo[2.2.1]heptane-2-carboxylate was prepared in a manner similar to that used in the synthesis of 5-(4-methylpiperazin-1-yl)pyridin-2-amine. ¹HNMR (600 MHz, DMSO-d6) δ ppm 1.31 (d, J=31.91 Hz, 11H) 1.83 (m, 2H) 2.71-2.82 (m, 1H) 3.44 (m, 1H) 4.30 (d, 2H) 5.08 (s, 2H) 6.35 (d, J=8.78 Hz, 1H) 6.77-6.91 (m, 1H) 7.33 (s, 1H). LCMS (ESI) 291 (M+H).

Example 36

Synthesis of N,N-dimethyl-1-(6-nitro-3-pyridyl)piperidin-4-amine, Compound 36

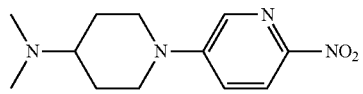 [SMILES: CN(C)C1CCN(c2ccc([N+](=O)[O-])nc2)CC1]

N,N-dimethyl-1-(6-nitro-3-pyridyl)piperidin-4-amine was synthesized in a manner similar to that used in the synthesis of 2-nitro-5-[4-(1-piperidyl)-1-piperidyl]pyridine. ¹HNMR (600 MHz, DMSO-d6) δ ppm 1.30-1.45 (m, 2H) 1.79 (m, 2H) 2.14 (s, 6H) 2.33 (m, 1H) 2.92-3.04 (m, 2H) 4.03 (d, J=13.76 Hz, 2H) 7.42 (dd, J=9.22, 3.07 Hz, 1H) 8.04-8.11 (m, 1H) 8.21 (d, J=2.93 Hz, 1H).

Example 37

Synthesis of 5-[4-(dimethylamino)-1-piperidyl]pyridin-2-amine, Compound 37

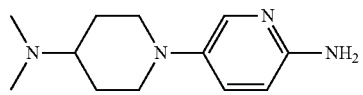

5-[4-(dimethylamino)-1-piperidyl]pyridin-2-amine was prepared in a manner similar to that used in the synthesis of 5-(4-methylpiperazin-1-yl)pyridin-2-amine. ¹HNMR (600 MHz, DMSO-d6) δ ppm 1.35-1.50 (m, 2H) 1.69-1.81 (m, 2H) 2.00-2.10 (m, 1H) 2.11-2.22 (s, 6H) 3.17-3.36 (m, 4H) 5.19-5.38 (s, 2H) 6.34 (d, J=8.78 Hz, 1H) 7.10 (dd, J=8.78, 2.93 Hz, 1H) 7.55 (d, J=2.63 Hz, 1H). LCMS (ESI) 221 (M+H).

Example 38

Synthesis of 4-(6-nitro-3-pyridyl) morpholine, Compound 38

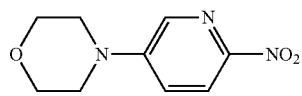 [SMILES: Nc1ccc(N2CCOCC2)cn1]

4-(6-nitro-3-pyridyl) morpholine was synthesized in a manner similar to that used in the synthesis of 2-nitro-5-[4-(1-piperidyl)-1-piperidyl] pyridine.

Example 39

Synthesis of 5-morpholinopyridin-2-amine, Compound 39

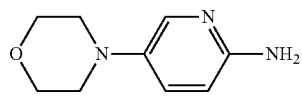

5-morpholinopyridin-2-amine was prepared in a manner similar to that used in the synthesis of 5-(4-methylpiperazin-1-yl) pyridin-2-amine. ¹HNMR (600 MHz, CHLOROFORM-d) δ ppm 2.91-3.00 (m, 4H) 3.76-3.84 (m, 4H) 4.19 (br. s., 2H) 6.45 (d, J=8.78 Hz, 1H) 7.12 (dd, J=8.78, 2.93 Hz, 1H) 7.72 (d, J=2.93 Hz, 1H).

Example 40

Synthesis of 5-(4-isobutylpiperazin-1-yl) pyridin-2-amine, Compound 40

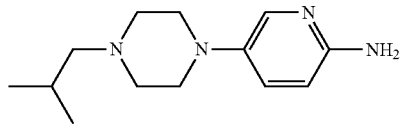 [SMILES: CC(C)CN1CCN(c2ccc(N)nc2)CC1]

1-isobutyl-4-(6-nitro-3-pyridyl)piperazine was synthesized in a manner similar to that used in the synthesis of 2-nitro-5-[4-(1-piperidyl)-1-piperidyl]pyridine which was then converted 5-(4-isobutylpiperazin-1-yl)pyridin-2-amine in a manner similar to that used in the synthesis of 5-(4-methylpiperazin-1-yl)pyridin-2-amine. ¹HNMR (600 MHz, CHLOROFORM-d) δ ppm 0.88 (d, J=6.73 Hz, 6H) 1.71-1.84 (m, 1H) 2.10 (d, J=7.32 Hz, 2H) 2.46-2.58 (m, 4H) 2.97-3.07 (m, 4H) 4.12 (s, 2H) 6.45 (d, J=8.78 Hz, 1H) 7.14 (dd, J=8.78, 2.93 Hz, 1H) 7.75 (d, J=2.93 Hz, 1H). LCMS (ESI) 235 (M+H).

Example 41

Synthesis of 5-(4-isopropylpiperazin-1-yl) pyridin-2-amine, Compound 41

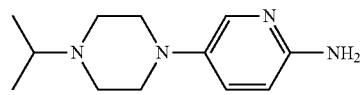

1-isopropyl-4-(6-nitro-3-pyridyl)piperazine was synthesized in a manner similar to that used in the synthesis of 2-nitro-5-[4-(1-piperidyl)-1-piperidyl]pyridine which was then converted to 5-(4-isopropylpiperazin-1-yl)pyridin-2-amine in a manner similar to that used in the synthesis of 5-(4-methylpiperazin-1-yl)pyridin-2-amine. ¹HNMR (600 MHz, CHLOROFORM-d) δ ppm 1.06 (d, J=6.44 Hz, 6H) 2.59-2.75 (m, 5H) 2.97-3.10 (m, 4H) 4.13 (s, 2H) 6.45 (d, J=8.78 Hz, 1H) 7.15 (dd, J=9.08, 2.93 Hz, 1H) 7.76 (d, J=2.93 Hz, 1H). LCMS (ESI) 221 (M+H).

Example 42

Synthesis of 5-[(2R,6S)-2,6-dimethylmorpholin-4-yl]pyridin-2-amine, Compound 42

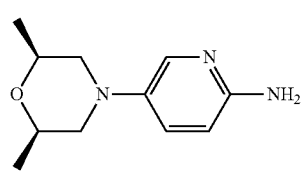

(2S,6R)-2,6-dimethyl-4-(6-nitro-3-pyridyl)morpholine was synthesized in a manner similar to that used in the synthesis of 2-nitro-5-[4-(1-piperidyl)-1-piperidyl]pyridine which was then converted to 5-[(2R,6S)-2,6-dimethylmorpholin-4-yl]pyridin-2-amine in a manner similar to that used in the synthesis of 5-(4-methylpiperazin-1-yl)pyridin-2-amine. ¹HNMR (600 MHz, CHLOROFORM-d) δ ppm 1.20 (d, J=6.44 Hz, 6H) 2.27-2.39 (m, 2H) 3.11-3.21 (m, 2H) 3.70-3.84 (m, 2H) 4.15 (s, 2H) 6.45 (d, J=8.78 Hz, 1H) 7.12 (dd, J=8.78, 2.93 Hz, 1H) 7.72 (d, J=2.63 Hz, 1H). LCMS (ESI) 208 (M+H).

Example 43

Synthesis of 5-[(3R,5S)-3,5-dimethylpiperazin-1-yl] pyridin-2-amine, Compound 43

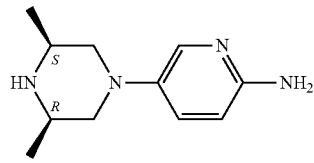

(3S,5R)-3,5-dimethyl-1-(6-nitro-3-pyridyl)piperazine was synthesized in a manner similar to that used in the synthesis of 2-nitro-5-[4-(1-piperidyl)-1-piperidyl]pyridine which was then converted to 5-[(3R,5S)-3,5-dimethylpiperazin-1-yl]pyridin-2-amine in a manner similar to that used in the synthesis of 5-(4-methylpiperazin-1-yl)pyridin-2-amine. ¹HNMR (600 MHz, CHLOROFORM-d) δ ppm 1.09 (d, J=6.44 Hz, 6H) 2.20 (t, J=10.83 Hz, 2H) 2.95-3.08 (m, 2H) 3.23 (dd, J=11.71, 2.05 Hz, 2H) 4.13 (s, 2H) 6.45 (d, J=8.78 Hz, 1H) 7.14 (dd, J=8.78, 2.93 Hz, 1H) 7.73 (d, J=2.63 Hz, 1H). LCMS (ESI) 207 (M+H).

Example 44

Synthesis of Compound 44

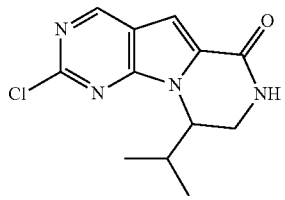 [SMILES: CC(C)C1CNC(=O)c2cc3cnc(Cl)nc3n21]

tert-butyl N-[2-[(5-bromo-2-chloro-pyrimidin-4-yl)amino]-3-methyl-butyl]carbamate

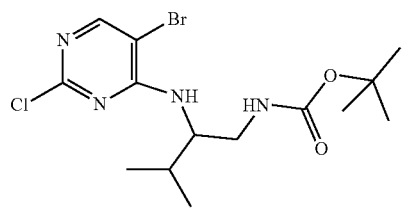 [SMILES: CC(C)C(CNC(=O)OC(C)(C)C)Nc1nc(Cl)ncc1Br]

A solution of intermediate A in ethanol (100 mL) was hydrogenated under 30 psi of hydrogen using 10% Pd/C (0.7 g) in a pressure bomb for 7 hrs. After filtration of the reaction mixture through CELITE™, the organic layer was concentrated under vacuum to afford tert-butyl N-(2-amino-3-methyl-butyl) carbamate (3.8 g).

To a solution of 5-bromo-2,4-dichloro-pyrimidine (7.11 g, 0.0312 mole) in ethanol (100 mL) was added diisopropylethyl amine (5.45 mL, 1.0 eq) and tert-butyl N-(2-amino-3-methyl-butyl) carbamate (6.31 g, 0.0312 mole). The reaction mixture was stirred at room temperature for 20 hrs. After concentration under vacuum, ethyl acetate and water were added. The organic layer was separated, dried with magnesium sulfate and then concentrated under vacuum. The crude product was purified by silica gel column chromatography using hexane/ethyl acetate (0-30%) to afford tert-butyl N-[2-[(5-bromo-2-chloro-pyrimidin-4-yl)amino]-3-methyl-butyl]carbamate. ¹HNMR (600 MHz, DMSO-d6) δ ppm 0.77-0.85 (d, J=6.5 Hz, 3H) 0.87 (d, J=6.73 Hz, 3H) 1.31-1.39 (m, 9H) 1.82-1.93 (m, 1H) 2.94 (d, J=5.56 Hz, 1H) 3.08-3.22 (m, 2H) 3.98 (d, J=8.20 Hz, 1H) 6.96 (d, J=8.78 Hz, 1H) 8.21 (s, 1H). LCMS (ESI) 393 (M+H).

tert-butyl N-[2-[2-chloro-6-(diethoxymethyl)pyrrolo[2,3-d]pyrimidin-7-yl]-3-methyl-butyl]carbamate

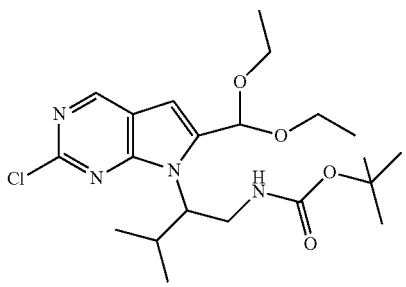 [SMILES: CCOC(OCC)c1cc2cnc(Cl)nc2n1C(CNC(=O)OC(C)(C)C)C(C)C]

tert-butyl N-[2-[2-chloro-6-(diethoxymethyl)pyrrolo[2,3-d]pyrimidin-7-yl]-3-methyl-butyl]carbamate was synthesized by hosting tert-butyl N-[2-[(5-bromo-2-chloro-pyrimidin-4-yl)amino]-3-methyl-butyl]carbamate to Sonogoshira conditions as described for tert-butyl N-[2-[[2-chloro-5-(3,3-diethoxyprop-1-ynyl)pyrimidin-4-yl]amino]ethyl]carbamate followed by subsequent treatment with TBAF as described in the synthesis of tert-butyl N-[2-[2-chloro-6-(diethoxymethyl)pyrrolo[2,3-d]pyrimidin-7-yl]ethyl]carbamate. ¹HNMR (600 MHz, DMSO-d6) δ ppm 1.11 (d, J=6.44 Hz, 3H) 1.18 (t, J=7.03 Hz, 6H) 1.21-1.26 (m, 12H) 2.88 (br. s., 1H) 3.43-3.78 (m, 6H) 3.97-4.08 (m, 1H) 5.61 (s, 1H) 6.65 (s, 1H) 6.71-6.78 (m, 1H) 8.87 (s, 1H). LCMS (ESI) 441 (M+H).

7-[1-[(tert-butoxycarbonylamino)methyl]-2-methyl-propyl]-2-chloro-pyrrolo[2,3-d]pyrimidine-6-carboxylic acid

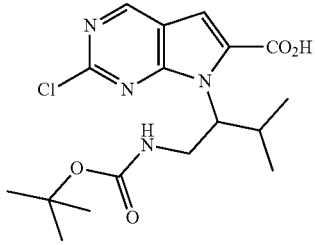 [SMILES: CC(C)C(CNC(=O)OC(C)(C)C)n1c(C(=O)O)cc2cnc(Cl)nc21]

To a solution tert-butyl N-[2-[[2-chloro-5-(3,3-diethoxy-prop-1-ynyl)pyrimidin-4-yl]amino]ethyl]carbamate in THF was added TBAF and the contents were heated at reflux for 3 hrs. Ethyl acetate and water were then added and the organic layer separated, dried with magnesium sulfate and then concentrated under vacuum. To this crude reaction was added acetic acid/water (9:1) and the contents were stirred for 12 hrs at room temperature. After concentration under vacuum, sat NaHCO₃ and ethyl acetate were added. The organic layer was separated, dried and then concentrated under vacuum. The crude reaction product thus obtained was dissolved in DMF, oxone was then added and the contents stirred for 3 hrs. After addition of ethyl acetate, the reaction mixture was filtered through CELITE™ and concentrated under vacuum. Column chromatography of the crude product over silica gel using hexane/ethyl acetate (0-100%) afforded 7-[1-[(tert-butoxycarbnylamino)methyl]-2-methyl-propyl]-2-chloro-pyrrrol[2,3-d]pyrimidine-6-carboxylic acid. 1HNMR (600 MHz, DMSO-d6) δ ppm 0.85 (d, J=7.03 Hz, 3H) 0.97 (d, J=6.73 Hz, 3H) 1.52 (s, 9H) 1.99-2.23 (m, 1H) 3.98 (dd, J=14.05, 3.51 Hz, 1H) 4.47-4.71 (m, 2H) 7.47 (s, 1H) 9.17 (s, 1H). LCMS (ESI) 383 (M+H).

Compound 44

To 7-[1-[(tert-butoxycarbonylamino)methyl]-2-methyl-propyl]-2-chloro-pyrrolo[2,3-d]pyrimidine-6-carboxylic acid (0.050 g, 0.00013 mole) in DCM (1.5 mL) was added DIC (32.7 mg) and DMAP (10 mg). The contents were stirred for 2 hrs. Trifluoroacetic acid (0.4 mL) was then added and stirring continued for an additional 30 minutes. After addition of satd NaHCO₃ to neutralize the excess acid, ethyl acetate was added and the organic layer separated, dried using magnesium sulfate and then concentrated under vacuum. The crude product was purified by silica gel column chromatography using hexane/ethyl acetate (0-100%) to afford the product. ¹HNMR (600 MHz, DMSO-d6) δ ppm 0.72 (d, J=6.73 Hz, 3H) 0.97 (d, J=6.73 Hz, 3H) 2.09-2.22 (m, 1H) 3.57 (dd, J=13.18, 4.98 Hz, 1H) 3.72 (dd, J=13.61, 4.25 Hz, 1H) 4.53 (dd, J=8.05, 3.95 Hz, 1H) 7.20 (s, 1H) 8.34 (d, J=4.98 Hz, 1H) 9.08 (s, 1H). LCMS (ESI) 265 (M+H).

Example 45

Synthesis of Compound 45

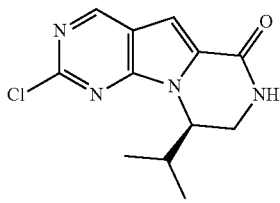 [SMILES: CC(C)[C@@H]1CNC(=O)c2cc3cnc(Cl)nc3n21]

Compound 14 was hydrogenated with 10% Pd/C to afford the intermediate tert-butyl N-[(2R)-2-amino-3-methyl-butyl]carbamate, which was then treated with 5-bromo-2,4-dichloro-pyrimidine using analogous reaction conditions as described for Compound 44 to afford Compound 45 The analytical data is consistent with that reported for the racemate (Intermediate 1A).

Example 46

Synthesis of Compound 46

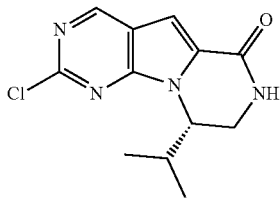 [SMILES: CC(C)[C@H]1CNC(=O)c2cc3cnc(Cl)nc3n21]

Compound 15 was hydrogenated with 10% Pd/C to afford the intermediate tert-butyl N-[(2S)-2-amino-3-methyl-butyl] carbamate, which was then treated with 5-bromo-2,4-dichloro-pyrimidine using analogous reaction conditions as described for Compound 44 to afford Compound 46. The analytical data (NMR and LCMS) was consistent with that reported for the racemate Compound 44.

Example 47

Synthesis of Compound 47

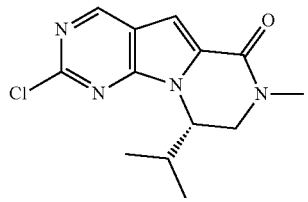 [SMILES: CC(C)[C@H]1CN(C)C(=O)c2cc3cnc(Cl)nc3n21]

To a solution of Compound 44 (80 mg, 0.00030 mole) in DMF (3 mL) was added a 60% dispersion of sodium hydride in oil (40 mg). After stirring for 15 minutes, methyl iodide (37 µL, 2 eq) was added. The contents were stirred at room temperature for 30 minutes. Saturated NaHCO₃ was then added followed by ethyl acetate. The organic layer was dried with magnesium sulfate and then concentrated under vacuum to afford the product. ¹HNMR (600 MHz, DMSO-d6) δ ppm 0.74 (d, J=6.73 Hz, 3H) 0.91 (d, J=6.73 Hz, 3H) 2.04-2.20 (m, 1H) 3.04 (s, 3H) 3.69 (dd, J=13.76, 1.17 Hz, 1H) 3.96 (dd, J=13.76, 4.68 Hz, 1H) 4.58 (dd, J=7.32, 3.51 Hz, 1H) 7.16 (s, 1H) 9.05 (s, 1H). LCMS (ESI) 279 (M+H).

Example 48

Synthesis of Compound 48

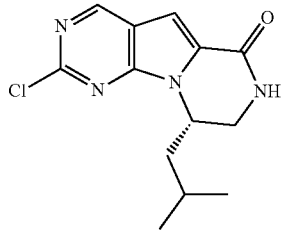 [SMILES: CC(C)C[C@H]1CNC(=O)c2cc3cnc(Cl)nc3n21]

tert-butyl N-[(2S)-2-[(5-bromo-2-chloro-pyrimidin-4-yl)amino]-4-methyl-pentyl]carbamate

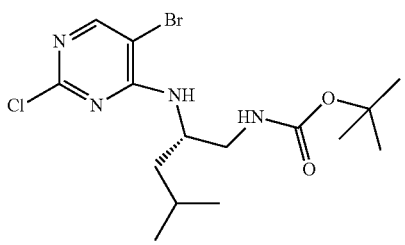 [SMILES: CC(C)C[C@@H](CNC(=O)OC(C)(C)C)Nc1nc(Cl)ncc1Br]

Compound 18 was hydrogenated with 10% Pd/C in ethanol under a blanket of hydrogen at 50 psi in a pressure bomb to afford tert-butyl N-[(2S)-2-amino-4-methyl-pentyl] carbamate which was then reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-4-methyl-pentyl]carbamate. ¹HNMR (600 MHz, CHLOROFORM-d) δ ppm 0.91 (d, J=6.44 Hz, 3H) 0.94 (d, J=6.44 Hz, 3H) 1.32-1.51 (m, 11H) 1.55-1.67 (m, 1H) 3.28 (t, J=5.86 Hz, 2H) 4.21-4.42 (m, 1H) 4.84 (s, 1H) 5.84 (d, J=7.32 Hz, 1H) 8.07 (s, 1H). LCMS (ESI) 407 (M+H).

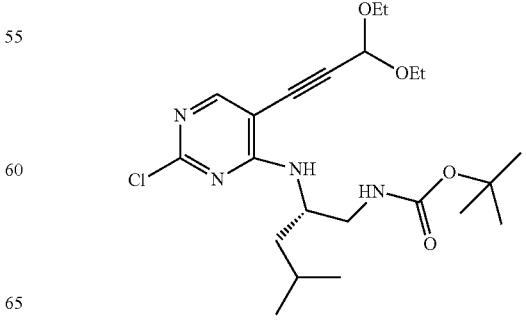

To a solution of tert-butyl N-[(2S)-2-[(5-bromo-2-chloro-pyrimidin-4-yl)amino]-4-methyl-pentyl]carbamate (5.0 g, 12.3 mmole) in tolune (36 mL) and triethylamine (7.2 mL) was added under nitrogen, 3,3-diethoxyprop-1-yne (2.8 mL, 19.7 mmole), Pd2(dba)3 (1.1 g, 1.23 mmole), and triphenylarsine (3.8 g, 12.3 mmole). The contents were heated to 70 degrees for 24 hrs. After cooling to room temperature, the reaction mixture was filtered through CELITE™ and then concentrated under vacuum. The crude product was purified by silica gel column chromatography using hexane/ethyl acetate (0-30%) to afford (2S)-N2-[2-chloro-5-(3,3-diethoxyprop-1-ynyl)pyrimidin-4-yl]-4-methyl-pentane-1,2-diamine. LCMS (ESI) 455 (M+H).

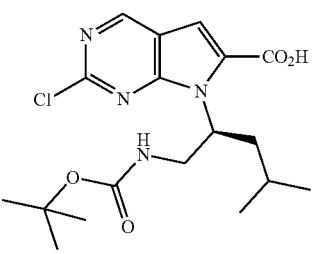 [SMILES: CC(C)C[C@@H](CNC(=O)OC(C)(C)C)n1c(C(=O)O)cc2cnc(Cl)nc21]

7-[(1S)-1-[(tert-butoxycarbonylamino)methyl]-3-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. ¹HNMR (600 MHz, DMSO-d6) δ ppm 0.88 (d, J=6.44 Hz, 3H) 0.97 (d, J=6.44 Hz, 3H) 1.47 (s, 9H) 1.49-1.54 (m, 1H) 1.56 (t, J=7.17 Hz, 2H) 3.98 (dd, J=13.91, 3.07 Hz, 1H) 3.76 (dd, J=13.31, 4.13 Hz, 1H) 4.38 (d, J=14.05 Hz, 1H) 4.90 (t, J=7.17 Hz, 1H) 7.41 (s, 1H) 9.11 (s, 1H). LCMS (M+H) 397.

Compound 48 was synthesized using an analogous synthetic sequence as that described for Compound 44. ¹HNMR (600 MHz, DMSO-d6) δ ppm 0.82 (d, J=6.73 Hz, 3H) 0.97 (d, J=6.44 Hz, 3H) 1.34-1.46 (m, 1H) 1.48-1.65 (m, 2H) 3.40 (dd, J=13.32, 5.42 Hz, 1H) 3.76 (dd, J=13.47, 4.10 Hz, 1H) 4.76-4.92 (m, 1H) 7.17 (s, 1H) 8.34 (d, J=5.27 Hz, 1H) 9.04 (s, 1H). LCMS (ESI) 279 (M+H).

Example 49

Synthesis of Compound 49

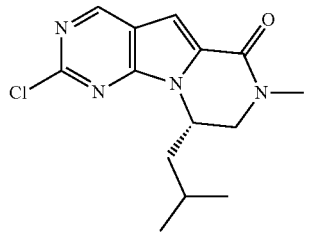 [SMILES: CC(C)C[C@H]1CN(C)C(=O)c2cc3cnc(Cl)nc3n21]

Compound 49 was synthesized in a manner similar to that described for Compound 47. ¹HNMR (600 MHz, DMSO-d6) δ ppm 0.82 (d, J=6.44 Hz, 3H) 0.97 (d, J=6.44 Hz, 3H) 1.37-1.68 (m, 3H) 3.04 (s, 3H) 3.56 (d, J=13.47 Hz, 1H) 4.00 (dd, J=13.32, 4.25 Hz, 1H) 4.82-4.94 (m, 1H) 7.16 (s, 1H) 9.03 (s, 1H). LCMS (ESI) 293 (M+H).

Example 50

Synthesis of Compound 50

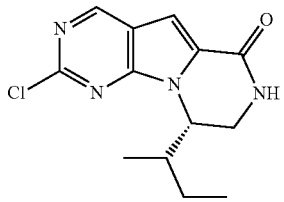 [SMILES: CCC(C)[C@H]1CNC(=O)c2cc3cnc(Cl)nc3n21]

tert-butyl N-[(2S)-2-[(5-bromo-2-chloro-pyrimidin-4-yl)amino]-3-methyl-pentyl]carbamate

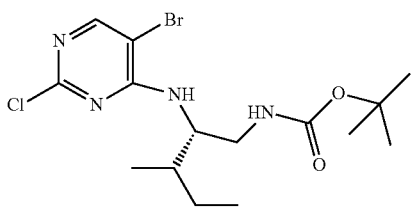 [SMILES: CCC(C)[C@@H](CNC(=O)OC(C)(C)C)Nc1nc(Cl)ncc1Br]

Compound 20 was hydrogenated using 10% Pd/C under hydrogen at 50 psi in a pressure vessel to afford tert-butyl N-[(2S)-2-amino-3-methyl-pentyl]carbamate which was reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-3-methyl-pentyl]carbamate. ¹HNMR (600 MHz, CHLOROFORM-d) δ ppm 0.88-0.95 (m, 6H) 1.11-1.20 (m, 1H) 1.34 (s, 9H) 1.44-1.54 (m, 1H) 1.64-1.72 (m, 1H) 3.17-3.27 (m, 1H) 3.33-3.43 (m, 1H) 4.11-4.21 (m, 1H) 4.81 (s, 1H) 5.92 (d, J=8.20 Hz, 1H) 8.05 (s, 1H). LCMS (ESI) 407.

tert-butyl N-[(2S)-2-[[2-chloro-5-(3,3-diethoxyprop-1-ynyl)pyrimidin-4-yl]amino]-3-methyl-pentyl]carbamate

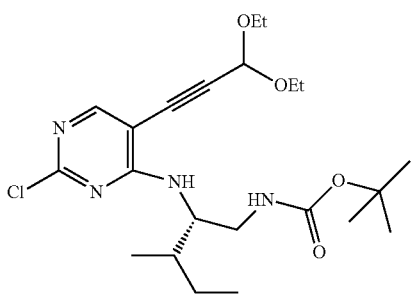 [SMILES: CCOC(C#Cc1cnc(Cl)nc1N[C@H](CNC(=O)OC(C)(C)C)C(C)CC)OCC]

tert-butyl N-[(2S)-2-[[2-chloro-5-(3,3-diethoxyprop-1-ynyl)pyrimidin-4-yl]amino]-3-methyl-pentyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2- diamine. ¹HNMR (600 MHz, DMSO-d6) δ ppm 0.76-0.89 (m, 6H) 1.03 (q, J=7.22 Hz, 3H) 1.10-1.17 (m, 3H) 1.25-1.42 (m, 11H) 1.59-1.73 (m, 1H) 3.35-3.47 (m, 4H) 3.51-3.73 (m, 2H) 3.99-4.11 (m, 1H) 5.52-5.56 (m, 1H) 6.76-7.03 (m, 2H) 8.12-8.23 (m, 1H). LCMS (ESI) 455 (M+H).

7-[(1S)-1-[(tert-butoxycarbonylamino)methyl]-2-methyl-butyl]-2-chloro-pyrrolo[2,3-d]pyrimidine-6-carboxylic acid

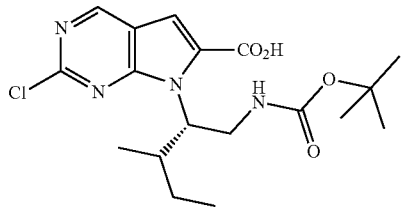 [SMILES: CCC(C)[C@@H](CNC(=O)OC(C)(C)C)n1c(C(=O)O)cc2cnc(Cl)nc21]

7-[(1S)-1-[(tert-butoxycarbonylamino)methyl]-2-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. ¹HNMR (600 MHz, DMSO-d6) δ ppm 0.80 (t, J=7.47 Hz, 3H) 0.86 (d, J=7.03 Hz, 3H) 1.06-1.30 (m, 2H) 1.48 (s, 9H) 1.79-1.96 (m, 1H) 3.95 (dd, J=14.05, 3.22 Hz, 1H) 4.52 (d, J=14.35 Hz, 1H) 4.61-4.73 (m, 1H) 7.43 (s, 1H) 9.13 (s, 1H). LCMS (ESI) 397 (M+H).

Compound 50 was synthesized using an analogous synthetic sequence as that described for Compound 44. ¹HNMR (600 MHz, DMSO-d6) δ ppm 0.74 (t, J=7.32 Hz, 3H) 0.89 (d, J=6.73 Hz, 3H) 1.00-1.12 (m, 2H) 1.82-1.94 (m, 1H) 3.55 (dd, J=13.91, 4.83 Hz, 1H) 3.70 (dd, J=13.61, 4.25 Hz, 1H) 4.57 (dd, J=7.91, 4.10 Hz, 1H) 7.17 (s, 1H) 8.31 (d, J=5.27 Hz, 1H) 9.05 (s, 1H). LCMS (ESI) 279 (M+H).

Example 51

Synthesis of Compound 51

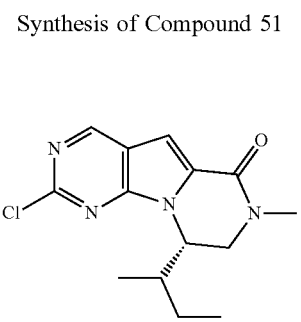

Compound 51 was synthesized in a manner similar to Compound 47. ¹HNMR (600 MHz, DMSO-d6) δ ppm 0.77 (t, J=7.47 Hz, 3H) 0.84 (d, J=6.73 Hz, 3H) 1.07-1.16 (m, 2H) 1.82-1.95 (m, 1H) 3.03 (s, 3H) 3.68 (d, J=13.76 Hz, 1H) 3.96 (dd, J=13.76, 4.39 Hz, 1H) 4.59-4.70 (m, 1H) 7.16 (s, 1H) 9.04 (s, 1H). LCMS (ESI) 293 (M+H).

Example 52

Synthesis of Compound 52

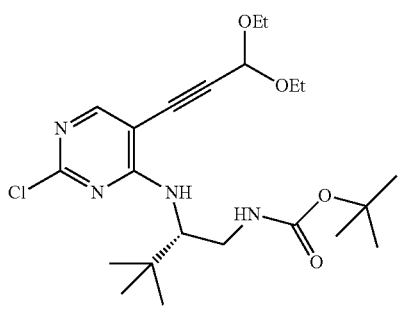 [SMILES: CCOC(C#Cc1cnc(Cl)nc1N[C@H](CNC(=O)OC(C)(C)C)C(C)(C)C)OCC]

tert-butyl N-[(2S)-2-[(5-bromo-2-chloro-pyrimidin-4-yl)amino]-3,3-dimethyl-butyl]carbamate Compound 21 was hydrogenated using 10% Pd/C under hydrogen at 50 psi in a pressure vessel to afford tert-butyl N-[(2S)-2-amino-3,3-dimethyl-butyl]carbamate which was then reacted with 5-bromo-2,4-dichloro-pyrimidine using analogous reaction conditions as described using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-3,3-dimethyl-butyl]carbamate. LCMS (ESI) 407 (M+H).

tert-butyl N-[(2S)-2-[[2-chloro-5-(3,3-diethoxyprop-1-ynyl)pyrimidin-4-yl]amino]-3,3-dimethyl-butyl]carbamate tert-butyl N-[(2S)-2-[[2-chloro-5-(3,3-diethoxyprop-1-ynyl)pyrimidin-4-yl]amino]-3,3-dimethyl-butyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. LCMS (ESI) 455 (M+H).

7-[(1S)-1-[(tert-butoxycarbonylamino)methyl]-2,2-dimethyl-propyl]-2-chloro-pyrrolo[2,3-d]pyrimidine-6-carboxylic acid tert-butyl N-[(2S)-2-[(5-bromo-2-chloro-pyrimidin-4-yl)amino]-2-phenyl-ethyl]carbamate

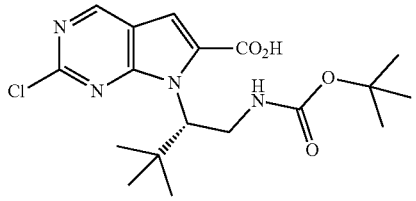 [SMILES: CC(C)(C)OC(=O)NC[C@@H](n1c(C(=O)O)cc2cnc(Cl)nc21)C(C)(C)C]

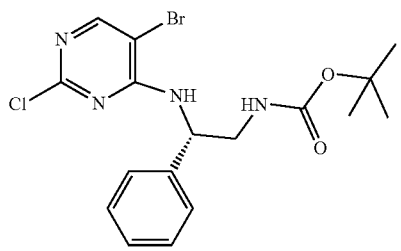

7-[(1S)-1-[(tert-butoxycarbonylamino)methyl]-2,2-dimethyl-propyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. LCMS (ESI) 397 (M+H). Intermediate 1F was synthesized using an analogous synthetic sequence as that described for intermediate 1A. LCMS (ESI) 279 (M+H).

Compound 21 was hydrogenated using 10% Pd/C under hydrogen at 50 psi in a pressure vessel to afford tert-butyl N-[(2S)-2-amino-2-phenyl-ethyl]carbamate which was then reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-2-phenyl-ethyl]carbamate. $^{1}$HNMR (600 MHz, DMSO-d6) δ ppm 1.32 (s, 9H) 3.29-3.50 (m, 2H) 5.12-5.24 (m, 1H) 7.10 (t, J=5.27 Hz, 1H) 7.21 (t, J=6.88 Hz, 1H) 7.26-7.34 (m, 4H) 7.89 (d, J=7.32 Hz, 1H) 8.24 (s, 1H). LCMS (ESI) 427 (M+H).

Example 53

Synthesis of Compound 53

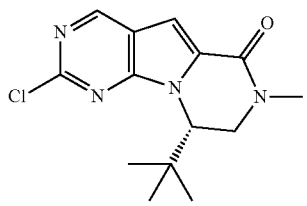 [SMILES: CN1C[C@H](C(C)(C)C)n2c(cc3cnc(Cl)nc32)C1=O]

tert-butyl N-[(2S)-2-[[2-chloro-5-(3,3-diethoxyprop-1-ynyl)pyrimidin-4-yl]amino]-2-phenyl-ethyl]carbamate Compound 53 was synthesized in a manner similar to that described for Intermediate 1CA. LCMS (ESI) 293 (M+H).

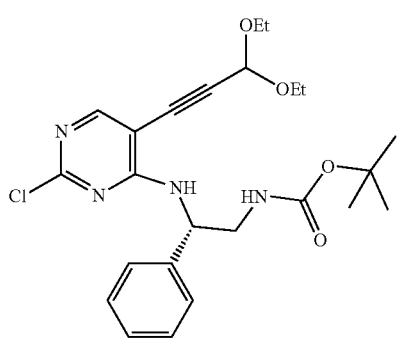

Example 54

Synthesis of Compound 54

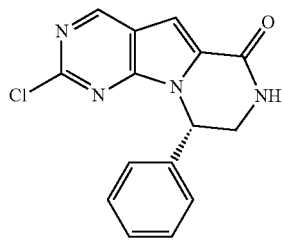 [SMILES: O=C1NC[C@H](c2ccccc2)n2c1cc1cnc(Cl)nc12]

tert-butyl N-[(2S)-2-[[2-chloro-5-(3,3-diethoxyprop-1-ynyl)pyrimidin-4-yl]amino]-2-phenyl-ethyl]carbamate was synthesized using similar experimental conditions to those used in the synthesis of (2S)-N2-[2-chloro-5-(3,3-diethoxyprop-1-ynyl)pyrimidin-4-yl]-4-methyl-pentane-1,2-diamine. $^{1}$HNMR (600 MHz, DMSO-d6) δ ppm 1.14 (t, J=7.03 Hz, 6H) 1.32 (s, 9H) 3.39 (s, 2H) 3.52-3.61 (m, 2H) 3.64-3.73 (m, 2H) 5.17-5.26 (m, 1H) 5.57 (s, 1H) 7.07-7.14 (m, 1H) 7.20-7.25 (m, 1H) 7.26-7.33 (m, 4H) 7.90 (d, J=7.61 Hz, 1H) 8.19 (s, 1H). LCMS (ESI) 475 (M+H).

7-[(1S)-2-(tert-butoxycarbonylamino)-1-phenyl-ethyl]-2-chloro-pyrrolo[2,3-d]pyrimidine-6-carboxylic acid

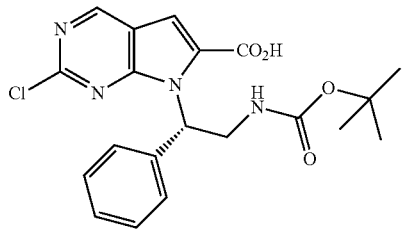 [SMILES: CC(C)(C)OC(=O)NC[C@H](c1ccccc1)n1c(C(=O)O)cc2cnc(Cl)nc21]

7-[(1S)-2-(tert-butoxycarbonylamino)-1-phenyl-ethyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. LCMS (ESI) 417 (M+H).

Compound 54

Compound 54 was synthesized using an analogous synthetic sequence as that described for Compound 44. $^1$HNMR (600 MHz, DMSO-d6) δ ppm 3.58-3.69 (m, 1H) 4.13 (dd, J=13.47, 4.39 Hz, 1H) 6.07 (d, J=3.81 Hz, 1H) 6.85 (d, J=7.32 Hz, 2H) 7.19-7.31 (m, 3H) 7.34 (s, 1H) 8.27 (d, J=5.27 Hz, 1H) 9.13 (s, 1H). LCMS (ESI) 299 (M+H).

Example 55

Synthesis of Compound 55

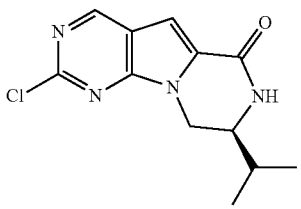 [SMILES: CC(C)[C@H]1Cn2c(cc3cnc(Cl)nc32)C(=O)N1]

tert-butyl N-[(1S)-1-[[(5-bromo-2-chloro-pyrimidin-4-yl)amino]methyl]-2-methyl-propyl]carbamate

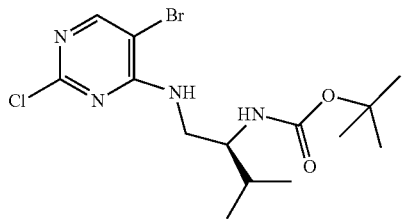 [SMILES: CC(C)[C@@H](CNc1nc(Cl)ncc1Br)NC(=O)OC(C)(C)C]

tert-butyl N-[(1S)-1-[[(5-bromo-2-chloro-pyrimidin-4-yl)amino]methyl]-2-methyl-propyl]carbamate was synthesized using 5-bromo-2,4-dichloro-pyrimidine and Intermediate E using analogous reaction conditions as described for tert-butyl N-[2-[(5-bromo-2-chloro-pyrimidin-4-yl)amino]-3-methyl-butyl]carbamate. $^1$HNMR (600 MHz, CHLOROFORM-d) δ ppm 0.95-1.02 (m, 6H) 1.35-1.45 (m, 9H) 1.75-1.90 (m, 1H) 3.35-3.48 (m, 1H) 3.52-3.61 (m, 1H) 3.64-3.76 (m, 1H) 4.56 (d, J=8.49 Hz, 1H) 6.47 (s, 1H) 8.07 (s, 1H). LCMS (ESI) 393 (M+H).

tert-butyl N-[(1S)-1-[[[2-chloro-5-(3,3-diethoxy-prop-1-ynyl)pyrimidin-4-yl]amino]methyl]-2-methyl-propyl]carbamate

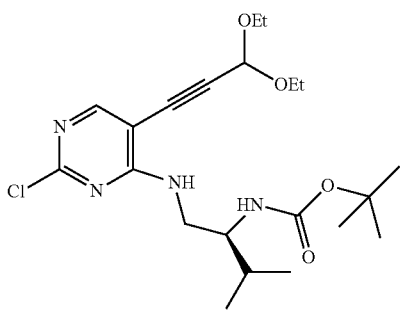 [SMILES: CCOC(C#Cc1cnc(Cl)nc1NC[C@@H](NC(=O)OC(C)(C)C)C(C)C)OCC]

tert-butyl N-[(1S)-1-[[[2-chloro-5-(3,3-diethoxypropyl-1-ynyl)pyrimidin-4-yl]amino]methyl]-2-methyl-propyl]carbamate was synthesized using similar experimental conditions to those used in the synthesis (2S)-N2-[2-chloro-5-(3,3-diethoxyprop-1-ynyl)pyrimidin-4-yl]-4-methyl-pentane-1,2-diamine. $^1$HNMR (600 MHz, CHLOROFORM-d) δ ppm 0.90-1.00 (m, 6H) 1.18-1.25 (m, 6H) 1.34-1.36 (m, 9H) 1.69-1.90 (m, 1H) 3.34-3.82 (m, 6H) 4.53-4.77 (m, 1H) 5.45-5.55 (m, 1H) 6.37 (dd, J=15.37, 6.59 Hz, 1H) 6.56 (s, 1H) 8.05 (s, 1H). LCMS (ESI) 441 (M+H).

7-[(2S)-2-(tert-butoxycarbonylamino)-3-methyl-butyl]-2-chloro-pyrrolo[2,3-d]pyrimidine-6-carboxylic acid

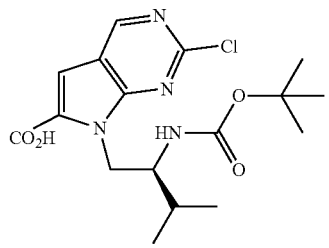 [SMILES: CC(C)[C@@H](Cn1c(C(=O)O)cc2cnc(Cl)nc21)NC(=O)OC(C)(C)C]

7-[(2S)-2-(tert-butoxycarbonylamino)-3-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, CHLOROFORM-d) δ ppm 0.90 (d, J=6.73 Hz, 3H) 0.96 (d, J=7.03 Hz, 3H) 1.55-1.66 (m, 10H) 4.14 (dd, J=13.61, 3.95 Hz, 1H) 4.52-4.63 (m, 1H) 4.84 (dd, J=13.61, 1.32 Hz, 1H) 7.37 (s, 1H) 8.95 (s, 1H). LCMS (ESI) 383 (M+H).

Compound 55

Compound 55 was synthesized using an analogous synthetic sequence as that described for Compound 44. LCMS (ESI) 265 (M+H).

Example 56

Synthesis of Compound 56

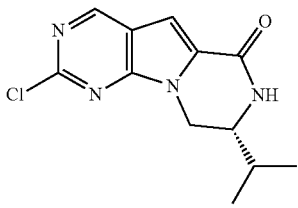 [SMILES: CC(C)[C@@H]1Cn2c(cc3cnc(Cl)nc32)C(=O)N1]

Compound 56 was synthesized using 5-bromo-2,4-dichloro-pyrimidine and Compound 17 as starting materials, and following a similar sequence of synthetic steps as for Compound 55. The analytical data was consistent with that described for its antipode (Compound 55). $^1$HNMR (600 MHz, DMSO-d6) δ ppm 0.88 (d, J=6.44 Hz, 6H) 1.73-1.86 (m, 1H) 3.67-3.76 (m, 2H) 4.11-4.21 (m, 1H) 7.13-7.19 (m, 1H) 8.56 (s, 1H) 9.05 (s, 1H). LCMS (ESI) 265 (M+H).

Example 57

Synthesis of Compound 57

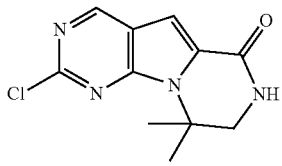 [SMILES: CC1(C)CNC(=O)c2cc3cnc(Cl)nc3n21]

tert-butyl N-[2-[(5-bromo-2-chloro-pyrimidin-4-yl)amino]-2-methyl-propyl]carbamate

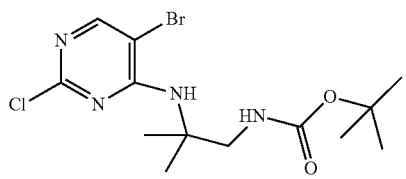 [SMILES: CC(C)(CNC(=O)OC(C)(C)C)Nc1nc(Cl)ncc1Br]

tert-butyl N-[2-[(5-bromo-2-chloro-pyrimidin-4-yl)amino]-2-methyl-propyl]carbamate was synthesized using 5-bromo-2,4-dichloro-pyrimidine and tert-butyl N-(2-amino-2-methyl-propyl)carbamate using analogous reaction conditions as described for tert-butyl N-[2-[(5-bromo-2-chloro-pyrimidin-4-yl)amino]-3-methyl-butyl]carbamate. LCMS (ESI) 379 (M+H).

tert-butyl N-[2-[[2-chloro-5-(3,3-diethoxyprop-1-ynyl)pyrimidin-4-yl]amino]-2-methyl-propyl]carbamate

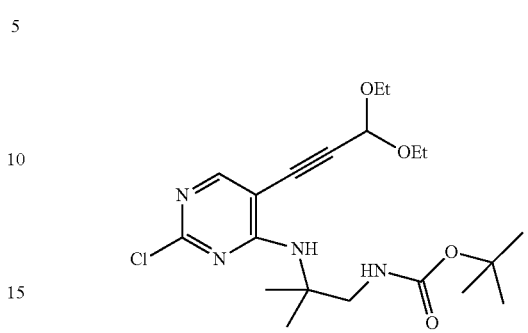

tert-butyl N-[2-[[2-chloro-5-(3,3-diethoxyprop-1-ynyl)pyrimidin-4-yl]amino]-2-methyl-propyl]carbamate was synthesized using similar experimental conditions to those used in the synthesis of (2S)-N2-[2-chloro-5-(3,3-diethoxyprop-1-ynyl)pyrimidin-4-yl]-4-methyl-pentane-1,2-diamine. $^1$HNMR (600 MHz, DMSO-d6) δ ppm 1.11-1.22 (m, 6H) 1.31-1.45 (m, 15H) 3.10-3.24 (m, 2H) 3.51-3.76 (m, 4H) 5.60 (s, 1H) 6.94 (s, 1H) 7.33 (t, J=6.44 Hz, 1H) 8.18 (s, 1H). LCMS (ESI) 427 (M+H).

7-[2-(tert-butoxycarbonylamino)-1,1-dimethyl-ethyl]-2-chloro-pyrrolo [2,3-d]pyrimidine-6-carboxylic acid

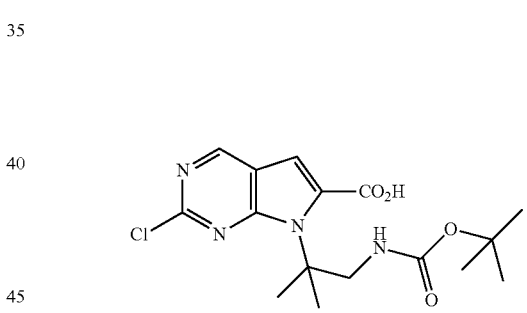

7-[2-(tert-butoxycarbonylamino)-1,1-dimethyl-ethyl]-2-chloro-pyrrolo [2,3-d]pyrimidine-6-carboxylic acid was synthesized using the analogous synthetic sequence as that described for 7-[1-[(tert-butoxycarbonylamino)methyl]-2-methyl-prpyl]-2-chloro-pyrroo[2,3-d]pyrimidine-6-carboxylic acid. $^1$HNMR (600 MHz, DMSO-d6) δ ppm 1.43 (s, 9H) 1.73 (s, 6H) 4.06 (s, 2H) 7.46 (s, 1H) 9.23 (s, 1H). LCMS (ESI) 369 (M+H).

Compound 57

Compound 57 was synthesized using an analogous synthetic sequence as that described for Compound 44. $^1$HNMR (600 MHz, DMSO-d6) δ ppm 1.73 (s, 6H) 3.50 (d, J=2.93 Hz, 2H) 7.25 (s, 1H) 8.46-8.55 (m, 1H) 9.07 (s, 1H). LCMS (ESI) 251 (M+H).

Example 58

Synthesis of Compound 58

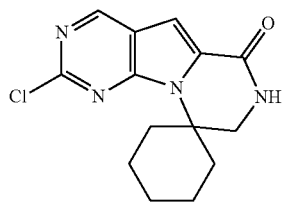 [SMILES: O=C1NCC2(CCCCC2)n2c1cc1cnc(Cl)nc12]

tert-butyl N-[[1-[(5-bromo-2-chloro-pyrimidin-4-yl)amino]cyclohexyl]methyl]carbamate

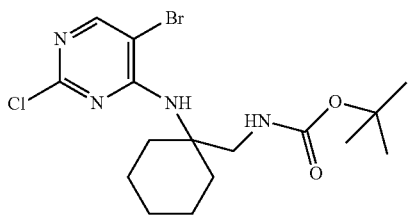 [SMILES: CC(C)(C)OC(=O)NCC1(Nc2nc(Cl)ncc2Br)CCCCC1]

tert-butyl N-[[1-[(5-bromo-2-chloro-pyrimidin-4-yl)amino]cyclohexyl]methyl]carbamate was synthesized using 5-bromo-2,4-dichloro-pyrimidine and Intermediate K using the analogous reaction conditions as described for tert-butyl N-[2-[(5-bromo-2-chloro-pyrimidin-4-yl)amino]-3-methyl-butyl]carbamate. $^1$HNMR (600 MHz, DMSO-d6) δ ppm 1.18-1.54 (m, 17H) 2.23 (d, J=14.35 Hz, 2H) 3.36 (d, J=6.44 Hz, 2H) 5.82 (s, 1H) 6.93 (s, 1H) 8.22 (s, 1H). LCMS (ESI) 419 (M+H).

tert-butyl N-[[1-[[2-chloro-5-(3,3-diethoxyprop-1-ynyl)pyrimidin-4-yl]amino]cyclohexyl]methyl]carbamate

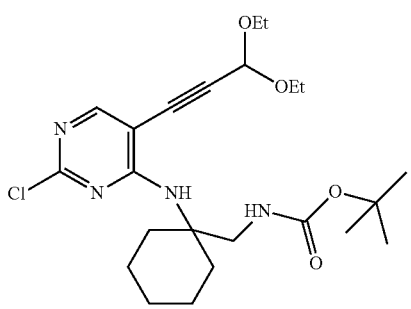 [SMILES: CCOC(C#Cc1cnc(Cl)nc1NC1(CNC(=O)OC(C)(C)C)CCCCC1)OCC]

tert-butyl N-[[1-[[2-chloro-5-(3,3-diethoxyprop-1-ynyl)pyrimidin-4-yl]amino]cyclohexyl]methyl]carbamate was synthesized using similar experimental conditions to those used in the synthesis of (2S)-N2-[2-chloro-5-(3,3-diethoxyprop-1-ynyl)pyrimidin-4-yl]-4-methyl-pentane-1,2-diamine. $^1$HNMR (600 MHz, DMSO-d6) δ ppm 1.08-1.16 (m, 6H) 1.17-1.54 (m, 17H) 2.13 (br. s., 2H) 3.36 (d, J=6.73 Hz, 2H) 3.50-3.69 (m, 4H) 5.72 (s, 1H) 6.94 (s, 1H) 5.72 (br. s., 1H) 8.17 (s, 1H). LCMS (ESI) 467 (M+H).

7-[1-[(tert-butoxycarbonylamino)methyl]cyclohexyl]-2-chloro-pyrrolo[2,3-d]pyrimidine-6-carboxylic acid

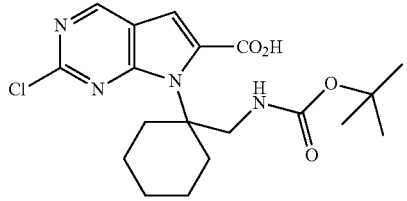 [SMILES: CC(C)(C)OC(=O)NCC1(n2c(C(=O)O)cc3cnc(Cl)nc32)CCCCC1]

7-[1-[(tert-butoxycarbonylamino)methyl]cyclohexyl]-2-chloro-pyrrol[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-d6) δ ppm 1.37-1.54 (m, 13H) 1.75 (br. s., 4H) 2.74 (br. s., 2H) 3.78-3.84 (m, 2H) 7.44-7.51 (m, 1H) 8.23 (s, 1H) 9.11 (s, 1H). LCMS (ESI) 409 (M+H).

Compound 58

Compound 58 was synthesized using an analogous synthetic sequence as that described for Compound 44. $^1$HNMR (600 MHz, DMSO-d6) δ ppm 1.28 (br. s., 2H) 1.42 (br. s., 2H) 1.70 (br. s., 4H) 1.85-1.95 (m, 2H) 2.69 (m, 2H) 7.16-7.25 (m, 1H) 8.41 (br. s., 1H) 9.04 (s, 1H). LCMS 291 (M+H).

Example 59

Synthesis of Compound 59

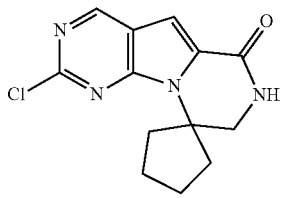 [SMILES: O=C1NCC2(CCCC2)n2c1cc1cnc(Cl)nc12]

tert-butyl N-[[1-[(5-bromo-2-chloro-pyrimidin-4-yl)amino]cyclopentyl]methyl]carbamate

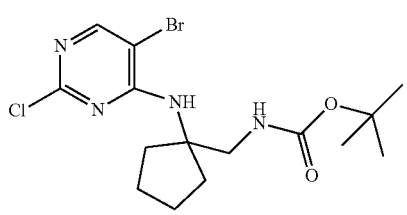 [SMILES: CC(C)(C)OC(=O)NCC1(Nc2nc(Cl)ncc2Br)CCCC1]

tert-butyl N-[[1-[(5-bromo-2-chloro-pyrimidin-4-yl)amino]cyclopentyl] methyl]carbamate was synthesized using 5-bromo-2,4-dichloro-pyrimidine and Intermediate L using analogous reaction conditions as described for tert-butyl N-[2-[(5-bromo-2-chloro-pyrimidin-4-yl)amino]-3-methyl-butyl]carbamate. ¹HNMR (600 MHz, DMSO-d6) δ ppm 1.34 (s, 9H) 1.50-1.58 (m, 2H) 1.63-1.78 (m, 4H) 1.96-2.06 (m, 2H) 3.25 (d, J=6.15 Hz, 2H) 6.71 (s, 1H) 7.18 (t, J=6.29 Hz, 1H) 8.20 (s, 1H). LCMS (ESI) 405 (M+H).

tert-butyl N-[[1-[[2-chloro-5-(3,3-diethoxyprop-1-ynyl)pyrimidin-4-yl]amino]cyclopentyl]methyl]carbamate

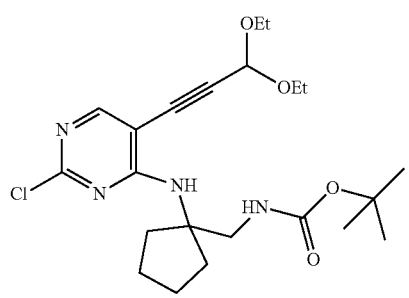 [SMILES: CCOC(C#Cc1cnc(Cl)nc1NC1(CNC(=O)OC(C)(C)C)CCCC1)OCC]

tert-butyl N-[[1-[[2-chloro-5-(3,3-diethoxyprop-1-ynyl)pyrimidin-4-yl]amino]cyclopentyl]methyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. LCMS (ESI) 453 (M+H).

7-[1-[(tert-butoxycarbonylamino)methyl]cyclopentyl]-2-chloro-pyrrolo[2,3-d]pyrimidine-6-carboxylic acid

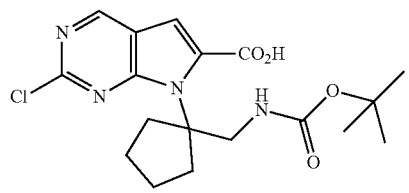 [SMILES: CC(C)(C)OC(=O)NCC1(n2c(C(=O)O)cc3cnc(Cl)nc32)CCCC1]

7-[1-[(tert-butoxycarbonylamino)methyl]cyclopentyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. ¹HNMR (600 MHz, DMSO-d6) δ ppm 1.47 (s, 9H) 1.74 (br. s., 2H) 1.88 (br. s., 2H) 2.04 (br. s., 2H) 2.41-2.45 (m, 2H) 4.06 (s, 2H) 7.45 (s, 1H) 9.11 (s, 1H). LCMS (ESI) 395 (M+H).

Compound 59

Compound 59 was synthesized using an analogous synthetic sequence as that described for Compound 44. ¹HNMR (600 MHz, DMSO-d6) δ ppm 1.72 (br. s., 2H) 1.86-1.93 (m, 2H) 1.99 (d, J=3.81 Hz, 2H) 2.40 (br. s., 2H) 3.48 (d, J=2.34 Hz, 2H) 7.22 (s, 1H) 8.53 (br. s., 1H) 9.05 (s, 1H). LCMS (ESI) 277 (M+H).

Example 60

Synthesis of Compound 60

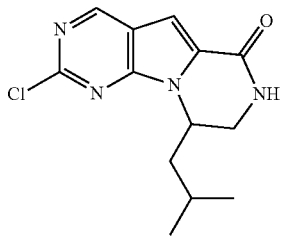 [SMILES: CC(C)CC1CNC(=O)c2cc3cnc(Cl)nc3n21]

tert-butyl N-[2-[(5-bromo-2-chloro-pyrimidin-4-yl)amino]-4-methyl-pentyl]carbamate

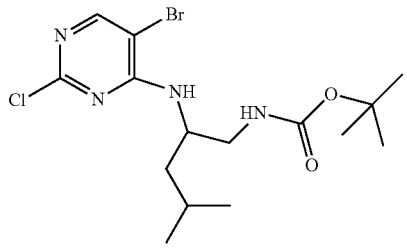 [SMILES: CC(C)CC(CNC(=O)OC(C)(C)C)Nc1nc(Cl)ncc1Br]

tert-butyl N-[2-[(5-bromo-2-chloro-pyrimidin-4-yl)amino]-4-methyl-pentyl]carbamate was synthesized using 5-bromo-2,4-dichloro-pyrimidine and Intermediate B using analogous reaction conditions as described for tert-butyl N-[2-[(5-bromo-2-chloro-pyrimidin-4-yl)amino]-3-methyl-butyl]carbamate. The analytical data is consistent with that described for the L-enantiomer. tert-butyl N-[2-[[2-chloro-5-(3,3-diethoxyprop-1-ynyl)pyrimidin-4-yl]amino]-4-methyl-pentyl]carbamate

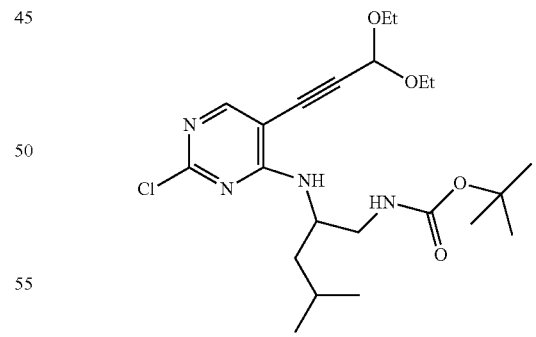

tert-butyl N-[2-[[2-chloro-5-(3,3-diethoxyprop-1-ynyl)pyrimidin-4-yl]amino]-4-methyl-pentyl]carbamate was synthesized using similar experimental conditions to that used in the synthesis of tert-butyl N-[2-[[2-chloro-5-(3,3-diethoxyprop-1-ynyl)pyrimidin-4-yl]amino]ethyl]carbamate. ¹HNMR (600 MHz, CHLOROFORM-d) δ ppm 1.21-1.31 (m, 12H) 1.38-1.46 (m, 11H) 1.70 (m, 1H) 3.24 (m, 2H) 3.65-3.82 (m, 4H) 4.86 (br s., 1H) 5.65 (s, 1H) 5.85 (br s., 1H) 6.94 (s, 1H) 8.21 (s, 1H). LCMS (ESI) 455 (M+H).

7-[1-[(tert-butoxycarbonylamino)methyl]-3-methyl-butyl]-2-chloro-pyrrolo[2,3-d]pyrimidine-6-carboxylic acid

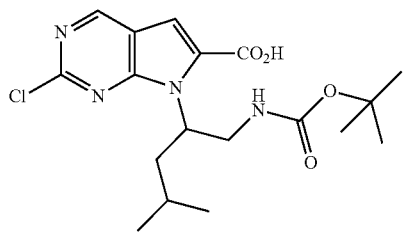 [SMILES: CC(C)CC(CNC(=O)OC(C)(C)C)n1c(C(=O)O)cc2cnc(Cl)nc21]

7-[1-[(tert-butoxycarbonylamino)methyl]-3-methyl-butyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. The analytical data was consistent with that described for the L-isomer.

Compound 60

Compound 60 was synthesized using an analogous synthetic sequence as that described for Compound 44. The analytical data was consistent with that described for the L-isomer.

Example 61

Synthesis of Compound 61

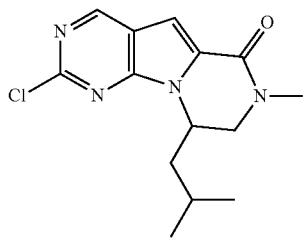 [SMILES: CC(C)CC1CN(C)C(=O)c2cc3cnc(Cl)nc3n21]

To a solution of Compound 60 (100 mg, 0.00024 mole) in DMF (3.0 mL) was added sodium hydride (60% dispersion in oil), (27.6 mg, 3 eq). After stirring for 15 mins, methyl iodide (30, 2 eq) was added. The contents were stirred at room temperature for 30 mins. After the addition of sat NaHCO$_3$, ethyl acetate was added. Separation of the organic layer followed by drying with magnesium sulfate and concentration under vacuum afforded the product. Analytical data was similar to the Compound 49.

Example 62

Synthesis of Compound 62

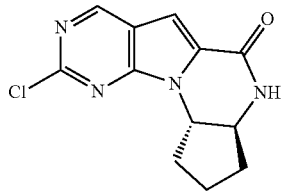 [SMILES: O=C1N[C@H]2CCC[C@@H]2n2c1cc1cnc(Cl)nc12]

tert-butyl N-[(1S,2S)-2-[(5-bromo-2-chloro-pyrimidin-4-yl)amino]cyclopentyl]carbamate

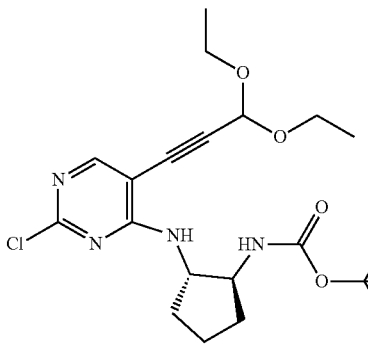

tert-butyl N-[(1S,2S)-2-[(5-bromo-2-chloro-pyrimidin-4-yl)amino]cyclopentyl]carbamate was synthesized by treating tert-butyl N-[(1S,2S)-2-aminocyclopentyl]carbamate with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate. $^1$HNMR (600 MHz, DMSO-d6) δ ppm 1.27 (s, 9H) 1.42-1.54 (m, 2H) 1.56-1.65 (m, 2H) 1.80-1.88 (m, 1H) 1.96-2.01 (m, 1H) 3.88-3.96 (m, 1H) 4.03-4.09 (m, 1H) 6.91 (d, J=8.20 Hz, 1H) 7.41 (d, J=7.32 Hz, 1H) 8.18 (s, 1H). LCMS (ESI) 391 (M+H).

tert-butyl N-[(1S,2S)-2-[[2-chloro-5-(3,3-diethoxy-prop-1-ynyl)pyrimidin-4-yl]amino]cyclopentyl]carbamate tert-butyl N-[(1S,2S)-2-[[2-chloro-5-(3,3-diethoxyprop-1-ynyl)pyrimidin-4-yl]amino]cyclopentyl]carbamate was synthesized using similar experimental conditions to that used in the synthesis of (2S)-N2-[2-chloro-5-(3,3-diethoxy-prop-1-ynyl)pyrimidin-4-yl]-4-methyl-pentane-1,2-diamine. 1HNMR (600 MHz, DMSO-d6) δ ppm 1.13 (t, 6H) 1.28 (s, 9H) 1.42-1.52 (m, 2H) 1.58-1.65 (m, 2H) 1.81-1.90 (m, 1H) 1.99-2.08 (m, 1H) 3.49-3.60 (m, 2H) 3.63-3.71 (m, 2H) 3.84-3.93 (m, 1H) 3.96-4.04 (m, 1H) 5.53 (s, 1H) 6.96 (d, J=7.90 Hz, 1H) 7.34 (d, J=7.03 Hz, 1H) 8.14 (s, 1H). LCMS (ESI) 439 (M+H).

7-[(1S,2S)-2-(tert-butoxycarbonylamino)cyclopentyl]-2-chloro-pyrrolo[2,3-d]pyrimidine-6-carboxylic acid

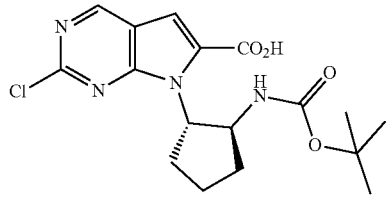 [SMILES: CC(C)(C)OC(=O)N[C@H]1CCC[C@@H]1n1c(C(=O)O)cc2cnc(Cl)nc21]

7-[(1S,2S)-2-(tert-butoxycarbonylamino)cyclopentyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-d6) δ ppm 1.41-1.52 (m, 9H) 1.55-1.68 (m, 1H) 1.88-2.00 (m, 2H) 2.05-2.15 (m, 1H) 2.26-2.35 (m, 1H) 2.71-2.89 (m, 1H) 4.01-4.16 (m, 1H) 4.28-4.45 (m, 1H) 7.41 (s, 1H) 9.11 (s, 1H). LCMS (ESI) 381 (M+H).

Compound 62

Compound 62 was synthesized using an analogous synthetic sequence as that described for Compound 44. $^1$HNMR (600 MHz, DMSO-d6) δ ppm 1.48-1.60 (m, 1H) 1.88-1.98 (m, 3H) 1.99-2.08 (m, 1H) 2.66-2.75 (m, 1H) 3.63-3.74 (m, 1H) 3.99-4.12 (m, 1H) 7.21 (s, 1H) 8.89 (s, 1H) 9.04 (s, 1H). LCMS (ESI) 263 (M+H).

Example 63

Synthesis of Compound 63

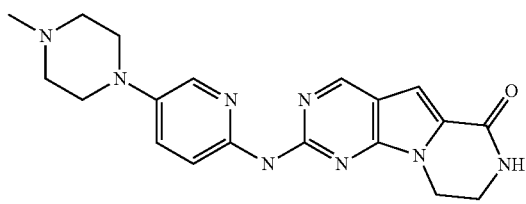 [SMILES: CN1CCN(c2ccc(Nc3ncc4cc5n(c4n3)CCNC5=O)nc2)CC1]

To chloro tricycliclactam (0.050 g, 0.225 mmole) in dioxane (2.0 mL) under nitrogen was added 5-(4-methylpiperazin-1-yl)pyridin-2-amine (0.052 g, 1.2 eq, 0.270 mmole) followed by the addition of Pd$_2$(dba)$_3$ (18.5 mg), BINAP (25 mg) and sodium-tert-butoxide (31 mg, 0.324 mmole). The contents of the flask are degassed for 10 minutes and then heated to 100 degrees for 12 hours. The crude reaction was loaded on a silica gel column and eluted with DCM/MeOH (0-15%) to afford the desired product (26 mg). To this compound dissolved in DCM/MeOH (10%) was added 3N HCl in iso-propanol (2 eq) and the reaction was stirred overnight. Concentration under vacuum afforded the hydrochloride salt. $^1$HNMR (d6-DMSO) δ ppm 11.13 (brs, 1H), 9.07 (s, 1H), 8.42 (s, 1H), 8.03 (br m 1H), 7.99 (s, 1H), 7.67 (brm, 1H), 7.18 (s, 1H), 4.33 (m, 2H), 3.79 (m, 2H), 3.64 (m, 2H), 3.50 (m, 2H), 3.16 (m, 4H), 2.79 (s, 3H). LCMS (ESI) 379 (M+H).

Example 64

Synthesis of Compound 64

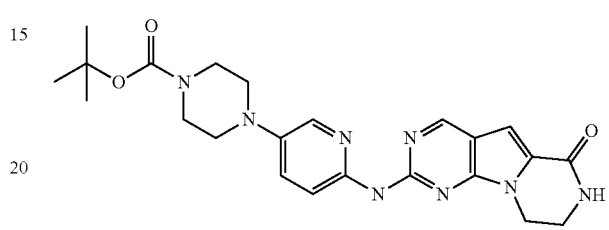

To chloro tricycliclactam (0.075 g, 0.338 mmole) in dioxane (3.5 mL) under nitrogen was added tert-butyl 4-(6-amino-3-pyridyl)piperazine-1-carboxylate (0.098 g, 1.05 eq) followed by the addition of Pd$_2$(dba)$_3$ (27 mg), BINAP (36 mg) and sodium-tert-butoxide (45 mg). The contents were heated at reflux for 11 hrs. The crude reaction was loaded onto a silica gel column and eluted with DCM/MeOH (0-10%) to afford the desired product (32 mg). $^1$HNMR (d6-DMSO) δ ppm 9.48 (s, 1H), 8.84 (s, 1H), 8.29 (s, 1H), 8.18 (s, 1H), 7.99 (s, 1H), 7.42 (m, 1H), 6.98 (s, 1H), 4.23 (m, 2H), 3.59 (m, 2H), 3.45 (m, 4H), 3.50 (m, 2H), 3.05 (m, 4H). LCMS (ESI) 465 (M+H).

Example 65

Synthesis of Compound 65

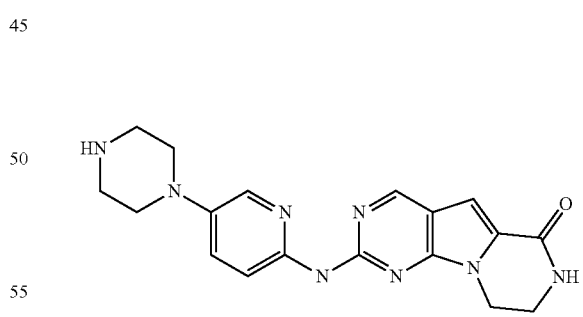

To a solution of Compound 64 (23 mg) in 10% DCM/MeOH was added 10 mL of a 3M solution of HCl in iso-propanol. The contents were stirred for 16 hrs. Concentration of the reaction mixture afforded the hydrochloride salt. $^1$HNMR (d6-DMSO) δ ppm 9.01 (s, 1H), 7.94 (m, 1H), 7.86 (m, 1H), 7.23 (s, 1H), 4.30 (m, 2H), 3.64 (m, 2H), 3.36 (m, 4H), 3.25 (m, 4H). LCMS (ESI) 465 (M+H).

Example 66

Synthesis of Compound 66

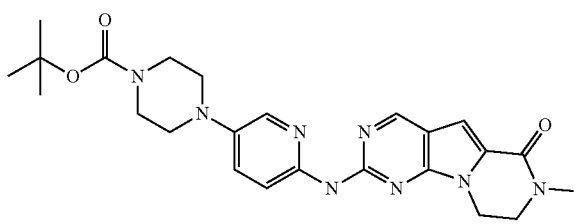 [SMILES: CN1CCn2c(cc3cnc(Nc4ccc(N5CCN(C(=O)OC(C)(C)C)CC5)cn4)nc32)C1=O]

To chloro-N-methyltricyclic amide (0.080 g, 0.338 mmole) in dioxane (3.5 mL) under nitrogen was added tert-butyl 4-(6-amino-3-pyridyl)piperazine-1-carboxylate 0.102 g (1.1 eq) followed by the addition of Pd$_2$(dba)$_3$ (27 mg), BINAP (36 mg) and sodium-tert-butoxide (45 mg). The contents were heated at reflux for 11 hrs. The crude product was purified using silica gel column chromatography with an eluent of dichloromethane/methanol (0-5%) to afford the desired product (44 mg). $^1$HNMR (d6-DMSO) δ ppm 9.49 (s, 1H), 8.85 (s, 1H), 8.32 (m, 1H), 8.02 (s, 1H), 7.44 (m, 1H), 7.00 (s, 1H), 4.33 (m, 2H), 3.80 (m, 2H), 3.48 (m, 4H), 3.07 (m, 4H), 3.05 (s, 3H), 1.42 (s, 9H). LCMS (ESI) 479 (M+H).

Example 67

Synthesis of Compound 67

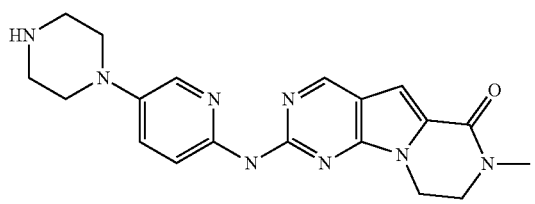 [SMILES: CN1CCn2c(cc3cnc(Nc4ccc(N5CCNCC5)cn4)nc32)C1=O]

To Compound 66 (32 mg) was added 3N HCL (10 mL) in isopropanol and the contents were stirred at room temperature overnight for 16 hrs. Concentration afforded the hydrochloride salt. $^1$HNMR (d6-DMSO) δ ppm 9.13 (m, 2H), 8.11 (m, 1H), 8.10 (s, 1H), 7.62 (m, 1H), 7.21 (s, 1H), 4.43 (m, 2H), 3.85 (m, 2H), 3.41 (m, 4H), 3.28 (m, 4H), 3.08 (s, 3H). LCMS (ESI) 379 (M+H).

Example 68

Synthesis of Compound 68

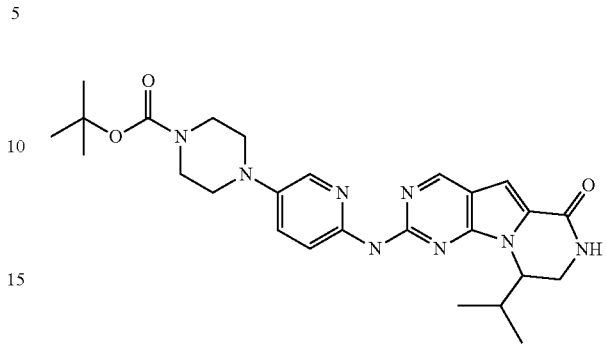

Compound 68 was synthesized using similar experimental conditions to that described for compound 64. $^1$HNMR (600 MHz, DMSO-d6) δ ppm 0.79 (d, J=7.03 Hz, 3H) 1.01 (d, J=6.73 Hz, 3H) 1.35-1.48 (m, 9H) 2.16 (dd, J=14.64, 6.73 Hz, 1H) 3.00-3.14 (m, 4H) 3.40-3.51 (m, 4H) 3.51-3.60 (m, 1H) 3.63-3.74 (m, 1H) 4.44 (dd, J=7.90, 3.81 Hz, 1H) 6.99 (s, 1H) 7.46 (dd, J=8.93, 2.78 Hz, 1H) 7.94-8.09 (m, 2H) 8.31 (dd, J=9.08, 1.46 Hz, 1H) 8.85 (s, 1H) 9.46 (s, 1H). LCMS (ESI) 507 (M+H).

Example 69

Synthesis of Compound 69

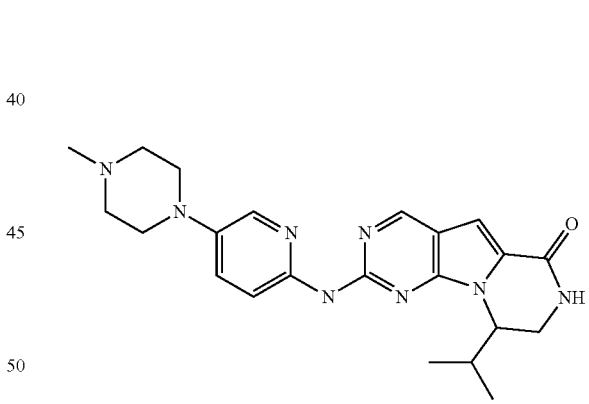

Compound 69 was synthesized using similar experimental conditions to those described for compound 63 and was recovered as an HCl salt. 1HNMR (600 MHz, DMSO-d6) δ ppm 0.77-0.86 (m, 3H) 0.96 (d, J=7.03 Hz, 3H) 2.10-2.24 (m, 1H) 3.07 (s, 3H) 3.37-3.79 (m, 8H) 4.00 (dd, J=13.61, 4.54 Hz, 2H) 4.63-4.73 (m, 1H) 7.20 (s, 1H) 7.58-7.71 (m, 1H) 7.99 (d, J=2.34 Hz, 1H) 8.12 (d, J=9.37 Hz, 1H) 9.11 (s, 1H) 9.41 (br. s., 2H) 11.76 (br. s., 1H). LCMS (ESI) 421 (M+H).

Example 70

Synthesis of Compound 70

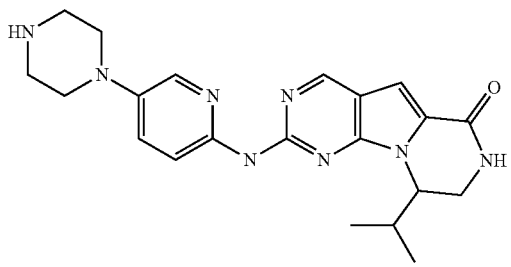 [SMILES: CC(C)C1CNC(=O)c2cc3cnc(Nc4ccc(N5CCNCC5)cn4)nc3n21]

Compound 70 was synthesized using similar experimental conditions to those described for compounds 64 and 65 and was recovered as an HCl salt. The characterization data (NMR and LCMS) was consistent with that reported for compound 71.

Example 71

Synthesis of Compound 71

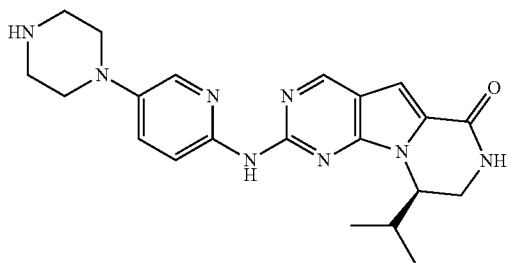 [SMILES: CC(C)[C@@H]1CNC(=O)c2cc3cnc(Nc4ccc(N5CCNCC5)cn4)nc3n21]

Compound 71 was synthesized using similar experimental conditions to those described for compounds 64 and 65 and was recovered as an HCl salt. $^1$HNMR (600 MHz, DMSO-d6) δ ppm 0.79 (d, J=6.73 Hz, 3H) 1.01 (d, J=6.73 Hz, 3H) 2.18 (dd, J=14.49, 7.17 Hz, 1H) 3.18-3.84 (m, 10H) 4.53-4.71 (m, 1H) 7.24 (s, 1H) 7.65 (d, J=9.37 Hz, 1H) 8.01 (d, J=2.64 Hz, 1H) 8.14 (d, J=1.46 Hz, 1H) 8.35 (d, J=5.27 Hz, 1H) 9.14 (s, 1H) 9.46 (s, 2H) 11.80 (s, 1H) LCMS (ESI) 407 (M+H).

Example 72

Synthesis of Compound 72 (Compound UUU)

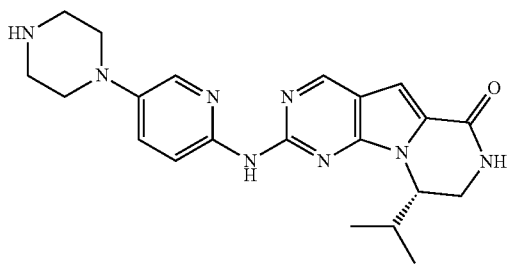

Compound 72 was synthesized using similar experimental conditions to that described for compounds 64 and 65 and was recovered as an HCl salt. $^1$HNMR (600 MHz, DMSO-d6) δ ppm 0.77 (d, J=7.03 Hz, 3H) 0.99 (d, J=6.73 Hz, 3H) 2.10-2.24 (m, 1H) 3.18-3.81 (m, 10H) 4.54-4.69 (m, 1H) 7.22 (s, 1H) 7.63 (d, J=9.08 Hz, 1H) 7.99 (d, J=2.63 Hz, 1H) 8.11 (s, 1H) 8.33 (d, J=5.27 Hz, 1H) 9.12 (s, 1H) 9.43 (s, 2H) 11.77 (s, 1H). LCMS (ESI) 407 (M+H).

Example 73

Synthesis of Compound 73

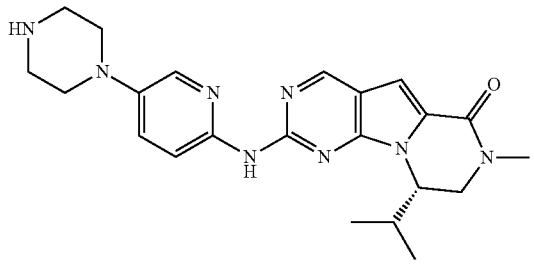 [SMILES: CC(C)[C@H]1CN(C)C(=O)c2cc3cnc(Nc4ccc(N5CCNCC5)cn4)nc3n21]

Compound 73 was synthesized using similar experimental conditions to those described for compounds 64 and 65 and was recovered as an HCl salt. $^1$HNMR (600 MHz, DMSO-d6) δ ppm 0.84 (d, J=6.73 Hz, 3H) 0.98 (d, J=6.73 Hz, 3H) 2.12-2.26 (m, 1H) 3.09 (s, 3H) 3.22-3.81 (m, 8H) 4.01 (dd, J=13.61, 4.25 Hz, 2H) 4.59-4.72 (m, 1H) 7.19 (s, 1H) 7.74 (s, 1H) 7.96-8.10 (m, 2H) 9.08 (s, 1H) 9.22 (s, 2H). LCMS (ESI) 421 (M+H).

Example 74

Synthesis of Compound 74

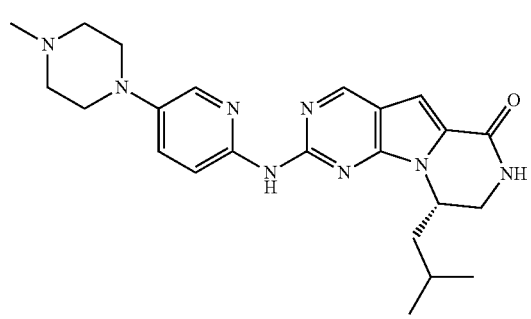 [SMILES: CC(C)C[C@H]1CNC(=O)c2cc3cnc(Nc4ccc(N5CCN(C)CC5)cn4)nc3n21]

Compound 74 was synthesized using similar experimental conditions to those described for compound 63 and was recovered as an HCl salt. $^1$HNMR (600 MHz, DMSO-d6) δ ppm 0.85 (d, J=4.98 Hz, 3H) 0.95 (d, J=4.98 Hz, 3H) 1.42-1.70 (m, 3H) 2.77 (d, J=2.93 Hz, 3H) 3.07-4.14 (m, 10H) 4.95 (s, 1H) 7.20 (s, 1H) 7.66 (d, J=9.66 Hz, 1H) 7.94 (s, 1H) 8.08-8.16 (m, 1H) 8.33 (d, J=4.68 Hz, 1H) 9.09 (s, 1H) 11.38 (s, 1H) 11.71 (s, 1H). LCMS (ESI) 435 (M+H).

Example 75

Synthesis of Compound 75

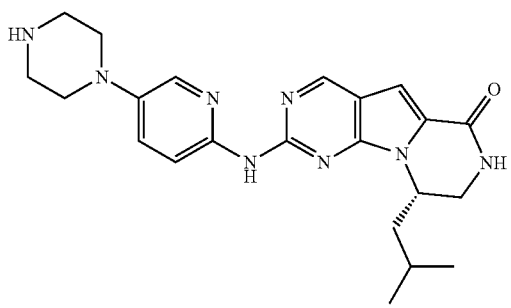 [SMILES: CC(C)C[C@H]1CNC(=O)c2cc3cnc(Nc4ccc(N5CCNCC5)cn4)nc3n21]

Compound 75 was synthesized using similar experimental conditions to those described for compounds 64 and 65 and was recovered as an HCl salt. $^1$HNMR (600 MHz, DMSO-d6) δ ppm 0.87 (d, J=6.15 Hz, 3H) 0.94 (d, J=6.15 Hz, 3H) 1.57 (d, J=84.61 Hz, 3H) 3.05 (s, 3H) 3.13-3.55 (m, 8H) 3.69 (d, J=78.17 Hz, 2H) 4.90 (s, 1H) 7.15 (s, 1H) 7.63-7.85 (m, 1H) 7.93 (s, 1H) 8.26 (s, 1H) 9.03 (s, 1H) 9.20 (s, 2H). LCMS (ESI) 421 (M+H).

Example 76

Synthesis of Compound 76

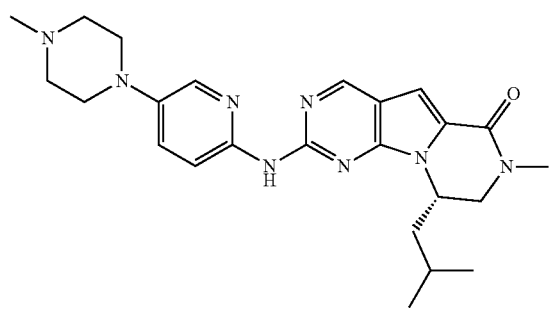

Compound 76 was synthesized using similar experimental conditions to those described for compound 63 and was recovered as an HCl salt. $^1$HNMR (600 MHz, DMSO-d6) δ ppm 0.85 (d, J=6.44 Hz, 3H) 0.95 (d, J=6.44 Hz, 3H) 1.43-1.70 (m, 3H) 2.78 (d, J=2.93 Hz, 3H) 3.05 (s, 3H) 3.24-3.84 (m, 8H) 4.01 (d, J=9.66 Hz, 2H) 4.89-5.01 (m, 1H) 7.15 (s, 1H) 7.77 (s, 1H) 7.91-8.05 (m, 2H) 9.03 (s, 1H) 10.96-11.55 (m, 2H). LCMS (ESI) 449 (M+H).

Example 77

Synthesis of Compound 77

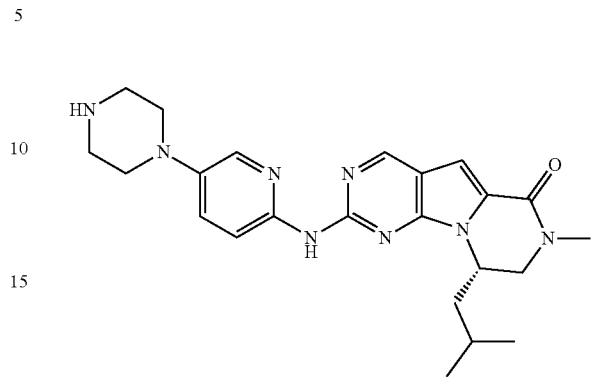

Compound 77 was synthesized using similar experimental conditions to those described for compounds 64 and 65 and was recovered as an HCl salt. $^1$HNMR (600 MHz, DMSO-d6) δ ppm 0.83-0.88 (d, J=6.15 Hz, 3H) 0.95 (d, J=6.15 Hz, 3H) 1.40-1.71 (m, 3H) 3.28-3.83 (m, 8H) 4.00 (d, J=3.22 Hz, 2H) 4.91-5.08 (m, 1H) 7.17 (s, 1H) 7.68 (d, J=9.66 Hz, 1H) 7.93 (s, 1H) 8.07 (s, 1H) 9.06 (s, 1H) 9.40 (s, 2H) 11.59 (s, 1H). LCMS (ESI) 435 (M+H).

Example 78

Synthesis of Compound 78

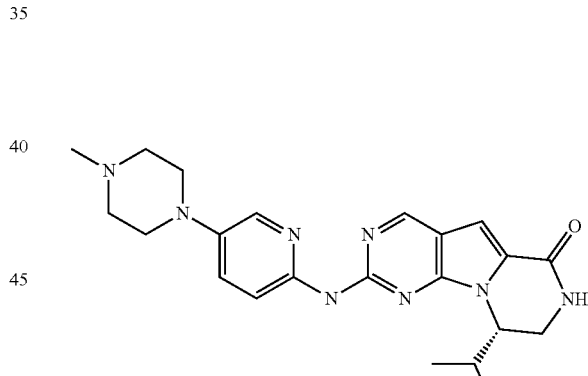

To Compound 50 0.060 g (0.205 mmole) was added 5-(4-methylpiperazin-1-yl)pyridin-2-amine (35.42 mg, 0.9 eq) followed by the addition of 1,4-dioxane (3 mL). After degassing with nitrogen, Pd$_2$dba$_3$ (12 mg), BINAP (16 mg) and sodium tert-butoxide (24 mg) were added. The contents were then heated at 90 degrees in a CEM Discovery microwave for 3 hrs. The reaction was then loaded onto a silica gel column and purified by eluting with DCM/MeOH (0-15%). 1HNMR (600 MHz, DMSO-d6) δ ppm 0.75 (t, J=7.47 Hz, 3H) 0.91 (d, J=6.73 Hz, 3H) 1.04-1.20 (m, 2H) 1.80-1.98 (m, 1H) 2.77 (d, J=3.81 Hz, 3H) 2.94-3.90 (m, 10H) 4.54-4.68 (m, 1H) 7.06-7.23 (m, 2H) 7.56-7.75 (m, 1H) 7.90-8.12 (m, 2H) 8.29 (s, 1H) 9.07 (s, 1H) 10.98-11.74 (m, 2H). LCMS (ESI) 435 (M+H).

Example 79

Synthesis of Compound 79

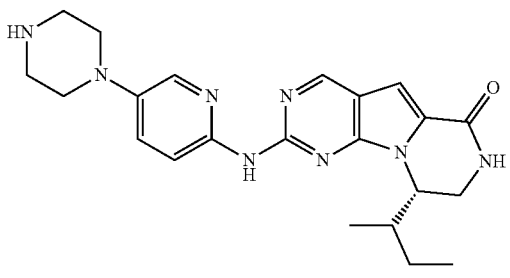 [SMILES: CCC(C)[C@H]1CNC(=O)c2cc3cnc(Nc4ccc(N5CCNCC5)cn4)nc3n21]

Compound 79 was synthesized in a similar manner to that described for compound 78 followed by the deblocking step described for compound 65 and was converted to an HCl salt. $^1$HNMR (600 MHz, DMSO-d6) δ ppm 0.75 (t, J=7.32 Hz, 3H) 0.90 (d, J=6.73 Hz, 3H) 1.07-1.15 (m, 2H) 1.85-1.94 (m, 1H) 3.17-3.75 (m, 10H) 4.58-4.67 (m, 1H) 7.17 (s, 1H) 7.71 (s, 1H) 7.96 (s, 1H) 7.98-8.05 (m, 1H) 8.28 (d, J=4.10 Hz, 1H) 9.06 (s, 1H) 9.39 (s, 2H). LCMS (ESI) 421 (M+H).

Example 80

Synthesis of Compound 80

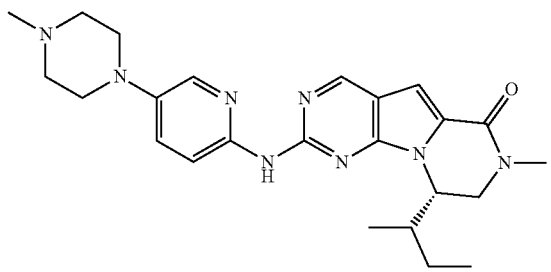

Compound 80 was synthesized in a similar manner to that described for compound 78. $^1$HNMR (600 MHz, DMSO-d6) δ ppm 0.78 (t, J=7.32 Hz, 3H) 0.86 (d, J=6.73 Hz, 3H) 1.13-1.21 (m, 2H) 1.84-1.96 (m, 1H) 2.77 (d, J=4.39 Hz, 3H) 3.04 (s, 3H) 3.11-3.84 (m, 8H) 3.98 (dd, J=13.61, 4.25 Hz, 2H) 4.66-4.74 (m, 1H) 7.17 (s, 1H) 7.64 (s, 1H) 7.96 (d, J=2.34 Hz, 1H) 8.03-8.13 (m, 1H) 9.08 (s, 1H) 11.26 (s, 1H) 11.66 (s, 1H). LCMS (ESI) 449 (M+H).

Example 81

Synthesis of Compound 81

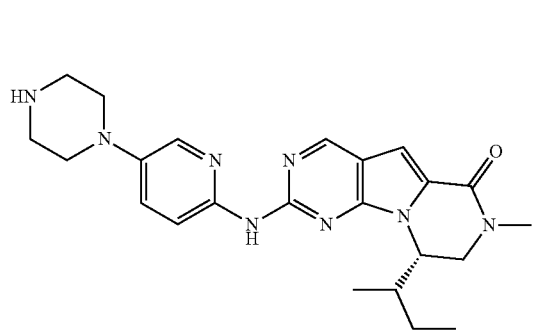 [SMILES: CCC(C)[C@H]1CN(C)C(=O)c2cc3cnc(Nc4ccc(N5CCNCC5)cn4)nc3n21]

The compound was synthesized in a similar manner to that described for compound 78 followed by the deblocking step described for compound 65 and was converted to an HCl salt. $^1$HNMR (600 MHz, DMSO-d6) δ ppm 0.78 (t, J=7.32 Hz, 3H) 0.85 (d, J=6.73 Hz, 3H) 1.10-1.27 (m, 2H) 1.82-1.99 (m, 1H) 3.04 (s, 3H) 3.28-3.77 (m, 8H) 3.97 (dd, J=13.91, 4.54 Hz, 2H) 4.62-4.75 (m, 1H) 7.07-7.24 (m, 1H) 7.62-7.75 (m, 1H) 7.94 (d, J=2.34 Hz, 1H) 7.97-8.08 (m, 1H) 9.05 (s, 1H) 9.29 (s, 2H). LCMS (ESI) 435 (M+H).

Example 82

Synthesis of Compound 82

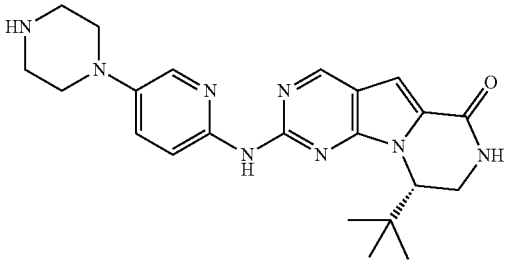 [SMILES: CC(C)(C)[C@H]1CNC(=O)c2cc3cnc(Nc4ccc(N5CCNCC5)cn4)nc3n21]

The compound was synthesized in a similar manner to that described for compound 78 followed by the deblocking step described for compound 65 and was converted to an HCl salt. $^1$HNMR (600 MHz, DMSO-d6) δ ppm 0.96 (s, 9H) 3.15-3.87 (m, 10H) 4.42-4.53 (m, 1H) 6.99 (s, 1H) 7.24 (s, 1H) 8.06 (s, 1H) 8.11-8.21 (m, 1H) 8.79-8.98 (m, 2H) 9.25 (s, 2H) 9.88 (s, 1H). LCMS (ESI) 421 (M+H).

Example 83

Synthesis of Compound 83

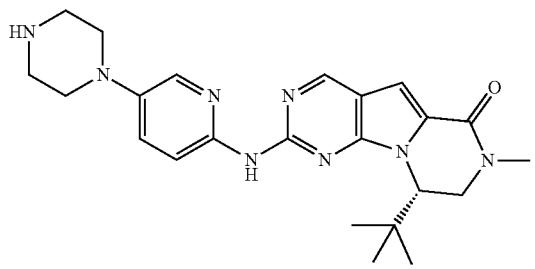 [SMILES: CN1C[C@H](C(C)(C)C)n2c(cc3cnc(Nc4ccc(N5CCNCC5)cn4)nc32)C1=O]

Compound 83 was synthesized in a similar manner to that described for compound 78 followed by the deblocking step described for compound 65 and was converted to an HCl salt. $^1$HNMR (600 MHz, DMSO-d6) δ ppm 0.95 (s, 9H) 2.79 (d, J=4.10 Hz, 3H) 3.06-3.86 (m, 10H) 4.56-4.67 (m, 1H) 7.17 (s, 1H) 7.70 (s, 1H) 7.96 (d, J=2.63 Hz, 1H) 7.99-8.08 (m, 1H) 8.26 (s, 1H) 9.06 (s, 1H) 10.80 (s, 1H). LCMS (ESI) 435 (M+H).

Example 84

Synthesis of Compound 84

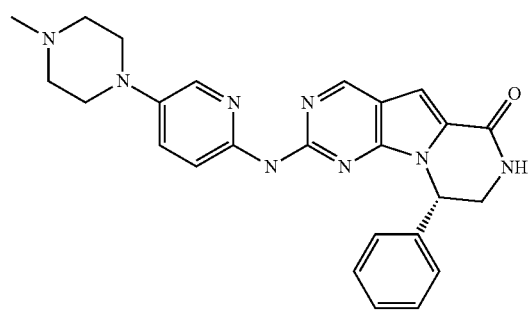 [SMILES: CN1CCN(c2ccc(Nc3ncc4cc5n(c4n3)[C@@H](c3ccccc3)CNC5=O)nc2)CC1]

Compound 84 was synthesized in a similar manner to that described for compound 78 and was converted to an HCl salt. $^1$HNMR (600 MHz, DMSO-d6) δ ppm 2.75-2.81 (m, 3H) 3.12-3.16 (m, 2H) 3.46-3.54 (m, 4H) 3.60-3.69 (m, 2H) 3.72-3.79 (m, 1H) 4.07-4.18 (m, 2H) 6.06-6.09 (m, 1H) 6.90 (d, J=7.61 Hz, 2H) 7.20-7.31 (m, 3H) 7.33 (s, 1H) 7.49-7.55 (m, 1H) 7.62-7.70 (m, 1H) 7.92 (d, J=2.93 Hz, 1H) 8.22 (s, 1H) 9.14 (s, 1H). LCMS (ESI) 455 (M+H).

Example 85

Synthesis of Compound 85

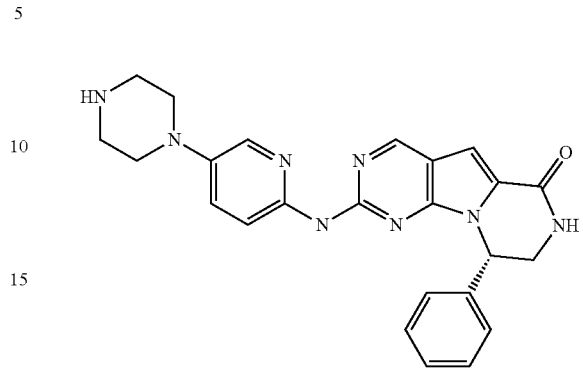

Compound 85 was synthesized in a similar manner to that described for compound 78 followed by the deblocking step described for compound 65 and was converted to an HCl salt. $^1$HNMR (600 MHz, DMSO-d6) δ ppm 3.21 (s, 4H) 3.35-3.67 (m, 5H) 4.07-4.20 (m, 2H) 6.13 (s, 1H) 6.90 (d, J=7.32 Hz, 2H) 7.22-7.31 (m, 3H) 7.36 (s, 1H) 7.48 (d, J=9.37 Hz, 1H) 7.93 (d, J=2.34 Hz, 1H) 8.04-8.11 (m, 1H) 8.25 (d, J=4.98 Hz, 1H) 9.17 (s, 1H) 11.77 (br, s., 1H). LCMS (ESI) 441 (M+H).

Example 86

Synthesis of Compound 86

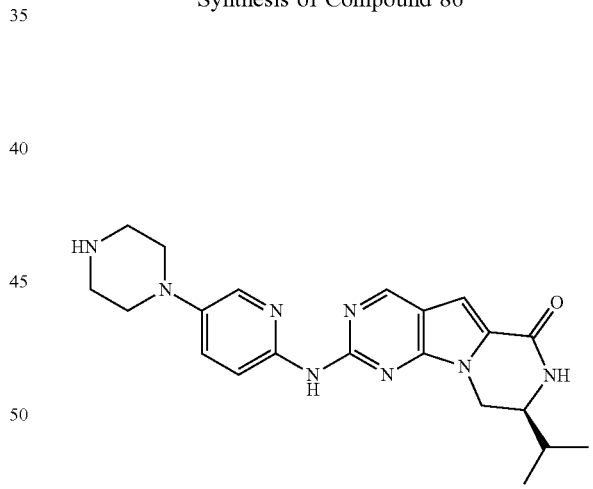

Compound 86 was synthesized in a similar manner to that described for compound 78 followed by the deblocking step described for compound 65 and was converted to an HCl salt. 1HNMR (600 MHz, DMSO-d6) δ ppm 0.90 (d, J=6.15 Hz, 6H) 1.72-1.89 (m, 1H) 3.15-3.92 (m, 9H) 4.10-4.46 (m, 2H) 7.18 (s, 1H) 7.59 (d, J=8.78 Hz, 1H) 8.00 (s, 1H) 8.13 (d, J=9.37 Hz, 1H) 8.55 (s, 1H) 9.09 (s, 1H) 9.67 (s, 2H) 11.91 (s, 1H). LCMS (ESI) 407 (ESI).

Example 87

Synthesis of Compound 87

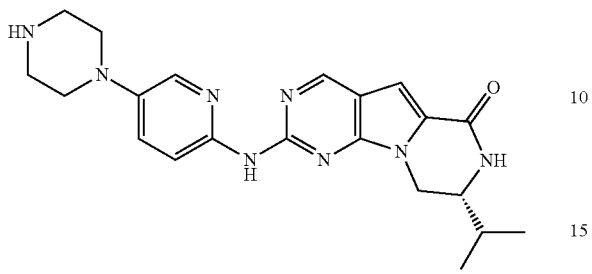

Compound 87 was synthesized in a manner similar to compound 86 and was converted to an HCl salt. The characterization data (NMR and LCMS) was similar to that obtained for the antipode compound 86.

Example 88

Synthesis of Compound 88

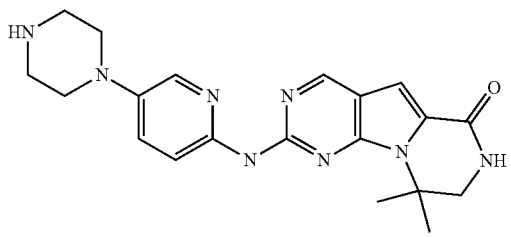 [SMILES: CC1(C)CNC(=O)c2cc3cnc(Nc4ccc(N5CCNCC5)cn4)nc3n21]

Compound 88 was synthesized in a similar manner to that described for compound 78 followed by the deblocking step described for compound 65 and was converted to an HCl salt. $^1$HNMR (600 MHz, DMSO-d6) δ ppm 1.78 (s, 6H) 3.40-3.53 (m, 6H) 3.64-3.73 (m, 4H) 7.27 (s, 1H) 7.66 (d, J=9.37 Hz, 1H) 7.98 (d, J=2.34 Hz, 1H) 8.12 (br. s., 1H) 8.47 (br. s., 1H) 9.11 (s, 1H) 9.45 (br. s., 2H) 11.62 (br. s., 1H). LCMS (ESI) 393 (M+H).

Example 89

Synthesis of Compound 89 (also referred to as Compound T)

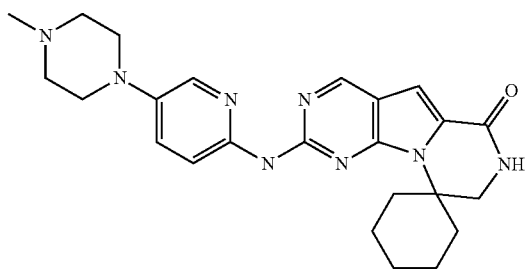 [SMILES: CN1CCN(c2ccc(Nc3ncc4cc5n(c4n3)C3(CCCCC3)CNC5=O)nc2)CC1]

Compound 89 was synthesized in a similar manner to that described for compound 78 and was converted to an HCl salt. $^1$HNMR (600 MHz, DMSO-d6) δ ppm 1.47 (br. s., 6H) 1.72 (br. s., 2H) 1.92 (br. s., 2H) 2.77 (br. s., 3H) 3.18 (br. s., 2H) 3.46 (br. s., 2H) 3.63 (br. s., 2H) 3.66 (d, J=6.15 Hz, 2H) 3.80 (br. s., 2H) 7.25 (s, 1H) 7.63 (br. s., 2H) 7.94 (br. s., 1H) 8.10 (br. s., 1H) 8.39 (br. s., 1H) 9.08 (br. s., 1H) 11.59 (br. s., 1H). LCMS (ESI) 447 (M+H).

Example 90

Synthesis of Compound 90 (also referred to as Compound Q)

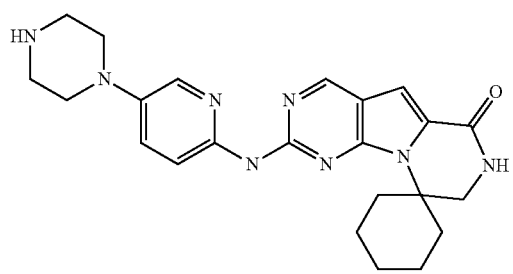 [SMILES: O=C1NCC2(CCCCC2)n2c1cc1cnc(Nc3ccc(N4CCNCC4)cn3)nc12]

Compound 90 was synthesized in a similar manner to that described for compound 78 followed by the deblocking step described for compound 65 and was converted to an HCl salt. $^1$HNMR (600 MHz, DMSO-d6) δ ppm 1.27-1.64 (m, 6H) 1.71 (br. s., 2H) 1.91 (br. s., 2H) 2.80 (br. s., 1H) 3.17-3.24 (m, 2H) 3.41 (br. s., 4H) 3.65 (br. s., 4H) 7.26 (br. s., 1H) 7.63 (br. s., 1 H) 7.94 (br. s., 1H) 8.13 (br. s., 1H) 8.40 (br. s., 1H) 9.09 (br. s., 1H) 9.62 (br. s., 1H) 11.71 (br. s., 1H). LCMS (ESI) 433 (M+H).

Example 91

Synthesis of Compound 91 (also referred to as Compound ZZ)

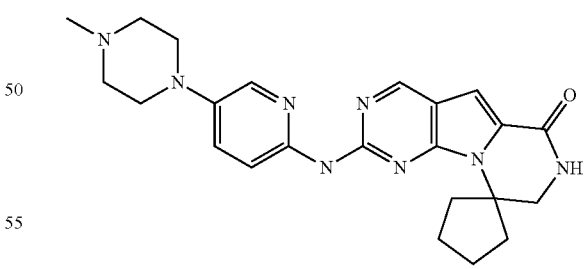

Compound 91 was synthesized using similar conditions to those described for compound 78 and was converted to an HCl salt. $^1$HNMR (600 MHz, DMSO-d6) δ ppm 1.64-1.75 (m, 2H) 1.83-1.92 (m, 2H) 1.96-2.06 (m, 2H) 2.49-2.58 (m, 2H) 2.79 (d, J=3.81 Hz, 3H) 3.06-3.18 (m, 4H) 3.59-3.69 (m, 2H) 3.73-3.83 (m, 2H) 4.04-4.12 (m, 2H) 7.17 (br. s., 1H) 7.60-7.70 (m, 2H) 7.70-7.92 (m, 2H) 7.96 (br. s., 1H) 8.41 (br. s., 1H) 8.98 (br. s., 1H) 10.77 (br. s., 1H). LCMS (ESI) 433 (M+H).

Example 92

Synthesis of Compound 92

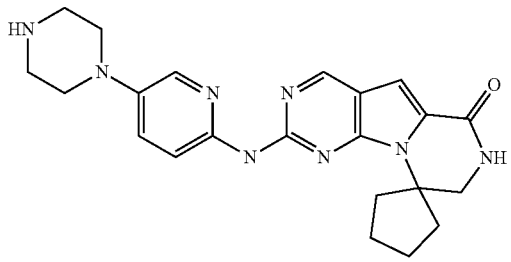 [SMILES: O=C1NCC2(CCCC2)n2c1cc1cnc(Nc3ccc(N4CCNCC4)cn3)nc12]

Compound 92 was synthesized in a similar manner to that described for compound 78 followed by the deblocking step described for compound 65 and was converted to an HCl salt. $^1$HNMR (600 MHz, DMSO-d6) δ ppm 1.64-1.75 (m, 2H) 1.84-1.92 (m, 2H) 1.96-2.05 (m, 2H) 2.48-2.56 (m, 2H) 3.22 (br. s., 4H) 3.42-3.48 (m, 4H) 3.60-3.69 (m, 2H) 4.05-4.13 (m, 1H) 7.18 (s, 1H) 7.65 (d, J=13.47 Hz, 1H) 7.70-7.77 (m, 1H) 7.94 (d, J=1.76 Hz, 1H) 8.42 (br. s., 1H) 9.00 (s, 1H) 9.15 (br. s., 2H). LCMS (ESI) 419 (M+H).

Example 93

Synthesis of Compound 93

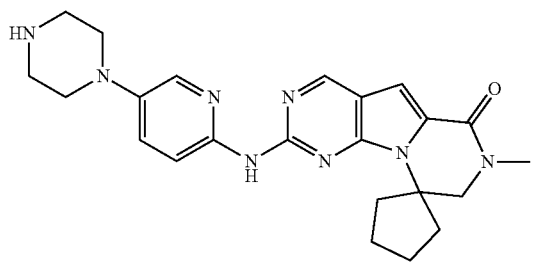 [SMILES: CN1CC2(CCCC2)n2c(cc3cnc(Nc4ccc(N5CCNCC5)cn4)nc32)C1=O]

Compound 93 was synthesized in a similar manner to that described for compound 78 followed by the deblocking step described for compound 65 and was converted to an HCl salt. $^1$HNMR (600 MHz, DMSO-d6) δ ppm 1.76 (br. s., 2H) 1.89 (br. s., 2H) 2.03 (br. s., 2H) 2.47-2.58 (m, 2H) 3.04 (s, 3H) 3.22 (br. s., 4H) 3.39 (br. s., 4H) 3.66 (s, 2H) 7.21 (s, 1H) 7.67 (d, J=9.37 Hz, 1H) 7.93 (br. s., 1H) 7.98-8.09 (m, 1H) 9.04 (s, 1H) 9.34 (br. s., 2H) 11.31 (br. s., 1H). LCMS (ESI) 433 (M+H).

Example 94

Synthesis of Compound 94

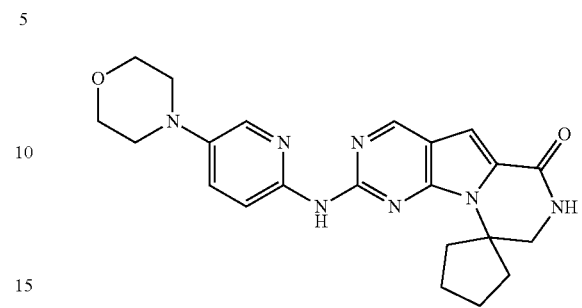

Compound 94 was synthesized using similar conditions to that described for compound 78 and was converted to an HCl salt. $^1$HNMR (600 MHz, DMSO-d6) δ ppm 1.66-1.77 (m, 2H) 1.84-1.94 (m, 2H) 1.96-2.08 (m, 2H) 2.48-2.57 (m, 2H) 3.36-3.52 (m, 4H) 3.60-3.80 (m, 6H) 7.21 (s, 1H) 7.53-7.74 (m, 2H) 7.86 (s, 1H) 8.02 (s, 1H) 8.45 (s, 1H) 9.03 (s, 1H) 11.19 (br. s., 1H). LCMS (ESI) 420 (M+H).

Example 95

Synthesis of Compound 95

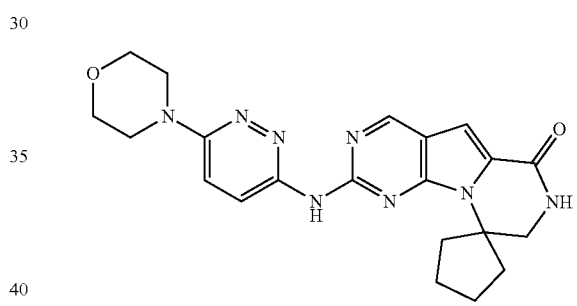

Compound 95 was synthesized using similar conditions to that described for compound 78 and was converted to an HCl salt. $^1$HNMR (600 MHz, DMSO-d6) δ ppm 1.65-1.79 (m, 2H) 1.85-1.95 (m, 2H) 1.97-2.08 (m, 2H) 2.47-2.54 (m, 2H) 3.40-3.58 (m, 5H) 3.65 (dd, J=21.67, 5.56 Hz, 1H) 3.69-3.78 (m, 4H) 7.24 (s, 1H) 7.97-8.17 (m, 2H) 8.48 (s, 1H) 9.08 (s, 1H) 11.81 (s, 1H). LCMS (ESI) 421 (M+H).

Example 96

Synthesis of Compound 96

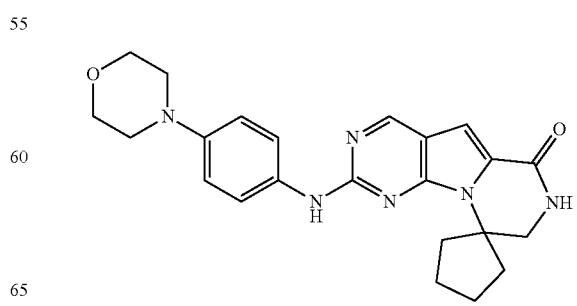

Compound 96 was synthesized using similar conditions to that described for compound 78 and was converted to an HCl salt. ¹HNMR (600 MHz, DMSO-d6) δ ppm 1.55-1.74 (m, 2H) 1.80-1.98 (m, 4H) 2.48-2.60 (m, 2H) 3.40-3.50 (m, 4H) 3.57-3.72 (m, 2H) 3.90-4.20 (m, 4H) 7.08 (s, 1H) 7.37-7.57 (m, 2H) 7.70 (m, 2H) 8.32 (s, 1H) 8.88 (s, 1H) 9.98 (s, 1H). LCMS (ESI) 419 (M+H).

Example 97

Synthesis of Compound 97 (also referred to as Compound III)

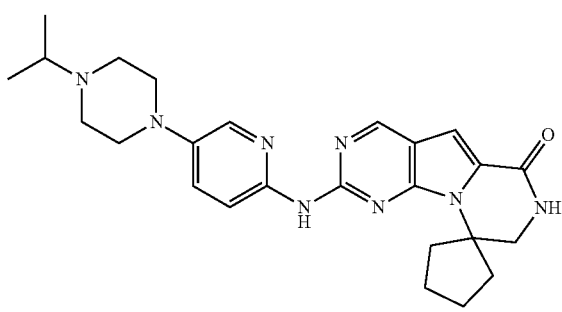 [SMILES: CC(C)N1CCN(c2ccc(Nc3ncc4cc5n(c4n3)C3(CCCC3)CNC5=O)nc2)CC1]

Compound 97 was synthesized using similar conditions to that described for compound 78 and was converted to an HCl salt. ¹HNMR (600 MHz, DMSO-d6) δ ppm 1.30 (d, J=5.27 Hz, 6H) 1.65-1.78 (m, 2H) 1.83-1.95 (m, 2H) 1.97-2.10 (m, 2H) 2.45-2.55 (m, 2H) 3.25-3.36 (m, 1H) 3.39-3.48 (m, 4H) 3.60-3.70 (m, 4H) 3.75-4.15 (m, 2H) 7.24 (s, 1H) 7.54-7.75 (m, 2H) 7.95 (s, 1H) 8.10 (s, 1H) 8.49 (s, 1H) 9.07 (s, 1H) 11.25 (s, 1H) 11.48 (s, 1H). LCMS (ESI) 461 (M+H).

Example 98

Synthesis of Compound 98

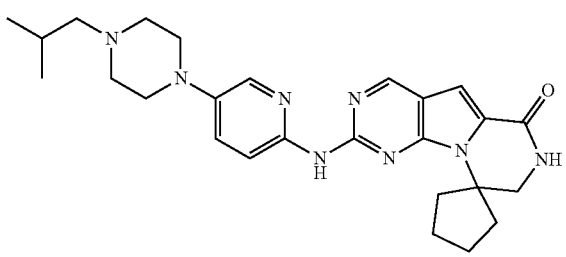 [SMILES: CC(C)CN1CCN(c2ccc(Nc3ncc4cc5n(c4n3)C3(CCCC3)CNC5=O)nc2)CC1]

Compound 98 was synthesized using similar conditions to that described for compound 78 and was converted to an HCl salt. ¹HNMR (600 MHz, DMSO-d6) δ ppm 0.99 (d, J=6.15 Hz, 6H) 1.65-1.78 (m, 2H) 1.90 (m, 2H) 1.97-2.08 (m, 2H) 2.08-2.17 (m, 1H) 2.45-2.55 (m, 2H) 2.88-3.02 (m, 2H) 3.33-3.48 (m, 4H) 3.50-3.90 (m, 6H) 7.24 (s, 1H) 7.67 (s, 2H) 7.94 (s, 1H) 8.12 (s, 1H) 8.49 (s, 1H) 9.07 (s, 1H) 10.77 (s, 1H) 11.51 (s, 1H). LCMS (ESI) 475 (M+H).

Example 99

Synthesis of Compound 99

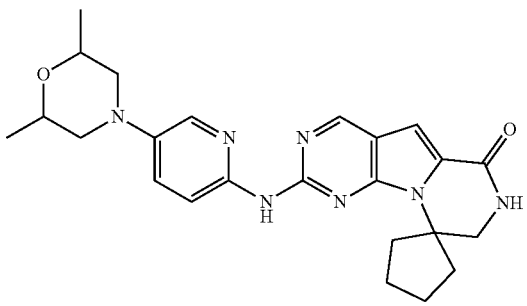 [SMILES: CC1CN(c2ccc(Nc3ncc4cc5n(c4n3)C3(CCCC3)CNC5=O)nc2)CC(C)O1]

Compound 99 was synthesized using similar conditions to those described for compound 78 and was converted to an HCl salt. ¹HNMR (600 MHz, DMSO-d6) δ ppm 1.13 (d, J=5.86 Hz, 6H) 1.66-1.77 (m, 2H) 1.84-1.94 (m, 2H) 1.97-2.09 (m, 2H) 2.40-2.53 (m, 2H) 3.37-3.49 (m, 2H) 3.50-3.59 (m, 2H) 3.59-3.73 (m, 4H) 7.23 (s, 1H) 7.64 (m, 3H) 7.85 (s, 1H) 8.11 (s, 1H) 8.47 (s, 1H) 9.05 (s, 1H). 11.35 (br s., 1H). LCMS (ESI) 448 (M+H).

Example 100

Synthesis of Compound 100

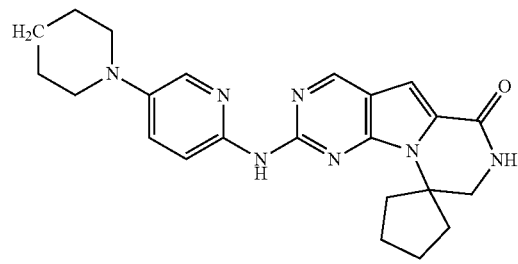 [SMILES: O=C1NCC2(CCCC2)n2c1cc1cnc(Nc3ccc(N4CCCCC4)cn3)nc12]

Compound 100 was synthesized using similar conditions to that described for compound 78 and was converted to an HCl salt. ¹HNMR (600 MHz, DMSO-d6) δ ppm 1.50-1.57 (m, 2H) 1.62-1.68 (m, 3H) 1.68-1.75 (m, 2H) 1.84-1.92 (m, 2H) 1.97-2.08 (m, 2H) 2.48-2.53 (m, 2H) 3.14-3.23 (m, 4H) 3.43-3.47 (m, 2H) 3.58-3.70 (m, 2H) 7.22 (s, 1H) 7.58-7.70 (m, 2H) 7.85-8.00 (m, 1H) 8.16 (d, 1H) 8.46 (s, 1H) 9.04 (s, 1H) 11.37 (br s., 1H). LCMS (ESI) 418 (M+H).

Example 101

Synthesis of Compound 101 (also referred to as Compound WW)

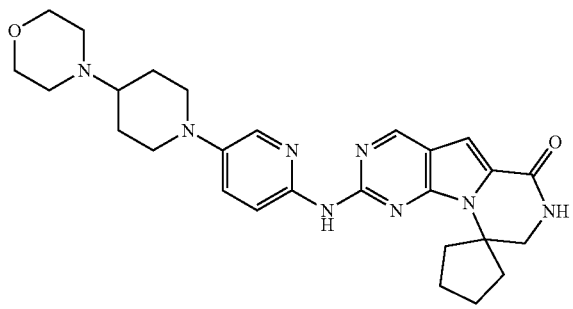 [SMILES: O=C1NCC2(CCCC2)n2c1cc1cnc(Nc3ccc(N4CCC(N5CCOCC5)CC4)cn3)nc12]

Compound 101 was synthesized using similar conditions to those described for compound 78 and was converted to an HCl salt. 1HNMR (600 MHz, DMSO-d6) δ ppm 1.72 (s, 2H) 1.90 (s, 4H) 2.03 (s, 2H) 2.21 (s, 2H) 2.48-2.54 (m, 2H) 2.73 (s, 2H) 3.03 (s, 2H) 3.25-3.35 (m, 1H) 3.38-3.48 (m, 4H) 3.65-3.99 (m, 5H) 7.23 (s, 1H) 7.63 (d, J=9.66 Hz, 1H) 7.90 (s, 1H) 8.13 (s, 1H) 8.47 (s, 1H) 9.06 (s, 1H) 10.50 (br s., 1H). LCMS (ESI) 503 (M+H).

Example 102

Synthesis of Compound 102 (also referred to as Compound HHH)

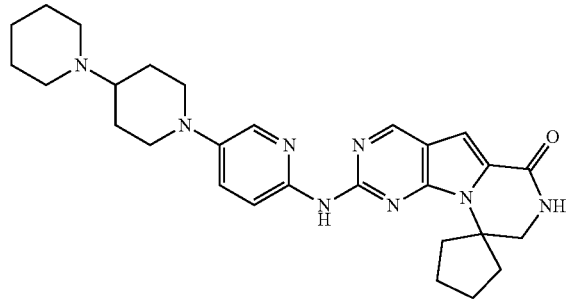 [SMILES: O=C1NCC2(CCCC2)n2c1cc1cnc(Nc3ccc(N4CCC(N5CCCCC5)CC4)cn3)nc12]

Compound 102 was synthesized using similar conditions to those described for compound 78 and was converted to an HCl salt. 1HNMR (600 MHz, DMSO-d6) δ ppm 1.63-1.85 (m, 6H) 1.87-1.92 (m, 2H) 1.99-2.06 (m, 2H) 2.15-2.23 (m, 2H) 2.47-2.53 (m, 1H) 2.69-2.79 (m, 2H) 2.81-2.91 (m, 2H) 2.98-3.08 (m, 2H) 3.32-3.48 (m, 4H) 3.57-3.72 (m, 4H) 3.77-3.85 (m, 2H) 7.22 (s, 1H) 7.60-7.68 (m, 2H) 7.90 (s, 1H) 8.07 (s, 1H) 8.46 (s, 1H) 9.04 (s, 1H). 11.41 (br s., 1H). LCMS (ESI) 501 (M+H).

Example 103

Synthesis of Compound 103

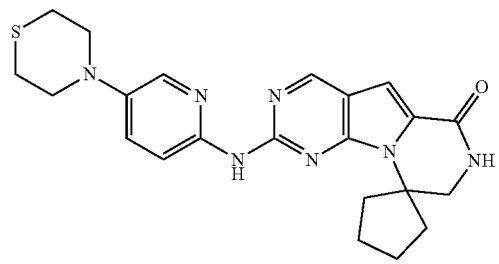 [SMILES: O=C1NCC2(CCCC2)n2c1cc1cnc(Nc3ccc(N4CCSCC4)cn3)nc12]

Compound 103 was synthesized using similar conditions to those described for compound 78 and was converted to an HCl salt. ¹HNMR (600 MHz, DMSO-d6) δ ppm 1.64-1.76 (m, 2H) 1.87-1.93 (m, 2H) 2.00-2.07 (m, 2H) 2.48-2.53 (m, 2H) 2.67-2.72 (m, 4H) 3.44-3.47 (m, 2H) 3.50-3.55 (m, 4H) 7.24 (s, 1H) 7.61 (d, J=9.37 Hz, 2H) 7.86 (d, J=2.63 Hz, 1H) 8.09 (d, J=12.88 Hz, 1H) 8.48 (s, 1H) 9.06 (s, 1H) 11.41 (br s., 1H). LCMS (ESI) 436 (M+H).

Example 104

Synthesis of Compound 104

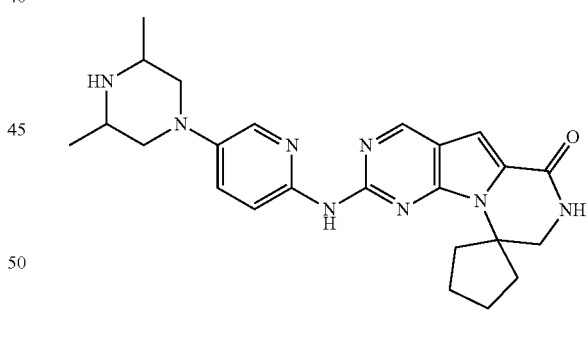

Compound 104 was synthesized using similar conditions to those described for compound 78 and was converted to an HCl salt. ¹HNMR (600 MHz, DMSO-d6) δ ppm 1.29 (d, J=6.73 Hz, 6H) 1.66-1.79 (m, 2H) 1.84-1.95 (m, 2H) 1.98-2.09 (m, 2H) 2.46-2.55 (m, 2H) 3.29-3.39 (m, 2H) 3.58-3.70 (m, 4H) 3.77-3.86 (m, 4H) 7.24 (s, 1H) 7.66 (d, J=9.37 Hz, 1H) 7.96 (d, J=2.93 Hz, 1H) 8.08 (s, 1H) 8.48 (s, 1H) 9.06 (s, 1H) 9.28 (s, 1H) 9.67 (s, 1H) 11.36 (s, 1H). LCMS (ESI) 447 (M+H).

Example 105

Synthesis of Compound 105

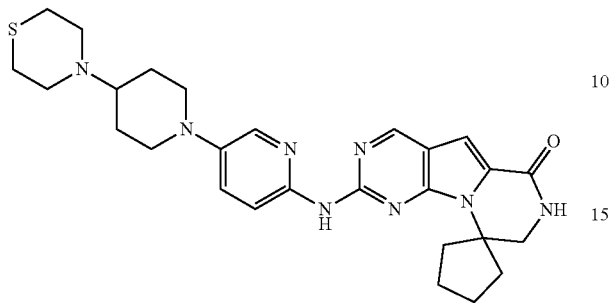

Compound 105 was synthesized using similar conditions to those described for compound 78 and was converted to an HCl salt. $^1$HNMR (600 MHz, DMSO-d6) δ ppm 1.73 (s, 2H) 1.76-1.85 (m, 2H) 1.85-1.94 (m, 2H) 1.98-2.07 (m, 2H) 2.19-2.26 (m, 2H) 2.48-2.52 (m, 1H) 2.70-2.81 (m, 4H) 3.13-3.20 (m, 1H) 3.30-3.48 (m, 3H) 3.58-3.71 (m, 4H) 3.78-3.84 (m, 4H) 7.24 (s, 1H) 7.62 (d, J=9.37 Hz, 2H) 7.89 (d, J=1.17 Hz, 1H) 8.09-8.18 (m, 1H) 8.48 (s, 1H) 9.06 (s, 1H) 11.46 (br s., 1H). LCMS (ESI) 519 (M+H).

Example 106

Synthesis of Compound 106

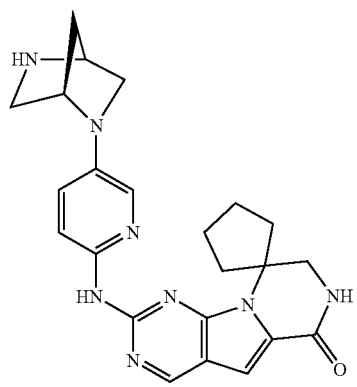 [SMILES: O=C1NCC2(CCCC2)n2c1cc1cnc(Nc3ccc(N4CC5C[C@@H]4CN5)cn3)nc12]

Compound 106 was synthesized using similar conditions to those described for compound 78 followed by the deblocking step described for compound 65 and was converted to an HCl salt. 1HNMR (600 MHz, DMSO-d6) δ ppm 1.65-1.75 (m, 2H) 1.85-1.93 (m, 2H) 1.93-1.99 (m, 1H) 2.00-2.06 (m, 2H) 2.08-2.14 (m, 1H) 2.47-2.55 (m, 2H) 3.07-3.25 (m, 2H) 3.25-3.69 (m, 5H) 4.46 (s, 1H) 4.67 (s, 1H) 7.22 (s, 1H) 7.58-7.69 (m, 2H) 8.46 (s, 1H) 9.02 (s, 1H) 9.34 (s, 1H) 9.65 (s, 1H). LCMS (ESI) 431 (M+H).

Example 107

Synthesis of Compound 107 (also referred to as Compound YY)

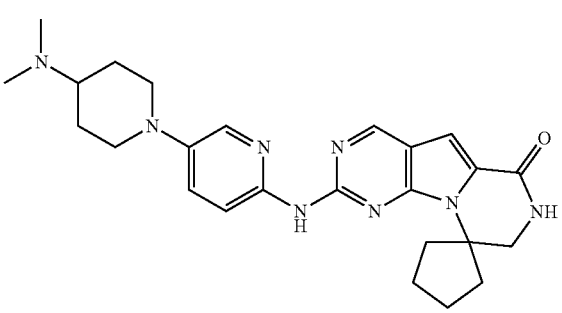 [SMILES: CN(C)C1CCN(c2ccc(Nc3ncc4cc5n(c4n3)C3(CCCC3)CNC5=O)nc2)CC1]

Compound 107 was synthesized using similar conditions to those described for compound 78 and was converted to an HCl salt. 1HNMR (600 MHz, DMSO-d6) δ ppm 1.65-1.82 (m, 3H) 1.89 (br. s., 2H) 1.98-2.08 (m, 2H) 2.13 (br. s., 2H) 2.47-2.55 (m, 2H) 2.68 (d, J=4.98 Hz, 6H) 2.71-2.80 (m, 2H) 3.29-3.71 (m, 10H) 7.16-7.26 (m, 1H) 7.67 (d, J=9.66 Hz, 2H) 7.91 (d, J=2.05 Hz, 1H) 8.14 (br. s., 1H) 8.48 (br. s., 1H) 9.05 (s, 1H) 11.14 (br. s., 1H) 11.43 (br. s., 1H). LCMS (ESI) 461 (M+H).

Example 108

Synthesis of Compound 108

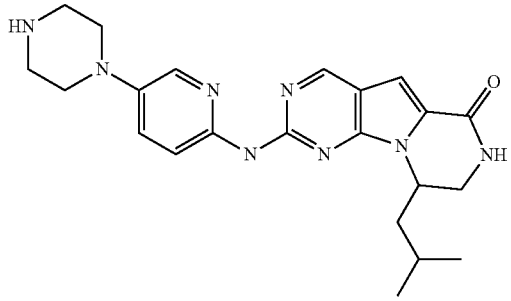 [SMILES: CC(C)CC1CNC(=O)c2cc3cnc(Nc4ccc(N5CCNCC5)cn4)nc3n21]

Compound 108 was synthesized in a manner similar to that described for compounds 64 and 65 and was recovered as an HCl salt. The analytical data was consistent with that described for the antipode compound 75.

Example 109

Synthesis of Compound 109

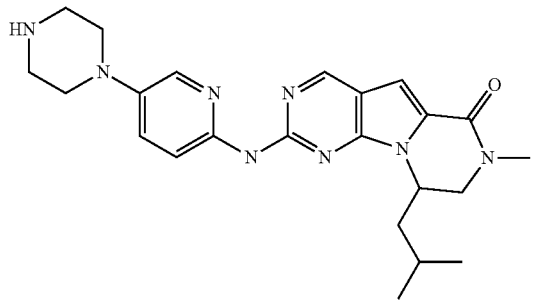 [SMILES: CC(C)CC1CN(C)C(=O)c2cc3cnc(Nc4ccc(N5CCNCC5)cn4)nc3n21]

Compound 109 was synthesized in a manner similar to that described for compounds 64 and 65 and was recovered as an HCl salt. The analytical data was consistent with that described for the antipode compound 75.

Example 110

Synthesis of Compound 110

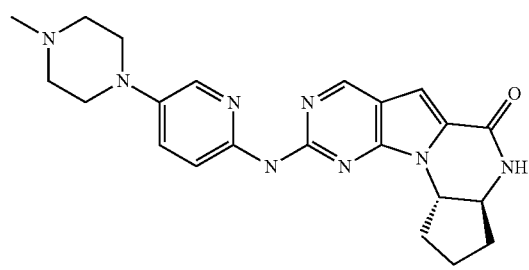 [SMILES: CN1CCN(c2ccc(Nc3ncc4cc5n(c4n3)[C@H]3CCC[C@@H]3NC5=O)nc2)CC1]

Compound 110 was synthesized in a similar manner to that described for compound 78 and then converted to its hydrochloride salt. $^1$HNMR (600 MHz, DMSO-d6) δ ppm 1.50-1.65 (m, 1H) 1.92-2.02 (m, 3H) 2.06-2.15 (m, 1H) 2.78 (d, J=3.81 Hz, 4H) 3.10-3.20 (m, 4H) 3.47-3.51 (m, 2H) 3.64-3.71 (m, 1H) 3.76-3.83 (m, 2H) 3.98-4.14 (m, 1H) 7.20 (s, 2H) 7.77 (s, 1H) 7.97 (s, 2H) 8.81 (s, 1H) 9.03 (s, 1H) 10.97 (br s., 1H). LCMS (ESI) 419 (M+H).

Example 111

Synthesis of Compound 111

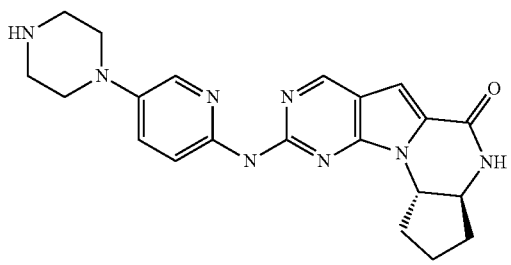 [SMILES: O=C1N[C@H]2CCC[C@@H]2n2c1cc1cnc(Nc3ccc(N4CCNCC4)cn3)nc12]

Compound 111 was synthesized in a similar manner to that described for compound 78 and then converted to its hydrochloride salt. $^1$HNMR (600 MHz, DMSO-d6) δ ppm 1.54-1.59 (m, 1H) 1.92-2.01 (m, 3H) 2.06-2.15 (m, 1H) 2.76-2.84 (m, 1H) 3.17-3.24 (m, 6H) 3.64-3.71 (m, 2H) 4.02-4.11 (m, 2H) 7.22 (s, 2H) 7.64 (s, 1H) 7.97 (s, 2H) 8.75 (s, 1H) 8.97 (s, 1H) 9.21 (s, 1H). LCMS (ESI) 405 (M+H).

Example 112

Synthesis of Compound 112

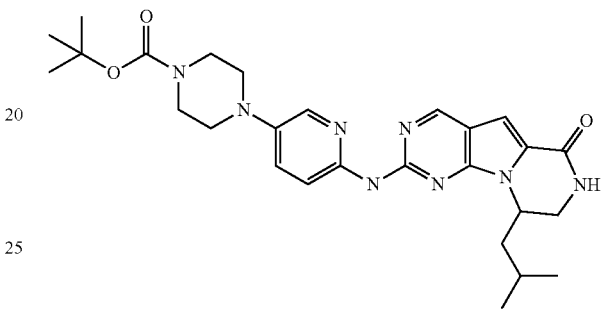

Compound 112 was synthesized using similar experimental conditions to that described for compound 64.

Example 113

Synthesis of tert-butyl N-[2-[(5-bromo-2-chloro-pyrimidin-4-yl)amino]ethyl]carbamate, Compound 113

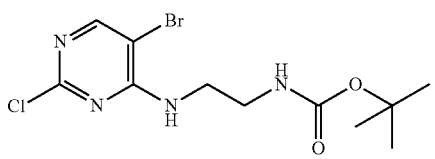 [SMILES: CC(C)(C)OC(=O)NCCNc1nc(Cl)ncc1Br]

To a solution of 5-bromo-2,4-dichloropyrimidine (12.80 g, 0.054 mole) in ethanol (250 mL) was added Hunig's base (12.0 mL) followed by the addition of a solution of N-(tert-butoxycarbonyl)-1,2-diaminoethane (10 g, 0.0624 mole) in ethanol (80 mL). The contents were stirred overnight for 20 hrs. The solvent was evaporated under vacuum. Ethyl acetate (800 mL) and water (300 mL) were added and the layers separated. The organic layer was dried with magnesium sulfate and then concentrated under vacuum. Column chromatography on silica gel using hexane/ethyl acetate (0-60%) afforded tert-butyl N-[2-[(5-bromo-2-chloro-pyrimidin-4-yl)amino]ethyl]carbamate. LCMS (ESI) 351 (M+H).

Example 114

Synthesis of tert-butyl N-[2-[[2-chloro-5-(3,3-diethoxyprop-1-ynyl)pyrimidin-4 yl]amino]ethyl]carbamate, Compound 114

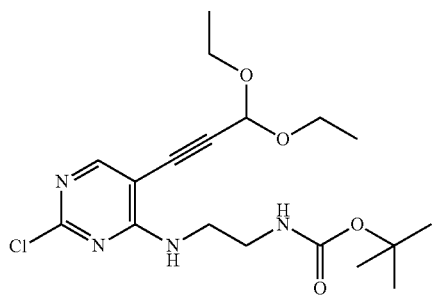 [SMILES: CCOC(C#Cc1cnc(Cl)nc1NCCNC(=O)OC(C)(C)C)OCC]

To tert-butyl N-[2-[(5-bromo-2-chloro-pyrimidin-4-yl)amino]ethyl]carbamate (5 g, 14.23 mmole) in toluene (42 mL) and triethylamine (8.33 mL) under nitrogen was added triphenyl arsine (4.39 g), 3,3-diethoxyprop-1-yne (3.24 mL) and Pddba (1.27 g). The contents were heated at 70 degrees for 24 hrs. After filtration through CELITE®, the crude reaction was columned using hexane/ethyl acetate (0-20%) to afford the desired product 3.9 g). Column chromatography of the resulting residue using hexane/ethyl acetate (0-30%) afforded tert-butyl N-[2-[[2-chloro-5-(3,3-diethoxyprop-1-ynyl)pyrimidin-4-yl]amino]ethyl]carbamate. LCMS (ESI) 399 (M+H).

Example 115

Synthesis of tert-butyl N-[2-[2-chloro-6-(diethoxymethyl)pyrrolo[2,3-d]pyrimidin-7-yl]ethyl]carbamate, Compound 115

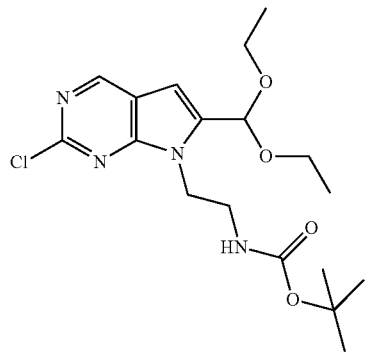 [SMILES: CCOC(OCC)c1cc2cnc(Cl)nc2n1CCNC(=O)OC(C)(C)C]

To a solution of Compound 114 (3.9 g, 0.00976 mole) in THF (60 mL) was added TBAF (68.3 mL, 7 eq). The contents were heated to 45 degrees for 2 hrs. Concentration followed by column chromatography using ethyl acetate/hexane (0-50%) afforded tert-butyl N-[2-[2-chloro-6-(diethoxymethyl)pyrrolo[2,3-d]pyrimidin-7-yl]ethyl]carbamate as a pale brown liquid (1.1 g). $^1$HNMR (d6-DMSO) δ ppm 8.88 (s, 1H), 6.95 (brs, 1H), 6.69 (s, 1H), 5.79 (s, 1H), 4.29 (m, 2H), 3.59 (m, 4H), 3.34 (m, 1H), 3.18 (m, 1H), 1.19 (m, 9H), 1.17 (m, 6H). LCMS (ESI) 399 (M+H).

Example 116

Synthesis of tert-butyl N-[2-[2-chloro-6-(diethoxymethyl)-5-iodo-pyrrolo[2,3-d]pyrimidin-7-yl]ethyl]carbamate, Compound 116

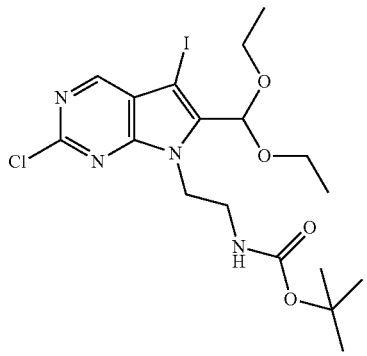 [SMILES: CCOC(OCC)c1c(I)c2cnc(Cl)nc2n1CCNC(=O)OC(C)(C)C]

To tert-butyl N-[2-[2-chloro-6-(diethoxymethyl)pyrrolo[2,3-d]pyrimidin-7-yl]ethyl]carbamate (0.1 g, 0.00025 mol) in acetonitrile (2 mL) was added 1,3-diiodo-5,5-dimethylhydantoin (95 mg, 1 eq), and solid NaHCO$_3$ (63 mg, 3 eq). The reaction was stirred at room temperature for 16 hrs. The reaction was filtered and concentrated in vacuo. The product was purified by silica gel column chromatography using hexane/ethylacetate (0-50%) to afford tert-butyl N-[2-[2-chloro-6-(diethoxymethyl)-5-iodo-pyrrolo[2,3-d]pyrimidin-7-yl]ethyl]carbamate as a pale yellow solid (0.03 g). LCMS (ESI) 525 (M+H).

Example 117

Synthesis of tert-Butyl N-[2-[2-chloro-6-(diethoxymethyl)-5-(o-tolyl)pyrrolo[2,3-d]pyrimidin-7-yl]ethyl]carbamate, Compound 117

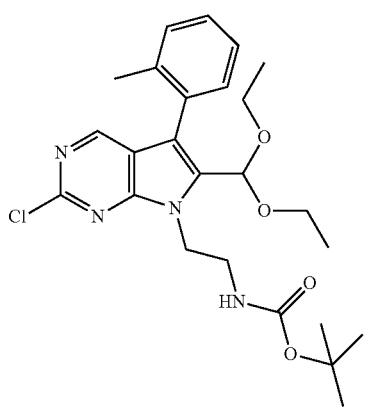 [SMILES: CCOC(OCC)c1c(-c2ccccc2C)c2cnc(Cl)nc2n1CCNC(=O)OC(C)(C)C]

To tert-butyl N-[2-[2-chloro-6-(diethoxymethyl)-5-iodo-pyrrolo[2,3-d]pyrimidin-7-yl]ethyl]carbamate (0.1 g, 0.19 mmole) in dioxane (3 mL) was added 2-methylphenylboronic acid (28 mg), tetrakis(triphenylphosphine)palladium (25 mg) and potassium phosphate (250 mg) in water (0.3 mL). The reaction was heated in a CEM Discovery microwave at 90° C. for 3 hrs. The crude reaction was loaded onto silica gel and columned using hexane/ethyl acetate (0-30%)

to afford tert-butyl N-[2-[2-chloro-6-(diethoxymethyl)-5-(o-tolyl)pyrrolo[2,3-d]pyrimidin-7-yl]ethyl]carbamate (0.06 g). LCMS (ESI) 489 (M+H).

Example 118

Synthesis of 7-[2-(tert-butoxycarbonylamino)ethyl]-2-chloro-5-(o-tolyl)pyrrolo [2,3-d]pyrimidine-6-carboxylic acid, Compound 118

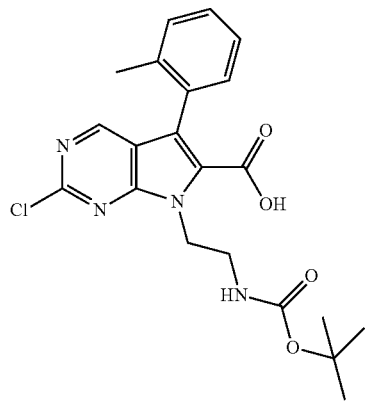 [SMILES: Cc1ccccc1-c1c(C(=O)O)n(CCNC(=O)OC(C)(C)C)c2nc(Cl)ncc12]

To tert-butyl N-[2-[2-chloro-6-(diethoxymethyl)-5-(o-tolyl)pyrrolo[2,3-d]pyrimidin-7-yl]ethyl]carbamate (0.85 g, 1.74 mmole) in AcOH (10 mL) was added water (1.5 mL). The reaction was stirred at room temperature for 16 hrs. The crude reaction was then concentrated under vacuum. After the addition of ethyl acetate (50 mL), the organic layer was washed with satd. NaHCO$_3$. The organic layer was dried with magnesium sulfate and then concentrated under vacuum to afford the crude intermediate, tert-butyl N-[2-[2-chloro-6-formyl-5-(o-tolyl)pyrrolo[2,3-d]pyrimidin-7-yl] ethyl]carbamate. To this crude intermediate in DMF (5 mL) was added oxone (1.3 g). After stirring for 2.5 hrs, water (20 mL) and ethyl acetate (100 mL) were added. The organic layer was separated, dried and then concentrated under vacuum to afford the crude product which was columned over silica gel using hexane/ethyl acetate (0-50%) to afford 7-[2-(tert-butoxycarbonylamino)ethyl]-2-chloro-5-(o-tolyl) pyrrolo[2,3-d]pyrimidine-6-carboxylic acid (0.112 g). LCMS (ESI) 431 (M+H).

Example 119

Synthesis of Compound 119

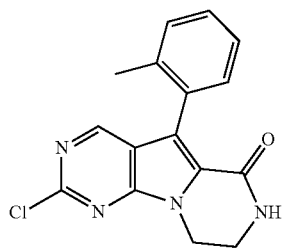 [SMILES: Cc1ccccc1-c1c2n(c3nc(Cl)ncc13)CCNC2=O]

To 7-[2-(tert-butoxycarbonylamino)ethyl]-2-chloro-5-(o-tolyl)pyrrolo[2,3-d]pyrimidine-6-carboxylic acid (0.1 g, 0.261 mmol) in DCM (4.1 mL) was added DMAP (20 mg) followed by the addition of N,N'-diisopropylcarbodiimide (0.081 mL, 2 eq). After stirring for 3 hrs, TFA (0.723 mL) was added. Stirring was then continued for another 30 minutes. The reaction mixture was neutralized with satd. NaHCO$_3$. DCM (20 mL) was then added and the organic layer separated, dried with magnesium sulfate and then concentrated under vacuum to afford the crude product which was columned using hexane/ethylacetate (0-100%) to afford chloro tricyclic amide Compound 119 (0.65 g). LCMS (ESI) 313 (M+H).

Example 120

Synthesis of Compound 120

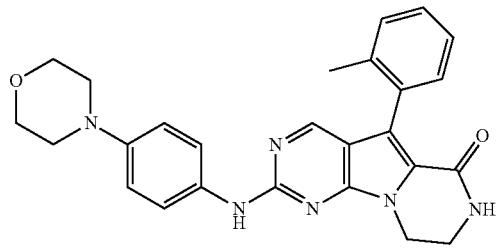 [SMILES: Cc1ccccc1-c1c2n(c3nc(Nc4ccc(N5CCOCC5)cc4)ncc13)CCNC2=O]

To the chloro tricyclic amide (0.040 g, 0.128 mmole) (Compound 119) in dioxane (2.5 mL) under nitrogen was added Pd$_2$(dba)$_3$ (12 mg), sodium tert-butoxide (16 mg), BINAP (16 mg) and 4-morpholinoaniline (22.7 mg, 1 eq). The reaction mixture was heated at 90° C. in a CEM Discovery microwave for 3.0 hrs. The crude reaction was loaded onto a silica gel column and the contents eluted with DCM/MeOH (0-6%) to afford the product (10 mg). LCMS (ESI) 455 (M+H). $^1$HNMR (600 MHz, DMSO-d6) δ ppm 2.14 (s, 3H) 3.23-3.50 (m, 2H) 3.57-3.73 (m, 2H), 3.81-3.92 (m, 8H), 7.11-7.31 (m, 4H) 7.31-7.48 (m, 1H) 7.58-7.73 (m, 1H) 7.77-7.95 (m, 2H) 8.05-8.21 (m, 1H) 8.44 (s, 1H) 9.85-10.01 (m, 1H).

Example 121

Synthesis of Compound 121

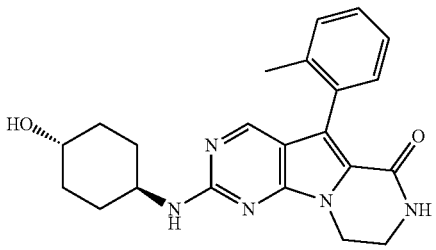 [SMILES: Cc1ccccc1-c1c2n(c3nc(N[C@H]4CC[C@H](O)CC4)ncc13)CCNC2=O]

To the chloro tricyclic amide (0.024 g) (Compound 119) in N-methyl-2-pyrrolidone (NMP) (1.5 mL) was added trans-4-aminocyclohexanol (0.0768 mmol, 26.54 mg, 3 eq) and Hunig's base (0.4 mL). The reaction was heated in a CEM Discovery microwave vessel at 150° C. for 1.2 hrs. The crude reaction was loaded onto a silica gel column and the contents eluted with DCM/MeOH (0-10%) to afford the product (21 mg). LCMS (ESI) 392 (M+H). $^1$HNMR (600

MHz, DMSO-d6) δ ppm 1.23 (d, J=8.78 Hz, 4H) 1.84 (br. s., 4H) 2.11 (s, 3H) 3.34-3.43 (m, 1H) 3.55 (br. s., 2H) 3.72 (br. s., 1H) 4.13 (br. s., 2H) 4.50 (br. s., 1H) 7.03 (br. s., 1H) 7.12-7.28 (m, 4H) 7.96 (br. s., 1H) 8.18 (br. s., 1H).

Example 122

Synthesis of 7-[2-(tert-butoxycarbonylamino)ethyl]-2-chloro-pyrrolo [2,3-d]pyrimidine-6-carboxylic acid, Compound 122

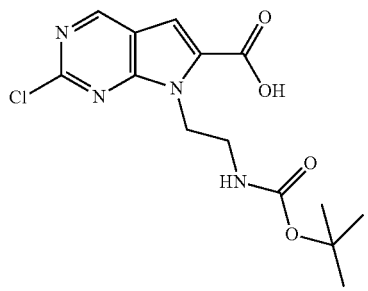 [SMILES: CC(C)(C)OC(=O)NCCn1c(C(=O)O)cc2cnc(Cl)nc21]

7-[2-(tert-butoxycarbonylamino)ethyl]-2-chloro-pyrrolo [2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 341 (M+H).

Example 123

Synthesis of Compound 123

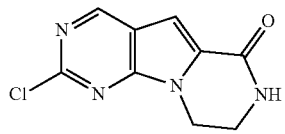 [SMILES: O=C1NCCn2c1cc1cnc(Cl)nc12]

Chloro tricyclic amide, Compound 123, was synthesized using a similar experimental procedure as that described for the synthesis of chloro tricyclic amide (Compound 119). LCMS (ESI) 223 (M+H).

Example 124

Synthesis of Compound 124

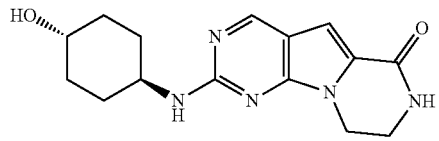 [SMILES: O=C1NCCn2c1cc1cnc(N[C@H]3CC[C@H](O)CC3)nc12]

To the chloro tricyclic amide, Compound 123 (0.035 g, 0.00157 mole) in NMP (1.5 mL) was added Hunig's base (0.3 mL) followed by the addition of the trans-4-aminocyclohexanol (54.2 mg). The reaction mixture was heated at 150° C. for 1.5 hrs. The crude reaction was loaded onto a silica gel column and the column was eluted with DCM/MeOH (0-10%) to afford the product (5 mg). LCMS (ESI) 302 (M+H).

Example 125

Synthesis of tert-butyl N-[2-[(5-bromo-2-chloro-pyrimidin-4-yl)amino]-2-methyl-propyl]carbamate, Compound 125

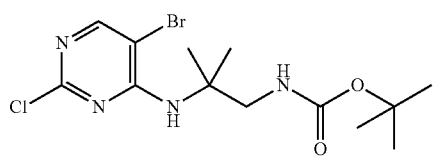 [SMILES: CC(C)(CNC(=O)OC(C)(C)C)Nc1nc(Cl)ncc1Br]

tert-butyl N-[2-[(5-bromo-2-chloro-pyrimidin-4-yl)amino]-2-methyl-propyl]carbamate was synthesized by treating 5-bromo-2,4-dichloropyrimidine with tert-butyl N-(2-amino-2-methyl-propyl)carbamate using similar experimental conditions as described for the synthesis of tert-butyl N-[2-[(5-bromo-2-chloro-pyrimidin-4-yl)amino]ethyl]carbamate. LCMS (ESI) (M+H) 379.

Example 126

Synthesis of tert-butyl N-[2-[[2-chloro-5-(3,3-diethoxyprop-1-ynyl)pyrimidin-4-yl]amino]-2-methyl-propyl]carbamate, Compound 126

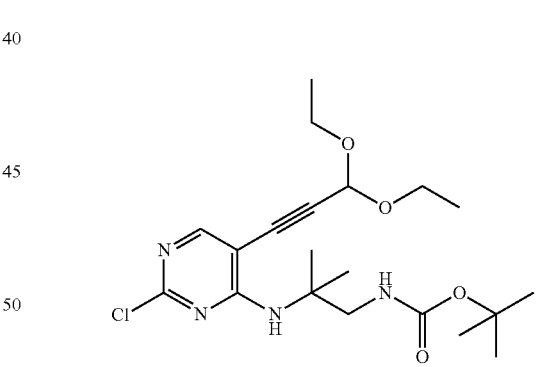

tert-butyl N-[2-[[2-chloro-5-(3,3-diethoxyprop-1-ynyl)pyrimidin-4-yl]amino]-2-methyl-propyl]carbamate was synthesized by treating tert-butyl N-[2-[(5-bromo-2-chloro-pyrimidin-4-yl)amino]-2-methyl-propyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate.

LCMS (ESI) (M+H) 427.

Example 127

Synthesis of tert-butyl N-[2-[2-chloro-6-(diethoxymethyl)pyrrolo[2,3-d]pyrimidin-7-yl]-2-methyl-propyl]carbamate, Compound 127

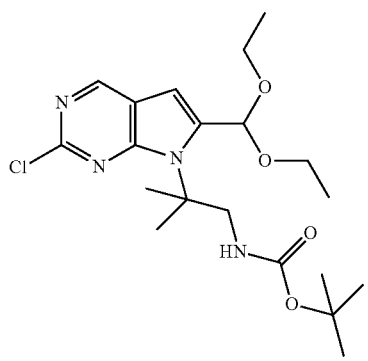 [SMILES: CCOC(OCC)c1cc2cnc(Cl)nc2n1C(C)(C)CNC(=O)OC(C)(C)C]

tert-butyl N-[2-[2-chloro-6-(diethoxymethyl)pyrrolo[2,3-d]pyrimidin-7-yl]-2-methyl-propyl]carbamate was synthesized by treating tert-butyl N-[2-[[2-chloro-5-(3,3-diethoxy-prop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3-d]pyrimidin-7-yl]ethyl]carbamate. LCMS (ESI) (M+H) 427.

Example 128

Synthesis of 7-[2-(tert-butoxycarbonylamino)-1,1-dimethyl-ethyl]-2-chloro-pyrrolo[2,3-d]pyrimidine-6-carboxylic acid, Compound 128

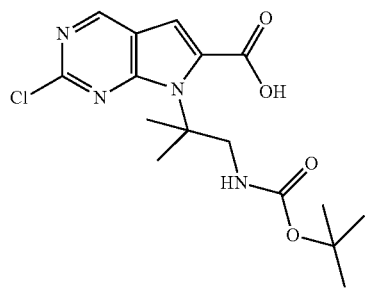 [SMILES: CC(C)(C)OC(=O)NCC(C)(C)n1c(C(=O)O)cc2cnc(Cl)nc21]

7-[2-(tert-butoxycarbonylamino)-1,1-dimethyl-ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 369 (M+H).

Example 129

Synthesis of Compound 129

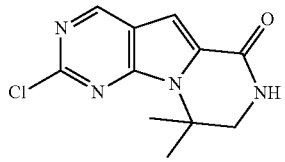 [SMILES: CC1(C)CNC(=O)c2cc3cnc(Cl)nc3n21]

Chloro tricyclic amide, Compound 129, was synthesized using a similar procedure as that described for the synthesis of chloro tricyclic amide, Compound 119. LCMS (ESI) 251 (M+H).

Example 130

Synthesis of Compound 130

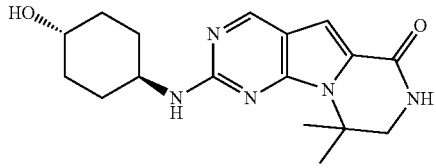 [SMILES: CC1(C)CNC(=O)c2cc3cnc(N[C@H]4CC[C@H](O)CC4)nc3n21]

Compound 130 was synthesized by treating chlorotricyclic amine Compound 129 with trans-4-aminocyclohexanol using similar experimental conditions as for compound 124. LCMS (ESI) 330 (M+H). $^1$HNMR (600 MHz, DMSO-d6) δ ppm 1.07-1.34 (m, 4H) 1.47-2.05 (m, 10H) 3.09 (m, 1H) 3.51 (d, J=2.91 Hz, 2H) 3.57 (m, 1H) 4.50 (br. s., 1H) 6.89 (s, 1H) 6.94-7.05 (m, 1H) 8.04 (br. s., 1H) 8.60 (s, 1H) 9.00 (br. s., 1H).

Example 131

Synthesis of benzyl N-[1-[[(5-bromo-2-chloro-pyrimidin-4-yl)amino]methyl]propyl]carbamate, Compound 131

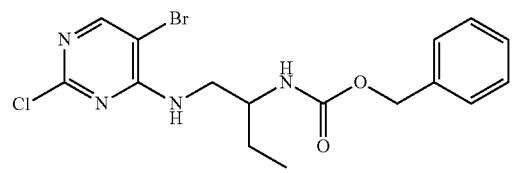 [SMILES: CCC(CNc1nc(Cl)ncc1Br)NC(=O)OCc1ccccc1]

Benzyl N-[1-[[(5-bromo-2-chloro-pyrimidin-4-yl)amino]methyl]propyl]carbamate was synthesized by treating 5-bromo-2,4-dichloropyrimidine with benzyl N-[1-(aminomethyl)propyl]carbamate using similar experimental conditions as described for the synthesis of tert-butyl N-[2-[(5-bromo-2-chloro-pyrimidin-4-yl)amino]ethyl]carbamate. LCMS (ESI) (M+H) 413.

Example 132

Synthesis of benzyl N-[1-[[[2-chloro-5-(3,3-diethoxyprop-1-ynyl)pyrimidin-4-yl]amino]methyl]propyl]carbamate, Compound 132

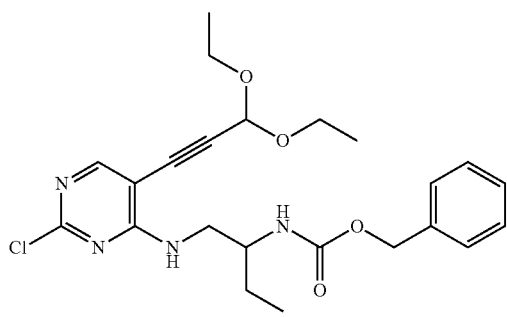 [SMILES: CCOC(C#Cc1cnc(Cl)nc1NCC(CC)NC(=O)OCc1ccccc1)OCC]

Benzyl N-[1-[[[2-chloro-5-(3,3-diethoxyprop-1-ynyl)pyrimidin-4-yl]amino]methyl]propyl]carbamate was prepared by treating benzyl N-[1-[[(5-bromo-2-chloro-pyrimidin-4-yl)amino]methyl]propyl]-carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4-yl]amino]ethyl]carbamate LCMS (ESI) (M+H) 461.

Example 133

Synthesis of benzyl N-[1-[[2-chloro-6-(diethoxymethyl)pyrrolo[2,3-d]pyrimidin-7-yl]methyl]propyl]carbamate, Compound 133

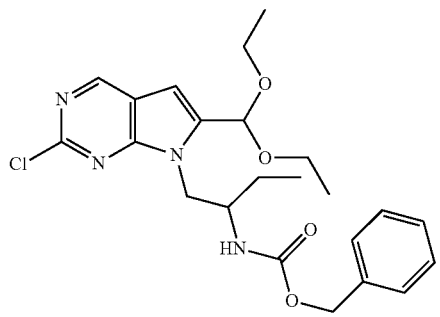 [SMILES: CCOC(OCC)c1cc2cnc(Cl)nc2n1CC(CC)NC(=O)OCc1ccccc1]

Benzyl N-[1-[[2-chloro-6-(diethoxymethyl)pyrrolo[2,3-d]pyrimidin-7-yl]methyl]propyl]carbamate was synthesized by treating benzyl N-[1-[[[2-chloro-5-(3,3-diethoxyprop-1-ynyl)pyrimidin-4-yl]amino]methyl]propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) (M+H) 461.

Example 134

Synthesis of 7-[2-(benzyloxycarbonylamino)butyl]-2-chloro-pyrrolo[2,3-d]pyrimidine-6-carboxylic acid, Compound 134

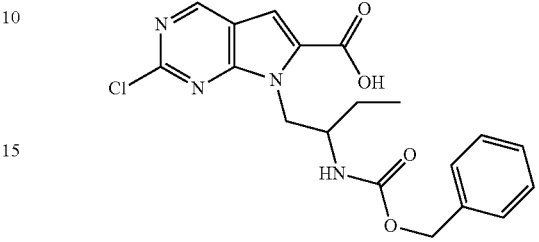

7-[2-(benzyloxycarbonylamino)butyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 403 (M+H).

Example 135

Synthesis of Compound 135

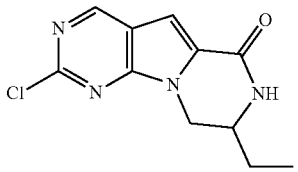 [SMILES: CCC1Cn2c(cc3cnc(Cl)nc32)C(=O)N1]

To a solution of 7-[2-(benzyloxycarbonylamino)butyl]-2-chloro-pyrrolo[2,3-d]pyrimidine-6-carboxylic acid in dichloromethane was added HBr, the reaction was stirred at 45 degrees for 3 hrs. After concentration, 2N NaOH was added to basify (pH=8.0) the reaction followed by the addition of THF (20 mL). Boc$_2$O was then added (1.2 eq) and the reaction was stirred for 16 hrs. To the crude reaction mixture was then added ethyl acetate (100 mL) and water (50 mL) and the organic phase was separated, dried (magnesium sulfate) and then concentrated under vacuum. To the crude product was added dichloromethane (30 mL) followed by DIC and DMAP. After stirring for 2 hrs, TFA was added and the contents stirred for an hour. The solvents were evaporated under vacuum and the residue basified with satd. NaHCO$_3$. Ethyl acetate was then added and the organic layer separated, dried (magnesium sulfate) and then concentrated under vacuum. Column chromatography with hexane/ethyl acetate (0-100%) afforded the desired chlorotricyclic core, Compound 135. LCMS (ESI) 251 (M+H).

Example 136

Synthesis of Compound 136

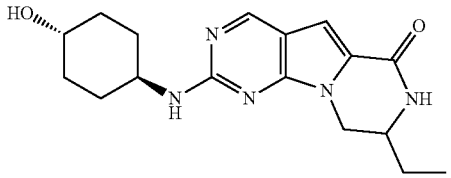 [SMILES: CCC1Cn2c(cc3cnc(N[C@H]4CC[C@H](O)CC4)nc32)C(=O)N1]

Compound 136 was synthesized by treating chlorotricyclic amine, Compound 135, with trans-4-aminocyclohexanol using similar experimental conditions as for compound 124. LCMS (ESI) 330 (M+H). $^1$HNMR (600 MHz, DMSO-d6) δ ppm 0.80-0.95 (m, 3H) 1.35-1.92 (m, 10H) 3.66 (br. m., 3H) 4.17 (br. s., 2H) 4.47 (br. s., 1H) 6.85 (s, 1H) 6.96 (br. s., 1H) 8.15 (br. s., 1H) 8.62 (br. s., 1H).

Example 137

Synthesis of tert-butyl N-[1-[[(5-bromo-2-chloro-pyrimidin-4-yl)amino]methyl]cyclopentyl]carbamate, Compound 137

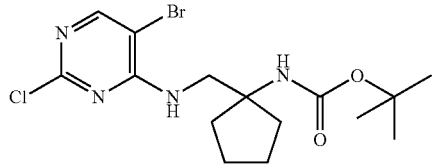 [SMILES: CC(C)(C)OC(=O)NC1(CNc2nc(Cl)ncc2Br)CCCC1]

tert-butyl N-[1-[[(5-bromo-2-chloro-pyrimidin-4-yl)amino]methyl]cyclopentyl]carbamate was synthesized by treating 5-bromo-2,4-dichloropyrimidine with tert-butyl N-[1-(aminomethyl)cyclopentyl]carbamate using similar experimental conditions as described for the synthesis of tert-butyl N-[2-[(5-bromo-2-chloro-pyrimidin-4-yl)amino]ethyl]carbamate. LCMS (ESI) 405 (M+H).

Example 138

Synthesis of tert-butyl N-[1-[[[2-chloro-5-(3,3-diethoxyprop-1-ynyl)pyrimidin-4-yl]amino]methyl]cyclopentyl]carbamate, Compound 138

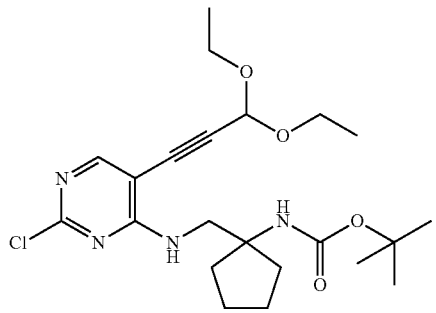 [SMILES: CCOC(C#Cc1cnc(Cl)nc1NCC1(NC(=O)OC(C)(C)C)CCCC1)OCC]

tert-butyl N-[1-[[[2-chloro-5-(3,3-diethoxyprop-1-ynyl)pyrimidin-4-yl]amino]methyl]cyclopentyl]carbamate was synthesized by treating tert-butyl N-[1-[[(5-bromo-2-chloro-pyrimidin-4-yl)amino]methyl]cyclopentyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate LCMS (ESI) 453 (M+H).

Example 139

Synthesis of tert-butyl N-[1-[[2-chloro-6-(diethoxymethyl)pyrrolo[2,3-d]pyrimidin-7-yl]methyl]cyclopentyl]carbamate, Compound 139

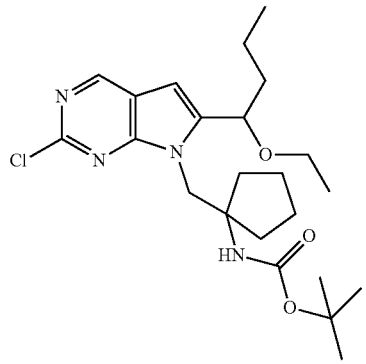 [SMILES: CCCC(OCC)c1cc2cnc(Cl)nc2n1CC1(NC(=O)OC(C)(C)C)CCCC1]

tert-butyl N-[1-[[2-chloro-6-(diethoxymethyl)pyrrolo[2,3-d]pyrimidin-7-yl]methyl]cyclopentyl]carbamate was synthesized by treating tert-butyl N-[2-[[2-chloro-5-(3,3-diethoxyprop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3 d]pyrimidin-7-yl] ethyl]carbamate. LCMS (ESI) 453 (M+H).

Example 140

Synthesis of 7-[[1-(tert-butoxycarbonylamino)cyclopentyl]methyl]-2-chloro-pyrrolo [2,3-d]pyrimidine-6-carboxylic acid, Compound 140

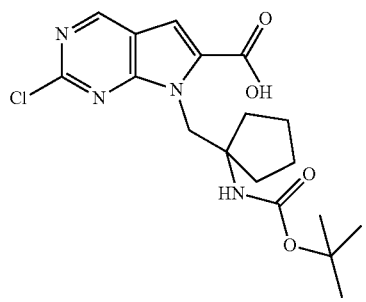 [SMILES: CC(C)(C)OC(=O)NC1(Cn2c(C(=O)O)cc3cnc(Cl)nc32)CCCC1]

7-[[1-(tert-butoxycarbonylamino)cyclopentyl]methyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 395 (M+H).

Example 141

Synthesis of Compound 141

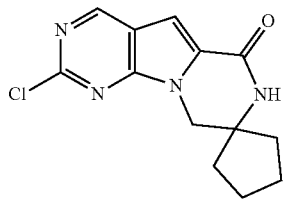 [SMILES: O=C1NC2(CCCC2)Cn2c1cc1cnc(Cl)nc12]

Chlorotricyclic core Compound 141 was synthesized using a similar experimental procedure as that described for the synthesis of chloro tricyclic amide Compound 119. LCMS (ESI) 277 (M+H).

Example 142

Synthesis of Compound 142

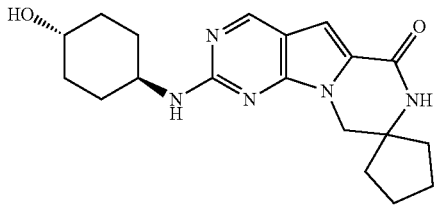 [SMILES: O=C1NC2(CCCC2)Cn2c1cc1cnc(N[C@H]3CC[C@H](O)CC3)nc12]

Compound 142 was synthesized by treating chlorotricyclic amine, Compound 141, with trans-4-aminocyclohexanol using similar experimental conditions as for Compound 124. LCMS (ESI) 356 (M+H). $^1$HNMR (600 MHz, DMSO-d6) δ ppm 1.08-1.32 (m, 8H) 1.60-2.09 (m, 8H) 3.03-3.17 (m, 1H) 3.35 (s, 2H) 3.54-3.62 (m, 1H) 4.51 (d, J=4.39 Hz, 1H) 6.88 (s, 1H) 6.96 (br. s., 1H) 8.07 (br. s., 1H) 8.58 (s, 1H).

Example 143

Synthesis of tert-butyl N-[[1-[(5-bromo-2-chloro-pyrimidin-4-yl)amino]cyclopentyl]methyl]carbamate, Compound 143

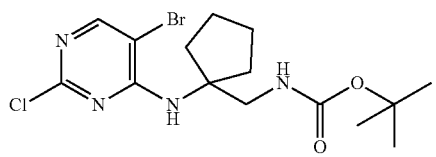 [SMILES: CC(C)(C)OC(=O)NCC1(Nc2nc(Cl)ncc2Br)CCCC1]

tert-butyl N-[[1-[(5-bromo-2-chloro-pyrimidin-4-yl)amino]cyclopentyl]methyl]carbamate was synthesized by treating 5-bromo-2,4-dichloropyrimidine with tert-butyl N-[(1-aminocyclopentyl)methyl]carbamate using similar experimental conditions as described for the synthesis of tert-butyl N-[2-[(5-bromo-2-chloro-pyrimidin-4-yl)amino]ethyl]carbamate. LCMS (ESI) 405 (M+H).

Example 144

Synthesis of tert-butyl N-[2-[[2-chloro-5-(3,3-diethoxyprop-1-ynyl)pyrimidin-4-yl]amino]-2-methyl-propyl]carbamate, Compound 144

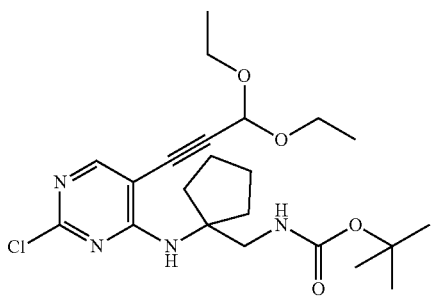 [SMILES: CCOC(C#Cc1cnc(Cl)nc1NC1(CNC(=O)OC(C)(C)C)CCCC1)OCC]

tert-butyl N-[[1-[[2-chloro-5-(3,3-diethoxyprop-1-ynyl)pyrimidin-4-yl]amino]cyclopentyl]methyl]carbamate was synthesized by treating tert-butyl N-[2-[(5-bromo-2-chloro-pyrimidin-4-yl)amino]-2-methyl-propyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate. LCMS (ESI) 453 (M+H).

Example 145

Synthesis of tert-butyl N-[[1-[2-chloro-6-(diethoxymethyl)pyrrolo[2,3-d]pyrimidin-7-yl]cyclopentyl]methyl]carbamate, Compound 145

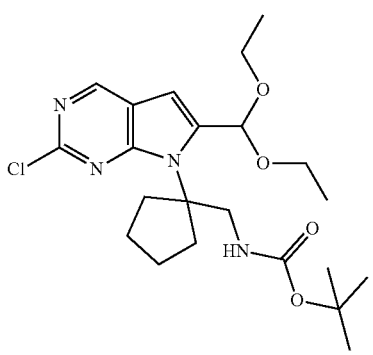 [SMILES: CCOC(OCC)c1cc2cnc(Cl)nc2n1C1(CNC(=O)OC(C)(C)C)CCCC1]

tert-Butyl N-[[1-[2-chloro-6-(diethoxymethyl)pyrrolo[2,3-d]pyrimidin-7-yl]cyclopentyl]methyl]carbamate was synthesized by treating tert-butyl N-[2-[[2-chloro-5-(3,3-diethoxyprop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) 4534 (M+H).

Example 146

Synthesis of 7-[2-(tert-butoxycarbonylamino)-1,1-dimethyl-ethyl]-2-chloro-pyrrolo[2,3-d]pyrimidine-6carboxylic acid, Compound 146

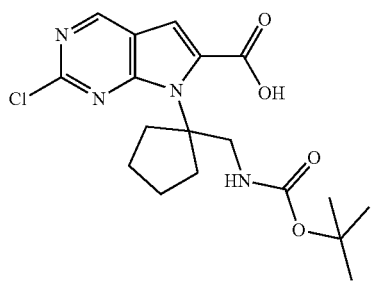 [SMILES: CC(C)(C)OC(=O)NCC1(n2c(C(=O)O)cc3cnc(Cl)nc32)CCCC1]

7-[2-(tert-Butoxycarbonylamino)-1,1-dimethyl-ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 395 (M+H).

Example 147

Synthesis of Compound 147

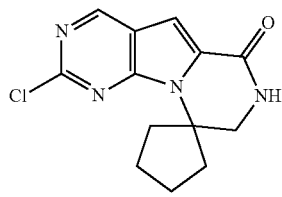 [SMILES: O=C1NCC2(CCCC2)n2c1cc1cnc(Cl)nc12]

Chloro tricyclic amide, Compound 147 was synthesized using a similar experimental procedure as that described for the chloro tricyclic amide, Compound 119. LCMS (ESI) 277 (M+H).

Example 148

Synthesis of Compound 148

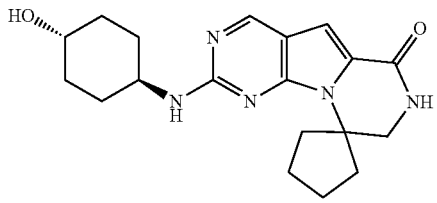 [SMILES: O=C1NCC2(CCCC2)n2c1cc1cnc(N[C@H]3CC[C@H](O)CC3)nc12]

Compound 148 was synthesized by treating chlorotricyclic amine, Compound 147, with trans-4-aminocyclohexanol using similar experimental conditions as for Compound 124. LCMS (ESI) 356 (M+H). $^1$HNMR (600 MHz, DMSO-$d_6$) δ ppm 1.06-1.35 (m, 8H) 1.45-1.95 (m, 8H) 3.10 (m, 1H) 3.58 (br. s., 2H) 3.95 (br. s., 1H) 4.49 (br. s., 1H) 6.84 (s, 1H) 6.85-6.93 (m, 1H) 8.29 (s, 1H) 8.61 (br. s., 1H).

Example 149

Synthesis of Compound 149

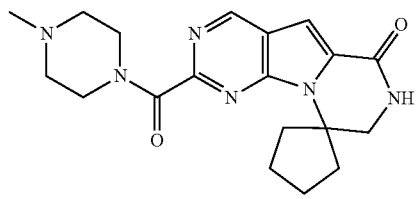 [SMILES: CN1CCN(C(=O)c2ncc3cc4n(c3n2)C2(CCCC2)CNC4=O)CC1]

Step 1: Compound 59 is Boc protected according to the method of A. Sarkar et al. (JOC, 2011, 76, 7132-7140).

Step 2: Boc-protected Compound 59 is treated with 5 mol % NiCl$_2$(Ph3)$_2$, 0.1 eq triphenylphosphine, 3 eq Mn, 0.1 eq tetraethylammonium iodide, in DMI under CO$_2$ (1 atm) at 25° C. for 20 hours to convert the aryl halide derivative into the carboxylic acid.

Step 3: The carboxylic acid from Step 2 is converted to the corresponding acid chloride using standard conditions.

Step 4: The acid chloride from Step 3 is reacted with N-methyl piperazine to generate the corresponding amide.

Step 5: The amide from Step 4 is deprotected using trifluoroacetic acid in methylene chloride to generate the target compound. Compound 149 is purified by silica gel column chromatography eluting with a dichloromethane-methanol gradient to provide Compound 149.

Each of Compounds 119 through 147 and corresponding compounds with various $R^8$, $R^1$ and Z definitions may be reacted with sodium hydride and an alkyl halide or other halide to insert the desired R substitution prior to reaction with an amine, such as described above for the synthesis of Compound 120, to produce the desired product of Formulae I, II, III, IV, or V.

Example 150

CDK4/6 Inhibition In Vitro Assay

Selected CDK4/6 inhibitor compounds disclosed herein were tested in CDK4/cyclinD1, CDK2/CycA and CDK2/cyclinE kinase assays by Nanosyn (Santa Clara, Calif.) to determine their inhibitory effect on these CDKs. The assays were performed using microfluidic kinase detection technology (Caliper Assay Platform). The compounds were tested in 12-point dose-response format in singlicate at Km for ATP. Phosphoacceptor substrate peptide concentration used was 1 M for all assays and Staurosporine was used as the reference compound for all assays. Specifics of each assay are as described below:

CDK2/CyclinA: Enzyme concentration: 0.2 nM; ATP concentration: 50 μM; Incubation time: 3 hr.

CDK2/CyclinE: Enzyme concentration: 0.28 nM; ATP concentration: 100 μM; Incubation time: 1 hr.

CDK4/CyclinD1: Enzyme concentration: 1 nM; ATP concentration: 200 μM; Incubation time: 10 hr.

The inhibitory IC$_{50}$ values for the compounds in Table 1 for CDK4/CycD1, CDK2/CycE, CDK2/CycA, as well as fold selectivity are presented in Table 2.

TABLE 2

Selective Inhibition of CDK4

| Structure | CDK4/CycD1 IC$_{50}$ [nM] | CDK2/CycE IC$_{50}$ [nM] | Fold Selectivity (CDK2/CycE/CDK4) | CDK2/CycA IC$_{50}$ [nM] | Fold Selectivity (CDK2/CycA/CDK4) |
|---|---|---|---|---|---|
| A | 4.2 | 6350 | 1516 | 3160 | 754 |
| B | 0.4 | 3040 | 6862 | 1890 | 4266 |
| C | 1.4 | 1920 | 1333 | 616 | 428 |
| D | 0.9 | 3480 | 3779 | 1500 | 1629 |
| E | 1 | 695 | 688 | 204 | 202 |
| F | 1.5 | 628 | 419 | 190 | 127 |
| G | 1.5 | 2580 | 1767 | 646 | 442 |
| H | 1.5 | 1520 | 1013 | 377 | 251 |
| I | 2 | 2120 | 1065 | 1130 | 568 |
| J | 0.7 | 5110 | 7707 | 4340 | 6546 |
| K | 1 | 1070 | 1019 | 738 | 703 |
| L | 5.7 | 4530 | 789 | 1490 | 260 |
| M | 2.3 | 2280 | 1004 | 1410 | 621 |
| N | 1 | 1500 | 1500 | ND | ND |
| O | 2.5 | 41410 | 1636 | 3150 | 1245 |
| P | 3.3 | 3560 | 1085 | 1010 | 308 |
| Q | 0.6 | 1080 | 1722 | 3030 | 4833 |
| R | 0.5 | 1920 | 3918 | 1360 | 2776 |
| S | 1.7 | 1250 | 718 | 342 | 197 |
| T | 0.8 | 1660 | 2022 | 1670 | 2034 |
| U | 0.7 | 1460 | 2229 | 857 | 1308 |
| V | 2.9 | 3500 | 1224 | 2130 | 745 |
| W | 2.7 | 3970 | 1481 | 539 | 201 |
| X | 0.9 | 11600 | 12975 | 1840 | 2058 |
| Y | 2.5 | 124 | 50 | 61 | 25 |
| Z | 3.2 | 3710 | 1174 | 647 | 205 |
| AA | 0.5 | 6100 | 13319 | 4630 | 10109 |
| BB | 0.8 | 1680 | 2017 | 502 | 603 |
| CC | 1.6 | 1250 | 791 | 755 | 478 |
| DD | 1.9 | 9620 | 5200 | 8360 | 4519 |
| EE | 3.8 | 1660 | 432 | 1110 | 289 |
| FF | 1.2 | 4620 | 3949 | 1400 | 1197 |
| GG | 1 | 3580 | 3377 | 1510 | 1425 |
| HH | 1.7 | 1280 | 766 | 265 | 159 |
| II | 2 | 367 | 184 | 239 | 120 |
| JJ | 1.4 | 288 | 204 | ND | ND |
| KK | 2.3 | 1760 | 762 | 915 | 396 |
| LL | 2 | 202 | 103 | 108 | 55 |
| MM | 1.8 | 3390 | 1863 | 597 | 328 |
| NN | 3.7 | 4700 | 1274 | 1560 | 423 |
| OO | 9 | 3980 | 442 | 570 | 63 |
| PP | 3.1 | 3600 | 1146 | 3090 | 984 |
| QQ | 4.1 | 3060 | 746 | 2570 | 627 |
| RR | 1.2 | 1580 | 1374 | 693 | 603 |
| SS | 0.8 | 1460 | 1865 | 1390 | 1775 |
| TT | 0.8 | 1260 | 1550 | 596 | 733 |
| UU | 7.3 | 3960 | 542 | ND | ND |
| VV | 3.3 | 2630 | 809 | 789 | 243 |
| WW | 0.7 | 1350 | 204 | ND | ND |
| XX | 1.3 | 7300 | 5615 | 6290 | 4838 |
| YY | 4.6 | 6900 | 1490 | ND | ND |
| ZZ | 10.5 | 9960 | 949 | ND | ND |
| AAA | 2.3 | 6010 | 2591 | 2130 | 918 |
| BBB | 2.8 | 187 | 68 | 85 | 31 |
| CCC | 2 | 2170 | 1074 | 457 | 226 |
| DDD | 9.5 | 9350 | 986 | ND | ND |
| EEE | 0.2 | 2950 | 1266 | 943 | 405 |
| FFF | 4.7 | 4540 | 966 | 1370 | 291 |
| GGG | 13.7 | 7610 | 555 | ND | ND |
| HHH | 6.8 | 2840 | 419 | ND | ND |
| III | 6 | 3770 | 626 | ND | ND |
| JJJ | 3.2 | 5200 | 1620 | 2830 | 882 |
| KKK | 1.3 | 291 | 231 | 87.3 | 69 |
| LLL | 3.2 | 1620 | 509 | 4530 | 1425 |
| MMM | 3.2 | 1890 | 600 | 990 | 314 |
| NNN | 1.4 | 2930 | 2154 | 1010 | 743 |
| OOO | 2.4 | 393 | 164 | 203 | 85 |
| PPP | 0.8 | 16500 | 21263 | 2640 | 3402 |
| QQQ | 10.5 | 11100 | 1057 | ND | ND |
| RRR | 2.6 | 4500 | 1758 | ND | ND |
| SSS | 2 | 2280 | 1112 | 1880 | 917 |
| TTT | 3.4 | 3030 | 899 | ND | ND |
| UUU | 18 | 16460 | 914 | ND | ND |
| VVV | 7.4 | 4380 | 589 | ND | ND |

TABLE 2-continued

| | Selective Inhibition of CDK4 | | | | |
|---|---|---|---|---|---|
| Structure | CDK4/ CycD1 IC$_{50}$ [nM] | CDK2/ CycE IC$_{50}$ [nM] | Fold Selectivity (CDK2/CycE/CDK4) | CDK2/CycA IC$_{50}$ [nM] | Fold Selectivity (CDK2/CycA/CDK4) |
| WWW | 18.5 | 2500 | 135 | ND | ND |
| XXX | 11.4 | 6620 | 581 | ND | ND |

To further characterize its kinase activity, Compound T was screened against 456 (395 non-mutant) kinases using DiscoveRx's KINOMEscan™ profiling service. The compound was screened using a single concentration of 1000 nM (>1000 times the IC50 on CDK4). Results from this screen confirmed the high potency against CDK4 and high selectivity versus CDK2. Additionally, the kinome profiling showed that Compound T was relatively selective for CDK4 and CDK6 compared to the other kinases tested. Specifically, when using an inhibitory threshold of 65%, 90%, or 99%, Compound T inhibited 92 (23.3%), 31 (7.8%) or 6 (1.5%) of 395 non-mutant kinases respectively.

In addition to CDK4 kinase activity, several compounds were also tested against CDK6 kinase activity. The results of the CDK6/CycD3 kinase assays, along with the CDK4/cyclinD1, CDK2/CycA and CDK2/cyclinE kinase assays, are shown for PD0332991 (Reference) and the compounds T, Q, GG, and U in Table 3. The IC$_{50}$ of 10 nM for CDK4/cyclinD1 and 10 uM for CDK12/CyclinE agrees well with previously published reports for PD0332991 (Fry et al. Molecular Cancer Therapeutics (2004) 3(11) 1427-1437; Toogood et al. Journal of Medicinal Chemistry (2005) 48, 2388-2406). Compounds T, Q, GG, and U are more potent (lower IC$_{50}$) with respect to the reference compound (PD0332991) and demonstrate a higher fold selectivity with respect to the reference compound (CDK2/CycE IC$_{50}$ divided by CDK4/CycD1 IC$_{50}$).

TABLE 3

| | Inhibition of CDK kinases by Compounds T, Q, GG, and U | | | | |
|---|---|---|---|---|---|
| Formula | CDK4/CycD1 IC$_{50}$ (nM) | CDK2/CycE IC$_{50}$ (uM) | Fold Selectivity CDK2/CDK4 | CDK2/CycA IC$_{50}$ (uM) | CDK6/CycD3 IC50 (nM) |
| PD0332991 Reference | 10 | 10 | 1000 | Not determined | Not determined |
| Compound T | 0.821 | 1.66 | 2022 | 1.67 | 5.64 |
| Compound Q | 0.627 | 1.08 | 1722 | 3.03 | 4.38 |
| Compound GG | 1.060 | 3.58 | 3377 | 1.51 | 4.70 |
| Compound U | 0.655 | 1.46 | 2229 | .857 | 5.99 |

Example 151

G1 Arrest (Cellular G1 and S-Phase) Assay

To show that CDK4/6 inhibitors described herein, when administered alone, do not have an inhibitory affect in Rb-negative (i.e., CDK-replication independent) cancers, CDK4/6 inhibitors were administered to various Rb-positive and Rb-negative cells and the cellular fractions in various stages of the cell cycle following treatment was assessed.

HS68 cells (human skin fibroblast cell line (Rb-positive)) were stained with propidium iodide staining solution and run on Dako Cyan Flow Cytometer. The fraction of cells in G0-G1 DNA cell cycle versus the fraction in S-phase DNA cell cycle was determined using FlowJo 7.2.2 analysis.

The compounds listed in Table 1 were tested for their ability to arrest HS68 cells at the G1 phase of the cell cycle. From the results of the cellular G1 arrest assay, the range of the inhibitory ECso values necessary for G1 arrest of HS68 cells was from 22 nM to 1500 nM (see column titled "Cellular G1 Arrest EC50" in Table 4).

Example 152

Inhibition of Cellular Proliferation

Further cellular proliferation assays were conducted using the following cancer cell lines: MCF7 (breast adenocarcinoma—Rb-positive), ZR-75-1 (breast ductal carcinoma—Rb-positive), H69 (human small cell lung cancer—Rb-negative) cells, or A2058 (human metastatic melanoma cells—Rb-negative). These cells were seeded in Costar (Tewksbury, Mass.) 3093 96 well tissue culture treated white walled/clear bottom plates. Cells were treated with the compounds of Table 1 as nine point dose response dilution series from 10 uM to InM. Cells were exposed to compounds and then cell viability was determined after either four (H69) or six (MCF7, ZR75-1, A2058) days as indicated using the CellTiter-Glo® luminescent cell viability assay (CTG; Promega, Madison, Wis., United States of America) following the manufacturer's recommendations. Plates were read on BioTek (Winooski, Vt.) Syngergy2 multi-mode plate reader. The Relative Light Units (RLU) were plotted as a result of variable molar concentration and data was analyzed using Graphpad (LaJolla, Calif.) Prism 5 statistical software to determine the EC50 for each compound.

The results of the cellular inhibition assays for the two Rb-positive breast cancer cell lines (MCF7 and ZR75-1) are shown in Table 4. The range of the inhibitory EC$_{50}$ values necessary for inhibition of MCF7 breast cancer cell proliferation was 28 nM to 257 nM. The range of the inhibitory EC$_{50}$ values necessary for inhibition of ZR75-1 breast cancer cell proliferation was 24 nM to 581 nM.

In addition to breast cancer cell lines, a number of the compounds disclosed herein were also evaluated against a small cell lung cancer cell line (H69) and a human metastatic melanoma cell line (A2058), two Rb-negative cell lines. The results of these cellular inhibition assays are shown in Table 4. The range of the inhibitory EC50 values necessary for inhibition of H69 small cell lung cancer cells was 2040 nM to >3000 nM. The range of the inhibitory EC50 values necessary for inhibition of A2058 malignant melanoma cell proliferation was 1313 nM to >3000 nM. In contrast to the significant inhibition seen on the two Rb-positive breast cancer cell lines, it was found that the compounds tested were not significantly effective at inhibiting proliferation of the Rb-negative small cell lung cancer or melanoma cells.

TABLE 4

Inhibition of Cancer Cell Proliferation

| Structure | Cellular G1 Arrest $EC_{50}$ (nM) | MCF7 Cellular $EC_{50}$ [nM] | ZR75-1 Cellular $EC_{50}$ [nM] | H69 Cellular $EC_{50}$ [nM] | A2058 Cellular $EC_{50}$ [nM] |
|---|---|---|---|---|---|
| A | 110 | 75 | 44 | >3000 | ND |
| B | 90 | 201 | 245 | ND | ND |
| C | 95 | 88 | 73 | ND | ND |
| D | 50 | 57 | 46 | 2911 | 1670 |
| E | 75 | 53 | 62 | 2580 | 1371 |
| F | 175 | ND | ND | ND | ND |
| G | 175 | ND | ND | ND | ND |
| H | 85 | 85 | 120 | 2040 | 1313 |
| I | 80 | 61 | 40 | 2950 | 1062 |
| J | 110 | 70 | 82 | >3000 | >3000 |
| K | 28 | 43 | ND | >3000 | 1787 |
| L | 65 | 506 | ND | 2161 | >3000 |
| M | 100 | ND | ND | ND | ND |
| N | 25 | 28 | 24 | >3000 | 1444 |
| O | 40 | 56 | 29 | >3000 | 2668 |
| P | 30 | 60 | 43 | >3000 | >3000 |
| Q | 100 | 49 | 35 | >3000 | 2610 |
| R | 70 | 36 | 50 | >3000 | 2632 |
| S | 150 | 76 | ND | >3000 | >3000 |
| T | 100 | 49 | 36 | >3000 | >3000 |
| U | 25 | 70 | 59 | >3000 | >3000 |
| V | 70 | 50 | 29 | >3000 | 1353 |
| W | 160 | 294 | ND | >3000 | >3000 |
| X | 65 | ND | ND | >3000 | >3000 |
| Y | 350 | ND | ND | ND | ND |
| Z | 110 | 141 | 54 | ND | ND |
| AA | 70 | 47 | 47 | >3000 | ND |
| BB | 75 | ND | ND | 2943 | 1635 |
| CC | 90 | 50 | 38 | >3000 | >3000 |
| DD | 100 | ND | ND | ND | ND |
| EE | 125 | 216 | 203 | ND | ND |
| FF | 80 | 140 | ND | ND | ND |
| GG | 80 | 52 | 62 | 2920 | 2691 |
| HH | 110 | ND | ND | ND | ND |
| II | 40 | 94 | 33 | >3000 | >3000 |
| JJ | 90 | 122 | ND | >3000 | >3000 |
| KK | 22 | 333 | ND | 2421 | 1379 |
| LL | 125 | 96 | ND | >3000 | >3000 |
| MM | 100 | 73 | 77 | >3000 | >3000 |
| NN | 110 | ND | ND | ND | ND |
| OO | 95 | 120 | 229 | >3000 | >3000 |
| PP | 100 | 164 | 66 | ND | ND |
| QQ | 120 | ND | ND | >3000 | >3000 |
| RR | 90 | 72 | ND | 2888 | 1617 |
| SS | 80 | 94 | 53 | 2948 | 1658 |
| TT | 75 | ND | ND | ND | ND |
| UU | 300 | ND | ND | ND | ND |
| VV | 200 | ND | ND | ND | ND |
| WW | 400 | ND | ND | ND | ND |
| XX | 225 | ND | ND | ND | ND |
| YY | 175 | 257 | 581 | ND | ND |
| ZZ | 500 | ND | ND | ND | ND |
| AAA | 275 | 320 | ND | >3000 | >3000 |
| BBB | 230 | 123 | ND | >3000 | >3000 |
| CCC | 250 | ND | ND | ND | ND |
| DDD | 350 | ND | ND | ND | ND |
| EEE | 250 | 453 | ND | >3000 | >3000 |
| FFF | 650 | ND | ND | ND | ND |
| GGG | 350 | ND | ND | ND | ND |
| HHH | 250 | ND | ND | ND | ND |
| III | 250 | ND | ND | ND | ND |
| JJJ | 240 | ND | ND | ND | ND |
| KKK | 190 | ND | ND | ND | ND |
| LLL | 250 | ND | ND | ND | ND |
| MMM | 200 | 134 | 141 | >3000 | >3000 |
| NNN | 210 | ND | ND | ND | ND |
| OOO | 200 | 138 | ND | >3000 | >3000 |
| PPP | 275 | ND | ND | ND | ND |
| QQQ | 500 | ND | ND | ND | ND |

TABLE 4-continued

Inhibition of Cancer Cell Proliferation

| Structure | Cellular G1 Arrest EC$_{50}$ (nM) | MCF7 Cellular EC$_{50}$ [nM] | ZR75-1 Cellular EC$_{50}$ [nM] | H69 Cellular EC$_{50}$ [nM] | A2058 Cellular EC$_{50}$ [nM] |
|---|---|---|---|---|---|
| RRR | 400 | ND | ND | ND | ND |
| SSS | 1500 | ND | ND | ND | ND |
| TTT | 350 | ND | ND | ND | ND |
| UUU | 300 | ND | ND | ND | ND |
| VVV | 300 | ND | ND | ND | ND |
| WWW | 300 | ND | ND | ND | ND |
| XXX | 300 | ND | ND | ND | ND |

Example 153

Pharmacokinetic and Pharmacodynamic Properties of Active Compounds

Compounds of the present invention demonstrate good pharmacokinetic and pharmacodynamic properties. Compound T, Q, GG, and U were dosed to mice at 30 mg/kg by oral gavage or 10 mg/kg by intravenous injection. Blood samples were taken at 0, 0.25, 0.5, 1.0, 2.0, 4.0, and 8.0 hours post dosing and the plasma concentration of compound T, Q, GG, or U were determined by HPLC. Compound T, GG, and U were demonstrated to have excellent oral pharmacokinetic and pharmacodynamic properties as shown in Table 5. This includes very high oral bioavailability (F (%)) of 52% to 80% and a plasma half-life of 3 to 5 hours following oral administration. Compound T, Q, GG, and U were demonstrated to have excellent pharmacokinetic and pharmacodynamic properties when delivered by intravenous administration.

TABLE 5

Pharmacokinetic and pharmacodynamic properties of active compounds

| Mouse PK | Compound T | Compound Q | Compound GG | Compound U |
|---|---|---|---|---|
| CL (mL/min/kg) | 35 | 44 | 82 | 52 |
| Vss (L/kg) | 2.7 | 5.2 | 7.5 | 3.4 |
| t$_{1/2}$ (h) p.o. | 5 | 0.8 | 3.5 | 3 |
| AUC$_{0\text{-}inf}$ (uM * h) i.v. | 1.3 | 0.95 | 1.1 | 0.76 |
| AUC (uM * h) p.o. | 2.9 | 0.15 | 1.9 | 3.3 |
| C$_{max}$ (uM) p.o. | 2.5 | 0.16 | 1.9 | 4.2 |
| T$_{max}$ (h) p.o. | 1 | 0.5 | 1 | 0.5 |
| F (%) | 80 | 2 | 52 | 67 |

Example 154

Cell Cycle Arrest by CDK 4/6 Inhibitors in CDK4/6-Dependent Cells

To test the ability of the disclosed CDK4/6 inhibitors to induce a clean G1-arrest, a cell based screening method was used consisting of two Rb-positive (tHS68 and WM2664) and one Rb-negative (A2058) cell line. Twenty-four hours after plating, each cell line was treated with Compound T in a dose dependent manner for 24 hours. At the conclusion of the experiment, cells were harvested, fixed, and stained with propidium iodide (a DNA intercalator), which fluoresces strongly red (emission maximum 637 nm) when excited by 488 nm light. Samples were run on Dako Cyan flow cytometer and >10,000 events were collected for each sample. Data were analyzed using FlowJo 2.2 software developed by TreeStar, Inc.

Figure 9A:
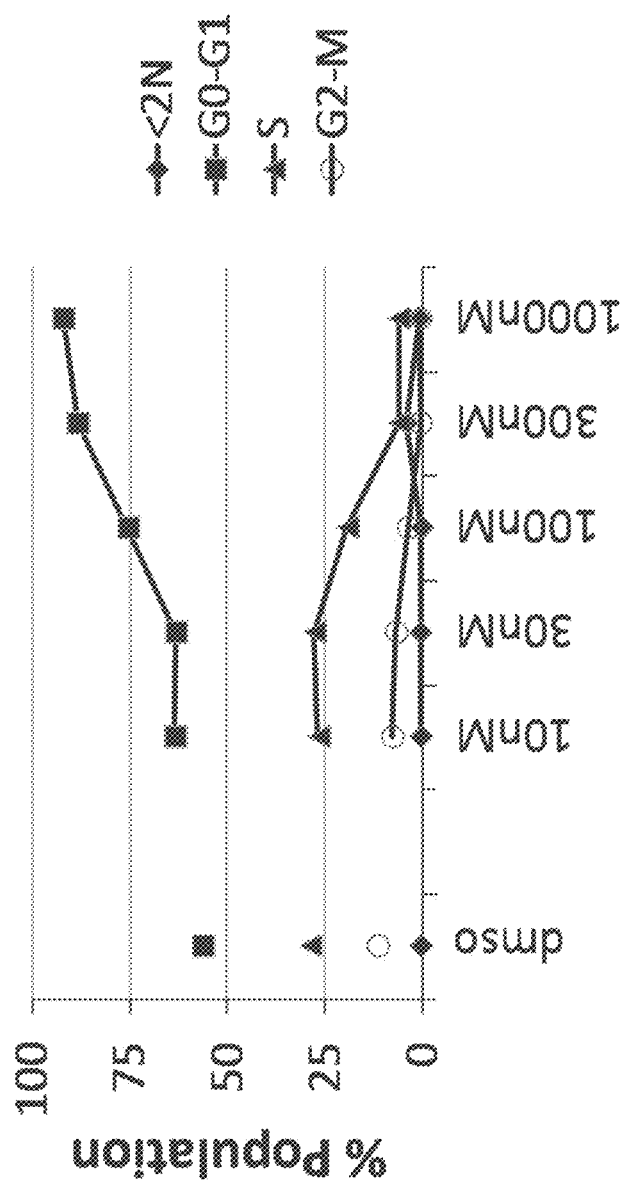
FIG. 9A is a graph of the percentage of cells in G2-M phase (open circles), S phase (triangles), G0-G1 phase (squares), <2N (diamonds) vs. variable concentration (nM) of compound T in tHS68 cells. The Rb-positive cell line (tHS68) was treated with the indicated concentrations of Compound T for 24 hours. Following treatment of Compound T, cells were harvested and analyzed for cell cycle distribution. As described in Example 153, tHS68 cells show a clean G1 arrest accompanied by a corresponding decrease in the number of cells in S-phase.
Figure 9C:
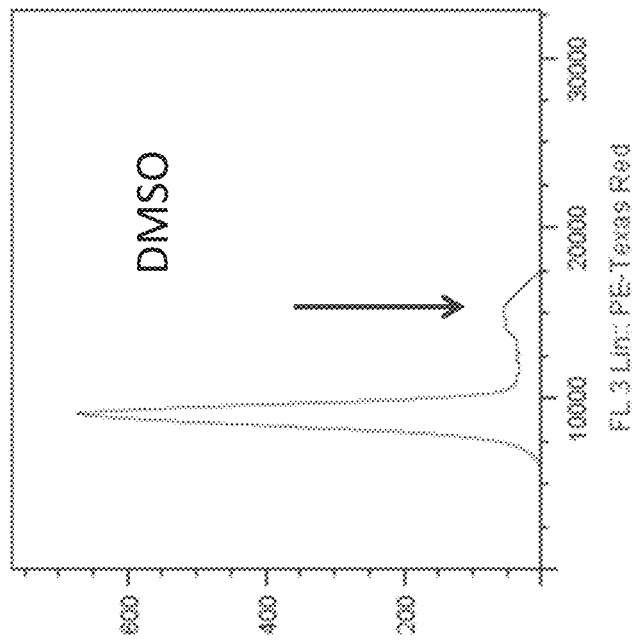
FIG. 9C is a graph of the number of WM2664 cells (Rb-positive cell line) vs. the DNA content of the cells (as measured by propidium iodide). Cells were treated with DMSO for 24 hours, harvested, and analyzed for cell cycle distribution.
Figure 9B:
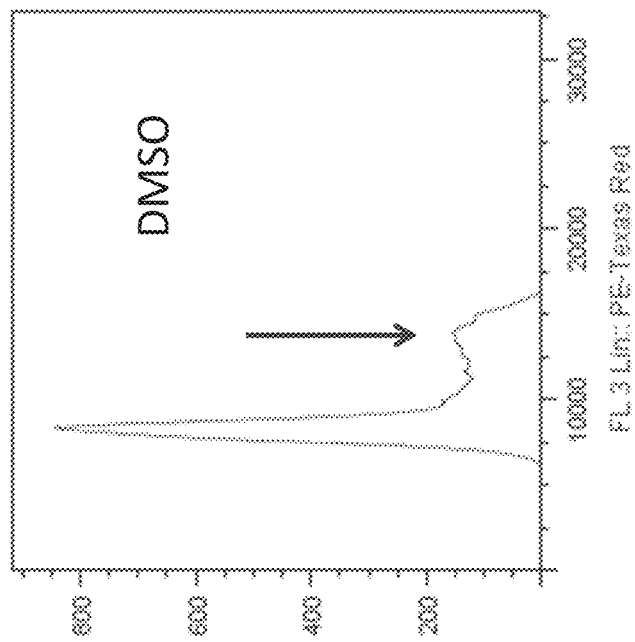
FIG. 9B is a graph of the number of tHS68 cells (Rb-positive cell line) vs. the DNA content of the cells (as measured by propidium iodide). Cells were treated with DMSO for 24 hours, harvested, and analyzed for cell cycle distribution.
Figures 9D, 9E:
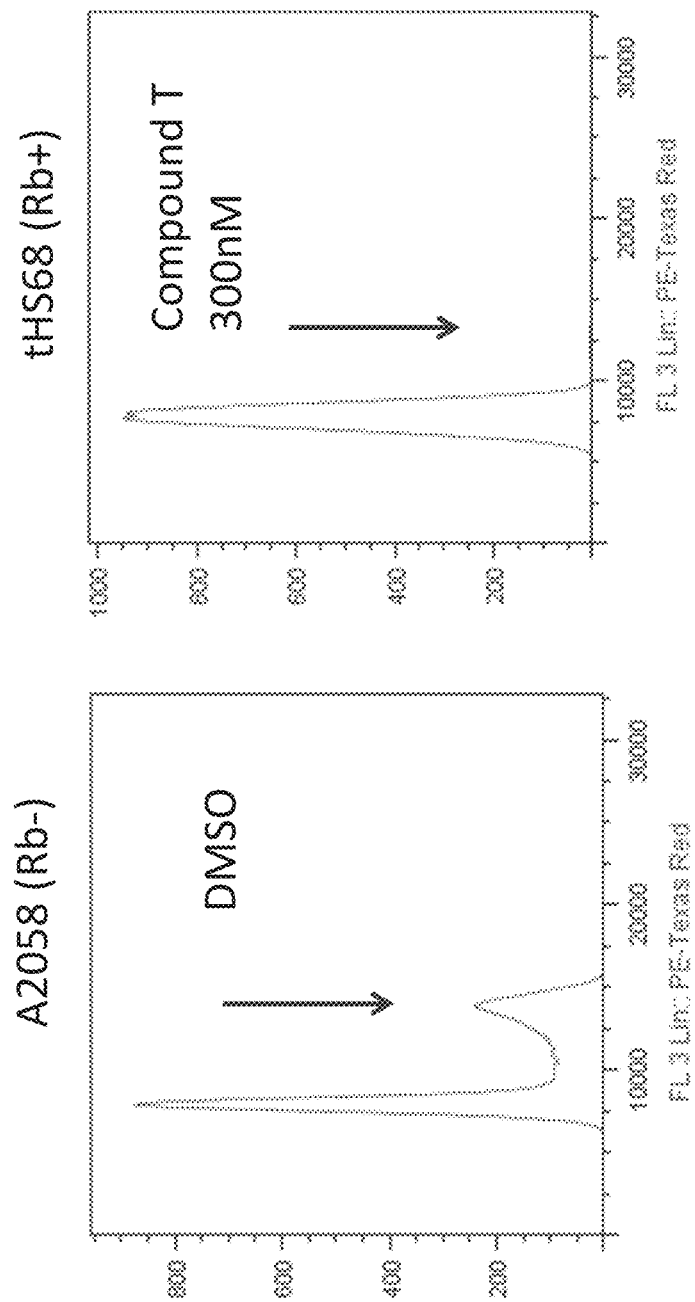
FIG. 9D is a graph of the number of A2058 cells (Rb-negative cell line) vs. the DNA content of the cells (as measured by propidium iodide). Cells were treated with DMSO for 24 hours, harvested, and analyzed for cell cycle distribution.
FIG. 9E is a graph of the number of tHS68 cells (Rb-positive cell line) vs. the DNA content of the cells (as measured by propidium iodide) after treatment with Compound T. Cells were treated with Compound T (300 nM) for 24 hours, harvested, and analyzed for cell cycle distribution. As described in Example 161, treatment of tHS68 cells with Compound T causes a loss of the S-phase peak (indicated by arrow).
Figures 9F, 9G:
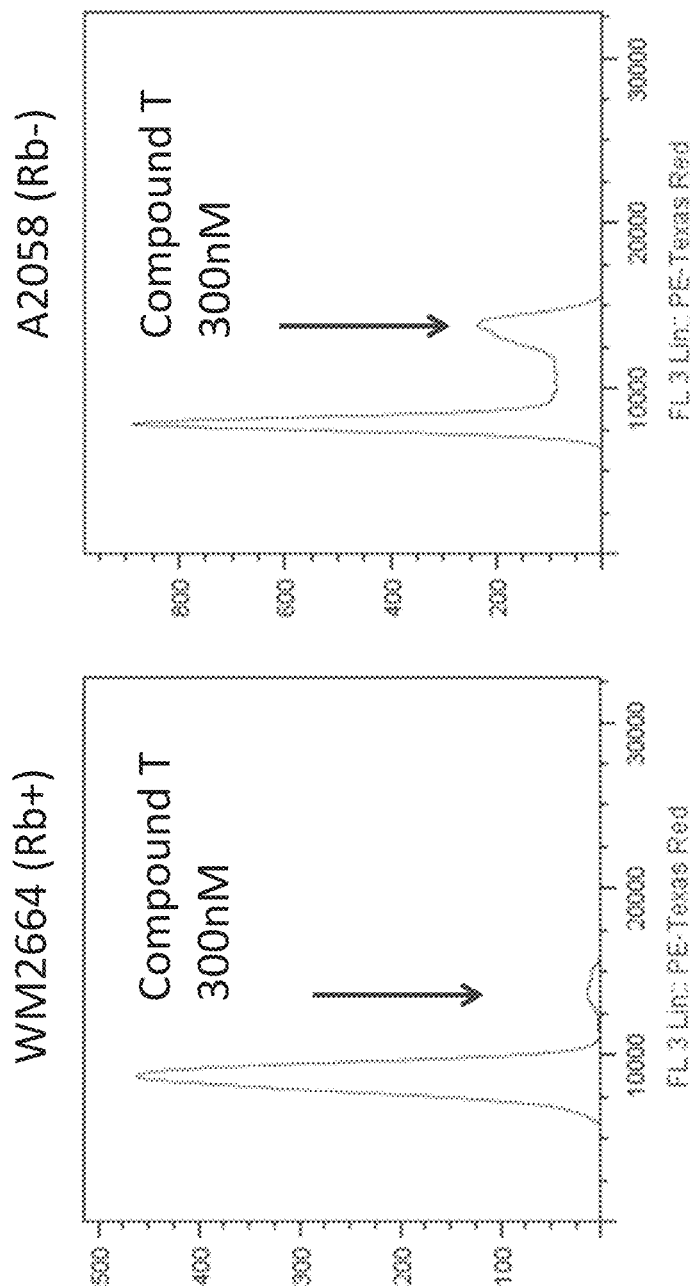
FIG. 9F is a graph of the number of WM2664 cells (Rb-positive cell line) vs. the DNA content of the cells (as measured by propidium iodide) after treatment with Compound T. Cells were treated with Compound T (300 nM) for 24 hours, harvested, and analyzed for cell cycle distribution. As described in Example 161, treatment of WM2664 cells with Compound T causes a loss of the S-phase peak (indicated by arrow).
FIG. 9G is a graph of the number of A2058 cells (Rb-negative cell line) vs. the DNA content of the cells (as measured by propidium iodide) after treatment with Compound T. Cells were treated with Compound T (300 nM) for 24 hours, harvested, and analyzed for cell cycle distribution. As described in Example 154, treatment of A2058 cells with Compound T does not cause a loss of the S-phase peak (indicated by arrow).

In FIG. 9A, results show that CDK 4/6 inhibitor Compound T induces a robust G1 cell cycle arrest, as nearly all cells are found in the G0-G1 phase upon treatment with increasing amounts of Compound T. In FIG. 9A, the results show that in Rb-positive cell lines, Compound T induced a robust G1 cell cycle arrest with an EC50 of 80 nM in tHS68 cells with a corresponding reduction in S-phase ranging from 28% at baseline to 6% at the highest concentration shown. Upon treatment with Compound T (300 nM), there was a similar reduction in the S-phase population and an increase in G1-arrested cells in both Rb-positive cell lines (tHS68 (Compare FIGS. 9B and 9E) and WM2664 (Compare FIGS. 9C and 9F)), but not in the Rb-negative (A2058; Compare FIGS. 9D and 9G) cell line. The Rb-negative cell line shows no effect in the presence of inhibitor.

Example 155

CDK 4/6 Inhibitor Compounds Inhibit Phosphorylation of RB

Figure 10:
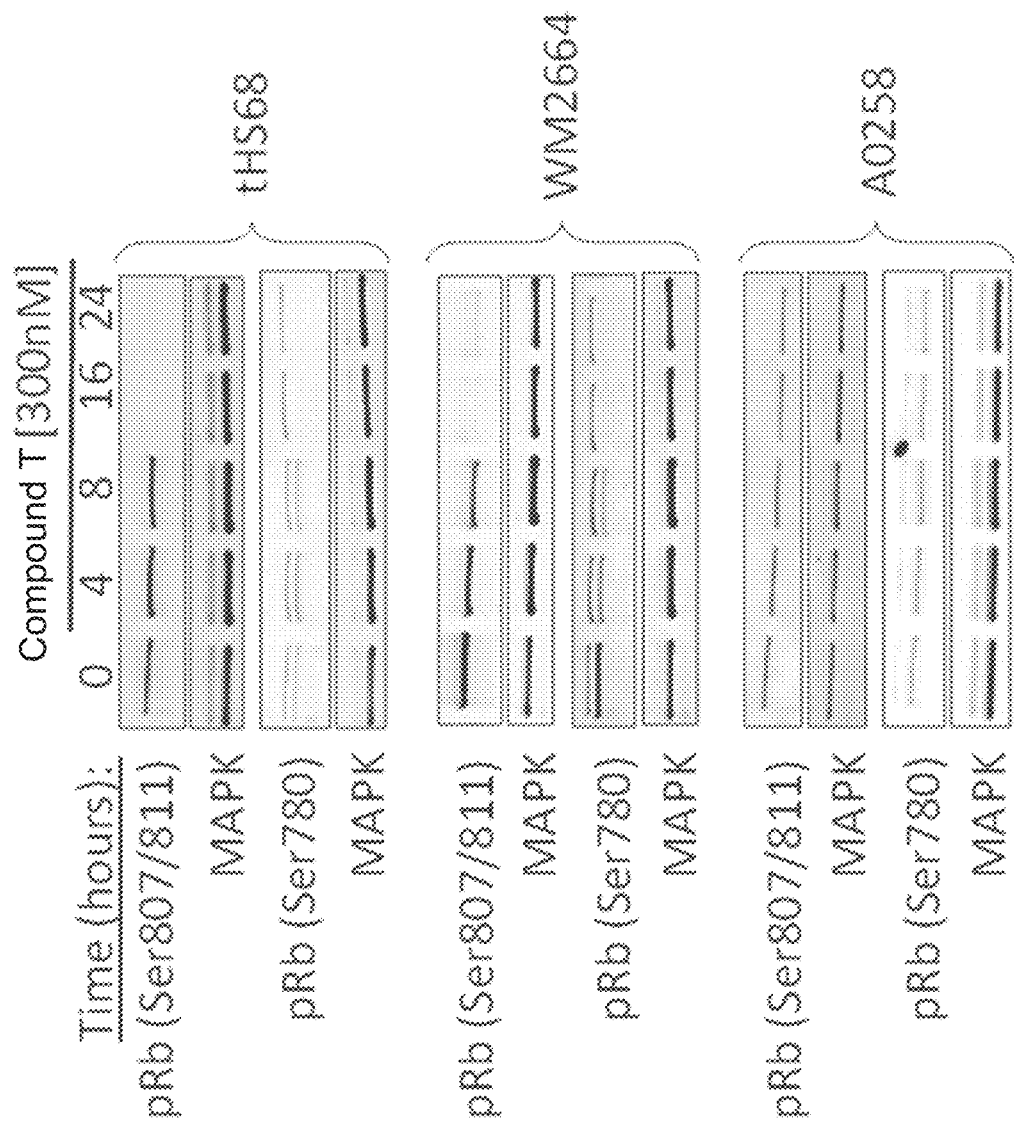
FIG. 10 is a Western blot showing the phosphorylation levels of Rb at Ser807/811 and Ser780 after treatment with Compound T. Rb-positive (tHS68 or WM2664) and Rb-negative cell lines (A2058) were treated with Compound T (300 nM) for the indicated times (0, 4, 8, 16, and 24 hours). MAPK levels are shown as a control for protein levels. Following treatment, cells were harvested and analyzed for Rb-phosphorylation by western blot analysis. As described in Example 155, Compound T treatment resulted in reduced Rb-phosphorylation starting 16 hours after treatment in Rb-positive cell lines (tHS68 and WM2664), but not in the Rb-negative cell line (A2058).

The CDK4/6-cyclin D complex is essential for progression from G1 to the S-phase of the DNA cell cycle. This complex phosphorylates the retinoblastoma tumor suppressor protein (Rb). To demonstrate the impact of CDK4/6 inhibition on Rb phosphorylation (pRb), CDK 4/6 inhibitor Compound T was exposed to three cell lines: two Rb-positive (tHS68, WM2664) and one Rb-negative (A2058). Twenty four hours after seeding, cells were treated with Compound T at 300 nM final concentration for 4, 8, 16, and 24 hours. Samples were lysed and protein was assayed by western blot analysis. Rb phosphorylation was measured at two sites targeted by the CDK4/6-cyclin D complex, Ser780 and Ser807/811 using species specific antibodies. Results demonstrate that Compound T blocks Rb phosphorylation in Rb-positive cell lines by 16 hours post exposure, while having no effect on Rb-negative cells (FIG. 10).

Example 156

CDK 4/6 Inhibitor Compounds Show Enhanced Efficacy Against CDK4/6 Independent Tumors in Combination with a Topoisomerase I Inhibitor The potential of the disclosed CDK 4/6 inhibitors to have advantageous, additive, or synergistic effects in combination with topoisomerase I inhibitors was examined in an Rb-negative tumor model. An Rb-negative model of small cell lung cancer was used in the following example. Briefly, xenografts of National Cancer Institute (NCI) H69 cells were grafted onto the mice. H69 cells are human small cell lung cancer cells and are Rb-negative cells.

Mice were enrolled in therapy studies when tumors reached a standard size (50-60 mm$^3$) that permitted easy serial assessment. Tumor-bearing mice were treated with vehicle control (N=8), carboplatin/etoposide (N=8), Compound T/carboplatin/etoposide (N=8), topotecan (N=8), or Compound T/topotecan (N=7). Carboplatin and etoposide were administered at 40 mg/kg and 4 mg/kg, respectively, and were administered by intraperitoneal injection twice per week for 3 weeks. Topotecan was administered at 0.6 mg/kg by intraperitoneal injection once daily for 5 days. Compound T was administered at 100 mg/kg by po, qdx5x4. On days when mice were treated with chemotherapeutic agents, Compound T was administered 30 minutes prior to each administration of carboplatin/etoposide or topotecan. Tumor size was examined twice per week for up to nine weeks.

Figure 11:
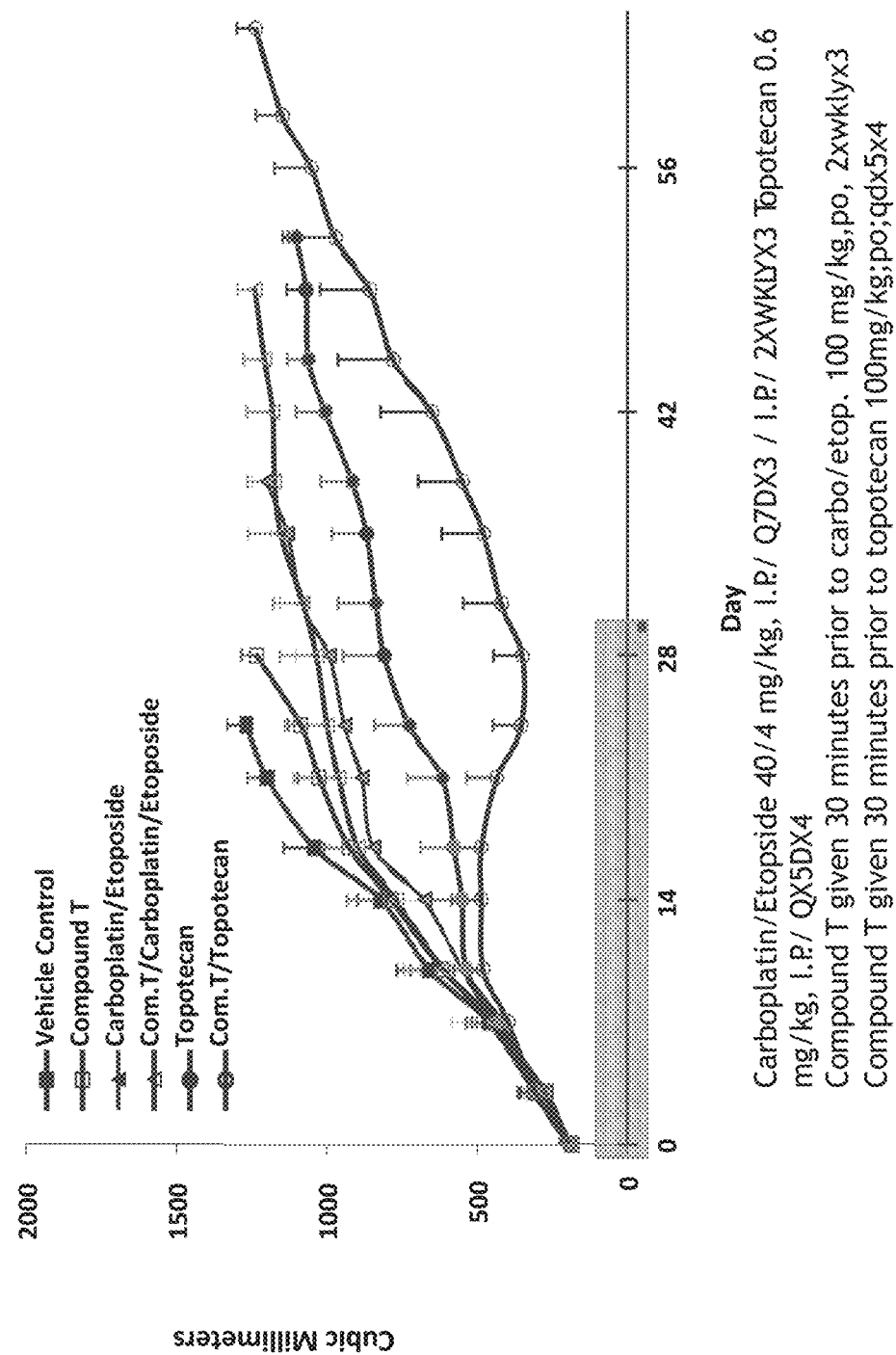
FIG. 11 is a graph showing the tumor size (in cubic millimeters) in a CDK4/6 independent mouse model (NCI-H69 SCLC xenograft model) treated with vehicle control (closed squares), Compound T (open squares), carboplatin/etoposide (closed triangles), Compound T/carboplatin/etoposide (open triangles), topotecan (closed circles), or Compound T/topotecan (open circles). As discussed in Example 156, Compound T showed enhanced efficacy in slowing tumor growth in combination with the chemotherapeutic agent topotecan. In contrast, Compound T did not result in increased efficacy in slowing tumor growth in combination with the chemotherapeutic agents carboplatin and etoposide.

As shown in FIG. 11, treatment of NCI-H69 xenograft mice with the CDk 4/6 inhibitor Compound T alone had very little effect of slowing tumor growth in the Rb-negative tumor model. When Compound T was administered in combination with the chemotherapeutic agents carboplatin and etoposide, there was no effect on tumor growth when compared to the use of carboplatin and etoposide without Compound T. While Compound T did not appear to show any synergistic effects in combination with carboplatin and etoposide, advantageously when Compound T was administered in combination with a topoisomerase I inhibitor, in this case topotecan, there was a significant decrease in tumor size in the H69 xenograft mouse model.

Example 157. CDK 4/6 Inhibitors Show Enhanced Efficacy Against CDK4/6 Independent Tumors in Combination with Toposiomerase I Inhibitors at Reduced CDK 4/6 Dosages The potential of the disclosed CDK 4/6 inhibitors to have advantageous, additive, or synergistic effects in combination with a topoisomerase I inhibitor compound, in this instance topotecan, was further examined in an Rb-negative tumor model. An Rb-negative model of small cell lung cancer was used in the following example. Briefly, xenografts of National Cancer Institute (NCI) H69 cells were grafted onto the mice (Athymic Nude (Crl:NU(NCr)-Foxn1$^{nu}$); 6-12 week old females) using the South Texas Accelerated Research Therapeutics (START) Cell-Based Xenograft (START-CBX) tumor model. H69 cells are human small cell lung cancer cells and are Rb-negative.

Data collected from the efficacy study included animal weights, observations and tumor dimensions. This information was used to determine agent tolerability based on weight change and gross physiologic changes and anticancer activity based on tumor growth delay or regression. The designated endpoint for this study was an individual tumor volume of 1 cm$^3$ or 60 days following treatment initiation.

Tumor fragments from NCI-H69 were harvested from host animals and implanted into immune-deficient mice and the study initiated at a mean tumor volume of approximately 150-250 mm$^3$. Tumor-bearing mice were treated with Compound T vehicle and topotecan vehicle (Group 1; N=7), Compound T (100 mg/kg) and topotecan vehicle (Group 2; N=7), Compound T (100 mg/kg) and topotecan (0.6 mg/kg) (Group 3; N=7), Compound T (50 mg/kg) and topotecan (0.6 mg/kg) (Group 4; N=7), Compound T (10 mg/kg) and topotecan (0.6 mg/kg) (Group 5; N=7) or Compound T vehicle and topotecan (0.6 mg/kg) (Group 6; N=7).

Importantly, the advantageous anti-tumor effects seen with the use of CDK4/6 inhibitor compounds described herein in combination with topoisomerase I inhibitors occurred at all doses of CDK4/6 inhibitor—100 mg/kg, 50 mg/kg, and 10 mg/kg. Thus, an advantageous anti-tumor effect can be achieved with low doses of CDK4/6 inhibitors described herein, for example about 10 mg/kg.

Additional details of the study are outlined in Table 6 below. On days when mice were treated with chemotherapeutic agents, Compound T was administered 30 minutes prior to topotecan. Tumor size was examined twice per week and the endpoint for this study was Day 59.

TABLE 6

Detailed Study Outline

| Group | Animals (N) | Treatment | Dose (mg/kg) | ROA/Schedule | Total Doses | Treatment Days | Endpoint |
|---|---|---|---|---|---|---|---|
| 1 | 7 | Compound T Vehicle | — | PO/qdx5x4 | 15 | 0-4, 7-11, 14-18 | 21 |
|   |   | Topotecan Vehicle | — | IP/qdx5x4 | 15 | 0-4, 7-11, 14-18 |   |
| 2 | 7 | Compound T | 100 | PO/qdx5x4 | 19 | 0-4, 7-11, 14-18, 21-23 | 24 |
|   |   | Topotecan Vehicle | — | IP/qdx5x4 | 19 | 0-4, 7-11, 14-18, 21-23 |   |
| 3 | 7 | Compound T | 100 | PO/qdx5x4 | 20 | 0-4, 7-11, 14-18, 21-24 | 59 |
|   |   | Topotecan | 0.6 | IP/qdx5x4 | 20 | 0-4, 7-11, 14-18, 21-24 |   |
| 4 | 7 | Compound T | 50 | PO/qdx5x4 | 20 | 0-4, 7-11, 14-18, 21-24 | 59 |
|   |   | Topotecan | 0.6 | IP/qdx5x4 | 20 | 0-4, 7-11, 14-18, 21-24 |   |
| 5 | 7 | Compound T | 10 | PO/qdx5x4 | 20 | 0-4, 7-11, 14-18, 21-24 | 59 |
|   |   | Topotecan | 0.6 | IP/qdx5x4 | 20 | 0-4, 7-11, 14-18, 21-24 |   |
| 6 | 7 | Compound T Vehicle | — | PO/qdx5x4 | 20 | 0-4, 7-11, 14-18, 21-24 | 59 |
|   |   | Topotecan | 0.6 | IP/qdx5x4 | 20 | 0-4, 7-11, 14-18, 21-24 |   |

Figure 12:
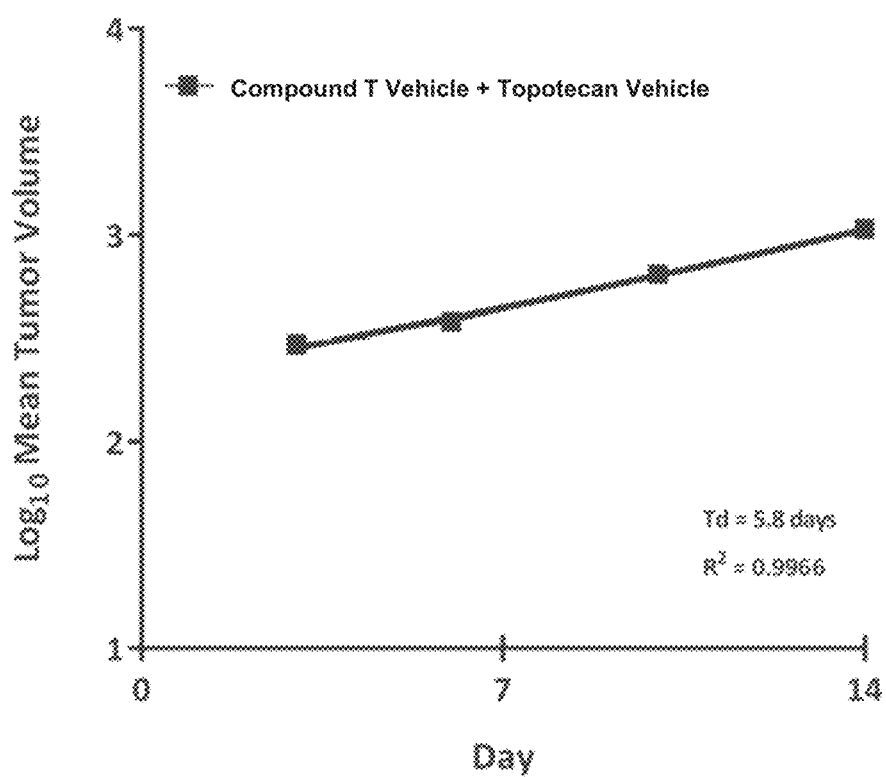
FIG. 12 is a graph showing the tumor size ($\log_{10}$ mean tumor volume) vs. time (days) in a CDK4/6 independent tumor mouse model (NCI-H69 SCLC xenograft model) treated with Compound T vehicle and topotecan vehicle control (closed squares). As discussed in Example 157, the tumor doubling time for the NCI-H69 SCLC xenograft model was 5.8 days.
Figure 13:
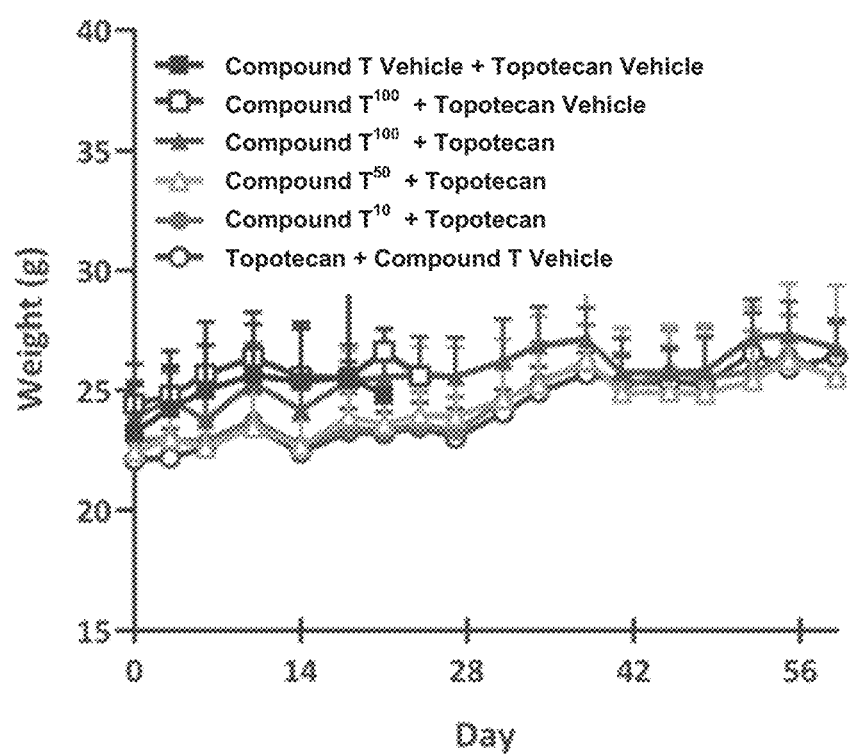
FIG. 13 is a graph showing animal weight (grams) vs. time (days) in a CDK4/6 independent tumor mouse model (NCI-H69 SCLC xenograft model). Tumor-bearing mice were treated with Compound T vehicle and topotecan vehicle (Group 1; closed squares), Compound T (100 mg/kg) and topotecan vehicle (Group 2; open squares), Compound T (100 mg/kg) and topotecan (0.6 mg/kg) (Group 3; closed triangles), Compound T (50 mg/kg) and topotecan (0.6 mg/kg) (Group 4; open triangles), Compound T (10 mg/kg) and topotecan (0.6 mg/kg) (Group 5; closed circles) or Compound T vehicle and topotecan (0.6 mg/kg) (Group 6; open circles). As discussed in Example 157, Compound T, administered alone or thirty minutes before topotecan, was well tolerated with no additive weight loss or toxicity.
Figure 14:
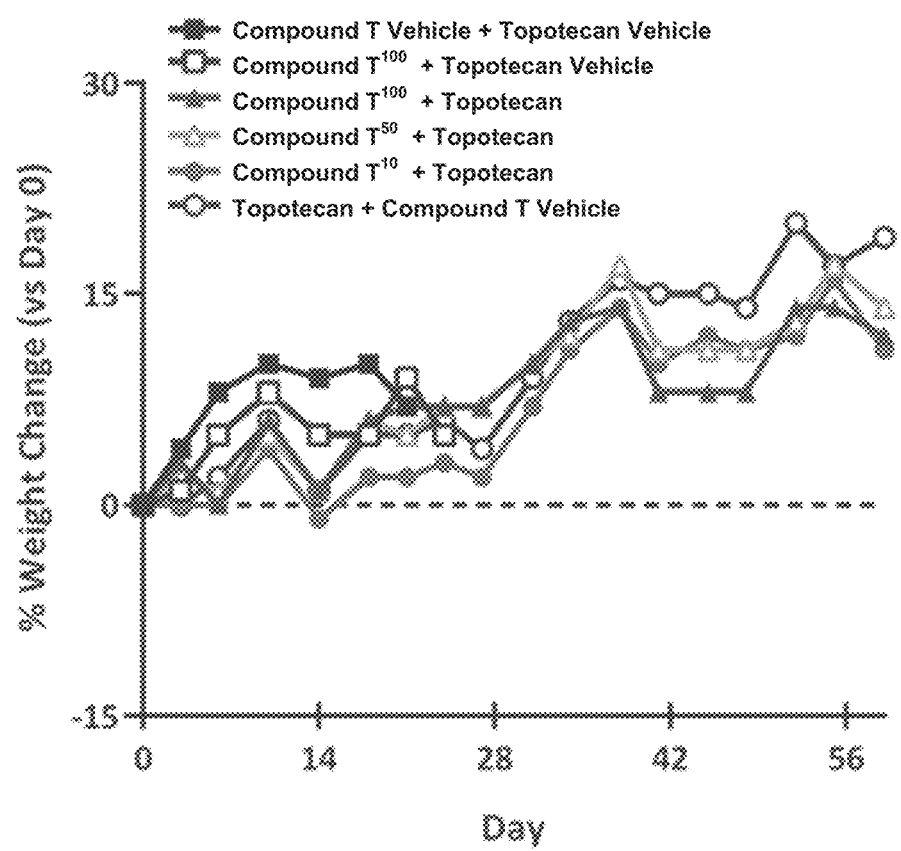

As shown in FIG. 12, the tumor doubling time of the NCI-H69 xenografts was 5.8 days. As shown in FIG. 13, Compound T, administered alone or thirty minutes before administration of a topoisomerase I inhibitor-topotecan, was well tolerated with no additive weight loss or toxicity. As shown in FIG. 14, there was no tumor burden associated with this model based on the percent weight gain versus Day 0 in control group animals.

Figure 15:
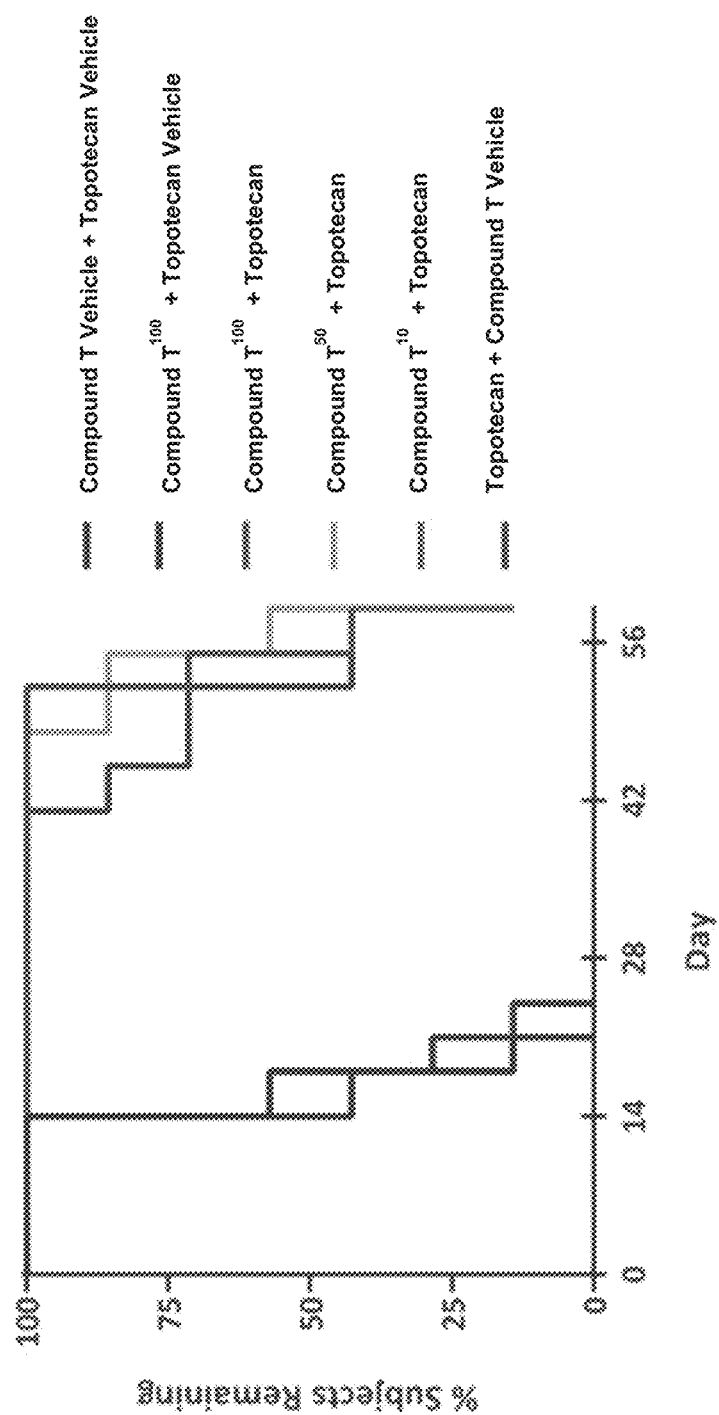
FIG. 15 is a graph showing survival (% subjects remaining) vs. time (days) in a CDK4/6 independent mouse model (NCI-H69 SCLC xenograft model). Tumor-bearing mice were treated with Compound T vehicle and topotecan vehicle (Group 1), Compound T (100 mg/kg) and topotecan vehicle (Group 2), Compound T (100 mg/kg) and topotecan (0.6 mg/kg) (Group 3), Compound T (50 mg/kg) and topotecan (0.6 mg/kg) (Group 4), Compound T (10 mg/kg) and topotecan (0.6 mg/kg) (Group 5) or Compound T vehicle and topotecan (0.6 mg/kg) (Group 6). As discussed in Example 157, mice treated with topotecan or topotecan plus Compound T survived significantly longer than mice treated with vehicle or Compound T only. The combination of topotecan with 100 mg/kg Compound T or 50 mg/kg Compound T led to increased survival rates in comparison to topotecan alone.

As shown in FIG. 15, mice treated with topotecan or topotecan/Compound T survived significantly longer than mice treated with vehicle or Compound T only. The combination of topotecan with 100 mg/kg Compound T or 50 mg/kg Compound T led to increased survival rates in comparison to topotecan alone.

Figure 16:
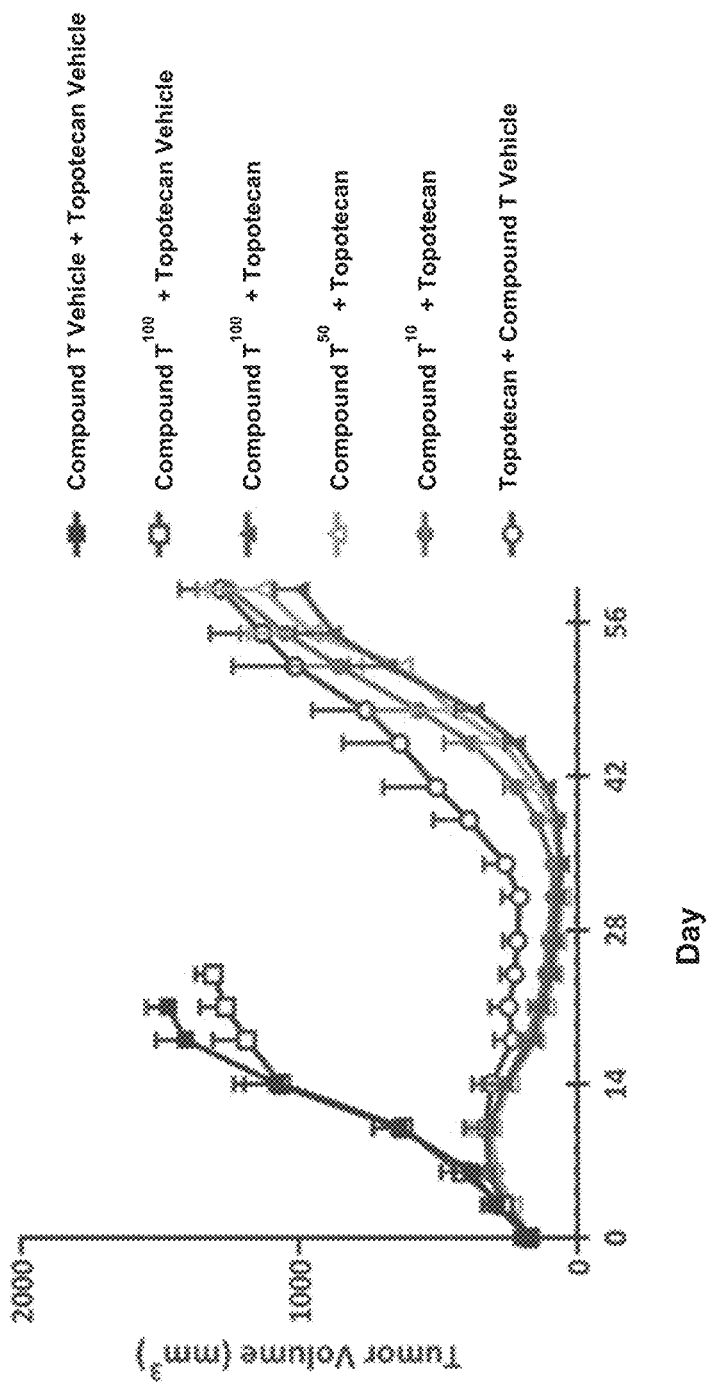
FIG. 16 is a graph showing tumor volume ($mm^3$) vs. time (days) in a CDK4/6 independent mouse model (NCI-H69 SCLC xenograft model). Tumor-bearing mice were treated with Compound T vehicle and topotecan vehicle (Group 1; closed squares), Compound T (100 mg/kg) and topotecan vehicle (Group 2; open squares), Compound T (100 mg/kg) and topotecan (0.6 mg/kg) (Group 3; closed triangles), Compound T (50 mg/kg) and topotecan (0.6 mg/kg) (Group 4; open triangles), Compound T (10 mg/kg) and topotecan (0.6 mg/kg) (Group 5; closed circles) or Compound T vehicle and topotecan (0.6 mg/kg) (Group 6; open circles). As discussed in Example 157, Compound T alone was inactive toward NCI-H69 xenografts, while topotecan alone was active and reduced tumor volumes (p<0.0001). Additionally, the combination of topotecan with each concentration of Compound T tested (100 mg/kg, 50 mg/kg, or 10 mg/kg) led to a reduction in tumor volume in comparison to treatment with vehicle alone (p<0.0001).

As shown in FIG. 16, Compound T alone was inactive toward NCI-H69 xenografts, while topotecan alone was active and reduced tumor volumes (p<0.0001; vs. vehicle control). Additionally, the combination of topotecan with each concentration of Compound T tested (100 mg/kg, 50 mg/kg, or 10 mg/kg) led to a reduction in tumor volume in comparison to treatment with vehicle (p<0.0001). The results of the experiments conducted in FIG. 16 are summarized in Table 7.

TABLE 7

Agent Efficacy and Tumor Volume Data

| Group | MTTE ± SD | T – C | *p-value | *Significant | LTS | PR (%) | CR | TFS |
|---|---|---|---|---|---|---|---|---|
| 1 | 18 ± 3 | — | — | — | 0 | 0 | 0 | 0 |
| 2 | 14 ± 4 | <0 | 0.8813 | N | 0 | 0 | 0 | 0 |
| 3 | 55 ± 3 | 37 | <0.0001 | Y | 3 | 4 | 0 | 0 |
| 4 | 59 ± 4 | 41 | <0.0001 | Y | 3 | 5 | 0 | 0 |
| 5 | 55 ± 4 | 37 | <0.0001 | Y | 1 | 3 | 0 | 0 |
| 6 | 52 ± 7 | 34 | <0.0001 | Y | 1 | 0 | 0 | 0 |

*Versus Vehicle Control
Group 1 = Compound T vehicle and topotecan vehicle
Group 2 = Compound T (100 mg/kg) and topotecan vehicle
Group 3 = Compound T (100 mg/kg) and topotecan (0.6 mg/kg)
Group 4 = Compound T (50 mg/kg) and topotecan (0.6 mg/kg)
Group 5 = Compound T (10 mg/kg) and topotecan (0.6 mg/kg)
Group 6 = Compound T vehicle and topotecan (0.6 mg/kg)
MTTE = Median timepoint in days for an individual mouse or group to reach a designated tumor volume or time endpoint, Mean ± SD used.
T – C = Difference in days between MTTE of treatment and control groups.
LTS = Individual tumor volume (TV) < volume endpoint at study time endpoint.
PR (%) = Tumor volume (TV) ≥ 50% regression versus Day 0 for two consecutive measurements over a period of ≥7 days during or at study completion.
CR = Tumor volume (TV) <15 mm³ for two consecutive measurements over a period of ≥7 days during or at study completion.
TFS = A designated complete responder at study endpoint; TFS animals are excluded from efficacy calculations.

This specification has been described with reference to embodiments of the invention. The invention has been described with reference to assorted embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the invention.

The invention claimed is:

1. A method for treating a human having Rb-negative triple negative breast cancer comprising:

a. administering to the human an effective amount of Cyclin Dependent Kinase (CDK) 4/6 inhibitor compound of the formula:

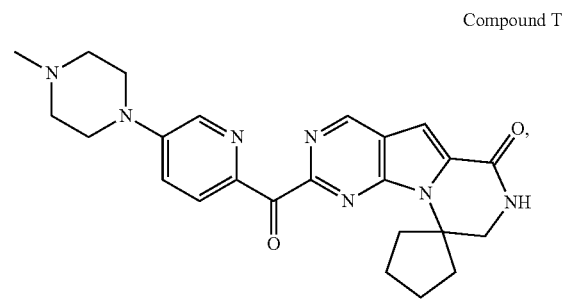 [SMILES: CN1CCN(c2ccc(C(=O)c3ncc4cc5n(c4n3)C3(CCCC3)CNC5=O)nc2)CC1]

Compound T or a pharmaceutically acceptable salt therein, and, b. administering to the human an effective amount of topotecan, wherein the topotecan is administered about 24 hours or less after the administration of the CDK 4/6 inhibitor.

2. The method of claim 1, wherein topotecan is administered about 4 hours or less after the administration of the CDK 4/6 inhibitor.

3. The method of claim 1, wherein topotecan is administered about 30 minutes or less after the administration of the CDK 4/6 inhibitor.

4. A method for treating a human having Rb-negative cervical cancer comprising:

a. administering to the human an effective amount of Cyclin Dependent Kinase (CDK) 4/6 inhibitor compound of the formula:

Compound T

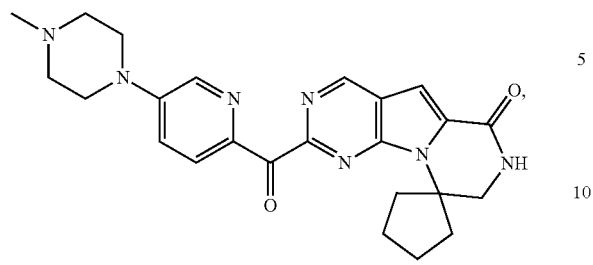

or a pharmaceutically acceptable salt therein, and,
  b. administering to the human an effective amount of topotecan,
wherein the topotecan is administered about 24 hours or less after the administration of the CDK 4/6 inhibitor.

5. The method of claim 4, wherein topotecan is administered about 4 hours or less after the administration of the CDK 4/6 inhibitor.

6. The method of claim 4, wherein topotecan is administered about 30 minutes or less after the administration of the CDK 4/6 inhibitor.

* * * * *

UNITED STATES PATENT AND TRADEMARK OFFICE
CERTIFICATE OF CORRECTION

| | |
|---|---|
| PATENT NO. | : 11,090,306 B2 |
| APPLICATION NO. | : 16/572418 |
| DATED | : August 17, 2021 |
| INVENTOR(S) | : Strum et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 133 days.

Signed and Sealed this
Seventh Day of February, 2023

Katherine Kelly Vidal
*Director of the United States Patent and Trademark Office*